US011274090B2

United States Patent
Wilson et al.

(10) Patent No.: US 11,274,090 B2
(45) Date of Patent: Mar. 15, 2022

(54) P300/CBP HAT INHIBITORS

(71) Applicant: Constellation Pharmaceuticals, Inc., Cambridge, MA (US)

(72) Inventors: Jonathan E. Wilson, Arlington, MA (US); Francois Brucelle, Cambridge, MA (US); Julian R. Levell, Arlington, MA (US)

(73) Assignee: Constellation Pharmaceuticals, Inc., Cambridge, MA (US)

( * ) Notice: Subject to any disclaimer, the term of this patent is extended or adjusted under 35 U.S.C. 154(b) by 0 days.

(21) Appl. No.: 16/970,169

(22) PCT Filed: Feb. 15, 2019

(86) PCT No.: PCT/US2019/018158
§ 371 (c)(1),
(2) Date: Aug. 14, 2020

(87) PCT Pub. No.: WO2019/161162
PCT Pub. Date: Aug. 22, 2019

(65) Prior Publication Data
US 2021/0115008 A1 Apr. 22, 2021

Related U.S. Application Data

(60) Provisional application No. 62/758,885, filed on Nov. 12, 2018, provisional application No. 62/631,596, filed on Feb. 16, 2018.

(51) Int. Cl.
| | | |
|---|---|---|
| C07D 401/04 | (2006.01) | |
| C07D 209/08 | (2006.01) | |
| C07D 213/75 | (2006.01) | |
| C07D 215/08 | (2006.01) | |
| C07D 231/12 | (2006.01) | |
| C07D 231/40 | (2006.01) | |
| C07D 237/08 | (2006.01) | |
| C07D 295/135 | (2006.01) | |
| C07D 401/14 | (2006.01) | |
| C07D 403/04 | (2006.01) | |
| C07D 405/04 | (2006.01) | |
| C07D 413/04 | (2006.01) | |
| C07D 417/04 | (2006.01) | |
| C07D 487/04 | (2006.01) | |
| C07D 491/107 | (2006.01) | |

(52) U.S. Cl.
CPC ......... *C07D 401/04* (2013.01); *C07D 209/08* (2013.01); *C07D 213/75* (2013.01); *C07D 215/08* (2013.01); *C07D 231/12* (2013.01); *C07D 231/40* (2013.01); *C07D 237/08* (2013.01); *C07D 295/135* (2013.01); *C07D 401/14* (2013.01); *C07D 403/04* (2013.01); *C07D 405/04* (2013.01); *C07D 413/04* (2013.01); *C07D 417/04* (2013.01); *C07D 487/04* (2013.01); *C07D 491/107* (2013.01)

(58) Field of Classification Search
CPC ............... C07D 231/40; C07D 237/08; C07D 295/135; C07D 401/14; C07D 403/04; C07D 405/04; C07D 413/04; C07D 417/04; C07D 487/04; C07D 491/107; C07D 401/04; C07D 209/08; C07D 213/75; C07D 215/08; C07D 231/12
See application file for complete search history.

(56) References Cited

U.S. PATENT DOCUMENTS

| | | |
|---|---|---|
| 8,309,700 B2 | 11/2012 | Mizutani et al. |
| 2014/0213586 A1 | 7/2014 | Bardiot et al. |
| 2021/0061762 A1 | 3/2021 | Wilson et al. |

FOREIGN PATENT DOCUMENTS

| | | |
|---|---|---|
| EP | 0415413 A1 | 3/1991 |
| WO | 2003/064397 A1 | 8/2003 |
| WO | 2010/021878 A1 | 2/2010 |
| WO | 2013/045516 A1 | 4/2013 |
| WO | 2015/054642 A2 | 4/2015 |
| WO | 2016/044770 A1 | 3/2016 |
| WO | 2016/044771 A1 | 3/2016 |
| WO | 2016/044777 A1 | 3/2016 |
| WO | 2016/196117 A1 | 12/2016 |
| WO | 2017/205536 A2 | 11/2017 |
| WO | 2019/161162 A1 | 8/2019 |

OTHER PUBLICATIONS

Hubbs et al., Amino acid derivatives as histone deacetylase inhibitors. Bioorg Med Chem Lett. Jan. 1, 2008;18(1):34-8.

Tria et al., Discovery of LSZ102, a Potent, Orally Bioavailable Selective Estrogen Receptor Degrader (SERD) for the Treatment of Estrogen Receptor Positive Breast Cancer. J Med Chem. 2018;61:2837-64.

(Continued)

*Primary Examiner* — Alicia L Otton

(74) *Attorney, Agent, or Firm* — McCarter & English, LLP; Steven G. Davis; Michael J. DeGrazia

(57) ABSTRACT

Provided are compounds of Formula (I): and pharmaceutically acceptable salts and compositions thereof, which are useful for treating a variety of conditions associated with histone acetyltransferase (HAT).

24 Claims, No Drawings

(56) References Cited

OTHER PUBLICATIONS

Copending U.S. Appl. No. 16/970,046, filed Aug. 14, 2020.
Golub et al., Molecular classification of cancer: class discovery and class prediction by gene expression monitoring. Science. Oct. 15, 1999;286(5439):531-7.
Lala et al., Role of nitric oxide in tumor progression: lessons from experimental tumors. Cancer Metastasis Rev. Mar. 1998;17(1):91-106.
Medline Plus, Cancer. Retrieved online at: http://nlm.nih.gov/medlineplus/cancer.html. 10 pages, Jun. 27, 2007.
Winterton et al., Discovery of Cytochrome P450 4F11 Activated Inhibitors of Stearoyl Coenzyme A Desaturase. J Med Chem. Jun. 28, 2018;61(12):5199-5221.
Copending U.S. Appl. No. 17/434,102, filed Aug. 26, 2021.

P300/CBP HAT INHIBITORS

RELATED APPLICATIONS

This application is a 35 U.S.C. § 371 national stage filing of International Application No. PCT/US2019/018158, filed Feb. 15, 2019, which claims priority to U.S. Provisional Application No. 62/631,596, filed Feb. 16, 2018 and U.S. Provisional Application No. 62/758,885, filed Nov. 12, 2018, the entire contents of each of which are incorporated herein by reference.

BACKGROUND

Chromatin is a complex combination of DNA and protein that makes up chromosomes. It is found inside the nuclei of eukaryotic cells and is divided between heterochromatin (condensed) and euchromatin (extended) forms. The major components of chromatin are DNA and proteins. Histones are the chief protein components of chromatin, acting as spools around which DNA winds. The functions of chromatin are to package DNA into a smaller volume to fit in the cell, to strengthen the DNA to allow mitosis and meiosis, and to serve as a mechanism to control expression and DNA replication. The chromatin structure is controlled by a series of post-translational modifications to histone proteins, notably histones H3 and H4, and most commonly within the "histone tails" which extend beyond the core nucleosome structure. Histone tails tend to be free for protein-protein interaction and are also the portion of the histone most prone to post-translational modification (Goll and Bestor, 2002, Genes Dev. 16:1739-1742; Grant, 2001, Genome Biol. 2:). These modifications include acetylation, methylation, phosphorylation, ubiquitinylation, SUMOylation. These epigenetic marks are written and erased by specific enzymes that place the tags on specific residues within the histone tail, thereby forming an epigenetic code, which is then interpreted by the cell to allow gene specific regulation of chromatin structure and thereby transcription.

Covalent modification of histones is a fundamental mechanism of control of gene expression, and one of the major epigenetic mechanisms at play in eukaryotic cells (Kouzarides, Cell, 128, 693-705 (2007)). Because distinct transcriptional states define fundamental cellular processes, such as cell type specification, lineage commitment, cell activation and cell death, their aberrant regulation is at the core of a range of diseases (Medzhitov et al., Nat. Rev. Immunol., 9, 692-703 (2009); Portela et al., Nat. Biotech., 28, 1057-1068 (2010)). Distinct classes of enzymes, namely histone acetyltransferases (HATS) and histone deacetylases (HDACs), acetylate or de-acetylate specific histone lysine residues (Struhl K., Genes Dev., 1998, 12, 5, 599-606).

Histone acetyltransferases (HATs) catalyze the acetylation (transfer of an acetyl group) on a ε-amino group of a target lysine side chain within a substrate histone, and histone deacetylases (HDACs) catalyze the removal of acetyl groups from lysine residues. Subsequently, acetylated core histones were shown to preferentially associate with transcriptionally active chromatin. See Nucleic Acids Res. 5:1863-1876 (1978); Proc. Natl. Acad. Sci. 75:2239-2243 (1978); and EMBO J, 7:1395-1402 (1988). HATs are categorized into four major families based on primary sequence homology, shared structural features, and functional roles: Gen5/PCAF (General control nonrepressed protein 5 and p300 and CBP associated factor); MYST (named for the founding members MOZ, Ybf2/Sas3, Sas2, and Tip60); p300/CBP (protein of 300 kDa and CREB Binding Protein); and Rtt109 (Regulator of Ty1 Transposition gene production 109).

Paralogs p300 and CBP (CREB binding protein) were originally identified as binding partners of the adenovirus early-region 1A (E1A) protein (Yee and Branton, 1985, Virology 147:142-153; Harlow et al., 1986, Mol. Cell Biol. 6:1579-1589), and the cAMP-regulated enhancer (CRE) binding proteins (Chrivia et al, 1993, Nature 365:855-859), respectively. p300 and CBP HAT domains have >90% sequence identity and are conserved in metazoans with many overlapping functions. In addition to the HAT domain, p300/CBP contains other protein interaction domains including three cysteine-histidine rich domains (CH1, CH2 and CH3), a KIX domain, a bromodomain, and a steroid receptor coactivator interaction domain (SID, also the SRC-1 interaction domain) (Arany et al, Cell. 1994 Jun. 17; 77(6):799-800) p300/CBP was found to have intrinsic HAT activity (Ogryzko et al., 1996, Cell 87:953-959; Bannister and Kouzarides, 1996, Nature 384:641-643). In addition to acetylating multiple lysines on all four core histones (H2A, H2B, H3 and H4), p300/CBP has been shown to have acetyltransferase activity towards >70 substrates (Wang et al., 2008, Curr. Opin. Struct. Biol. 18:741-747), including, for example, p53 (Gu et al., 1997, Cell 90:595-606), MyoD (Polesskaya et al., 2002, J. Biol. Chem. 275:34359-64), STAT3 (Yuan et al., 2005, Science 307:269-73) and NFκβ (Chen et al., 2002, EMBO J. 21:6539-48). These two acetyltransferases are responsible for the majority of histone H3 lysine 18 acetylation (H3K18ac) and H3K27ac, modifications associated with active promoters and enhancers (Horwitz et al. 2008; Jin et al. 2011).

Besides acting as an acetyltransferase, p300 also acts as a scaffold for transcription factors or a bridge to connect the transcription factors and the basal transcriptional machinery to activate transcription (Chan and Thangue, 2001, J. Cell Sci. 114:2363-2373; Chen and Li, 2011, Epigenetics 6:957-961). P300/CBP proteins are involved in many cellular processes, including cell growth, proliferation, and differentiation (reviewed in Chan and Thangue, 2001, J. Cell Sci. 114:2363-2373). Mutations in p300/CBP have been observed in number of human diseases, particularly cancer with frequencies up to 30%. A higher frequency of these mutations occur within the HAT domain, suggesting a selective pressure to alter this activity in cancers. These mutations are mostly mono-allelic, with loss of heterozygosity of the second allele, consistent with Knudson's hypothesis of a classical tumor suppressor gene. See Nature 376, 348-351, 1995; Oncogene 12, 1565-1569, 1996; and Proc. Natl. Acad. Sci. USA 94, 8732-8737, 1997. Heterozygous mutations in CBP were first described in RTS, an autosomal-dominant disease, characterised by mental retardation, skeletal abnormalities and a high incidence of neoplasia (Nature 376, 348-351, 1995). This suggests that a full complement of CBP gene dosage is required for normal development. P300/CBP genes are also involved in various chromosomal translocations, particularly in hematological malignancies and possibly contribute to aberrant growth through gain of function (Kitabayashi et al. 2001; Panagopoulos et al. 2001)

High p300 expression, correlating with poor survival and aggressive phenotypes, has been observed in prostate cancer (Debes et al 2003; Cancer Res. 63: 7638-7640; Heemers et al., 2008, Adv. Exp. Med. Biol. 617:535-40; Isharwal et al., 2008, Prostate 68:1097-104), liver cancer (Yokomizo et al., 2011, Cancer Lett. 310:1407; Li et al., 2011, J. Transl. Med. 9:5), breast cancer (Lermento et al., 2010, Exp. Mol. Pathol.

88:256-64), esophageal carcinoma (Li et al, 2011, Ann Thorac Surg. 91: 1531-1538) and cutaneous squamous cell carcinoma (Chen et al, 2014, Br J Dermatol. 172: 111-119). Inhibition of p300/CBP has therapeutic potential in cancer (Iyer et al., 2004, Proc. Natl. Acad. Sci. USA 101:7386-7391; Stimson et al., 2005, Mol. Cancer Ther. 4:1521-1532; Zheng et al., 2004, Methods Enzymol. 376:188-199), cardiac disease (Davidson et al., 2005, Chembiochem. 6:162-170); diabetes mellitus (Zhou et al., 2004, Nat. Med. 10:633-637), and HIV (Varier and Kundu, 2006, Curr. Pharm. Des. 12:1975-1993). P300/CBP is also involved in regulating inflammatory mediators (Deng et al., 2004, Blood WO 2016/044770 PCT/US2015/051028 103:2135-42; Tumer-Brannen et al., 2011, J. Immunol. 186:7127-7135). P300/CBP has also been linked to other diseases, such as fibrosis (Ghosh and Varga, 2007, J. Cell. Physiol. 213:663-671), metabolic syndrome (Bricambert et al., 2010, J. Clin. Invest. 120:4316-4331), and progressive neurodegenerative diseases, such as Huntington Disease (Cong et al., 2005, Mol. Cell. Neurosci. 30:12-23), Kennedy's disease (Lieberman et al., 2002, Hum. Mol. Genet. 11:1967-76), and Alzheimer's disease (Lrancis et al., 2007, Neurosci. Lett. 413:137-140).

The association of p300/CBP activity in disease pathogenesis suggests potential utility of p300/CBP as a therapeutic target. However, the identification of potent, specific histone acetyltransferase inhibitors has been challenging (Cole, 2008, Nat. Chem. Biol. 4:590-97). P300 HAT inhibitors derived from natural compounds have moderate potency but lack specificity (Dekker and Haisma, 2009, Dmg Disc. Today 14:942-8). Lys-CoA, converted to a cell-permeable form with a Tat peptide attachment, is more selective, but has limited use in pharmacological studies due to its complexity. Recently, a selective p300 inhibitor C646 was identified using the Lys-CoA/p300 HAT structure in a virtual ligand screening approach (Bowers et al., 2010, Chemistry & Biology 17:471-482). While progress has been made in this field, there remains a need in the art for improved HAT inhibitors.

SUMMARY

Provided herein are compounds having the Formula I:

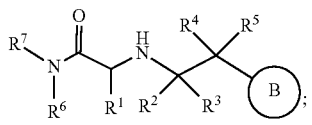

(I)

and pharmaceutically acceptable salts and compositions thereof, wherein B, $R^1$, $R^2$, $R^3$, $R^4$, $R^5$, $R^6$, and $R^7$ are as described herein. The disclosed compounds and compositions modulate histone acetyltranferases (see e.g., Table 8), and are useful in a variety of therapeutic applications such as, for example, in treating cancer.

DETAILED DESCRIPTION

1. General Description of Compounds

Provided herein is a compound of Formula I:

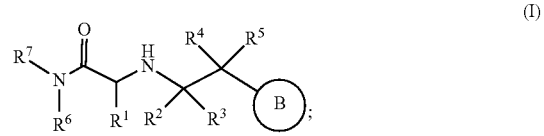

(I)

or a pharmaceutically acceptable salt thereof, wherein

Ring B is aryl, heterocyclyl, or heteroaryl each of which may be optionally substituted with 1 to 4 groups selected from $R^b$;

$R^6$ is a hydrogen or $C_{1-6}$alkyl;

$R^7$ is aryl or heteroaryl, each of which is substituted with one group selected from $R^f$, and wherein said aryl and heteroaryl for $R^7$ may also be optionally substituted with 1 to 4 groups selected from $R^a$; or $R^6$ and $R^7$ taken together with the nitrogen ring to which they are attached form a fused bicyclic heterocyclyl optionally substituted with 1 to 4 groups selected from $R^a$;

$R^1$ is $C_{1-6}$alkyl, $C_{1-6}$haloalkyl, $C_{2-6}$alkenyl, —$C_{1-6}$alkylOR$^c$, —$C_{1-6}$alkylN(R$^d$)$_2$, —$C_{1-6}$alkylC(O)OR$^d$, —$C_{1-6}$alkylOC$_{1-6}$alkylN(R$^d$)$_2$, —$C_{1-6}$alkylSOR$^d$, —$C_{1-6}$alkylS(O)$_2$R$^d$, —$C_{1-6}$alkylSON(R$^d$)$_2$, —$C_{1-6}$alkylSO$_2$N(R$^d$)$_2$, —$C_{1-6}$alkylcycloalkyl, —$C_{1-6}$alkylheterocyclyl, —$C_{1-6}$alkylheteroaryl, —$C_{1-6}$alkylaryl, cycloalkyl, aryl, heteroaryl, or heterocyclyl, wherein each of said cycloalkyl, heterocyclyl, aryl, and heteroaryl alone and in connection with —$C_{1-6}$alkylcycloalkyl, —$C_{1-6}$alkylaryl, —$C_{1-6}$alkylheteroaryl, and —$C_{1-6}$alkylheterocyclyl are optionally substituted with 1 to 3 groups selected from $R^c$;

each of $R^2$, $R^3$, $R^4$, and $R^5$ are independently hydrogen or $C_{1-6}$alkyl, wherein said $C_{1-6}$alkyl is optionally substituted with 1 or 2 groups selected from halo, —C(O)OR$^d$, —OC$_{1-6}$alkylN(R$^d$)$_2$, —$C_{1-6}$alkylN(R$^d$)$_2$, —N(R$^d$)$_2$, —NR$^d$C$_{1-6}$alkylOR$^d$, —SOR$^d$, —S(O)$_2$R$^d$, —SON(R$^d$)$_2$, —SO$_2$N(R$^d$)$_2$, $C_{3-10}$cycloalkyl, $C_{5-10}$heterocyclyl, $C_{5-10}$heteroaryl, and $C_{6-10}$aryl;

each of $R^a$, $R^b$, and $R^c$ are each independently halo, CN, oxo, NO$_2$, $C_{1-6}$alkyl, $C_{2-6}$alkenyl, $C_{1-6}$alkoxy, $C_{1-6}$haloalkoxy, $C_{1-6}$haloalkyl, —$C_{1-6}$alkylOR$^d$, —C(O)R$^d$, —C(O)OR$^d$, —$C_{1-6}$alkylC(O)OR$^d$, —C(O)N(R$^d$)$_2$, —C(O)NR$^d$C$_{1-6}$alkylOR$^d$, —OC$_{1-6}$alkylN(R$^d$)$_2$, —$C_{1-6}$alkylC(O)N(R$^d$)$_2$, —$C_{1-6}$alkylN(R$^d$)$_2$, —N(R$^d$)$_2$, —C(O)NR$^d$C$_{1-6}$alkylN(R$^d$)$_2$, —NR$^d$C$_{1-6}$alkylN(R$^d$)$_2$, —NR$^d$C$_{1-6}$alkylOR$^d$, —SOR$^d$, —S(O)$_2$R$^d$, —SON(R$^d$)$_2$, —SO$_2$N(R$^d$)$_2$, SF$_5$, -Ocycloalkyl, —O—$C_{1-4}$alkylaryl, —$C_{1-6}$alkylcycloalkyl, —$C_{1-6}$alkylaryl, —$C_{1-6}$alkylheteroaryl, —$C_{1-6}$alkylheterocyclyl, cycloalkyl, heterocyclyl, heteroaryl, or aryl, wherein each of said cycloalkyl, heterocyclyl, aryl, and heteroaryl alone and in connection with -Ocycloalkyl, —$C_{1-6}$alkylcycloalkyl, —$C_{1-6}$alkylaryl, —$C_{1-6}$alkylheteroaryl, and —$C_{1-6}$alkylheterocyclyl are optionally substituted with 1 to 3 groups selected from halo, $C_{1-6}$alkyl, $C_{1-6}$haloalkyl, $C_{1-6}$alkoxy, $C_{1-6}$haloalkoxy, —N(R$^d$)$_2$, —C(O)R$^d$, and —$C_{1-6}$alkylOR$^d$;

each $R^d$ is independently hydrogen, $C_{1-6}$haloalkyl, or $C_{1-6}$alkyl; and each $R^f$ is independently cycloalkyl, heterocyclyl, heteroaryl, or aryl, wherein each of said cycloalkyl, heterocyclyl, aryl, and heteroaryl are optionally substituted with 1 to 3 groups selected from halo, CN, oxo, $NO_2$, $C_{1-6}$alkyl, $C_{2-6}$alkenyl, $C_{1-6}$alkoxy, $C_{1-6}$haloalkoxy, $C_{1-6}$haloalkyl, —$C_{1-6}$alkyl$OR^d$, —$C(O)R^d$, —$C(O)OR^d$, —$C_{1-6}$alkyl$C(O)OR^d$, —$C(O)N(R^d)_2$, —$C(O)NR^dC_{1-6}$alkyl$OR^d$, —$OC_{1-6}$alkyl$N(R^d)_2$, —$C_{1-6}$alkyl$C(O)N(R^d)_2$, —$C_{1-6}$alkyl$N(R^d)_2$, —$N(R^d)_2$, —$C(O)NR^dC_{1-6}$alkyl$N(R^d)_2$, —$NR^dC_{1-6}$alkyl$N(R^d)_2$, —$NR^dC_{1-6}$alkyl$OR^d$, —$SOR^d$, —$S(O)_2R^d$, —$SON(R^d)_2$, —$SO_2N(R^d)_2$, $SF_5$, -Ocycloalkyl; provided the compound is not N-[1,1'-biphenyl]-2-yl-2-[[2-(3,4-dimethoxyphenyl)ethyl]amino]-propanamide, or 2-[(2-phenylpropyl)amino]-N-[4-(1H-1,2,4-triazol-1-yl)phenyl]-propanamide, or a salt thereof.

2. Definitions

When used in connection to describe a chemical group that may have multiple points of attachment, a hyphen (-) designates the point of attachment of that group to the variable to which it is defined. For example, —$N(R^d)_2$ and —$NR^dC_{1-6}$alkyl$OR^d$ mean that the point of attachment for this group occurs on the nitrogen atom.

The terms "halo" and "halogen" refer to an atom selected from fluorine (fluoro, —F), chlorine (chloro, —Cl), bromine (bromo, —Br), and iodine (iodo, —I).

The term "alkyl" when used alone or as part of a larger moiety, such as "haloalkyl", "alkyl$C_{5-10}$heterocyclyl", and the like, means saturated straight-chain or branched monovalent hydrocarbon radical. Unless otherwise specified, an alkyl group typically has 1-6 carbon atoms, i.e., ($C_1$-$C_6$) alkyl.

"Alkoxy" means an alkyl radical attached through an oxygen linking atom, represented by —O-alkyl. For example, "($C_1$-$C_4$)alkoxy" includes methoxy, ethoxy, proproxy, and butoxy.

The term "haloalkyl" includes mono, poly, and perhaloalkyl groups where the halogens are independently selected from fluorine, chlorine, bromine, and iodine.

"Haloalkoxy" is a haloalkyl group which is attached to another moiety via an oxygen atom such as, e.g., but are not limited to —$OCHCF_2$ or —$OCF_3$.

The term "oxo" refers to the diradical =O

The term "aryl" refers to an aromatic carbocyclic single ring or two fused ring system containing 6 to 10 carbon atoms. Examples include phenyl, indanyl, tetrahydronaphthalene, and naphthyl.

The term "carbocyclyl" means a monocyclic, bicyclic (e.g., a bridged or spiro bicyclic ring), polycyclic (e.g., tricyclic), or fused hydrocarbon ring system that is completely saturated or that contains one or more units of unsaturation, but where there is no aromatic ring. Cycloalkyl is a completely saturated carbocycle. Monocyclic cycloalkyl groups include, without limitation, cyclopropyl, cyclobutyl, cyclopentyl, cyclohexyl, cycloheptyl, and cyclooctyl. Bridged bicyclic cycloalkyl groups include, without limitation, bicyclo[3.2.1]octane, bicyclo[2.2.1]heptane, bicyclo[3.1.0]hexane, bicyclo[1.1.1]pentane, and the like. Spiro bicyclic cycloalkyl groups include, e.g., spiro[3.6]decane, spiro[4.5]decane, and the like. Fused cycloalkyl rings include, e.g., decahydronaphthalene, octahydropentalene, and the like. It will be understood that when specified, optional substituents on a carbocyclyl (e.g., in the case of an optionally substituted cycloalkyl) may be present on any substitutable position and, include, e.g., the position at which the carbocyclyl group is attached.

The term "heteroaryl" used alone or as part of a larger moiety refers to a 5- to 12-membered aromatic radical containing 1-4 heteroatoms selected from N, O, and S. A heteroaryl group may be mono- or bi-cyclic. Monocyclic heteroaryl includes, for example, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, etc. Bi-cyclic heteroaryls include groups in which a monocyclic heteroaryl ring is fused to one or more aryl or heteroaryl rings. Nonlimiting examples include indolyl, imidazopyridinyl, benzooxazolyl, benzooxodiazolyl, indazolyl, benzimidazolyl, benzthiazolyl, quinolyl, quinazolinyl, quinoxalinyl, pyrrolopyridinyl, pyrrolopyrimidinyl, pyrazolopyridinyl, thienopyridinyl, thienopyrimidinyl, indolizinyl, purinyl, naphthyridinyl, and pteridinyl. It will be understood that when specified, optional substituents on a heteroaryl group may be present on any substitutable position and, include, e.g., the position at which the heteroaryl is attached.

The term "heterocyclyl" means a 5- to 12-membered saturated or partially unsaturated heterocyclic ring containing 1 to 4 heteroatoms independently selected from N, O, and S. It can be mononcyclic, bicyclic (e.g., a bridged, fused, or spiro bicyclic ring), or tricyclic. A heterocyclyl ring can be attached to its pendant group at any heteroatom or carbon atom that results in a stable structure. Examples of such saturated or partially unsaturated heterocyclic radicals include, without limitation, tetrahydrofuranyl, tetrahydrothienyl, terahydropyranyl, pyrrolidinyl, pyridinonyl, pyrrolidonyl, piperidinyl, oxazolidinyl, piperazinyl, dioxanyl, dioxolanyl, morpholinyl, dihydrofuranyl, dihydropyranyl, dihydropyridinyl, tetrahydropyridinyl, dihydropyrimidinyl, oxetanyl, azetidinyl and tetrahydropyrimidinyl. A heterocyclyl group may be mono- or bicyclic. The term "heterocyclyl" also includes, e.g., unsaturated heterocyclic radicals fused to another unsaturated heterocyclic radical or aryl or heteroaryl ring, such as for example, tetrahydronaphthyridine, indolinone, dihydropyrrolotriazole, imidazopyrimidine, quinolinone, dioxaspirodecane. It will also be understood that when specified, optional substituents on a heterocyclyl group may be present on any substitutable position and, include, e.g., the position at which the heterocyclyl is attached (e.g., in the case of an optionally substituted heterocyclyl or heterocyclyl which is optionally substituted).

The term "spiro" refers to two rings that shares one ring atom (e.g., carbon).

The term "fused" refers to two rings that share two adjacent ring atoms with one another.

The term "bridged" refers to two rings that share three ring atoms with one another.

The disclosed compounds exist in various stereoisomeric forms. Stereoisomers are compounds that differ only in their spatial arrangement. Enantiomers are pairs of stereoisomers whose mirror images are not superimposable, most commonly because they contain an asymmetrically substituted carbon atom that acts as a chiral center. "Enantiomer" means one of a pair of molecules that are mirror images of each other and are not superimposable. Diastereomers are stereoisomers that contain two or more asymmetrically substituted carbon atoms. The symbol in a structural formula represents the presence of a chiral carbon center. "R" and "S" represent the configuration of substituents around one or more chiral carbon atoms. Thus, "R*" and "S*" denote the relative configurations of substituents around one or more chiral carbon atoms.

"Racemate" or "racemic mixture" means a compound of equimolar quantities of two enantiomers, wherein such mixtures exhibit no optical activity, i.e., they do not rotate the plane of polarized light.

The compounds of the herein may be prepared as individual enantiomers by either enantio-specific synthesis or resolved from an enantiomerically enriched mixture. Conventional resolution techniques include forming the salt of a free base of each isomer of an enantiomeric pair using an optically active acid (followed by fractional crystallization and regeneration of the free base), forming the salt of the acid form of each enantiomer of an enantiomeric pair using an optically active amine (followed by fractional crystallization and regeneration of the free acid), forming an ester or amide of each of the enantiomers of an enantiomeric pair using an optically pure acid, amine or alcohol (followed by chromatographic separation and removal of the chiral auxiliary), or resolving an enantiomeric mixture of either a starting material or a final product using various well known chromatographic methods. Additionally, the compounds can be prepared as individual enantiomers by separating a racemic mixture using conventional chiral chromatography techniques.

When the stereochemistry of a disclosed compound is named or depicted by structure, the named or depicted stereoisomer is at least 60%, 70%, 80%, 90%, 99% or 99.9% by weight pure relative to all of the other stereoisomers. Percent by weight pure relative to all of the other stereoisomers is the ratio of the weight of one stereoisomer over the weight of the other stereoisomers. When a single enantiomer is named or depicted by structure, the depicted or named enantiomer is at least 60%, 70%, 80%, 90%, 99% or 99.9% by weight optically pure. Percent optical purity by weight is the ratio of the weight of the enantiomer over the weight of the enantiomer plus the weight of its optical isomer.

When the stereochemistry of a disclosed compound is named or depicted by structure, and the named or depicted structure encompasses more than one stereoisomer (e.g., as in a diastereomeric pair), it is to be understood that one of the encompassed stereoisomers or any mixture of the encompassed stereoisomers are included. It is to be further understood that the stereoisomeric purity of the named or depicted stereoisomer is at least 60%, 70%, 80%, 90%, 99% or 99.9% by weight pure relative to all of the other stereoisomers. The stereoisomeric purity in this case is determined by dividing the total weight in the mixture of the stereoisomers encompassed by the name or structure by the total weight in the mixture of all of the stereoisomers.

When a disclosed compound is named or depicted by structure without indicating the stereochemistry, and the compound has one chiral center, it is to be understood that the name or structure encompasses one enantiomer of compound free from the corresponding optical isomer, a racemic mixture of the compound, or mixtures enriched in one enantiomer relative to its corresponding optical isomer.

When a disclosed compound is named or depicted by structure without indicating the stereochemistry and e.g., the compound has more than one chiral center (e.g., at least two chiral centers), it is to be understood that the name or structure encompasses one stereoisomer free of other stereoisomers, mixtures of stereoisomers, or mixtures of stereoisomers in which one or more stereoisomers is enriched relative to the other stereoisomer(s). For example, the name or structure may encompass one stereoisomer free of other diastereomers, mixtures of stereoisomers, or mixtures of stereoisomers in which one or more diastereomers is enriched relative to the other diastereomer(s).

Unless otherwise specified, when only some of the stereochemical centers in a disclosed compound are depicted or named by structure, the named or depicted configuration is enriched relative to the remaining configurations, for example, by a molar excess of at least 60%, 70%, 80%, 90%, 99% or 99.9%. For example, the structure:

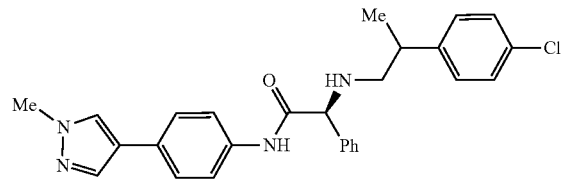 [SMILES: CC(CN[C@H](C(=O)Nc1ccc(-c2cnn(C)c2)cc1)c1ccccc1)c1ccc(Cl)cc1]

means that that the configuration about the chiral carbon where the stereochemistry is depicted is stereochemically enriched as S (e.g., by a molar excess of at least 60%, 70%, 80%, 90%, 99% or 99.9%) and that the stereochemistry at the other chiral center, to which the stereochemistry is not identified, may be R or S, or a mixture thereof.

The terms "subject" and "patient" may be used interchangeably, and means a mammal in need of treatment, e.g., companion animals (e.g., dogs, cats, and the like), farm animals (e.g., cows, pigs, horses, sheep, goats and the like) and laboratory animals (e.g., rats, mice, guinea pigs and the like). Typically, the subject is a human in need of treatment.

The term "inhibit," "inhibition" or "inhibiting" includes a decrease in the baseline activity of a biological activity or process.

As used herein, the terms "treatment," "treat," and "treating" refer to reversing, alleviating, delaying the onset of, or inhibiting the progress of a disease or disorder, or one or more symptoms thereof, as described herein. In some aspects, treatment may be administered after one or more symptoms have developed, i.e., therapeutic treatment. In other aspects, treatment may be administered in the absence of symptoms. For example, treatment may be administered to a susceptible individual prior to the onset of symptoms (e.g., in light of a history of symptoms and/or in light of exposure to a particular organism, or other susceptibility factors), i.e., prophylactic treatment. Treatment may also be continued after symptoms have resolved, for example to delay their recurrence.

The term "pharmaceutically acceptable carrier" refers to a non-toxic carrier, adjuvant, or vehicle that does not destroy the pharmacological activity of the compound with which it is formulated. Pharmaceutically acceptable carriers, adjuvants or vehicles that may be used in the compositions described herein include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

The term "effective amount" or "therapeutically effective amount" refers to an amount of a compound described herein that will elicit a biological or medical response of a subject e.g., a dosage of between 0.01-100 mg/kg body weight/day.

3. Compounds

In a first embodiment, provided herein is a compound of Formula I:

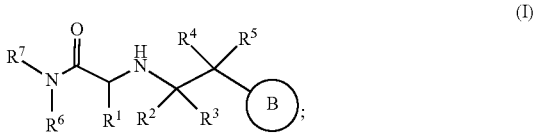

or a pharmaceutically acceptable salt thereof, wherein the variables are as described above.

In a second embodiment, the compound of Formula I is of the Formula II or III:

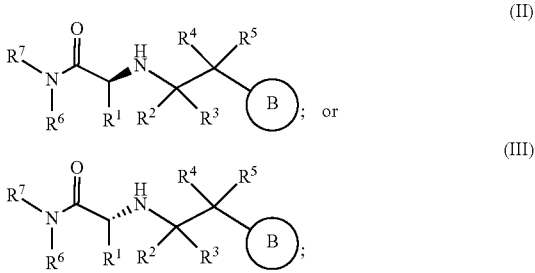

or a pharmaceutically acceptable salt thereof, wherein the remaining variables are as described for Formula I.

In a third embodiment, $R^6$ in the compounds of Formula I, II, or III is hydrogen; and $R^7$ is aryl or heteroaryl, each of which is substituted with one group selected from $R^f$, and wherein said aryl and heteroaryl for $R^7$ may also be optionally substituted with 1 to 4 groups selected from $R^a$; or $R^6$ and $R^7$ taken together with the nitrogen ring to which they are attached form a fused bicyclic heterocyclyl optionally substituted with 1 to 4 groups selected from $R^a$, wherein the remaining variables are as described above for Formula I. Alternatively, $R^6$ in the compounds of Formula I, II, or III is hydrogen; and $R^7$ is phenyl, pyridyl, pyrimidinyl, or quinolinyl, each of which is substituted with one group selected from $R^f$, and wherein said phenyl, pyridyl, pyrimidinyl, and quinolinyl for $R^7$ may also be optionally substituted with 1 to 4 groups selected from $R^a$; or $R^6$ and $R^7$ taken together with the nitrogen ring to which they are attached form a 5,6- or 6,6-fused bicyclic heterocyclyl optionally substituted with 1 to 4 groups selected from $R^a$, wherein the remaining variables are as described above for Formula I. In another alternative, $R^6$ in the compounds of Formula I, II, or III is hydrogen; $R^7$ is selected from phenyl, 2-pyridinyl, 3-pyridinyl, pyrimidin-5-yl, and quinolin-6-yl, each of which is substituted with one group from $R^f$, and wherein said phenyl, 2-pyridinyl, 3-pyridinyl, pyrimidin-5-yl, and quinolin-6-yl for $R^7$ may also be optionally substituted with 1 to 4 groups selected from $R^a$; or $R^6$ and $R^7$ taken together with the nitrogen ring to which they are attached form indolin-1-yl or dihydroquinolin-1(2H)-yl, each of which may be optionally substituted with 1 to 4 groups selected from $R^a$, wherein the remaining variables are as described above for Formula I.

In a fourth embodiment, Ring B in the compounds of Formula I, II, or III is phenyl optionally substituted with 1 to 3 groups selected from $R^b$, wherein the remaining variables are as described above for Formula I or the third embodiment.

In a fifth embodiment, $R^1$ in the compounds of Formula I, II, or III is phenyl optionally substituted with 1 to 3 groups selected from $R^c$, wherein the remaining variables are as described above for Formula I or the third or fourth embodiment.

In a sixth embodiment, $R^3$ in the compounds of Formula I, II, or III is hydrogen, wherein the remaining variables are as described above for Formula I or the third, fourth, or fifth embodiment.

In a seventh embodiment, $R^5$ in the compounds of Formula I, II, or III is hydrogen, wherein the remaining variables are as described above for Formula I or the third, fourth, fifth, or sixth embodiment.

In an eighth embodiment, $R^2$ in the compounds of Formula I, II, or III is hydrogen or $C_{1-4}$alkyl, wherein the remaining variables are as described above for Formula I or the third, fourth, fifth, sixth, or seventh embodiment. Alternatively, $R^2$ in the compounds of Formula I, II, or III is hydrogen or methyl, wherein the remaining variables are as described above for Formula I or the third, fourth, fifth, sixth, or seventh embodiment. In another alternative, $R^2$ in the compounds of Formula I, II, or III is hydrogen, wherein the remaining variables are as described above for Formula I or the third, fourth, fifth, sixth, or seventh embodiment.

In a ninth embodiment, $R^4$ in the compounds of Formula I, II, or III is hydrogen or $C_{1-4}$alkyl, wherein the remaining variables are as described above for Formula I or the third, fourth, fifth, sixth, seventh, or eighth embodiment. Alternatively, $R^4$ in the compounds of Formula I, II, or III is hydrogen, methyl, or ethyl, wherein the remaining variables are as described above for Formula I or the third, fourth, fifth, sixth, seventh, or eighth embodiment. In another alternative, $R^4$ in the compounds of Formula I, II, or III is hydrogen, wherein the remaining variables are as described above for Formula I or the third, fourth, fifth, sixth, seventh, or eighth embodiment.

In a tenth embodiment, the compound of Formula I is of the Formula IV or V:

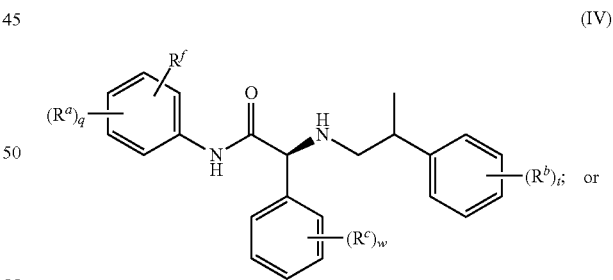

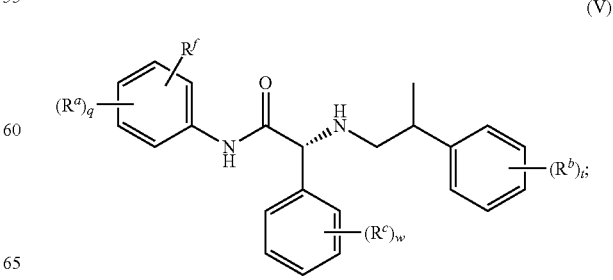

or a pharmaceutically acceptable salt thereof, wherein w, q, and t are each independently 0, 1, or 2, and wherein the remaining variables are as described above for Formula I or the third, fourth, fifth, sixth, seventh, eighth, or ninth embodiment. Alternatively, the compound of Formula I is of the Formula VI or VII:

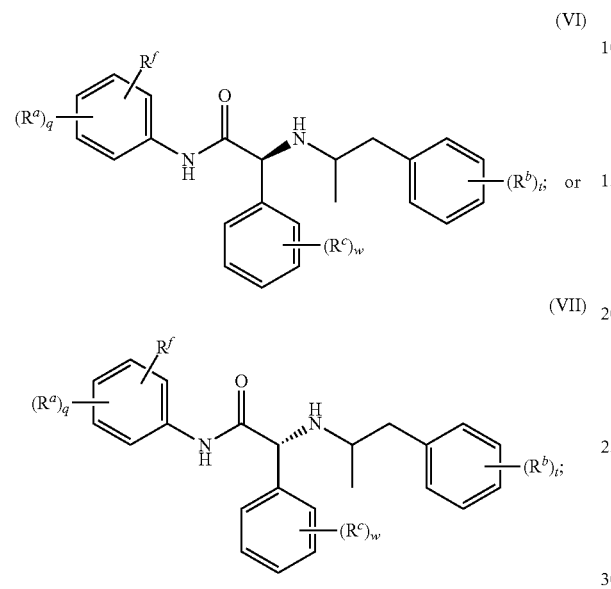

or a pharmaceutically acceptable salt thereof, wherein w, q, and t are each independently 0, 1, or 2, and wherein the remaining variables are as described above for Formula I or the third, fourth, fifth, sixth, seventh, eighth, or ninth embodiment. In another alternative, the compound of Formula I is of the Formula VIII or IX:

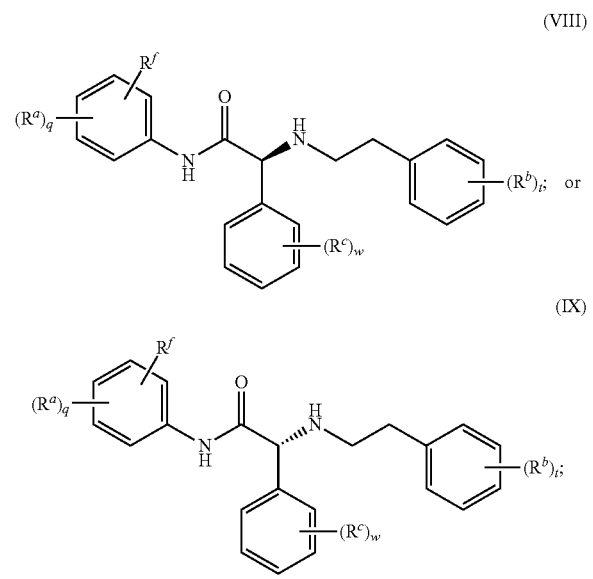

or a pharmaceutically acceptable salt thereof, wherein w, q, and t are each independently 0, 1, or 2, and wherein the remaining variables are as described above for Formula I or the third, fourth, fifth, sixth, seventh, eighth, or ninth or tenth embodiment.

In an eleventh embodiment, $R^c$, if present, in the compounds of Formula I, II, III, IV, V, VI, VII, VIII, or IX is $C_{1-6}$alkyl, $C_{1-6}$alkoxy, $C_{1-6}$haloalkoxy, or $C_{1-6}$haloalkyl, wherein the remaining variables are as described above for Formula I or the third, fourth, fifth, sixth, seventh, eighth, or ninth embodiment.

In a twelfth embodiment, compound of Formula I is of the Formula X or XI:

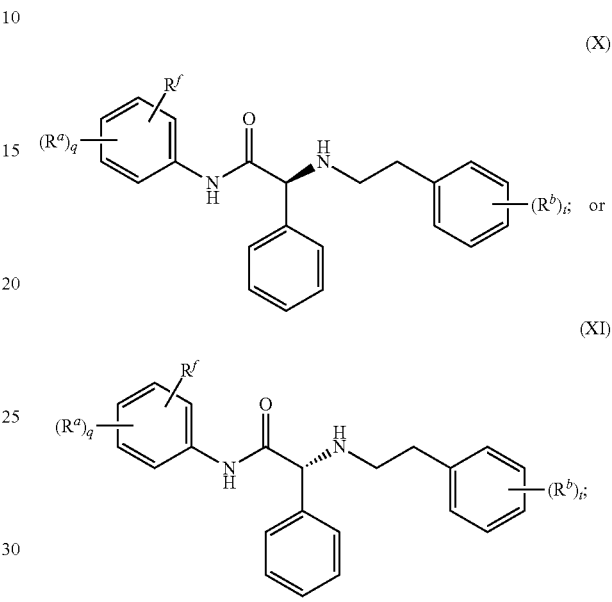

or a pharmaceutically acceptable salt thereof, wherein the remaining variables are as described above for Formula I or the third, fourth, fifth, sixth, seventh, eighth, ninth, tenth, or eleventh embodiment.

In a thirteenth embodiment, q in the compounds of Formula IV, V, VI, VII, VIII, or IX is 0 or 1, wherein the remaining variables are as described above for Formula I or the third, fourth, fifth, sixth, seventh, eighth, ninth, tenth, eleventh, or twelfth embodiment.

In a fourteenth embodiment, $R^a$ in the compounds of Formula I, II, III, IV, V, VI, VII, VIII, IX, X, and XI is $C_{1-4}$alkoxy or halo, wherein the remaining variables are as described above for Formula I or the third, fourth, fifth, sixth, seventh, eighth, ninth, tenth, eleventh, twelfth, or thirteenth embodiment.

In a fifteenth embodiment, $R^f$ in the compounds of Formula I, II, III, IV, V, VI, VII, VIII, IX, X, and XI is heteroaryl or heterocyclyl, each of which may be optionally substituted with 1 to 3 groups selected from selected from halo, CN, oxo, $NO_2$, $C_{1-6}$alkyl, $C_{2-6}$alkenyl, $C_{1-6}$alkoxy, $C_{1-6}$haloalkoxy, $C_{1-6}$haloalkyl, —$C_{1-6}$alkyl$OR^d$, —C(O)$R^d$, —C(O)O$R^d$, —$C_{1-6}$alkylC(O)O$R^d$, —C(O)N($R^d$)$_2$, —C(O)N$R^d C_{1-6}$alkylO$R^d$, —O$C_{1-6}$alkylN($R^d$)$_2$, —$C_{1-6}$alkylC(O)N($R^d$)$_2$, —$C_{1-6}$alkylN($R^d$)$_2$, —N($R^d$)$_2$, —C(O)N$R^d C_{1-6}$alkylN($R^d$)$_2$, —N$R^d C_{1-6}$alkylN($R^d$)$_2$, —N$R^d C_{1-6}$alkylO$R^d$, —SO$R^d$, —S(O)$_2 R^d$, —SON($R^d$)$_2$, —SO$_2$N($R^d$)$_2$, $SF_5$, -Ocycloalkyl, wherein the remaining variables are as described above for Formula I or the third, fourth, fifth, sixth, seventh, eighth, ninth, tenth, eleventh, twelfth, thirteenth, or fourteenth embodiment. Alternatively, $R^f$ in the compounds of Formula I, II, III, IV, V, VI, VII, VIII, IX, X, and XI is pyrazolyl, imidazolyl, pyridazinyl, piperazinyl, or piperidinyl, each of which may be optionally substituted with 1 to 3 groups selected from selected from halo, CN, oxo, NO₂, C₁₋₆alkyl, C₂₋₆alkenyl, C₁₋₆alkoxy, C₁₋₆haloalkoxy, C₁₋₆haloalkyl, —C₁₋₆alkylOR$^d$, —C(O)R$^d$, —C(O)OR$^d$, —C₁₋₆alkylC(O)OR$^d$, —C(O)N(R$^d$)₂, —C(O)NR$^d$C₁₋₆alkylOR$^d$, —OC₁₋₆alkylN(R$^d$)₂, —C₁₋₆alkylC(O)N(R$^d$)₂, —C₁₋₆alkylN(R$^d$)₂, —N(R$^d$)₂, —C(O)NR$^d$C₁₋₆alkylN(R$^d$)₂, —NR$^d$C₁₋₆alkylN(R$^d$)₂, —NR$^d$C₁₋₆alkylOR$^d$, —SOR$^d$, —S(O)₂R$^d$, —SON(R$^d$)₂, —SO₂N(R$^d$)₂, SF₅, -Ocycloalkyl, wherein the remaining variables are as described above for Formula I or the third, fourth, fifth, sixth, seventh, eighth, ninth, tenth, eleventh, twelfth, thirteenth, or fourteenth embodiment.

In a sixteenth embodiment, R$^f$ in the compounds of Formula I, II, III, IV, V, VI, VII, VIII, IX, X, and XI is pyrazolyl, imidazolyl, pyridazinyl, piperazinyl, or piperidinyl, each of which may be optionally substituted with 1 to 3 groups selected from selected from C₁₋₄alkyl and —C(O)R$^d$, wherein R$^d$ is C₁₋₄alkyl, wherein the remaining variables are as described above for Formula I or the third, fourth, fifth, sixth, seventh, eighth, ninth, tenth, eleventh, twelfth, thirteenth, fourteenth, or fifteenth embodiment.

In a seventeenth embodiment, R$^b$ in the compounds of Formula I, II, III, IV, V, VI, VII, VIII, IX, X, and XI is halo, wherein the remaining variables are as described above for Formula I or the third, fourth, fifth, sixth, seventh, eighth, ninth, tenth, eleventh, twelfth, thirteenth, fourteenth, fifteenth, or sixteenth embodiment.

In an eighteenth embodiment, the compound of Formula I is of the Formula XII or XIII:

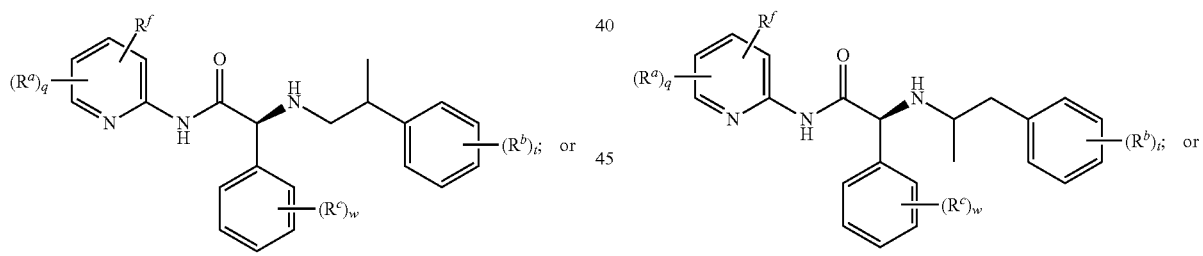

or a pharmaceutically acceptable salt thereof, wherein w, q, and t are each independently 0, 1, or 2, and wherein the remaining variables are as described above for Formula I or the third, fourth, fifth, sixth, seventh, eighth, or ninth embodiment. Alternatively, the compound of Formula I is of the Formula XIV or XV:

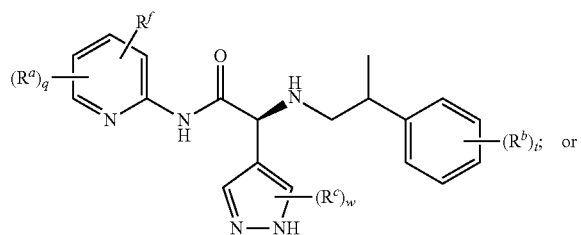

or a pharmaceutically acceptable salt thereof, wherein w, q, and t are each independently 0, 1, or 2, and wherein the remaining variables are as described above for Formula I or the third, fourth, fifth, sixth, seventh, eighth, or ninth embodiment. In another alternative, the compound of Formula I is of the Formula XVI or XVII:

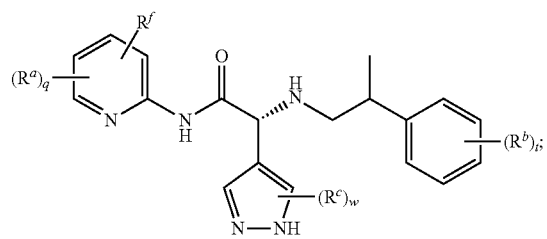

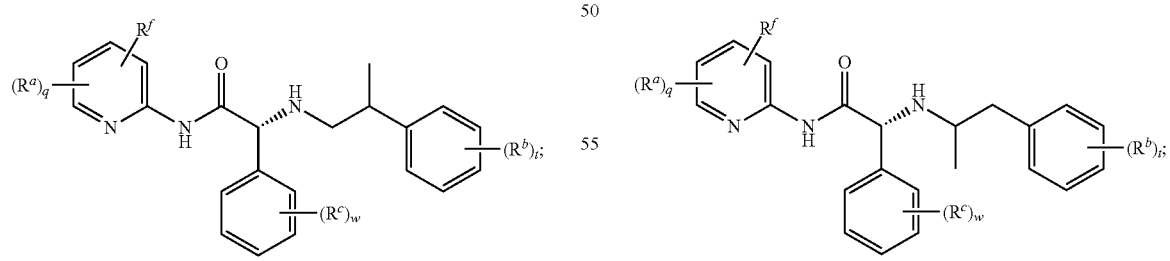

or a pharmaceutically acceptable salt thereof, wherein w, q, and t are each independently 0, 1, or 2, and wherein the remaining variables are as described above for Formula I or the third, fourth, fifth, sixth, seventh, eighth, or ninth embodiment. In another alternative, the compound of Formula I is of the Formula XVIII or XIX:

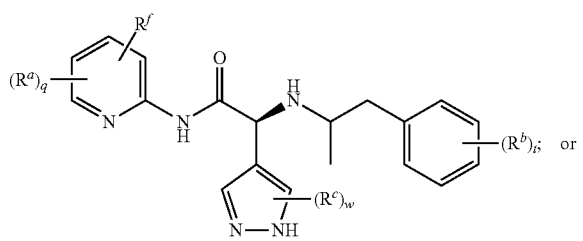

(XVIII)

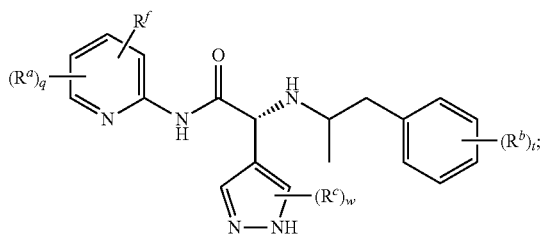

(XIX)

or a pharmaceutically acceptable salt thereof, wherein w, q, and t are each independently 0, 1, or 2, and wherein the remaining variables are as described above for Formula I or the third, fourth, fifth, sixth, seventh, eighth, or ninth embodiment. In another alternative, the compound of Formula I is of the Formula XX or XXI:

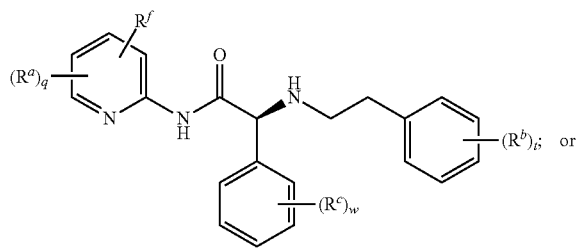

(XX)

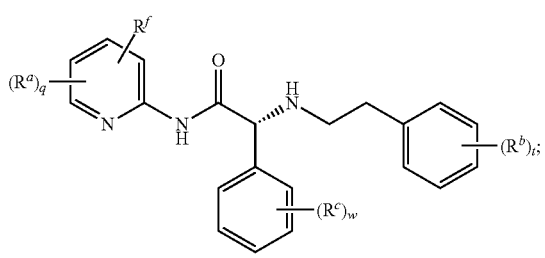

(XXI)

or a pharmaceutically acceptable salt thereof, wherein w, q, and t are each independently 0, 1, or 2, and wherein the remaining variables are as described above for Formula I or the third, fourth, fifth, sixth, seventh, eighth, or ninth embodiment. In another alternative, the compound of Formula I is of the Formula XXII or XXIII:

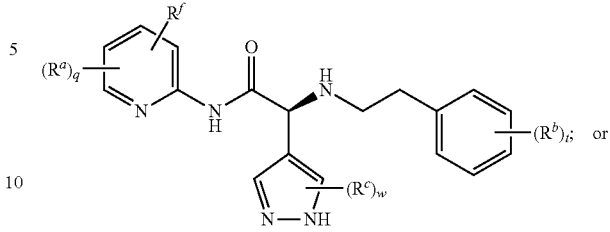

(XXII)

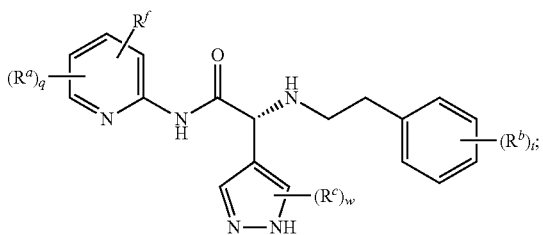

(XXIII)

or a pharmaceutically acceptable salt thereof, wherein w, q, and t are each independently 0, 1, or 2, and wherein the remaining variables are as described above for Formula I or the third, fourth, fifth, sixth, seventh, eighth, or ninth embodiment.

In a nineteenth embodiment, $R^c$, if present, in the compounds of Formula XII, XIII, XIV, XV, XVI, XVII, XVIII, XIX, XX, XXI, XXII, and XXIII is independently $C_{1-6}$alkyl, halo, or CN, wherein the remaining variables are as described above for Formula I or the third, fourth, fifth, sixth, seventh, eighth, ninth, or eighteenth embodiment. Alternatively, $R^c$, if present, in the compounds of Formula XII, XIII, XIV, XV, XVI, XVII, XVIII, XIX, XX, XXI, XXII, and XXIII is $C_{1-4}$alkyl, wherein the remaining variables are as described above for Formula I or the third, fourth, fifth, sixth, seventh, eighth, ninth, or eighteenth embodiment.

In a twentieth embodiment, w in the compounds of Formula XII, XIII, XIV, XV, XVI, XVII, XVIII, XIX, XX, XXI, XXII, and XXIII is 0 or 1, wherein the remaining variables are as described above for Formula I or the third, fourth, fifth, sixth, seventh, eighth, ninth, eighteenth, or nineteenth embodiment.

In a twenty-first embodiment, $R^b$ in the compounds of Formula XII, XIII, XIV, XV, XVI, XVII, XVIII, XIX, XX, XXI, XXII, and XXIII is cyano, wherein the remaining variables are as described above for Formula I or the third, fourth, fifth, sixth, seventh, eighth, ninth, eighteenth, nineteenth, or twentieth embodiment.

In a twenty-second embodiment, t in the compounds of Formula XII, XIII, XIV, XV, XVI, XVII, XVIII, XIX, XX, XXI, XXII, and XXIII is 1, wherein the remaining variables are as described above for Formula I or the third, fourth, fifth, sixth, seventh, eighth, ninth, eighteenth, nineteenth, twentieth, or twenty-first embodiment.

In a twenty-third embodiment, q in the compounds of Formula XII, XIII, XIV, XV, XVI, XVII, XVIII, XIX, XX, XXI, XXII, and XXIII is 1, wherein the remaining variables are as described above for Formula I or the third, fourth, fifth, sixth, seventh, eighth, ninth, eighteenth, nineteenth, twentieth, twenty-first, or twenty second embodiment.

In a twenty-fourth embodiment, $R^f$ in the compounds of Formula XII, XIII, XIV, XV, XVI, XVII, XVIII, XIX, XX, XXI, XXII, and XXIII is cycloalkyl, phenyl, heteroaryl, or heterocyclyl, each of which may be optionally substituted with 1 to 3 groups selected from halo, CN, oxo, NO$_2$, C$_{1-6}$alkyl, C$_{2-6}$alkenyl, C$_{1-6}$alkoxy, C$_{1-6}$haloalkoxy, C$_{1-6}$haloalkyl, —C$_{1-6}$alkylOR$^d$, —C(O)R$^d$, —C(O)OR$^d$, —C$_{1-6}$alkylC(O)OR$^d$, —C(O)N(R$^d$)$_2$, —C(O)NR$^d$C$_{1-6}$alkylOR$^d$, —OC$_{1-6}$alkylN(R$^d$)$_2$, —C$_{1-6}$alkylC(O)N(R$^d$)$_2$, —C$_{1-6}$alkylN(R$^d$)$_2$, —N(R$^d$)$_2$, —C(O)NR$^d$C$_{1-6}$alkylN(R$^d$)$_2$, —NR$^d$C$_{1-6}$alkylN(R$^d$)$_2$, —NR$^d$C$_{1-6}$alkylOR$^d$, —SOR$^d$, —S(O)$_2$R$^d$, —SON(R$^d$)$_2$, —SO$_2$N(R$^d$)$_2$, SF$_5$, -Ocycloalkyl, wherein the remaining variables are as described above for Formula I or the third, fourth, fifth, sixth, seventh, eighth, ninth, eighteenth, nineteenth, twentieth, twenty-first, twenty-second, or twenty-third embodiment. Alternatively, R$^f$ in the compounds of Formula XII, XIII, XIV, XV, XVI, XVII, XVIII, XIX, XX, XXI, XXII, and XXIII is pyrimidinyl, phenyl, cyclobutanyl, cyclopropyl, pyrazolyl, imidazolyl, azetidinyl, piperidinyl, pyrrolidinyl, piperazinyl, triazolopyrazinyl, triazolyl, imidazolidinyl, thiadiazolidinyl, morpholinyl, oxaazaspiroheptanyl, oxaazaspirooctanyl, dihydropyrimidinyl, oxadiazolyl, isoxazolyl, or dihydropyridazinyl, each of which may be optionally substituted with 1 to 3 groups selected from halo, CN, oxo, NO$_2$, C$_{1-6}$alkyl, C$_{2-6}$alkenyl, C$_{1-6}$alkoxy, C$_{1-6}$ haloalkoxy, C$_{1-6}$haloalkyl, —C$_{1-6}$alkylOR$^d$, —C(O)R$^d$, —C(O)OR$^d$, —C$_{1-6}$alkylC(O)OR$^d$, —C(O)N(R$^d$)$_2$, —C(O)NR$^d$C$_{1-6}$alkylOR$^d$, —OC$_{1-6}$alkylN(R$^d$)$_2$, —C$_{1-6}$alkylC(O)N(R$^d$)$_2$, —C$_{1-6}$alkylN(R$^d$)$_2$, —N(R$^d$)$_2$, —C(O)NR$^d$C$_{1-6}$alkylN(R$^d$)$_2$, —NR$^d$C$_{1-6}$alkylN(R$^d$)$_2$, —NR$^d$C$_{1-6}$alkylOR$^d$, —SOR$^d$, —S(O)$_2$R$^d$, —SON(R$^d$)$_2$, —SO$_2$N(R$^d$)$_2$, SF$_5$, -Ocycloalkyl, wherein the remaining variables are as described above for Formula I or the third, fourth, fifth, sixth, seventh, eighth, ninth, eighteenth, nineteenth, twentieth, twenty-first, twenty-second, or twenty-third embodiment. In another alternative, R$^f$ in the compounds of Formula XII, XIII, XIV, XV, XVI, XVII, XVIII, XIX, XX, XXI, XXII, and XXIII is pyrimidinyl, phenyl, pyrazolyl, imidazolyl, azetidinyl, piperidinyl, pyrrolidinyl, piperazinyl, triazolopyrazinyl, triazolyl, imidazolidinyl, thiadiazolidinyl, morpholinyl, oxaazaspiroheptanyl, oxaazaspirooctanyl, dihydropyrimidinyl, oxadiazolyl, isoxazolyl, or dihydropyridazinyl, each of which may be optionally substituted with 1 to 3 groups selected from halo, oxo, C$_{1-6}$alkyl, C$_{1-6}$alkoxy, C$_{1-6}$haloalkyl, —C$_{1-6}$alkylOR$^d$, —C(O)R$^d$, —C(O)N(R$^d$)$_2$, —C$_{1-6}$alkylC(O)N(R$^d$)$_2$, and —S(O)$_2$R$^d$, wherein the remaining variables are as described above for Formula I or the third, fourth, fifth, sixth, seventh, eighth, ninth, eighteenth, nineteenth, twentieth, twenty-first, twenty-second, or twenty-third embodiment. In another alternative, R$^f$ in the compounds of Formula XII, XIII, XIV, XV, XVI, XVII, XVIII, XIX, XX, XXI, XXII, and XXIII is pyrazolyl or triazolyl, each of which may be optionally substituted with C$_{1-3}$alkyl or —C(O)N(R$^d$)$_2$, wherein the remaining variables are as described above for Formula I or the third, fourth, fifth, sixth, seventh, eighth, ninth, eighteenth, nineteenth, twentieth, twenty-first, twenty-second, or twenty-third embodiment.

In a twenty-fifth embodiment, R$^d$ in the compounds of Formula XII, XIII, XIV, XV, XVI, XVII, XVIII, XIX, XX, XXI, XXII, and XXIII is hydrogen or C$_{1-3}$alkyl, wherein the remaining variables are as described above for Formula I or the third, fourth, fifth, sixth, seventh, eighth, ninth, eighteenth, nineteenth, twentieth, twenty-first, twenty-second, twenty-third, or twenty-fourth embodiment. Alternatively, R$^d$ in the compounds of Formula XII, XIII, XIV, XV, XVI, XVII, XVIII, XIX, XX, XXI, XXII, and XXIII is C$_{1-3}$alkyl, wherein the remaining variables are as described above for Formula I or the third, fourth, fifth, sixth, seventh, eighth, ninth, eighteenth, nineteenth, twentieth, twenty-first, twenty-second, twenty-third, or twenty-fourth embodiment.

In a twenty-sixth embodiment, the compound of Formula XX or XXI excludes a compound having the Formula:

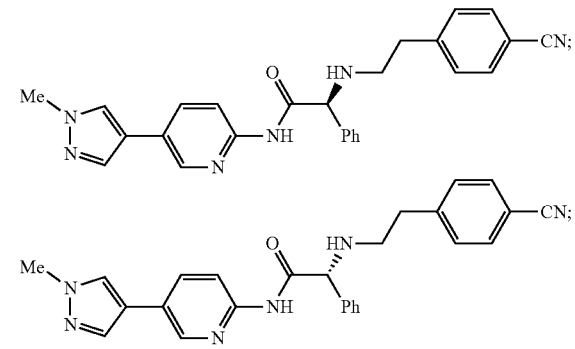

or a pharmaceutically acceptable salt thereof, wherein the remaining variables are as described above for Formula I or the third, fourth, fifth, sixth, seventh, eighth, ninth, eighteenth, nineteenth, twentieth, twenty-first, twenty-second, twenty-third, twenty-fourth, or twenty-fifth embodiment.

In a twenty-seventh embodiment, the compound of Formula I is selected from the following formula:

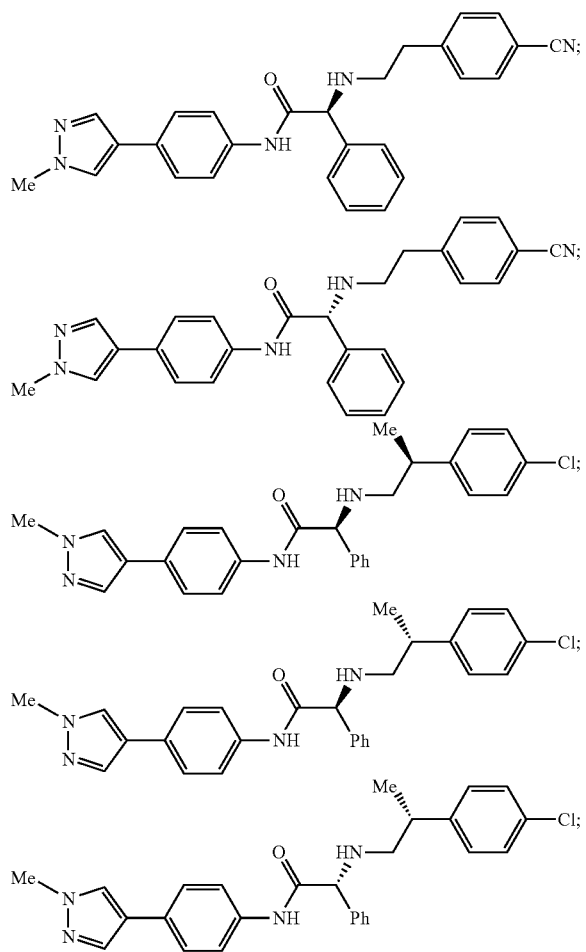

-continued

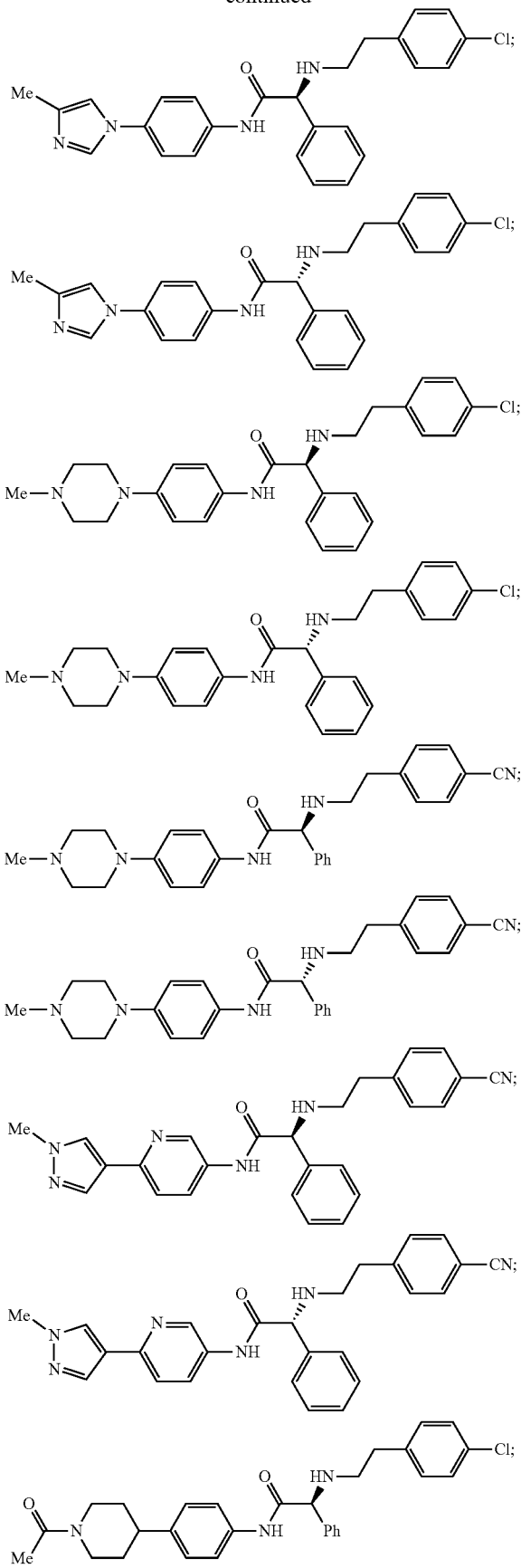
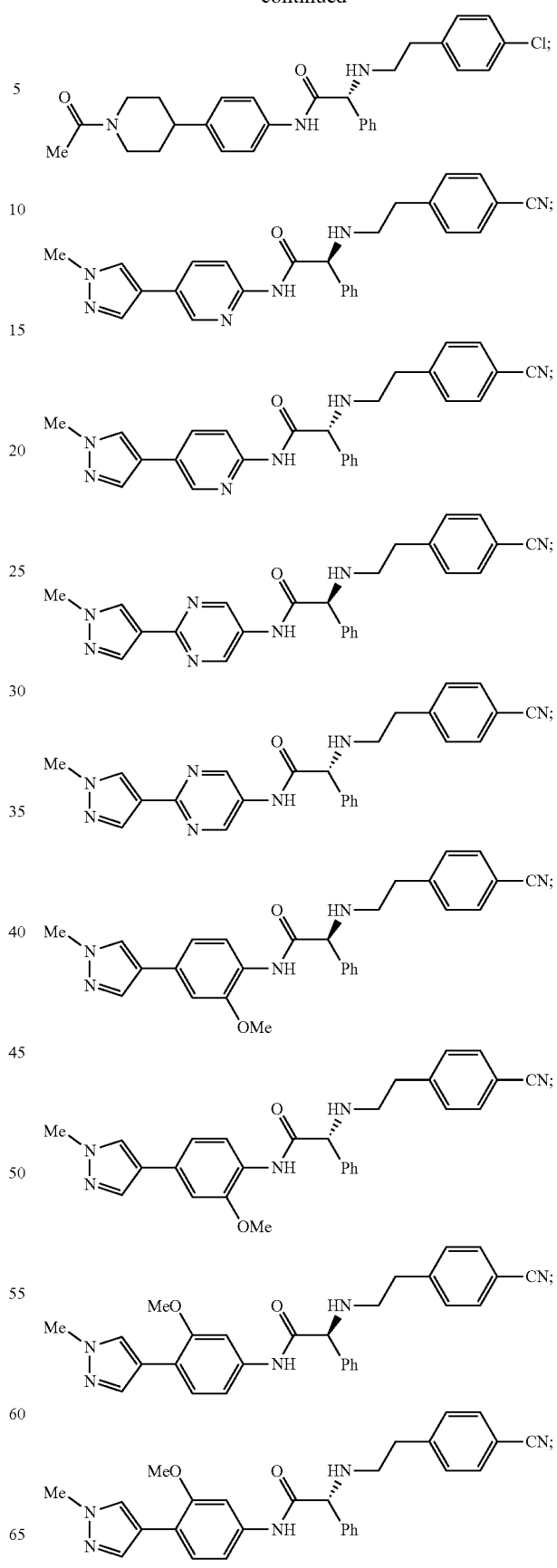

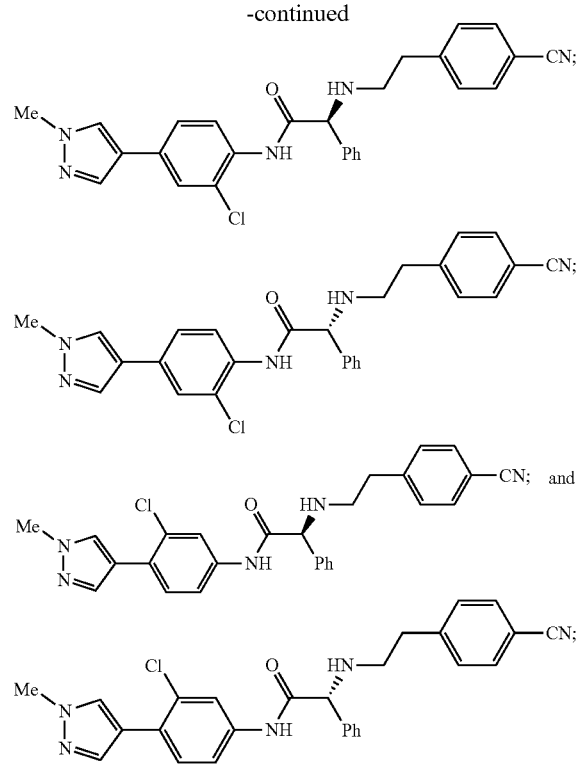
or a pharmaceutically acceptable salt thereof of any of the foregoing.
In a twenty-eighth embodiment, the compound of Formula I is selected from the following formula:
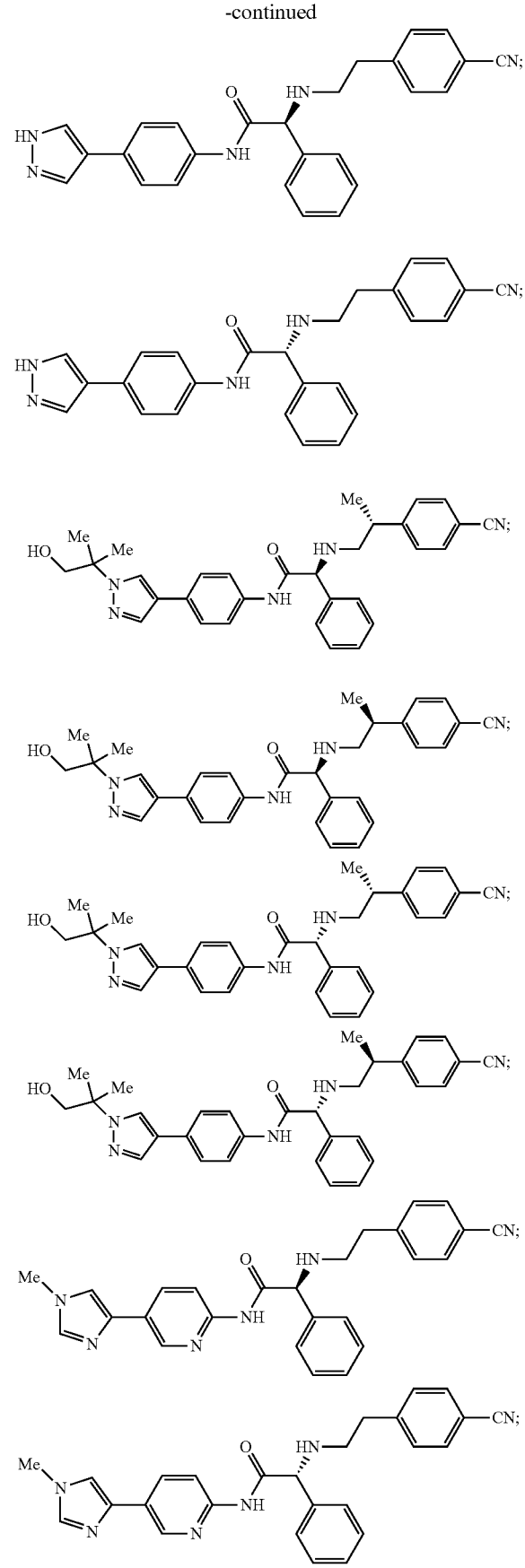

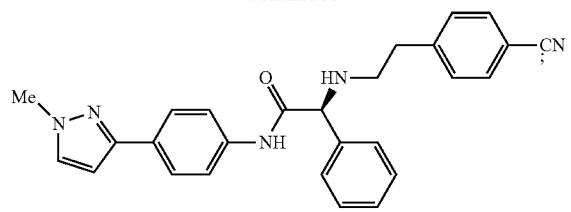
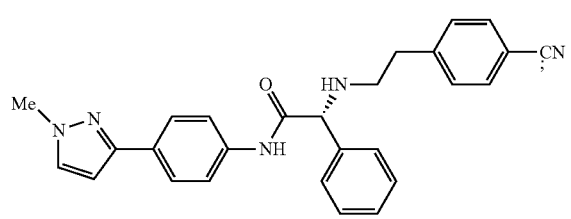
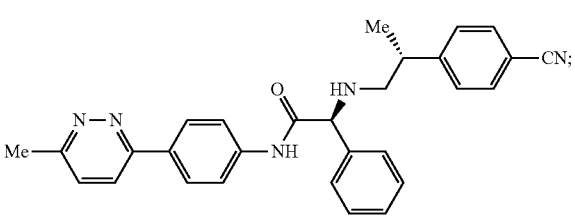
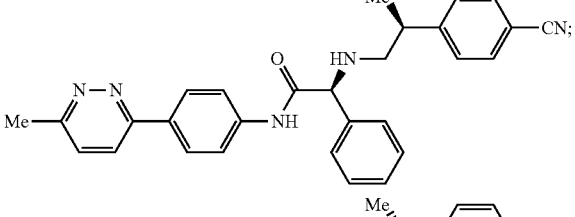
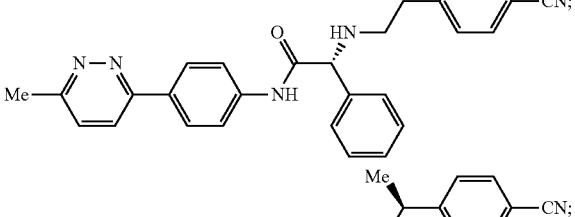
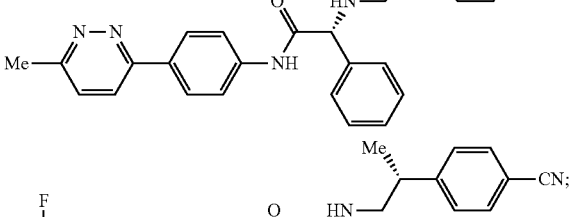
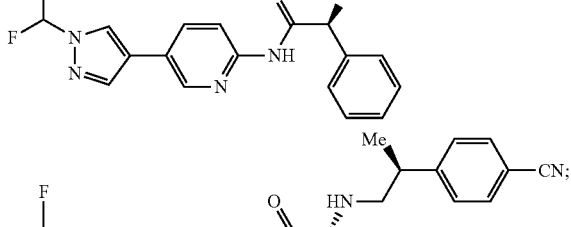
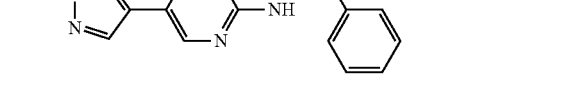
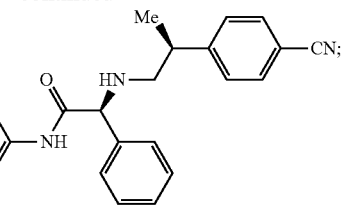
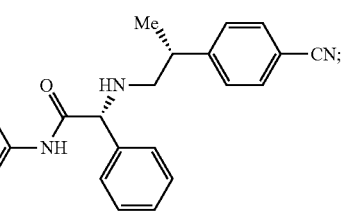
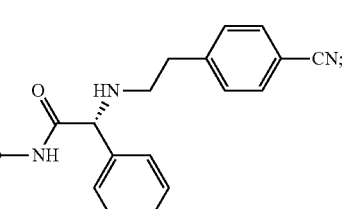
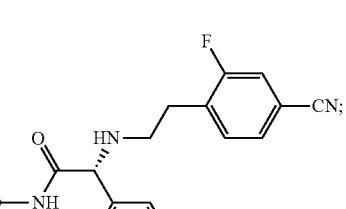
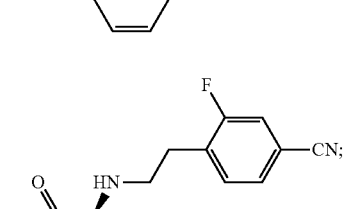
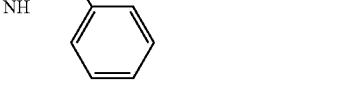

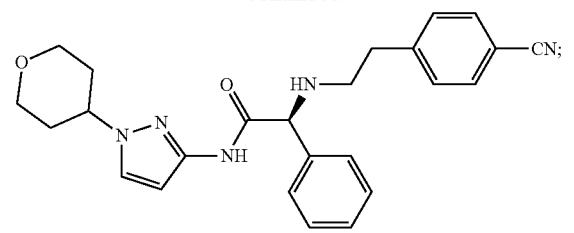
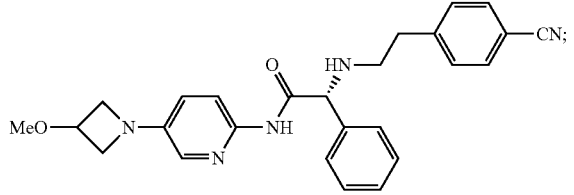
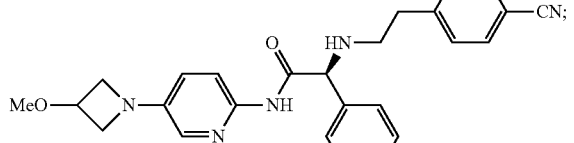
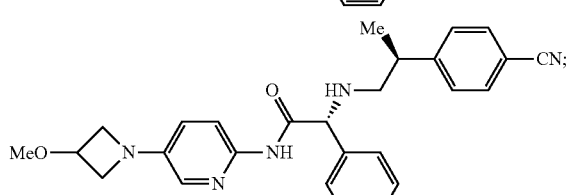
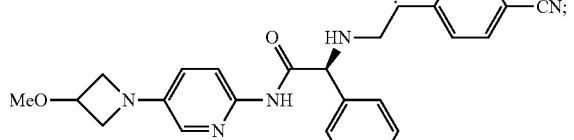
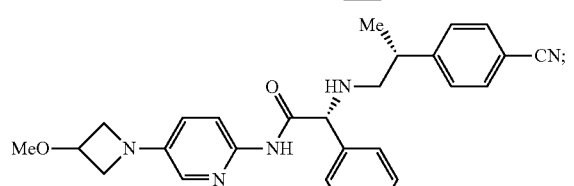
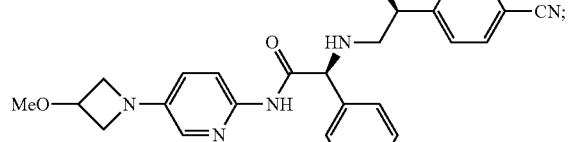
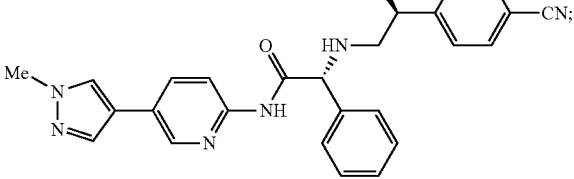
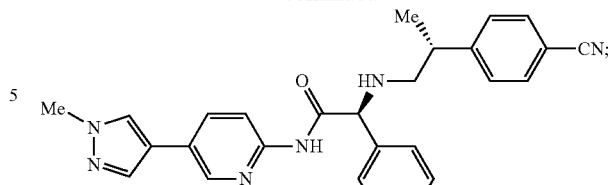
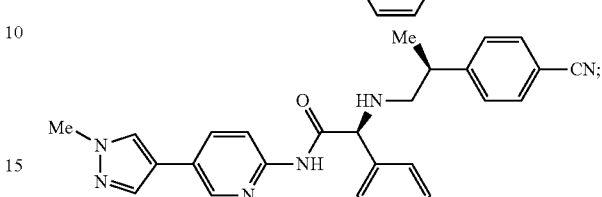
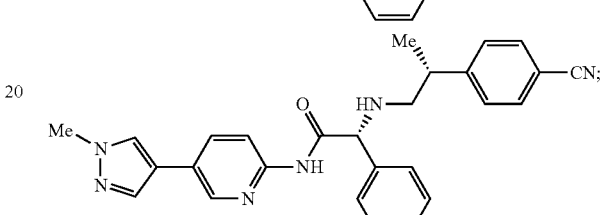
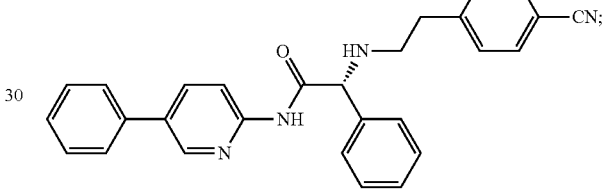
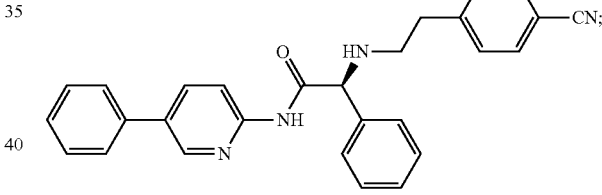
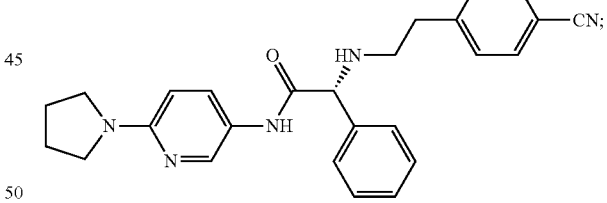
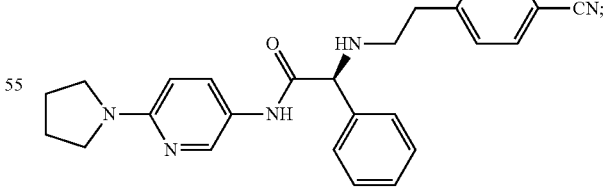
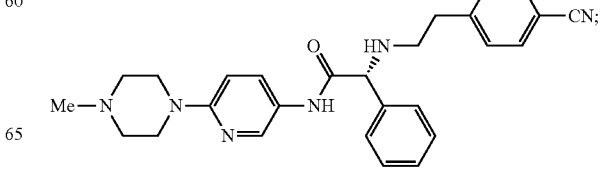

-continued
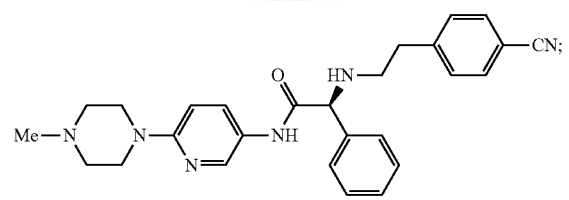
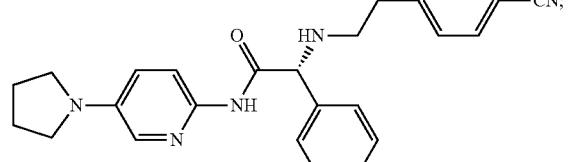
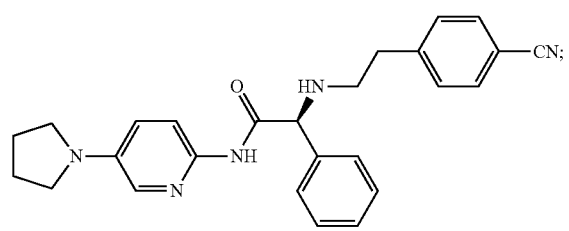
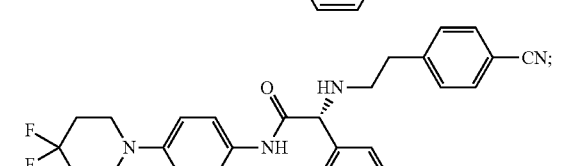
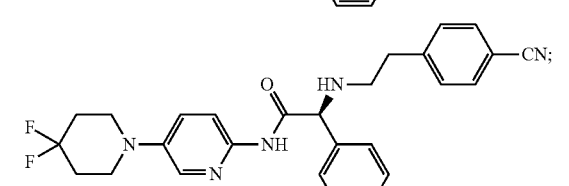
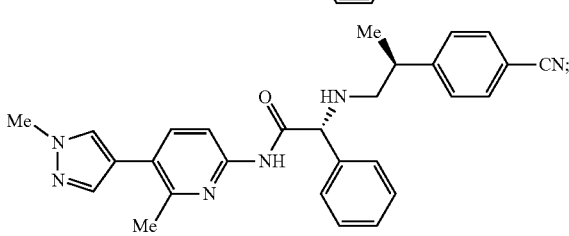
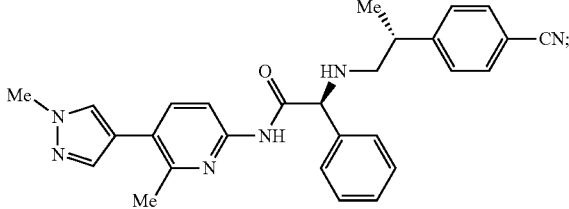
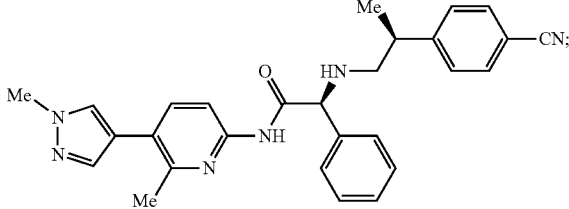
-continued
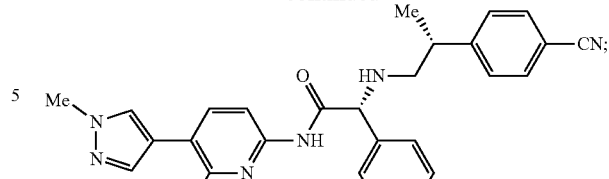
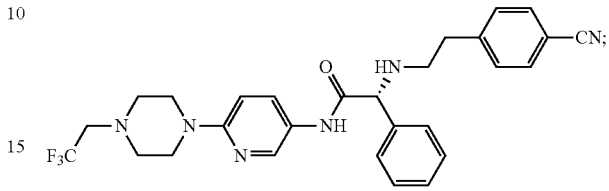
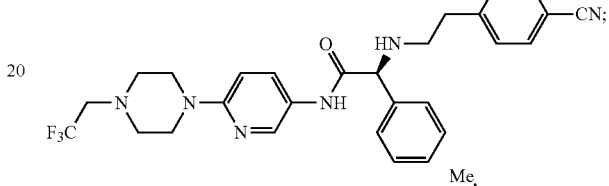
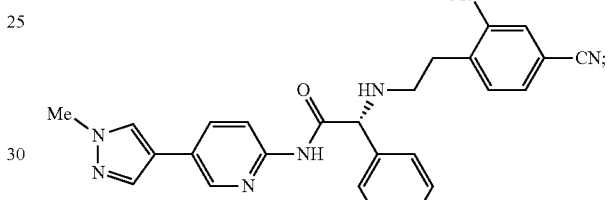
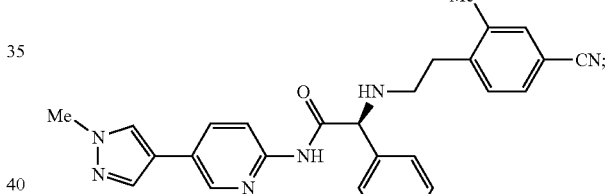
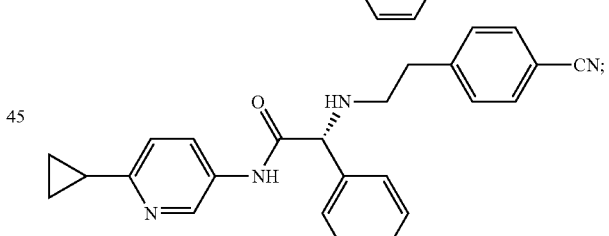
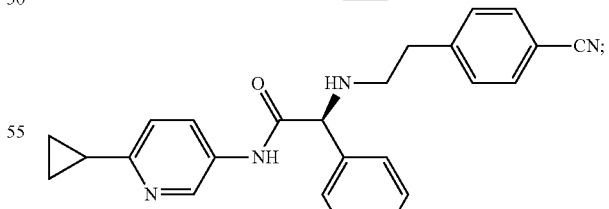
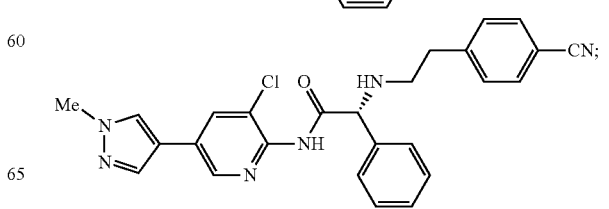

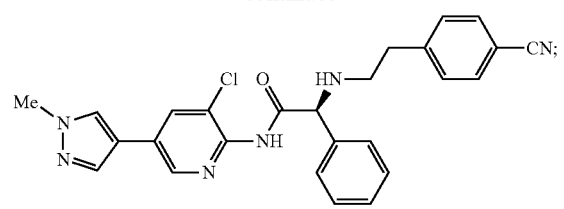
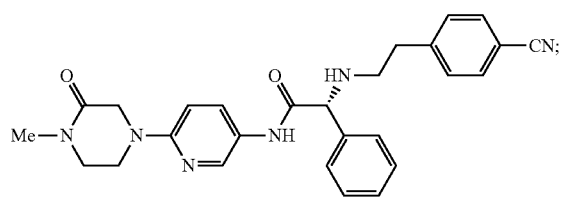
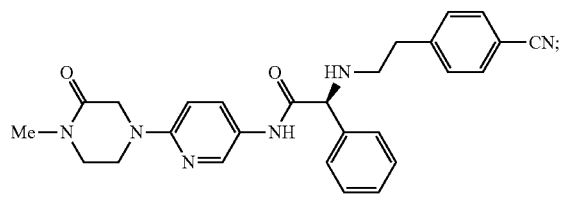
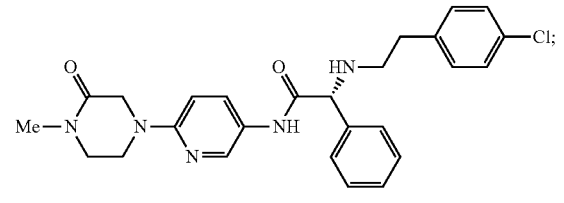
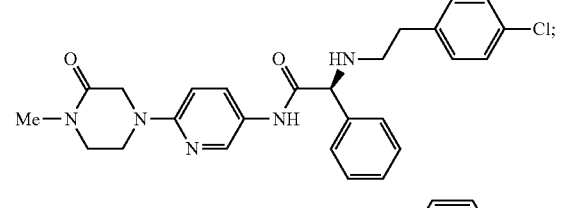
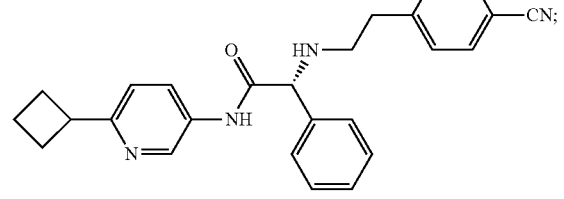
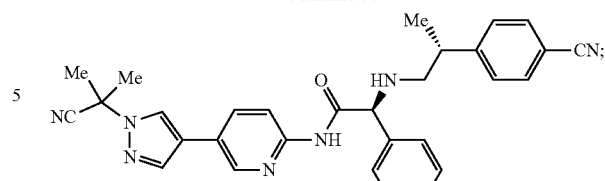
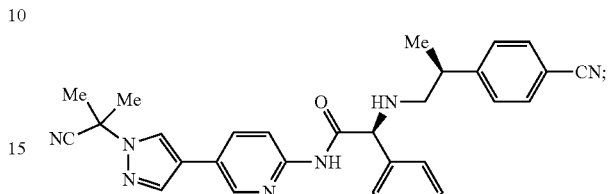
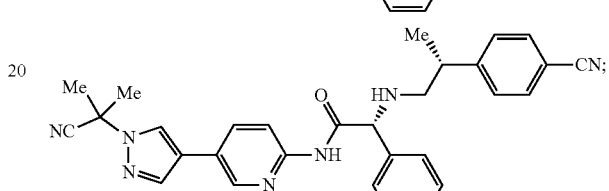
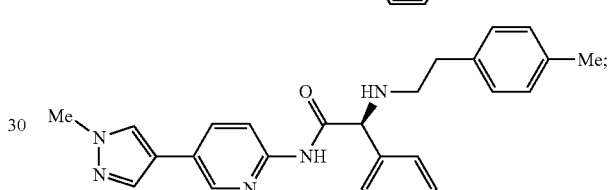
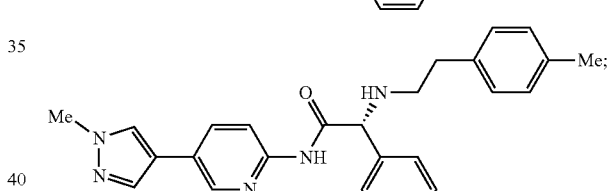
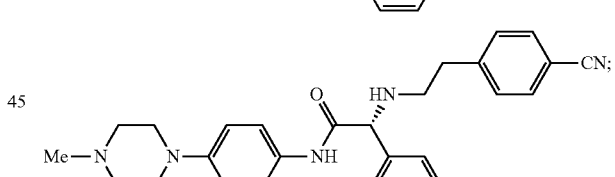
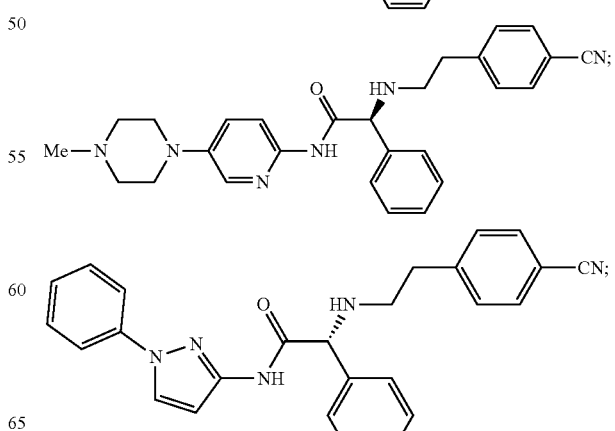

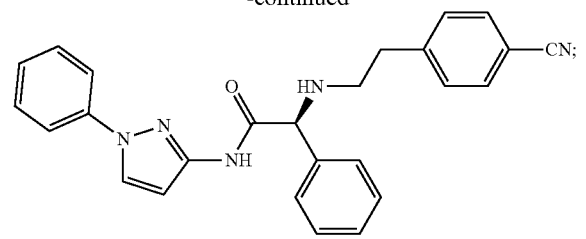
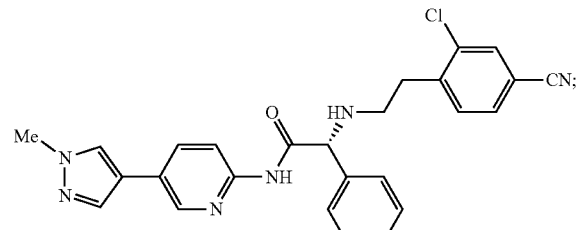
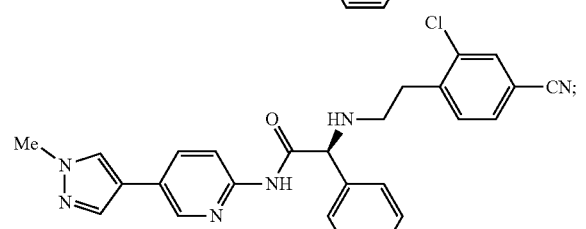
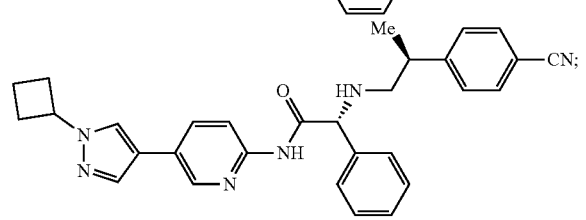
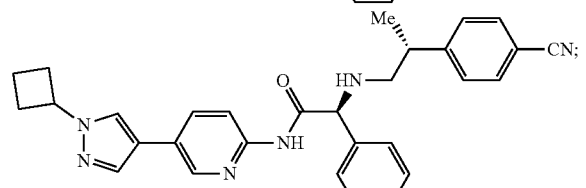
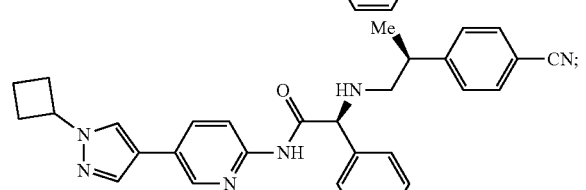
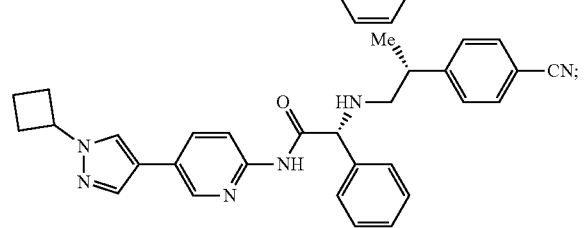
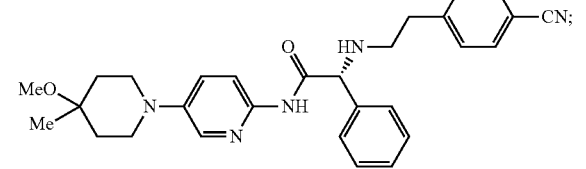
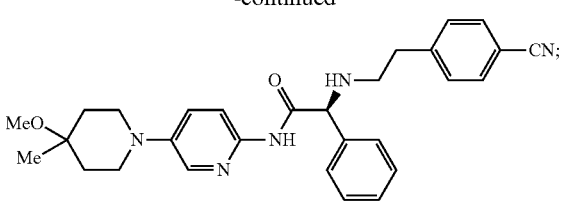
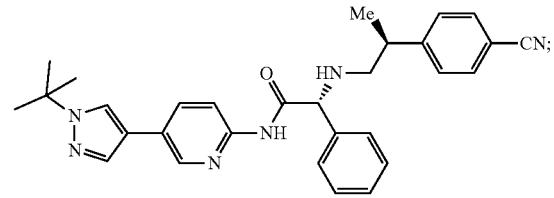
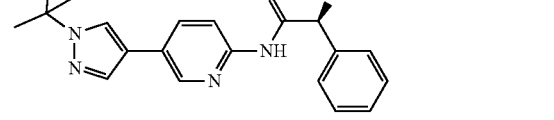
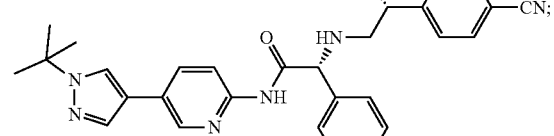
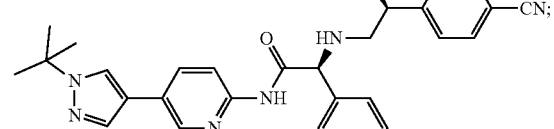
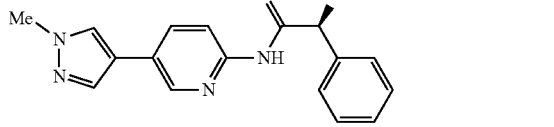
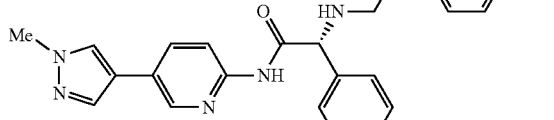
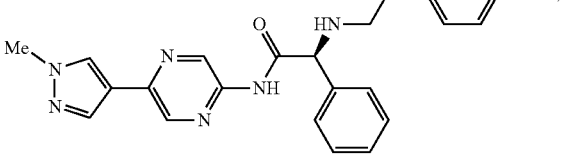

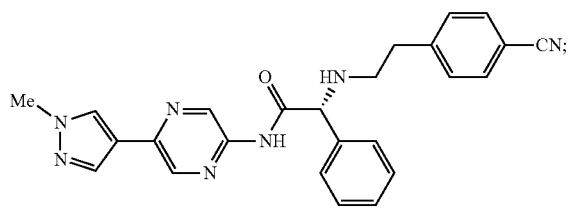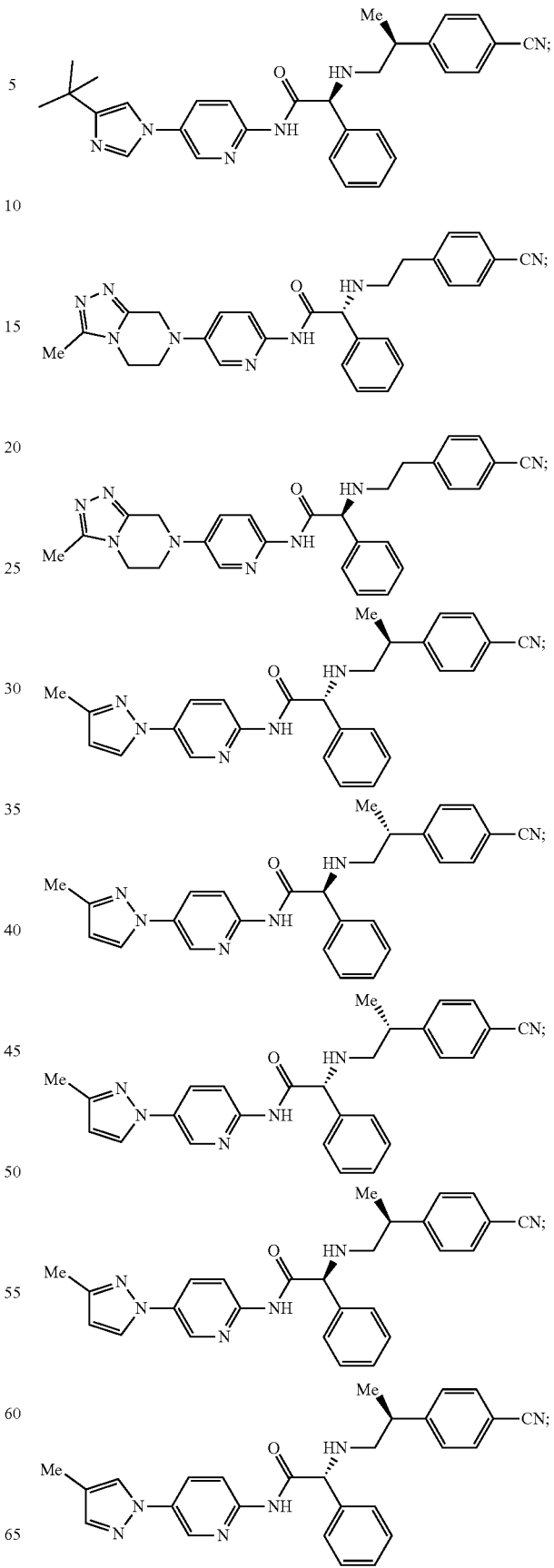

-continued
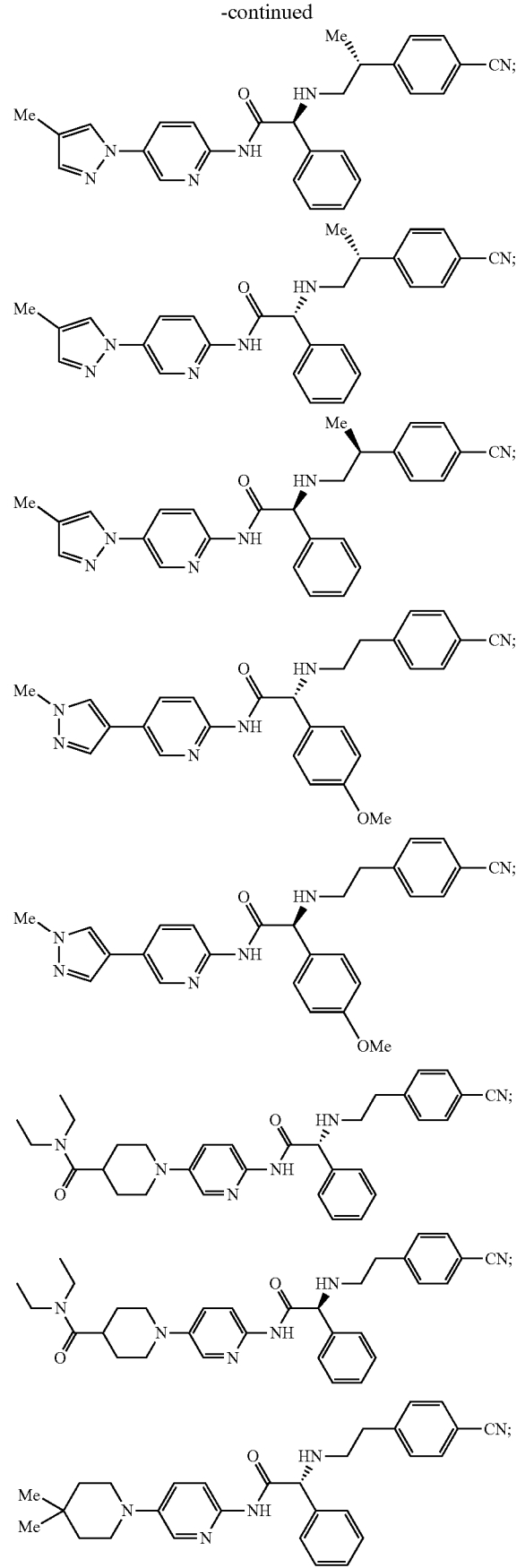
-continued
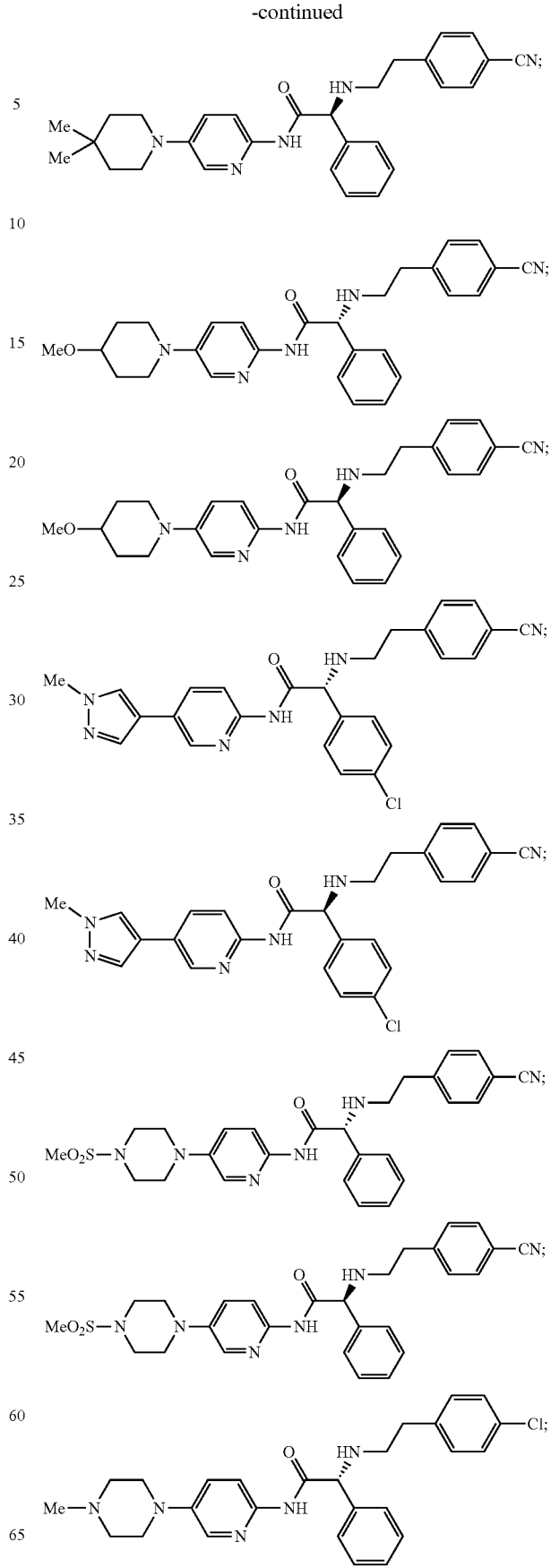

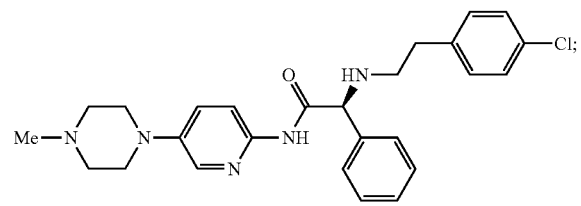
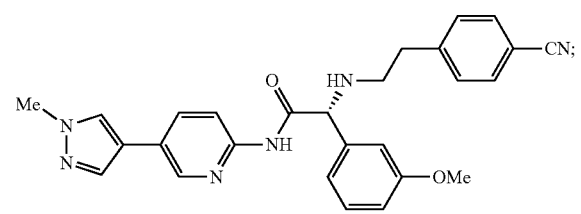
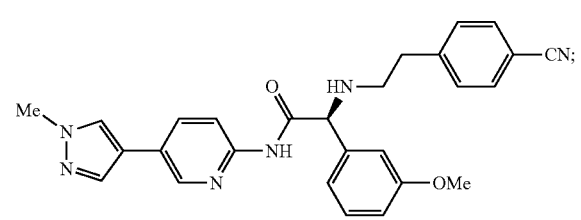
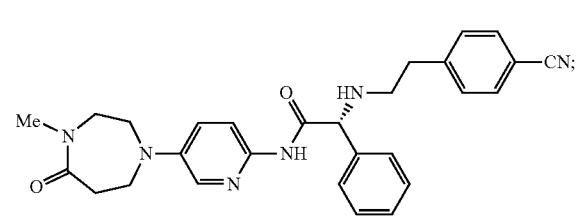
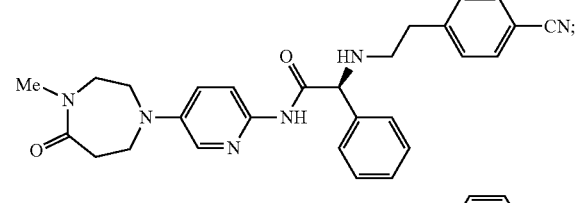
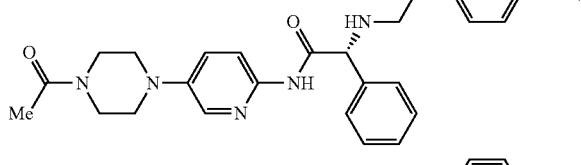
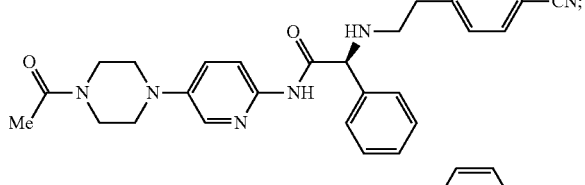
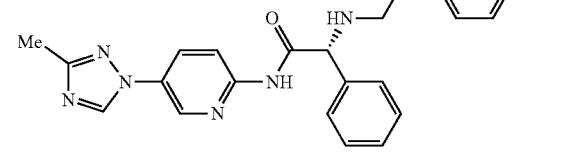
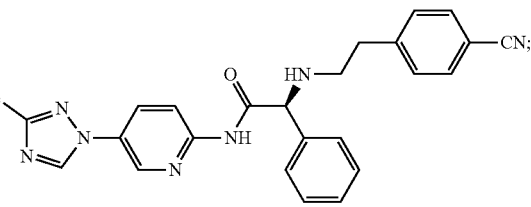
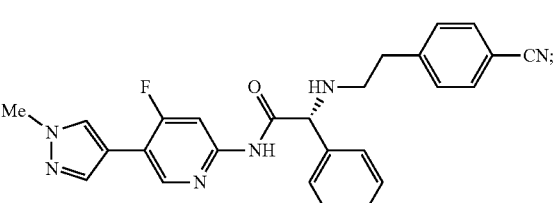
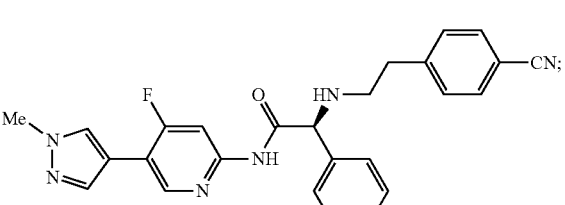
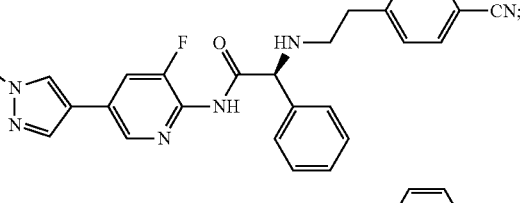
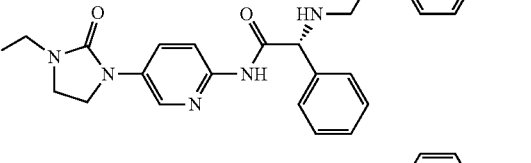
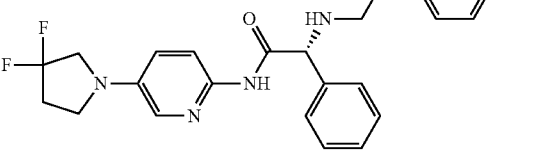

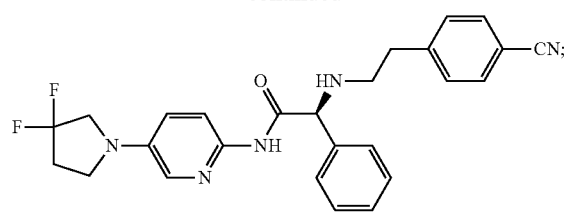
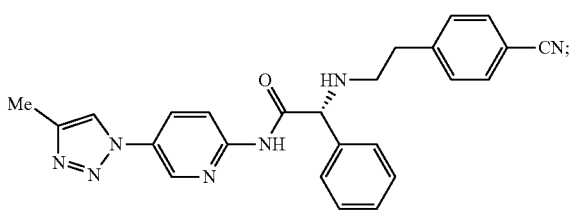
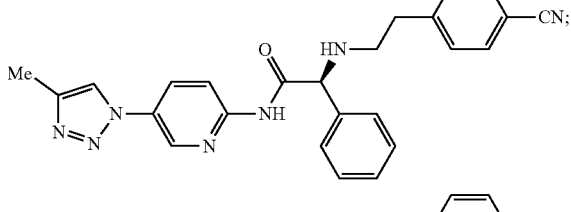
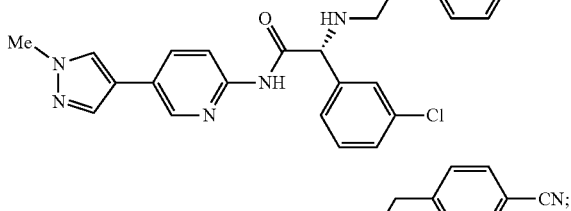
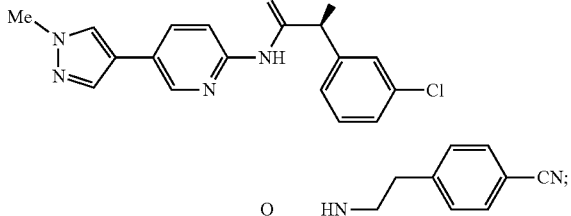
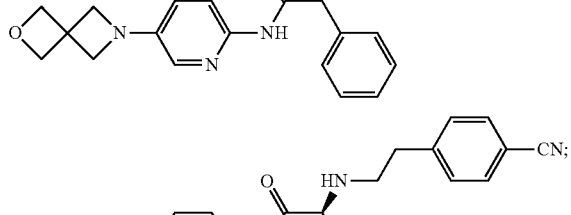
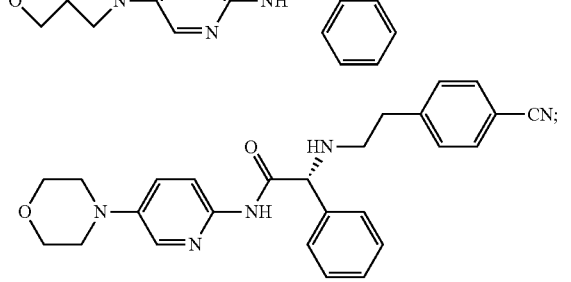
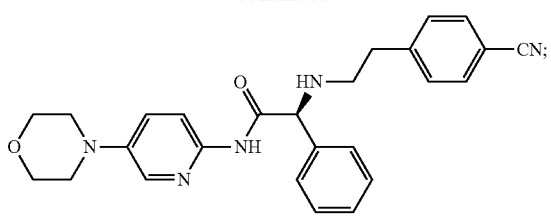
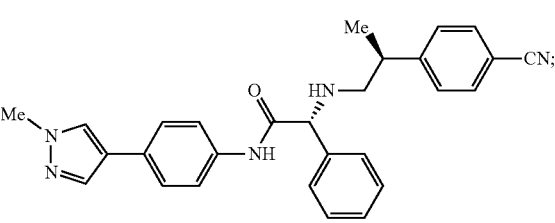
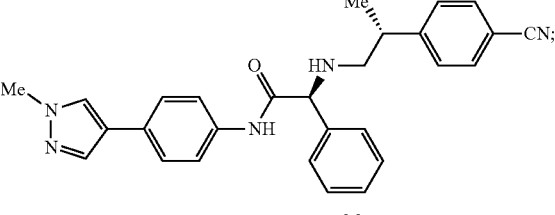
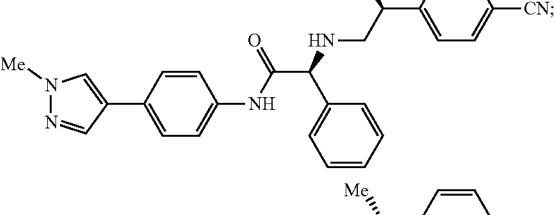
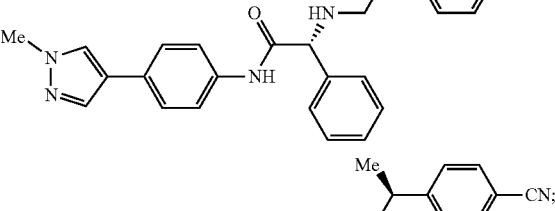
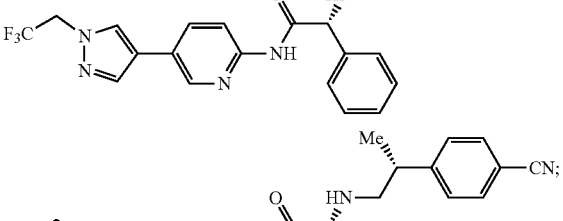
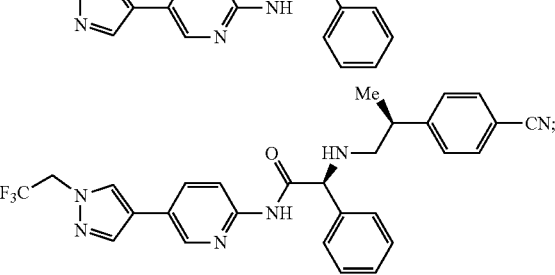

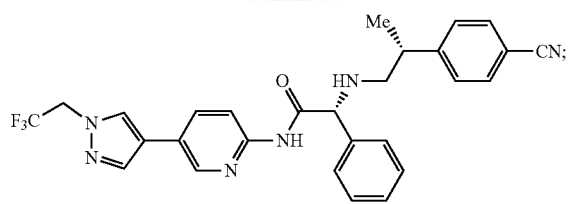
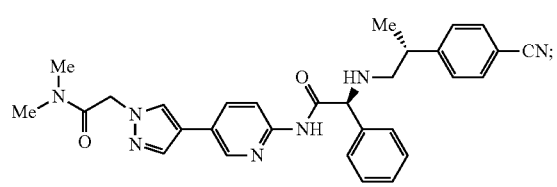
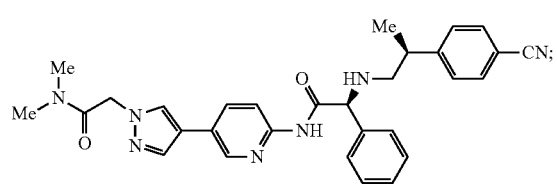
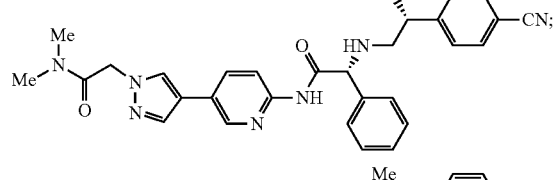
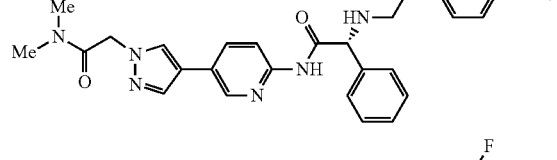
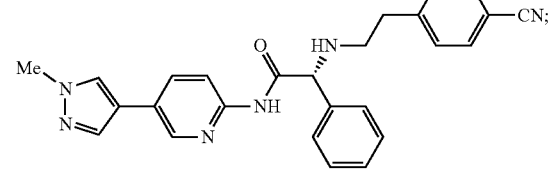
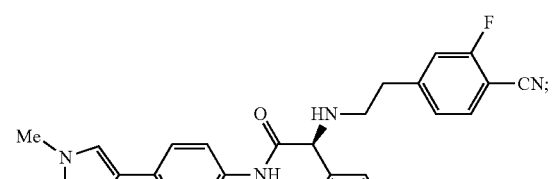
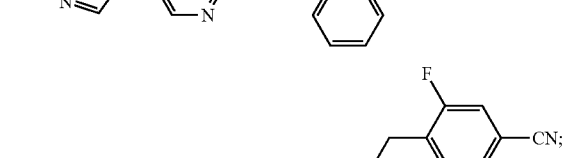
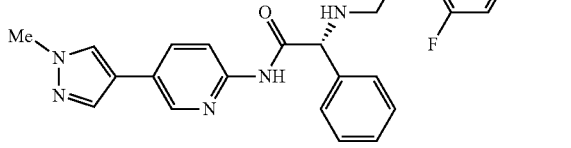
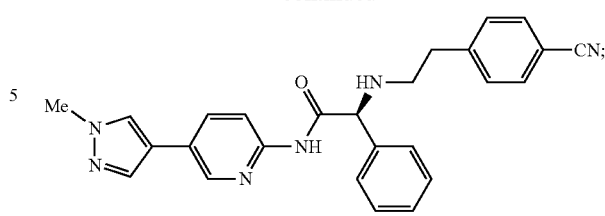
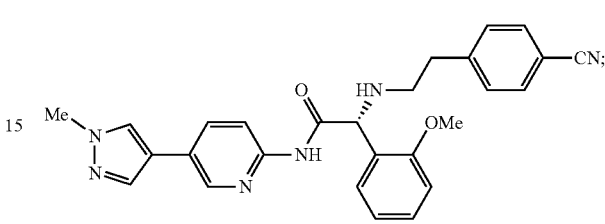
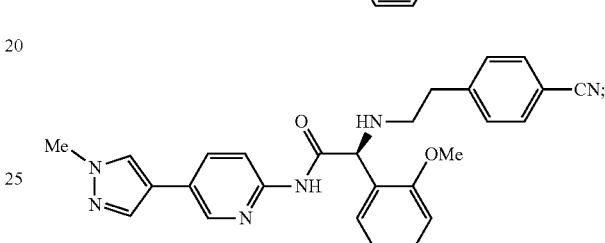
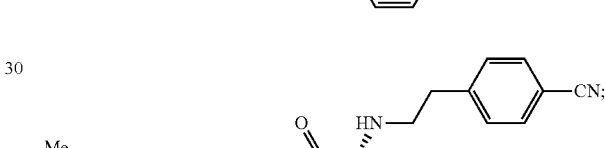
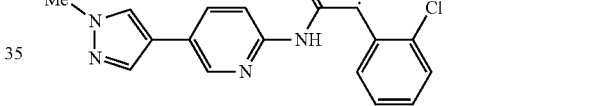
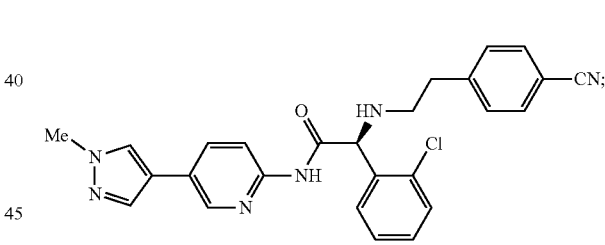
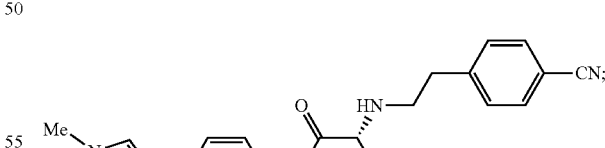
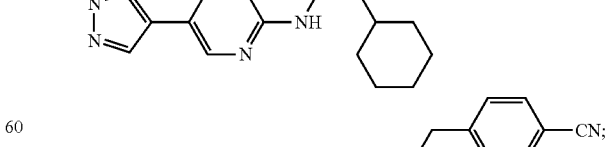
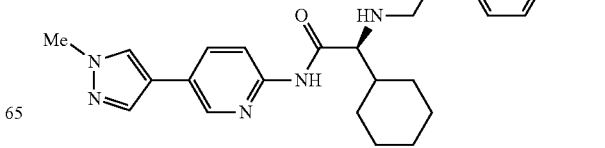

-continued
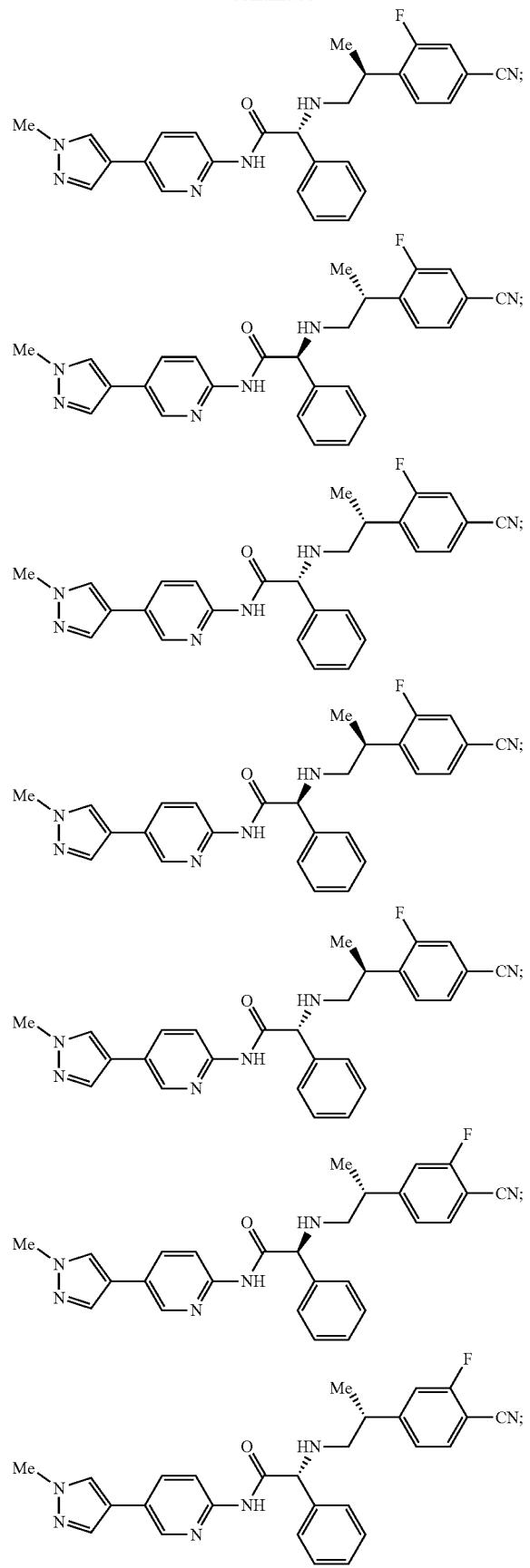
-continued
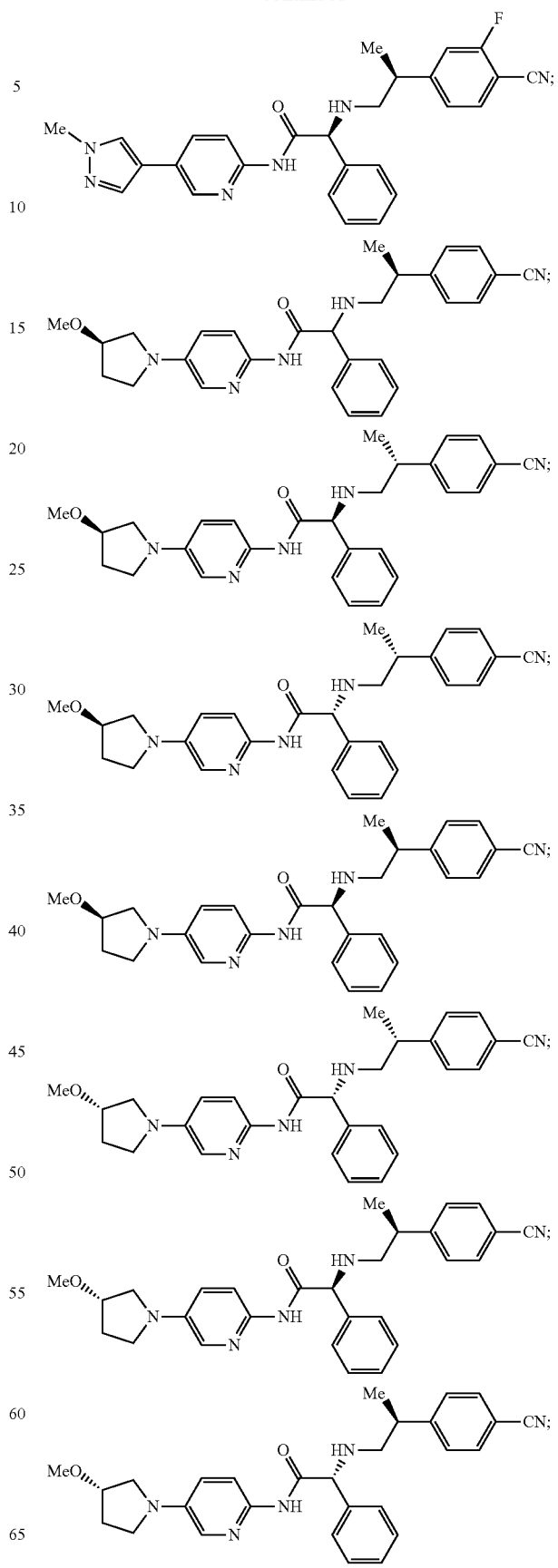

-continued

-continued
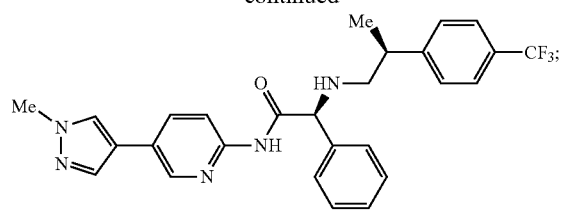
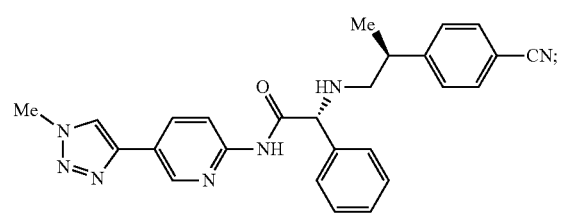
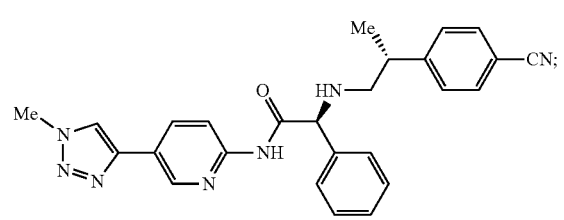
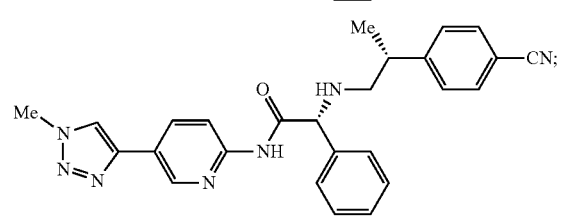
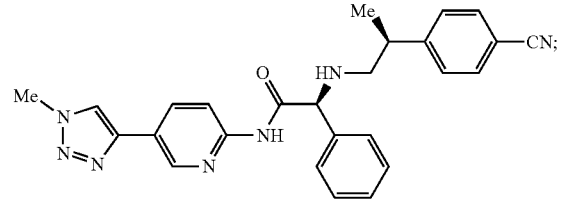
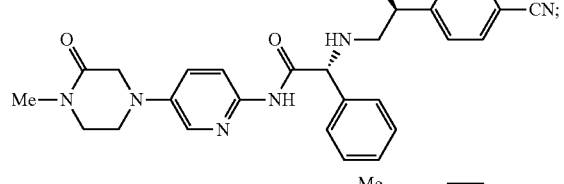
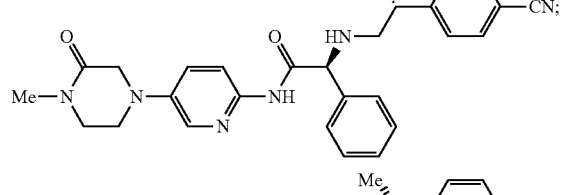
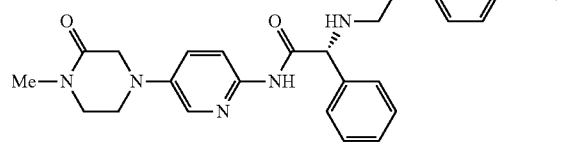
-continued
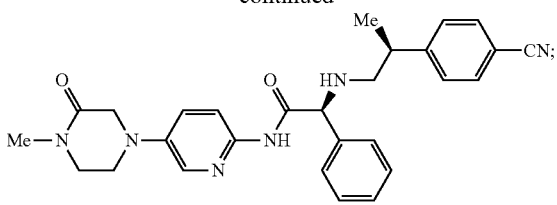
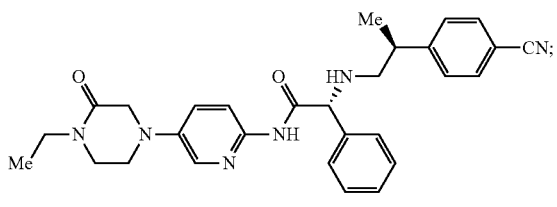
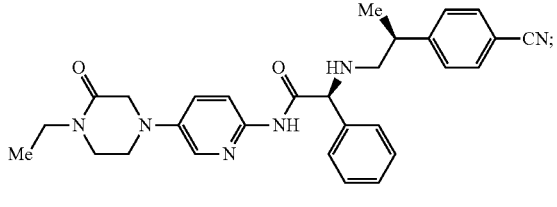
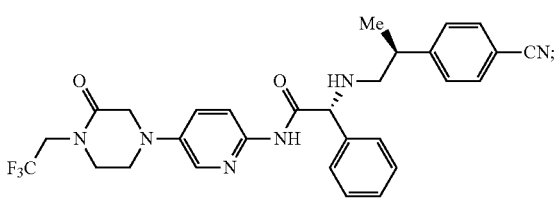
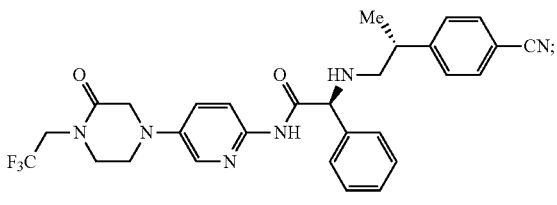
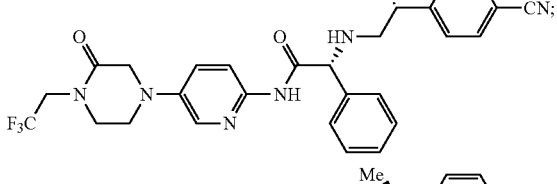
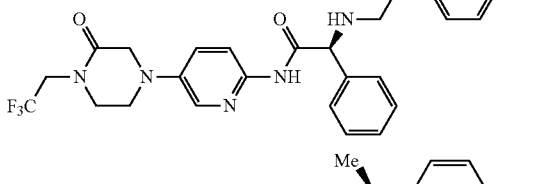
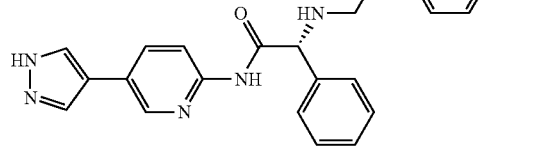

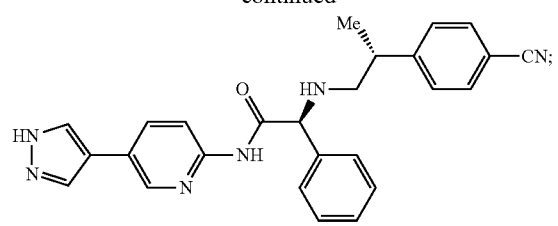
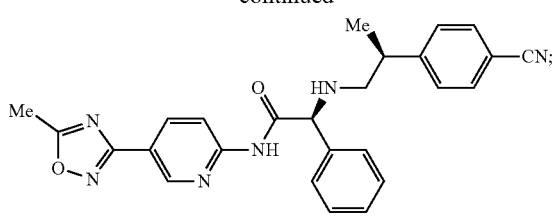
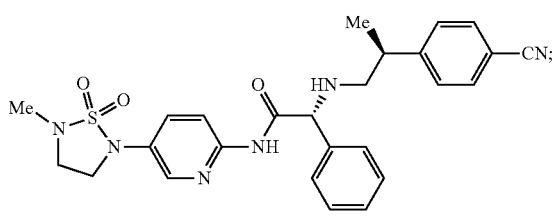
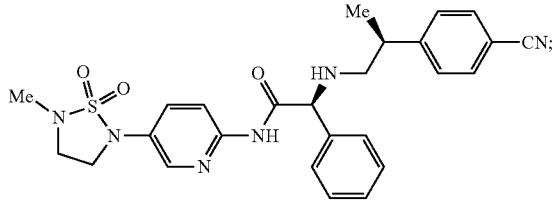
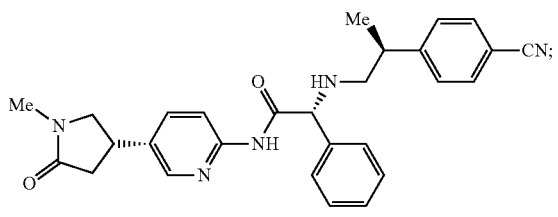
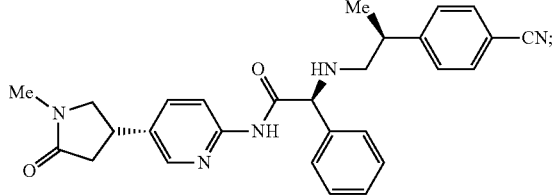
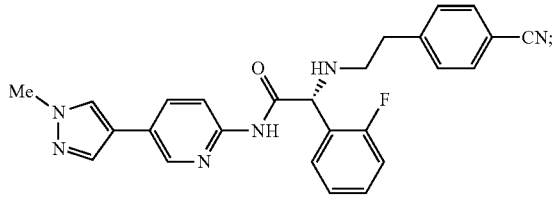

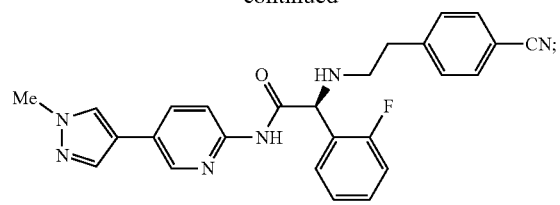
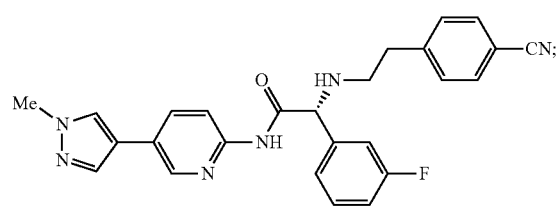
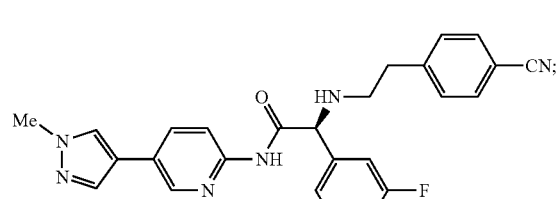
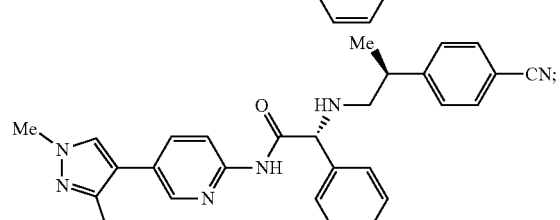
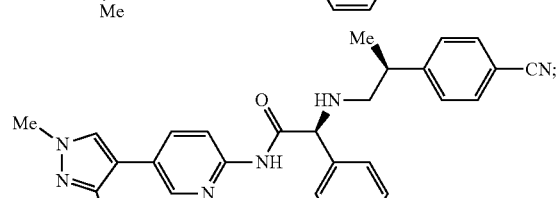
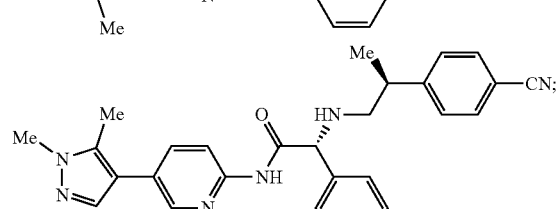
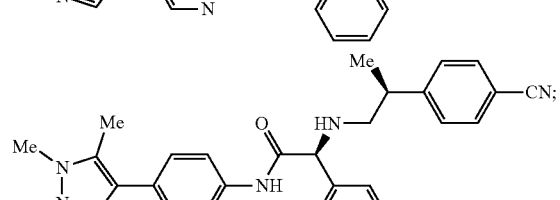
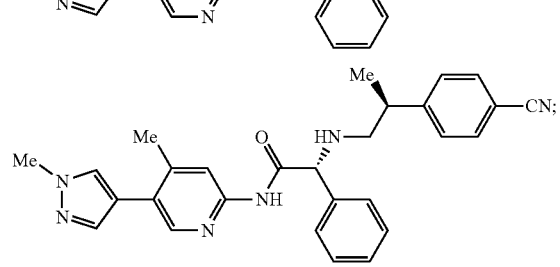

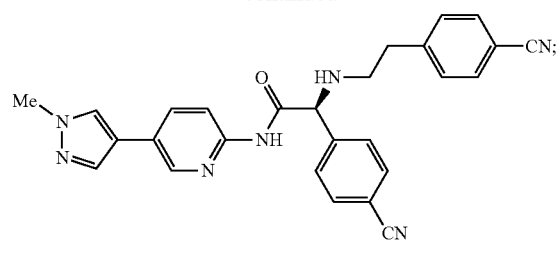
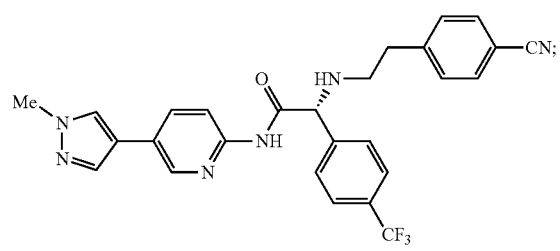
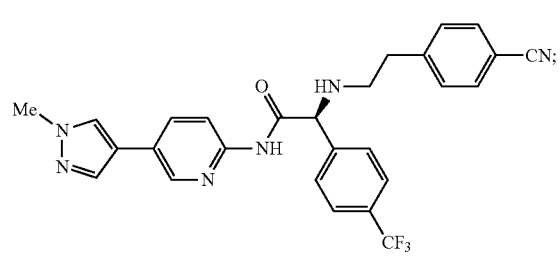
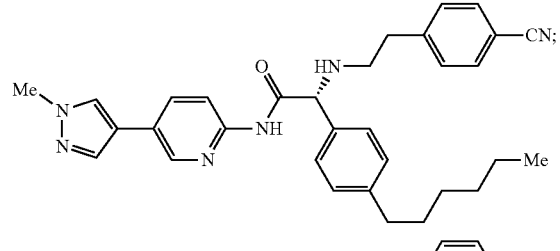
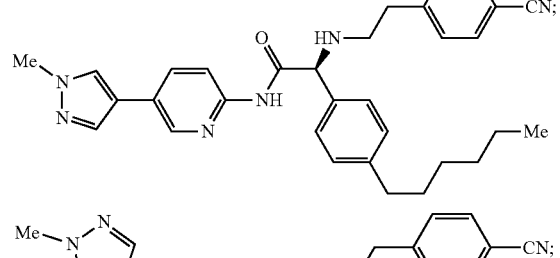
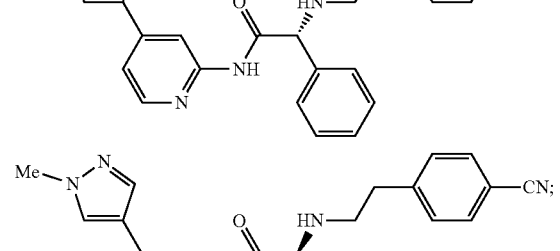
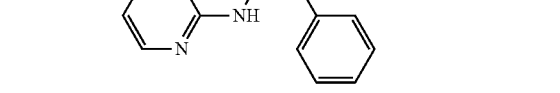
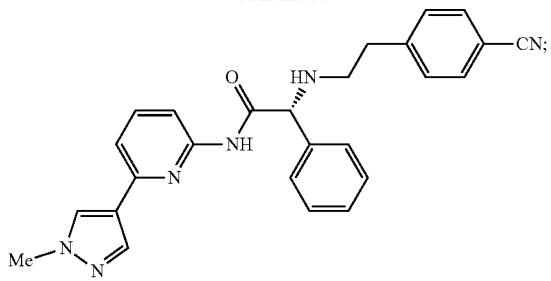
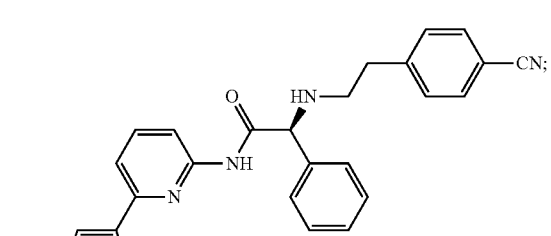
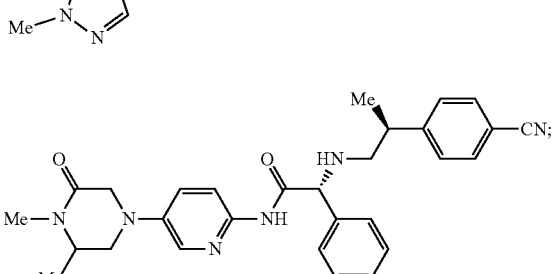
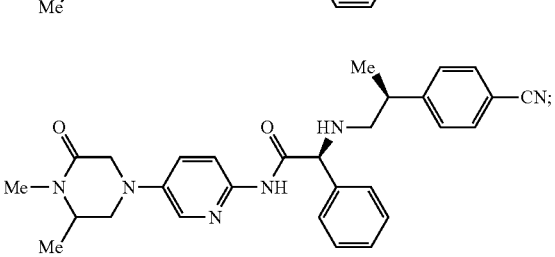
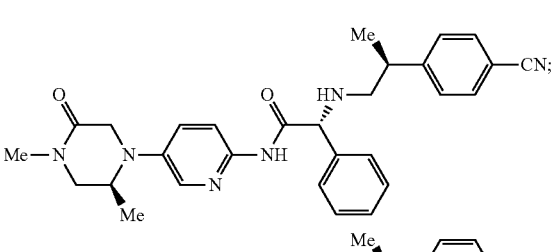
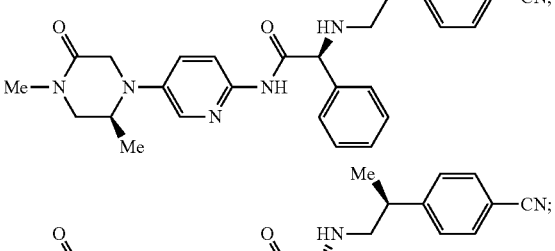
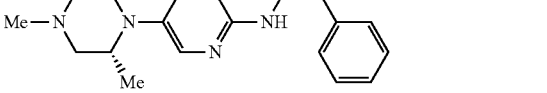

57
-continued
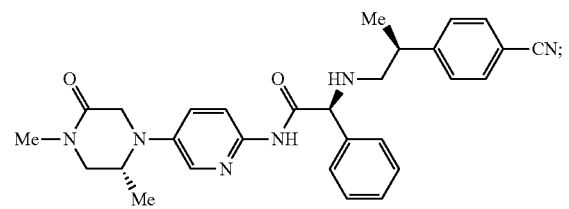
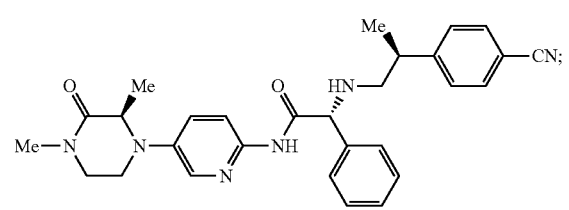
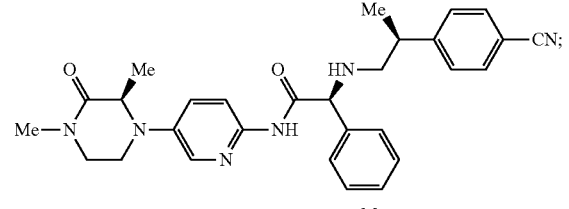
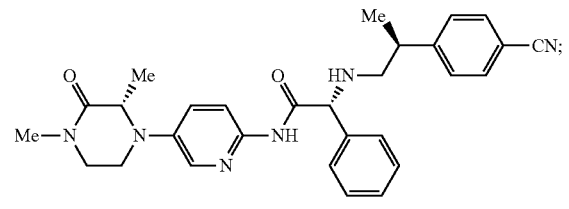
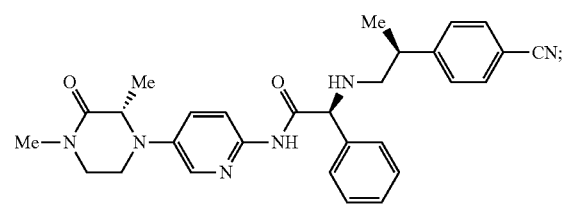
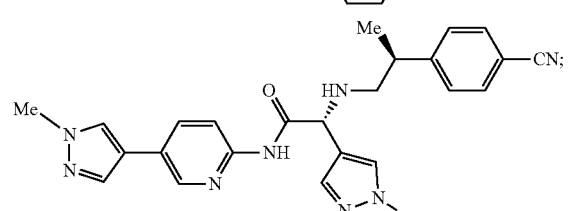
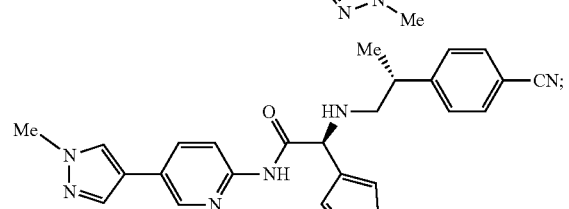
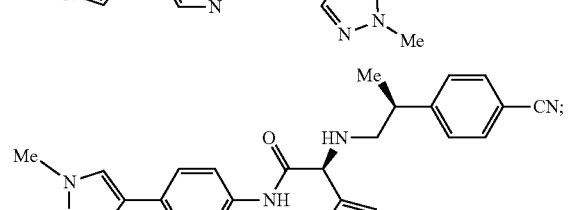
58
-continued
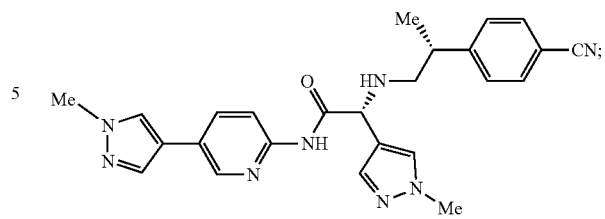
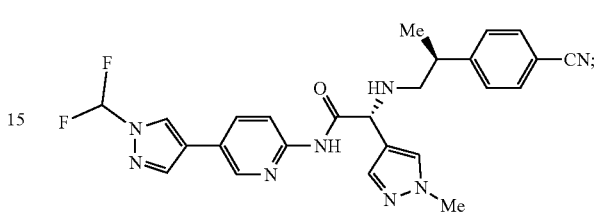
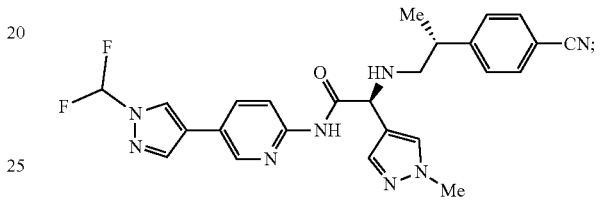
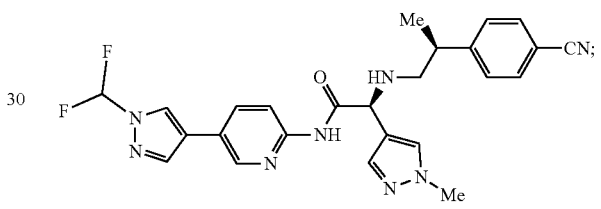
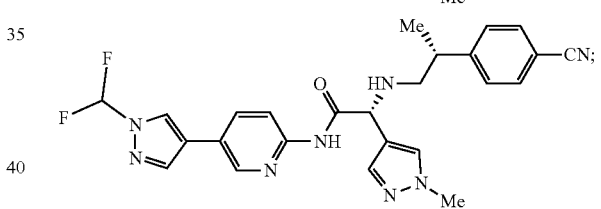
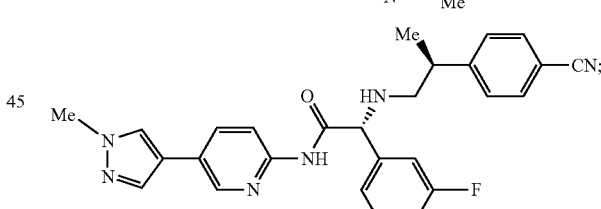
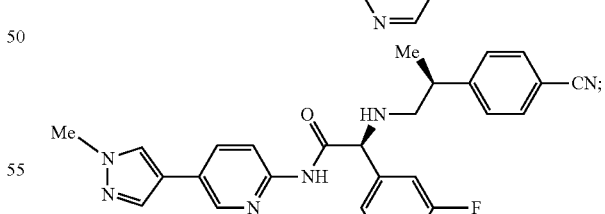
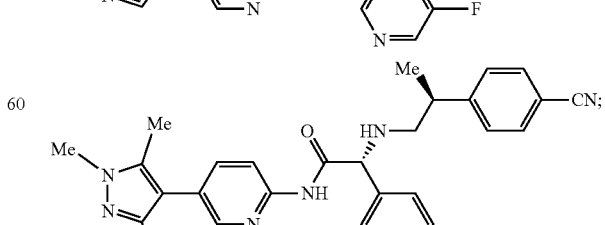

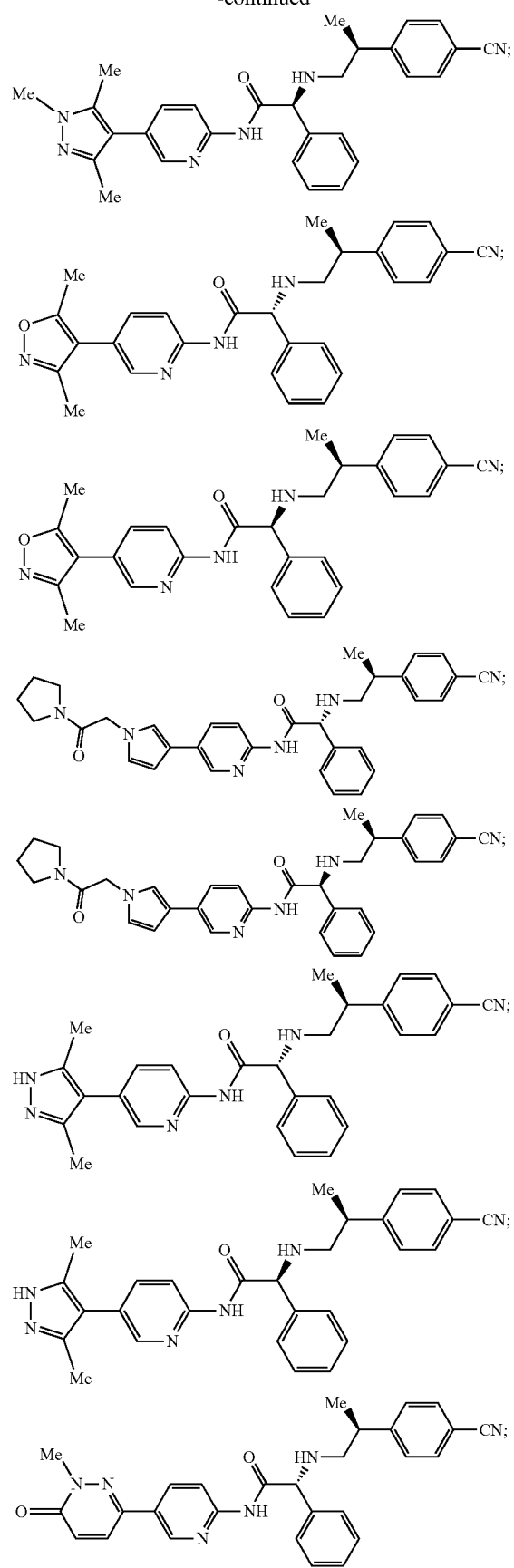
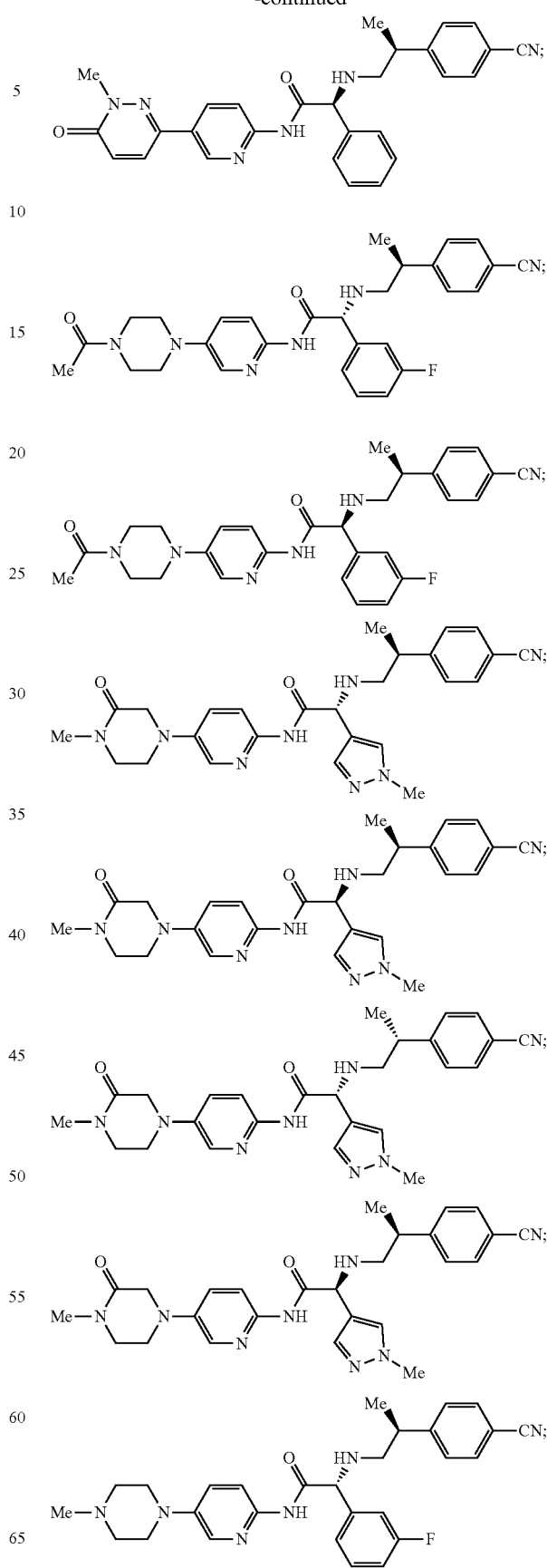

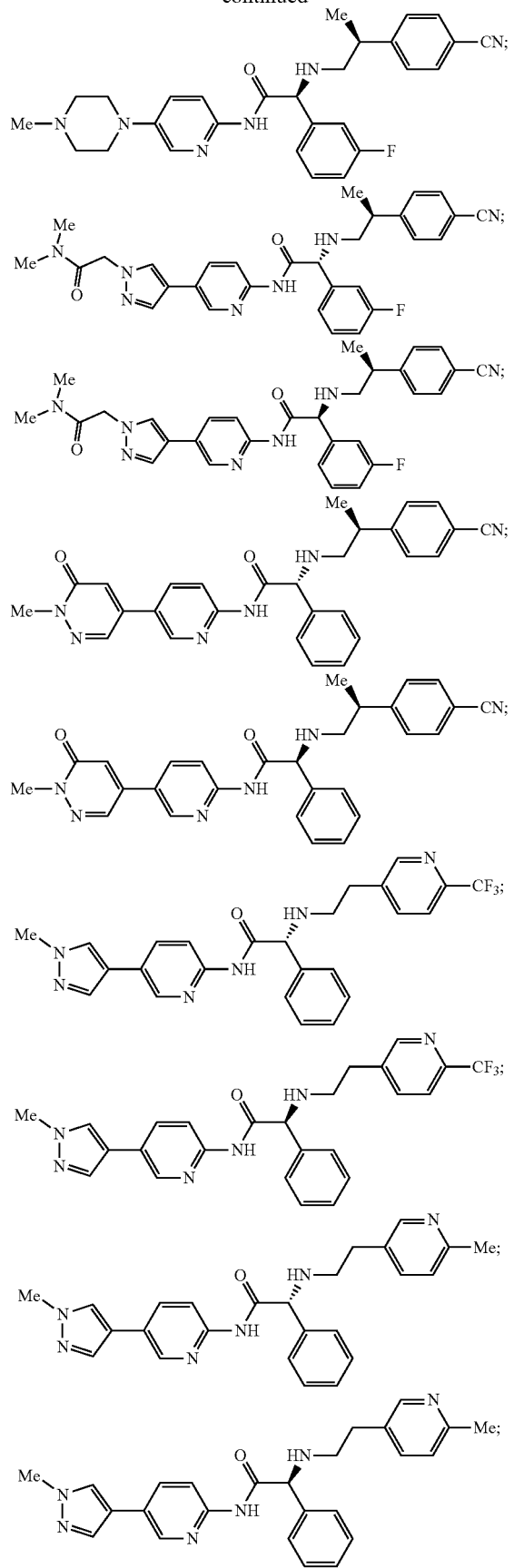
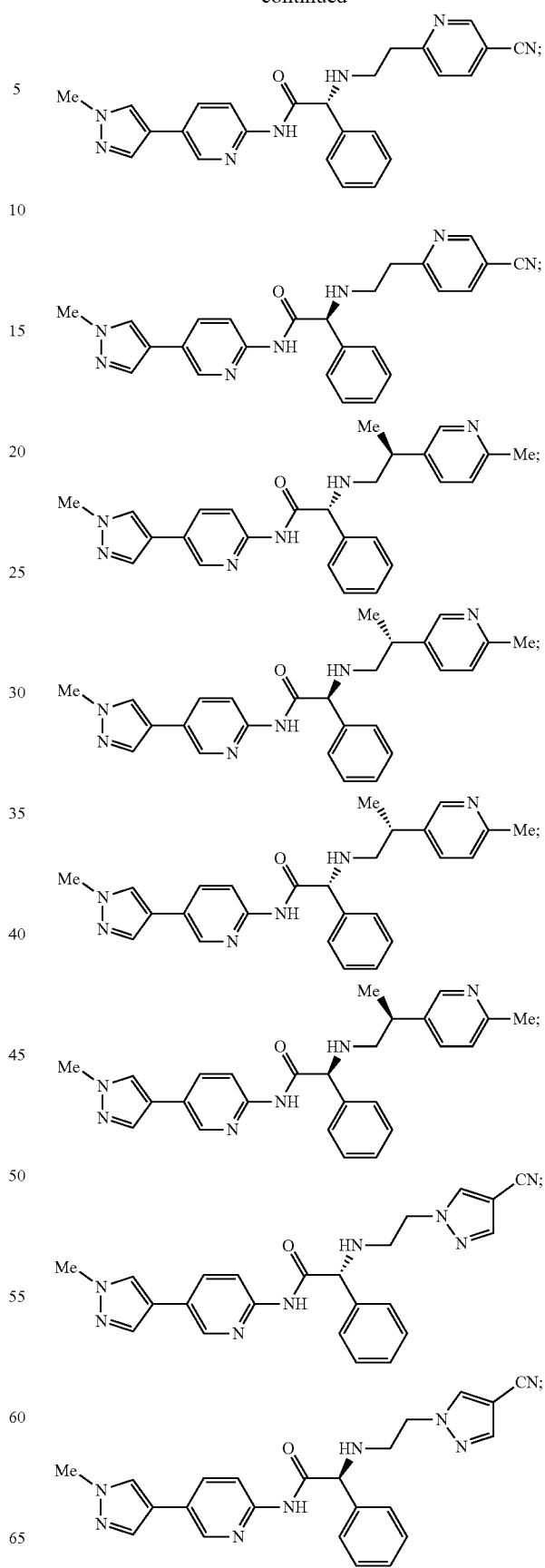

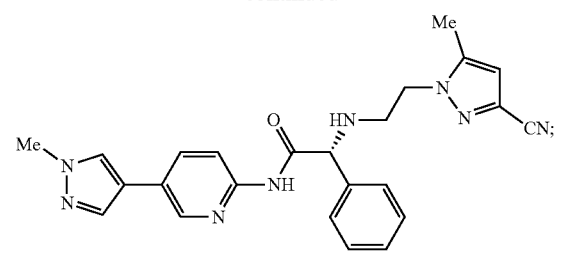
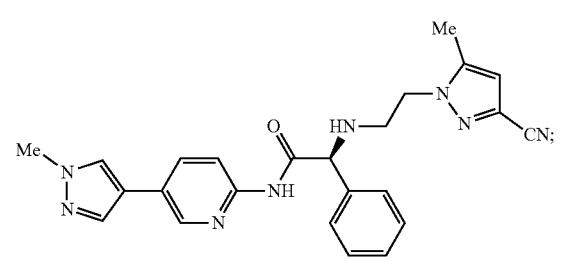
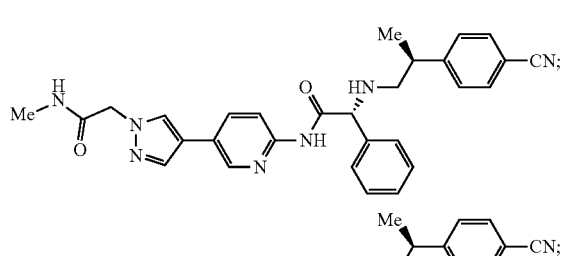
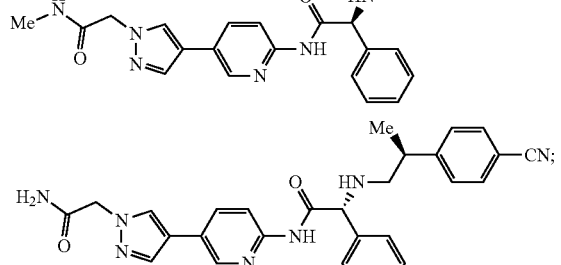
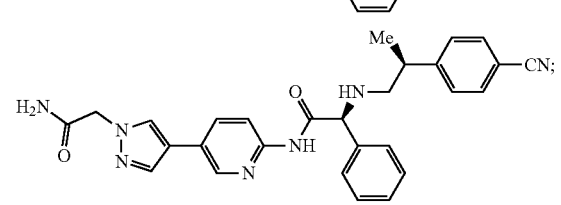
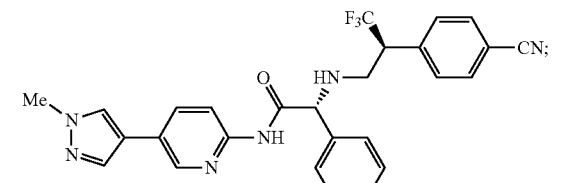
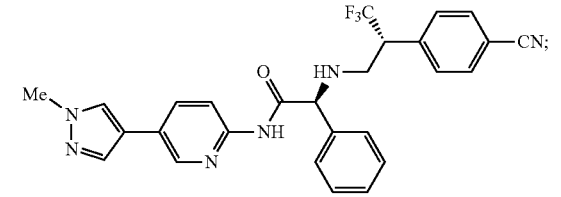
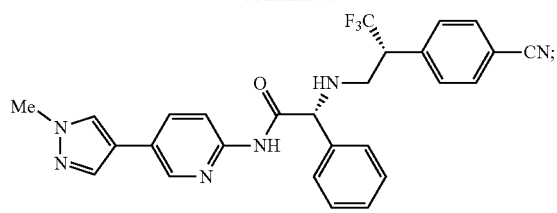
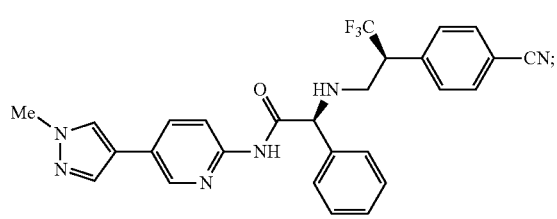
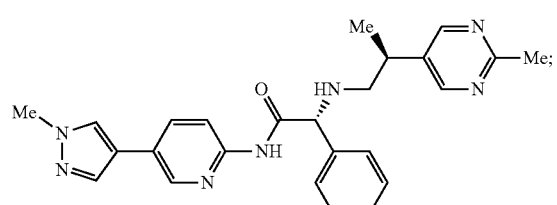
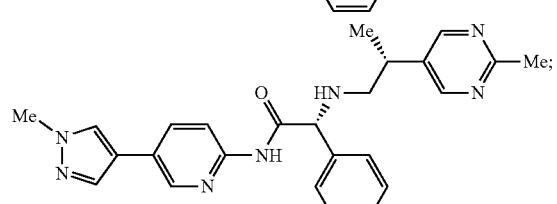
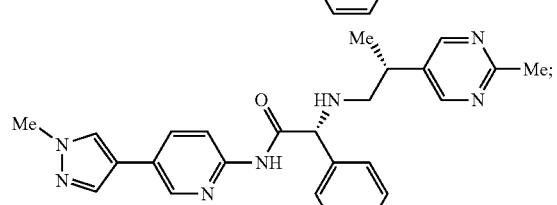
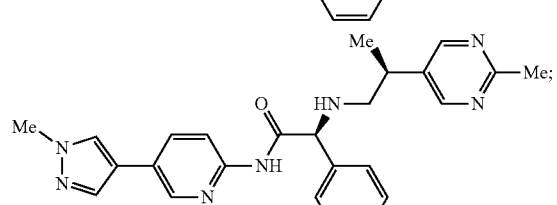
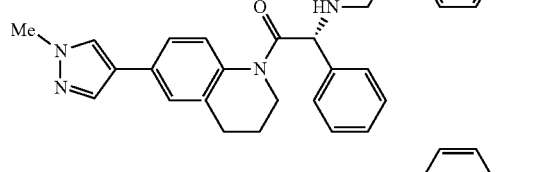

-continued

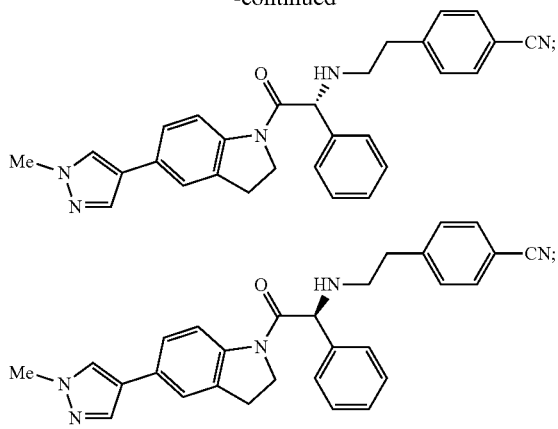

or a pharmaceutically acceptable salt thereof of any of the foregoing.

Specific examples of compounds are provided in the EXEMPLIFICATION section and are included as part of a twenty-ninth embodiment herein. Pharmaceutically acceptable salts as well as the neutral forms of these compounds are also included.

Also provided herein are pharmaceutical compositions comprising 1) a compound having the Formula I:

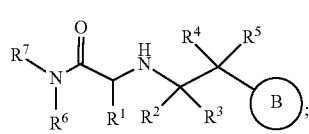

(I)

or a pharmaceutically acceptable salt thereof, wherein

Ring B is aryl, heterocyclyl, or heteroaryl each of which may be optionally substituted with 1 to 4 groups selected from $R^b$;

$R^6$ is a hydrogen or $C_{1-6}$alkyl;

$R^7$ is aryl or heteroaryl, each of which is substituted with one group selected from $R^f$, and wherein said aryl and heteroaryl for $R^7$ may also be optionally substituted with 1 to 4 groups selected from $R^a$; or $R^6$ and $R^7$ taken together with the nitrogen ring to which they are attached form a fused bicyclic heterocyclyl optionally substituted with 1 to 4 groups selected from $R^a$;

$R^1$ is $C_{1-6}$alkyl, $C_{1-6}$haloalkyl, $C_{2-6}$alkenyl, —$C_{1-6}$alkylOR$^c$, —$C_{1-6}$alkylN(R$^d$)$_2$, —$C_{1-6}$alkylC(O)OR$^d$, —$C_{1-6}$alkylOC$_{1-6}$alkylN(R$^d$)$_2$, —$C_{1-6}$alkylSOR$^d$, —$C_{1-6}$alkylS(O)$_2$R$^d$, —$C_{1-6}$alkylSON(R$^d$)$_2$, —$C_{1-6}$alkylSO$_2$N(R$^d$)$_2$, —$C_{1-6}$alkylcycloalkyl, —$C_{1-6}$alkylheterocyclyl, —$C_{1-6}$alkylheteroaryl, —$C_{1-6}$alkylaryl, cycloalkyl, aryl, heteroaryl, or heterocyclyl, wherein each of said cycloalkyl, heterocyclyl, aryl, and heteroaryl alone and in connection with —$C_{1-6}$alkylcycloalkyl, —$C_{1-6}$alkylaryl, —$C_{1-6}$alkylheteroaryl, and —$C_{1-6}$alkylheterocyclyl are optionally substituted with 1 to 3 groups selected from $R^c$;

each of $R^2$, $R^3$, $R^4$, and $R^5$ are independently hydrogen or $C_{1-6}$alkyl, wherein said $C_{1-6}$alkyl is optionally substituted with 1 or 2 groups selected from halo, —C(O)OR$^d$, —OC$_{1-6}$alkylN(R$^d$)$_2$, —$C_{1-6}$alkylN(R$^d$)$_2$, —N(R$^d$)$_2$, —NR$^d$C$_{1-6}$alkylOR$^d$, —SOR$^d$, —S(O)$_2$R$^d$, —SON(R$^d$)$_2$, —SO$_2$N(R$^d$)$_2$, $C_{3-10}$cycloalkyl, $C_{5-10}$heterocyclyl, $C_{5-10}$heteroaryl, and $C_{6-10}$aryl;

each of $R^a$, $R^b$, and $R^c$ are each independently halo, CN, oxo, NO$_2$, $C_{1-6}$alkyl, $C_{2-6}$alkenyl, $C_{1-6}$alkoxy, $C_{1-6}$haloalkoxy, $C_{1-6}$haloalkyl, —$C_{1-6}$alkylOR$^d$, —C(O)R$^d$, —C(O)OR$^d$, —$C_{1-6}$alkylC(O)OR$^d$, —C(O)N(R$^d$)$_2$, —C(O)NR$^d$C$_{1-6}$alkylOR$^d$, —OC$_{1-6}$alkylN(R$^d$)$_2$, —$C_{1-6}$alkylC(O)N(R$^d$)$_2$, —$C_{1-6}$alkylN(R$^d$)$_2$, —N(R$^d$)$_2$, —C(O)NR$^d$C$_{1-6}$alkylN(R$^d$)$_2$, —NR$^d$C$_{1-6}$alkylN(R$^d$)$_2$, —NR$^d$C$_{1-6}$alkylOR$^d$, —SOR$^d$, —S(O)$_2$R$^d$, —SON(R$^d$)$_2$, —SO$_2$N(R$^d$)$_2$, SF$_5$, -Ocycloalkyl, —O—$C_{1-4}$alkylaryl, —$C_{1-6}$alkylcycloalkyl, —$C_{1-6}$alkylaryl, —$C_{1-6}$alkylheteroaryl, —$C_{1-6}$alkylheterocyclyl, cycloalkyl, heterocyclyl, heteroaryl, or aryl, wherein each of said cycloalkyl, heterocyclyl, aryl, and heteroaryl alone and in connection with -Ocycloalkyl, —$C_{1-6}$alkylcycloalkyl, —$C_{1-6}$alkylaryl, —$C_{1-6}$alkylheteroaryl, and —$C_{1-6}$alkylheterocyclyl are optionally substituted with 1 to 3 groups selected from halo, $C_{1-6}$alkyl, $C_{1-6}$haloalkyl, $C_{1-6}$alkoxy, $C_{1-6}$haloalkoxy, —N(R$^d$)$_2$, —C(O)R$^d$, and —$C_{1-6}$alkylOR$^d$;

each $R^d$ is independently hydrogen, $C_{1-6}$haloalkyl, or $C_{1-6}$alkyl; and each $R^f$ is independently cycloalkyl, heterocyclyl, heteroaryl, or aryl, wherein each of said cycloalkyl, heterocyclyl, aryl, and heteroaryl are optionally substituted with 1 to 3 groups selected from halo, CN, oxo, NO$_2$, $C_{1-6}$alkyl, $C_{2-6}$alkenyl, $C_{1-6}$alkoxy, $C_{1-6}$haloalkoxy, $C_{1-6}$haloalkyl, —$C_{1-6}$alkylOR$^d$, —C(O)R$^d$, —C(O)OR$^d$, —$C_{1-6}$alkylC(O)OR$^d$, —C(O)N(R$^d$)$_2$, —C(O)NR$^d$C$_{1-6}$alkylOR$^d$, —OC$_{1-6}$alkylN(R$^d$)$_2$, —$C_{1-6}$alkylC(O)N(R$^d$)$_2$, —$C_{1-6}$alkylN(R$^d$)$_2$, —N(R$^d$)$_2$, —C(O)NR$^d$C$_{1-6}$alkylN(R$^d$)$_2$, —NR$^d$C$_{1-6}$alkylN(R$^d$)$_2$, —NR$^d$C$_{1-6}$alkylOR$^d$, —SOR$^d$, —S(O)$_2$R$^d$, —SON(R$^d$)$_2$, —SO$_2$N(R$^d$)$_2$, SF$_5$, -Ocycloalkyl; and 2) a pharmaceutically acceptable carrier.

In one aspect, the compound(s) and variable(s) of Formula I in the disclosed compositions are selected from any one of those described in the first, second, third, fourth, fifth, sixth, seventh, eighth, ninth, tenth, eleventh, twelfth, thirteenth, fourteenth, fifteenth, sixteenth, eighteenth, nineteenth, twentieth, twenty-first, twenty-second, twenty-third, twenty-fourth, twenty-fifth, or twenty-sixth embodiments, or as provided in the Exemplification section below.

4. Uses, Formulation and Administration

Compounds and compositions described herein are generally useful for modulating the activity of p300 and/or CBP HAT. In some aspects, the compounds and compositions described herein inhibit the activity of p300 and/or CBP HAT.

In some aspects, compounds and compositions described herein are useful in treating a disorder associated with p300 and/or CBP HAT function. Thus, provided herein are methods of treating a disorder associated with p300 and/or CBP HAT function, comprising administering to a subject in need thereof, a therapeutically effective amount of a compound described herein, or a pharmaceutically acceptable salt thereof, or a composition comprising a disclosed compound or pharmaceutically acceptable salt thereof. Also provided is the use of a compound described herein, or a pharmaceutically acceptable salt thereof, or a composition comprising a disclosed compound or pharmaceutically acceptable salt thereof, for the manufacture of a medicament for treating a disorder associated with p300 and/or CBP HAT function. Also provided is a compound described herein, or a pharmaceutically acceptable salt thereof, or a composition comprising a disclosed compound or pharmaceutically acceptable salt thereof, for use in treating a disorder associated with p300 and/or CBP HAT.

In some aspects, compounds and compositions described herein are useful in treating a disorder associated with chromatin acetylation at H3K27, H3K18, and other acetylation sites on the basic residues of chromatin acted upon by the p300 and/or CBP enzyme. Thus, provided herein are methods of treating a disorder associated with chromatin acetylation at H3K27, H3K18, and other acetylation sites on the basic residues of chromatin acted upon by the p300 and/or CBP enzyme, comprising administering to a subject in need thereof, a therapeutically effective amount of a compound described herein, or a pharmaceutically acceptable salt thereof, or a composition comprising a disclosed compound or pharmaceutically acceptable salt thereof. Also provided is the use of a compound described herein, or a pharmaceutically acceptable salt thereof, or a composition comprising a disclosed compound or pharmaceutically acceptable salt thereof, for the manufacture of a medicament for treating a disorder associated with chromatin acetylation at H3K27, H3K18, and other acetylation sites on the basic residues of chromatin acted upon by the p300 and/or CBP enzyme. Also provided is a compound described herein, or a pharmaceutically acceptable salt thereof, or a composition comprising a disclosed compound or pharmaceutically acceptable salt thereof, for use in treating a disorder associated with chromatin acetylation at H3K27, H3K18, and other acetylation sites on the basic residues of chromatin acted upon by the p300 and/or CBP enzyme.

In some aspects, compounds and compositions described herein are useful in treating a disorder associated with hyperacetylation of chromatin and/or hyperacetylation of proteins that are known to be acetylated by p300 and/or CBP. Thus, provided herein are methods of treating a disorder associated with hyperacetylation of chromatin and/or hyperacetylation of proteins that are known to be acetylated by p300 and/or CBP, comprising administering to a subject in need thereof, a therapeutically effective amount of a compound described herein, or a pharmaceutically acceptable salt thereof, or a composition comprising a disclosed compound or pharmaceutically acceptable salt thereof. Also provided is the use of a compound described herein, or a pharmaceutically acceptable salt thereof, or a composition comprising a disclosed compound or pharmaceutically acceptable salt thereof, for the manufacture of a medicament for treating a disorder associated with hyperacetylation of chromatin and/or hyperacetylation of proteins that are known to be acetylated by p300 and/or CBP. Also provided is a compound described herein, or a pharmaceutically acceptable salt thereof, or a composition comprising a disclosed compound or pharmaceutically acceptable salt thereof, for use in treating a disorder associated with hyperacetylation of chromatin and/or hyperacetylation of proteins that are known to be acetylated by p300 and/or CBP.

In some aspects, the compounds and compositions described herein are useful in treating cancer, cardiac disease, metabolic disease, fibrotic disease, inflammatory disease, or viral infections.

In some aspects, the cancer treated by the compounds and compositions described herein is selected from adenocarcinoma of the breast, prostate, and colon; bronchogenic carcinoma of the lung; myeloid; melanoma; hepatoma; neuroblastoma; papilloma; apudoma; choristoma; branchioma; malignant carcinoid syndrome; carcinoid heart disease; carcinoma (e.g., Walker, basal cell, basosquamous, Brown-Pearce, ductal, Ehrlich tumor, Krebs 2, merkel cell, mucinous, non-small cell lung, oat cell, papillary, scirrhous, bronchiolar, bronchogenic, squamous cell, and transitional cell); histiocytic disorders; leukemia; histiocytosis malignant; Hodgkin's disease; immunoproliferative small; non-Hodgkin's lymphoma; plasmacytoma; reticuloendotheliosis; melanoma; chondroblastoma; chondroma; chondrosarcoma; fibroma; fibrosarcoma; giant cell tumors; histiocytoma; lipoma; liposarcoma; mesothelioma; myxoma; myxosarcoma; osteoma; osteosarcoma; chordoma; craniopharyngioma; dysgerminoma; hamartoma; mesenchymoma; mesonephroma; myosarcoma; ameloblastoma; cementoma; odontoma; teratoma; thymoma; trophoblastic tumor; adenoma; cholangioma; cholesteatoma; cyclindroma; cystadenocarcinoma; cystadenoma; granulosa cell tumor; gynandroblastoma; hepatoma; hidradenoma; islet cell tumor; Leydig cell tumor; papilloma; sertoli cell tumor; theca cell tumor; leimyoma; leiomyosarcoma; myoblastoma; myomma; myosarcoma; rhabdomyoma; rhabdomyosarcoma; ependymoma; ganglioneuroma; glioma; medulloblastoma; meningioma; neurilemmoma; neuroblastoma; neuroepithelioma; neurofibroma; neuroma; paraganglioma; paraganglioma nonchromaffin; angiokeratoma; angiolymphoid hyperplasia with eosinophilia; angioma sclerosing; angiomatosis; glomangioma; hemangioendothelioma; hemangioma; hemangiopericytoma; hemangiosarcoma; lymphangioma; lymphangiomyoma; lymphangiosarcoma; pinealoma; carcinosarcoma; chondrosarcoma; cystosarcoma phyllodes; fibrosarcoma; hemangiosarcoma; leiomyosarcoma; leukosarcoma; liposarcoma; lymphangiosarcoma; myosarcoma; myxosarcoma; ovarian carcinoma; rhabdomyosarcoma; sarcoma; neoplasms; nerofibromatosis; and cervical dysplasia.

In other aspects, the cancer treated by the compounds and compositions described herein is selected from acoustic neuroma, acute leukemia, acute lymphocytic leukemia, acute myelocytic leukemia, acute T-cell leukemia, basal cell carcinoma, bile duct carcinoma, bladder cancer, brain cancer, breast cancer, bronchogenic carcinoma, cervical cancer, chondrosarcoma, chordoma, choriocarcinoma, chronic leukemia, chronic lymphocytic leukemia, chronic myelocytic leukemia, chronic myelogenous leukemia, colon cancer, colorectal cancer, craniopharyngioma, cystadenocarcinoma, diffuse large B-cell lymphoma, dysproliferative changes, embryonal carcinoma, endometrial cancer, endotheliosarcoma, ependymoma, epithelial carcinoma, erythroleukemia, esophageal cancer, estrogen-receptor positive breast cancer, essential thrombocythemia, Ewing's tumor, fibrosarcoma, follicular lymphoma, germ cell testicular cancer, glioma, glioblastoma, gliosarcoma, heavy chain disease, head and neck cancer, hemangioblastoma, hepatoma, hepatocellular cancer, hormone insensitive prostate cancer, leiomyosarcoma, leukemia, liposarcoma, lung cancer, lymphagioendotheliosarcoma, lymphangiosarcoma, lymphoblastic leukemia, lymphoma, lymphoid malignancies of T-cell or B-cell origin, medullary carcinoma, medulloblastoma, melanoma, meningioma, mesothelioma, multiple myeloma, myelogenous leukemia, myeloma, myxosarcoma, neuroblastoma, NUT midline carcinoma (NMC), non-small cell lung cancer, oligodendroglioma, oral cancer, osteogenic sarcoma, ovarian cancer, pancreatic cancer, papillary adenocarcinomas, papillary carcinoma, pinealoma, polycythemia vera, prostate cancer, rectal cancer, renal cell carcinoma, retinoblastoma, rhabdomyosarcoma, sarcoma, sebaceous gland carcinoma, seminoma, skin cancer, small cell lung carcinoma, solid tumors (carcinomas and sarcomas), small cell lung cancer, stomach cancer, squamous cell carcinoma, synovioma, sweat gland carcinoma, thyroid cancer, Waldenstrom's macroglobulinemia, testicular tumors, uterine cancer, and Wilms' tumor.

In some aspects, the cancer treated by the compounds and compositions described herein is selected from colon cancer, gastric cancer, thyroid cancer, lung cancer, leukemia, pancreatic cancer, melanoma, multiple melanoma, brain cancer, CNS cancer, renal cancer, prostate cancer, ovarian cancer, leukemia, and breast cancer.

In some aspects, the cancer treated by the compounds and compositions described herein is selected from lung cancer, breast cancer, pancreatic cancer, colorectal cancer, and melanoma.

In some aspects, the cancer treated by the compounds and compositions described herein is selected from prostate cancer, enhancer drive cancers, multiple myeloma, and lymphoma (e.g., mantle cell lymphoma). See e.g., Santer et al 2011, Mol Cancer Ther. 10: 1644-1655; Lasko et al, 2017, Nature. Oct. 5; 550(7674):128-132; Tie F, et al. 2009 Development 136:3131-3141; Bergsagel P L, Kuehl W M 2001, Oncogene, 20(40):5611-22; Chesi and Bergsagel 2013, Int J Hematol. 97(3): 313-323; and Jares P et al 2007, Nat Rev Cancer. 7(10):750-762.

In one aspect, the cardiac disease treated by the compound and compositions described herein is selected from cardiac hypertrophy and heart failure.

In one aspect, the metabolic disease treated by the compound and compositions described herein is selected from obesity, hepatic steatosis, dyslipidemia, hypertension, coronary heart disease, hepatic inflammation, and diabetes mellitus type 2.

In one aspect, the fibrotic disease treated by the compound and compositions described herein is selected from radiation-induced pneumonitis, radiation fibrosis, acute respiratory distress syndrome, chronic obstructive pulmonary disease, idiopathic pulmonary fibrosis, interstitial lung disease, myocardial infarction, ischemic stroke, ischemic kidney disease, transplant rejection, Leishmaniasis, type I diabetes, rheumatoid arthritis, chronic hepatitis, cirrhosis, inflammatory bowel disease, Crohn's disease, scleroderma, keloid, post-operative fibrosis, chemotherapy induced fibrosis (e.g., chemotherapy induced pulmonary fibrosis or ovarian cortical fibrosis), nephrogenic systemic fibrosis, retroperitoneal fibrosis, myelofibrosis, mediastinal fibrosis, cystic fibrosis, asbestosis, asthma, and pulmonary hypertension.

In one aspect, the inflammatory disease treated by the compound and compositions described herein is selected from asthma, inflammatory bowel disease (Crohn's disease or ulcerative colitis), chronic obstructive pulmonary disease, rheumatoid arthritis, and psoriasis. In another aspect, the inflammatory disease treated by the compound and compositions described herein is selected from Addison's disease, acute gout, ankylosing spondylitis, asthma, atherosclerosis, Behcet's disease, bullous skin diseases, chronic obstructive pulmonary disease, Crohn's disease, dermatitis, eczema, giant cell arteritis, fibrosis, glomerulonephritis, hepatic vascular occlusion, hepatitis, hypophysitis, immunodeficiency syndrome, inflammatory bowel disease, Kawasaki disease, lupus nephritis, multiple sclerosis, myocarditis, myositis, nephritis, organ transplant rejection, osteoarthritis, pancreatitis, pericarditis, Polyarteritis nodosa, pneumonitis, primary biliary cirrhosis, psoriasis, psoriatic arthritis, rheumatoid arthritis, scleritis, sclerosing cholangitis, sepsis, systemic lupus erythematosus, Takayasu's Arteritis, toxic shock, thyroiditis, type I diabetes, ulcerative colitis, uveitis, vitiligo, vasculitis, and Wegener's granulomatosis.

In one aspect, the viral infection treated by the compound and compositions described herein is selected from human immunodeficiency virus, hepatitis C virus, and human papilloma virus.

In certain aspects, a composition described herein is formulated for administration to a patient in need of such composition. Compositions described herein may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. In some embodiments, the compositions are administered orally, intraperitoneally or intravenously.

Sterile injectable forms of the compositions described herein may be aqueous or oleaginous suspension. These suspensions may be formulated according to techniques known in the art using suitable dispersing or wetting agents and suspending agents.

In some aspects, the compositions are administered orally.

A specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of a compound described herein in the composition will also depend upon the particular compound in the composition.

The compounds described herein may be present in the form of pharmaceutically acceptable salts. For use in medicines, the salts of the compounds described herein refer to non-toxic "pharmaceutically acceptable salts." Pharmaceutically acceptable salt forms include pharmaceutically acceptable acidic/anionic or basic/cationic salts. Suitable pharmaceutically acceptable acid addition salts of the compounds described herein include e.g., salts of inorganic acids (such as hydrochloric acid, hydrobromic, phosphoric, nitric, and sulfuric acids) and of organic acids (such as, acetic acid, benzenesulfonic, benzoic, methanesulfonic, and p-toluenesulfonic acids). Compounds of the present teachings with acidic groups such as carboxylic acids can form pharmaceutically acceptable salts with pharmaceutically acceptable base(s). Suitable pharmaceutically acceptable basic salts include e.g., ammonium salts, alkali metal salts (such as sodium and potassium salts) and alkaline earth metal salts (such as magnesium and calcium salts). Compounds with a quaternary ammonium group also contain a counteranion such as chloride, bromide, iodide, acetate, perchlorate and the like. Other examples of such salts include hydrochlorides, hydrobromides, sulfates, methanesulfonates, nitrates, benzoates and salts with amino acids such as glutamic acid.

Combination therapies using a therapeutically effective amount of a compound of Formula I, or a pharmaceutically acceptable salt thereof, and an effective amount of one or more additional pharmaceutically active agents are also included herein. Additional active agents that can be combined with a compound of Formula I, or a pharmaceutically acceptable salt thereof, include e.g., those which target the estrogen receptor (ER). These include, but are not limited to selective estrogen receptor degraders (SERDs), ER antagonists, selective estrogen receptor modulators (SERMs), and aromatase inhibitors (AIs). Examples of SERDs and ER antagonists include, but are not limited to, fulvestrant, RAD-1901 (elacestrant), GDC-0927 ((2S)-2-(4-{2-[3-(fluoromethyl)-1-azetidinyl]ethoxy}phenyl)-3-(3-hydroxyphenyl)-4-methyl-2H-chromen-6-ol), GDC-0810 (brilanestrant), AZD-9496 ((2E)-3-[3,5-difluoro-4-[(1R,3R)-2-(2-fluoro-2-methylpropyl)-2,3,4,9-tetrahydro-3-methyl-1H-pyrido[3,4-b]indol-1-yl]phenyl]-2-propenoic acid), OP-1250 (a prodrug of (S)-3-(4-hydroxyphenyl)-4-methyl-2-(4-(2-((R)-3-methylpyrrolidin-1-yl)ethoxy)phenyl)-2H-chromen-7-ol found in U.S. Pat. No. 9,018,244, the contents of which are incorporated herein by reference), (S)-3-(4-hydroxyphenyl)-4-methyl-2-(4-(2-((R)-3-methylpyrrolidin-1-yl)ethoxy)phenyl)-2H-chromen-7-ol, also found in U.S. Pat. No. 9,018,244, the contents of which are incorporated herein by reference), LSZ102 ((E)-3-(4-((2-(2-(1,1-difluoroethyl)-4-fluorophenyl)-6-hydroxybenzo[b]thiophen-3-yl)oxy)phenyl)acrylic acid), and H3B-6545 ((E)-N,N-dimethyl-4-((2-((5-((Z)-4,4,4-trifluoro-1-(3-fluoro-1H-indazol-5-yl)-2-phenylbut-1-en-1-yl)pyridin-2-yl)oxy)ethyl)amino)but-2-enamide). Examples of SERMs include, but are not limited to, tamoxifen, toremifene, raloxifene, bazedoxifene, ospemifene, and nafoxidene. Examples of AIs include, but are not limited to, anastrozole, letrozole, exemestane, vorozole, formestane and fadrozole. In one aspect, provided is a compound of Formula I, or a pharmaceutically acceptable salt thereof, and an additional therapeutic agent selected from fulvestrant, RAD-1901, GDC-0927, GDC-0810, AZD-9496, OP-1250, LSZ102, H3B-6545, tamoxifen, toremifene, raloxifene, bazedoxifene, ospemifene, nafoxidene, anastrozole, letrozole, exemestane, vorozole, formestane and fadrozole. In one aspect, the additional therapeutic agent is fulvestrant. The use of one or more of the combination therapies discussed above for treating a condition recited herein is also included within the scope of the present disclosure.

For example, in one aspect, the combination treatments meantion above are useful in the treatment of cancer e.g., breast cancer.

EXEMPLIFICATION

Representative examples of the disclosed compounds are illustrated in the following non-limiting methods, schemes, and examples.

General starting materials used were obtained from commercial sources or prepared in other examples, unless otherwise noted.

The following abbreviations have the indicated meanings: Ac=acetyl; ACN=acetonitrile; AcO acetate; BOC=t-butyloxycarbonyl; CBZ=carbobenzoxy; CDI=carbonyldiimidazole; DBU=1,8-Diazabicycloundec-7-ene; DCC=1,3-dicyclohexylcarbodiimide; DCE=1,2-dichloroethane; DI=de-ionized; DIAD=Diisopropyl azodicarboxylate; DIBAL=diisobutyl aluminum hydride; DIPA=diisopropylamine; DIPEA or DIE A=N,N-diisoproylethylamine, also known as Hunig's base; DMA=dimethylacetamide; DMAP=4-(dimethylamino)pyridine; DMF=dimethylformamide; DMP=Dess-Martin periodinane; DPPA=Diphenylphosphoryl azide; DPPP=1,3-bis(diphenylphosphino)propane; Dtbbpy=4,4'-di-/e/7-butyl-2,2'-dipyridyl; EDC or EDCI=1-(3-dimethylaminopropyl)-3-ethylcarbodiimide hydrochloride; EDTA=ethylenediaminetetraacetic acid, tetrasodium salt; EtOAc=ethyl acetate; FAB=fast atom bombardment; FMOC=9-fluorenylmethoxycarbonyl; HMPA=hexamethylphosphoramide; HATU=(9-(7-Azabenzotriazol-1-yl)-N, N, N, N-tetramethyluroniumhexafluorophosphate; HOAt=1-Hydroxy-7-azabenzotriazole or 3H-[1,2,3]triazolo[4,5-b]pyridin-3-ol; HOBt=1-hydroxybenzotriazole; HRMS=high resolution mass spectrometry; KHMDS=potassium hexamethyldisilazane; LC-MS=Liquid chromatography-mass spectrometry; LDA=lithium diisopropylamide; LiHMDS=lithium hexamethyldisilazane; MCPBA=meta-chloroperbenzoic acid; MMPP=magnesium monoperoxyphthlate hexahydrate; Ms=methanesulfonyl=mesyl; MsO=methanefulfonate=mesylate; MTBE=Methyl t-butyl ether; NBS=N-bromosuccinimide; NMM=4-methylmorpholine; NMP=N-methylpyrrolidinone; NMR=Nuclear magnetic resonance; PCC=pyridinium chlorochromate; PDC=pyridinium dichromate; Ph=phenyl; PPTS=pyridinium p-toluene sulfonate; pTSA=p-toluene sulfonic acid; r.t./RT=room temperature; rac.=racemic; T3P=2,4,6-Tripropyl-1,3,5,2,4,6-trioxatriphosphinane 2,4,6-trioxide; TEA=triethylamine; TFA=trifluoroacetic acid; TfO=trifluoromethanesulfonate=triflate; THF=tetrahydrofuran; TLC=thin layer chromatography; TMSCl=trimethylsilyl chloride.

Unless otherwise stated, the absolute configuration of each eluting stereoisomer in the following examples was not identified.

The progress of reactions was often monitored by TLC or LC-MS. The LC-MS was recorded using one of the following methods.

| METHOD-C3: | | | | |
|---|---|---|---|---|
| Mobile Phase | (A) 2 mM Ammonium acetate + 0.1% Formic Acid in Water | | | |
| | (B) 0.1% Formic Acid in Acetonitrile | | | |
| Column | : BEH C18 (50*2.1 mm) 1.7 um | | | |
| Column Flow | : 0.55 ml/min | | | |
| Gradient | : | Time (min) | % A | % B |
| | | 0.01 | 98 | 2 |
| | | 0.30 | 98 | 2 |
| | | 0.60 | 50 | 50 |
| | | 1.10 | 25 | 75 |
| | | 2.00 | 0 | 100 |
| | | 2.70 | 0 | 100 |
| | | 2.71 | 98 | 2 |
| | | 3.00 | 98 | 2 |

| PDS Method-J: | | | | |
|---|---|---|---|---|
| Mobile Phase | (A) 5 mM Ammonium Acetate + 0.1% Formic Acid in Water | | | |
| | (B) 0.1% Formic Acid in Acetonitrile | | | |
| Column | : BEH C18 (50*2.1 mm), 1.7 um or Equivalent | | | |
| Column Flow | : 0.45 ml/min | | | |
| Gradient | : | Time (min) | % A | % B |
| | | 0.01 | 98 | 2 |
| | | 0.50 | 98 | 2 |
| | | 5.00 | 10 | 90 |
| | | 6.00 | 5 | 95 |
| | | 7.00 | 5 | 95 |
| | | 7.01 | 98 | 2 |
| | | 8.00 | 98 | 2 |

| Method-H: | | | | |
|---|---|---|---|---|
| Mobile Phase | (A) 5 mM Ammonium bicarbonate in water | | | |
| | (B) Acetonitrile | | | |
| Column | : X-Bridge C18 (50*4.6 mm), 3.5 um | | | |
| Column Flow | : 1.0 ml/min | | | |
| Gradient | : | Time (min) | % A | % B |
| | | 0.01 | 95 | 5 |
| | | 5.00 | 10 | 90 |
| | | 5.80 | 5 | 95 |
| | | 7.20 | 5 | 95 |

Method-H:

| | | |
|---|---|---|
| 7.21 | 95 | 5 |
| 10.00 | 95 | 5 |

Method-F:

| Mobile Phase | (A) 10 mM Ammonium Acetate in WATER |
| --- | --- |
| | (B) 100% Acetonitrile |
| Column | : X-Bridge C18 (150*4.6 mm), 5 um or Equivalent |
| Column Flow | : 1.0 ml/min |

| Gradient | : | Time (min) | % A | % B |
|---|---|---|---|---|
| | | 0.01 | 90 | 10 |
| | | 5.00 | 10 | 90 |
| | | 7.00 | 0 | 100 |
| | | 11.00 | 0 | 100 |
| | | 11.01 | 90 | 10 |
| | | 12.00 | 90 | 10 |

Method-G:

| Mobile Phase | (A) 10 mM Ammonium Acetate in Water |
| --- | --- |
| | (B) 100% Acetonitrile |
| Column | : X-Bridge C18 (150*4.6 mm), 5 um or Equivalent |
| Column Flow | : 1.0 ml/min |

| Gradient | : | Time (min) | % A | % B |
|---|---|---|---|---|
| | | 0.01 | 100 | 0 |
| | | 7.00 | 50 | 50 |
| | | 9.00 | 0 | 100 |
| | | 11.00 | 0 | 100 |
| | | 11.01 | 100 | 0 |
| | | 12.00 | 100 | 0 |

NMR was recorded at room temperature unless noted otherwise on Varian Inova 400 or 500 MHz spectrometers with the solvent peak used as the reference or on Bruker 300 or 400 MHz spectrometers with the TMS peak used as internal reference.

The compounds described herein may be prepared using the following methods and schemes. Unless specified otherwise, all starting materials used are commercially available.

Method 1

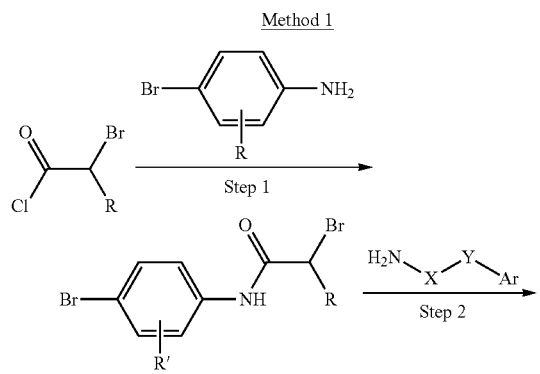

Method 1 is a 2-step protocol, consisting of an acylation reaction with a 2-bromoacylchloride and a subsequent alkylation reaction with a substituted ethylamine, for the preparation of N-(haloaryl)-2-(arylethylamino)-2-substitutedacetamides or N-(haloheteroaryl)-2-(arylethylamino)-2-substitutedacetamides, that is useful for the synthesis of intermediates en route to the compounds described herein.

Method 2

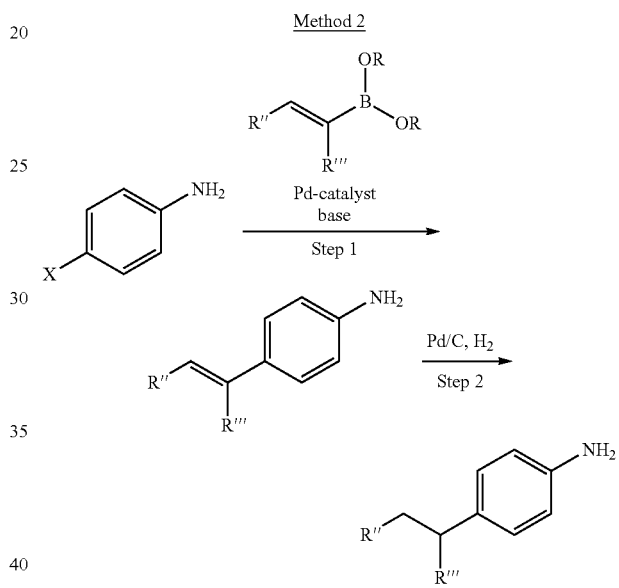

Method 2 is a 2-step protocol, which consists of a Suzuki cross-coupling reaction and a palladium-catalyzed hydrogenation reaction, for the preparation of methyl 4-alkylanilines starting from a haloaniline and an alkenylboronic ester that is useful for the synthesis of intermediates en route to the compounds described herein.

Method 3

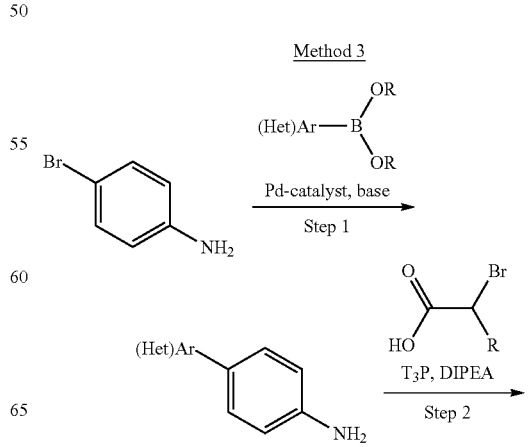

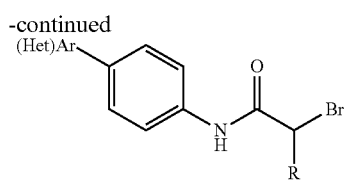

Method 3 is a 2-step protocol, which consists of a Suzuki cross-coupling reaction and an amide coupling, for the preparation of 2-bromo-N-(4-heteroaryl)-2-substitutedacetamides starting from a haloaniline and an heteroarylboronic ester that is useful for the synthesis of intermediates en route to the compounds described herein.

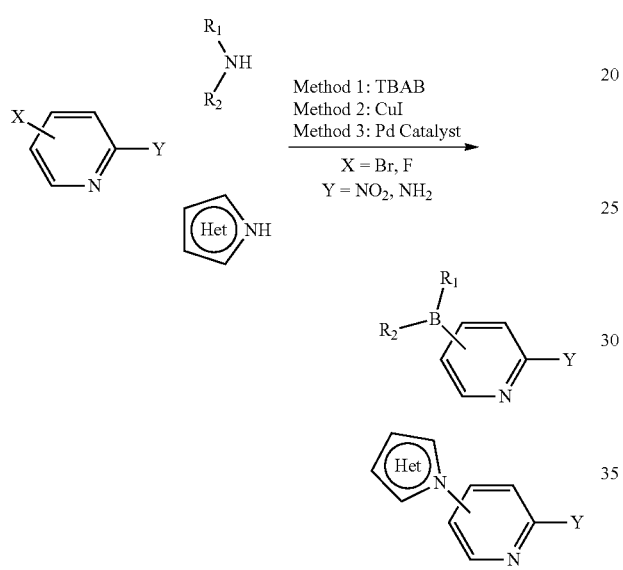

Methods 4, 5, and 6 are protocols for the coupling of substituted nitropyridines or aminopyridines with aliphatic and heteroaromatic amines for the preparation of substituted pyridines that are useful for the synthesis of intermediates en route to the compounds described herein

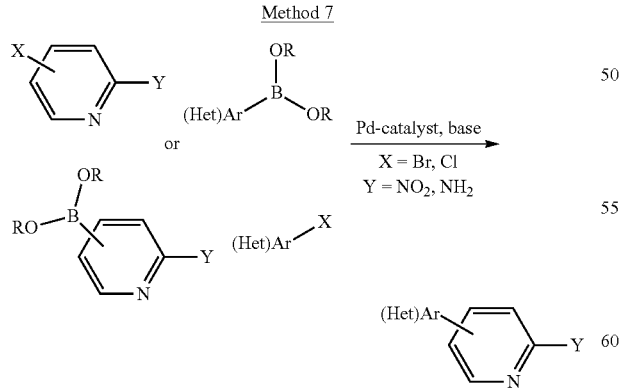

Method 7 is a protocol for the preparation of substituted pyridines, a Suzuki cross-coupling reaction of pyridine boronic acids and esters with aryl- and heteroaryl halides or a Suzuki cross coupling reaction of halopyridines with aryl- or heteroaryl boronic acids and esters, that is useful for the synthesis of intermediates en route to the compounds described herein.

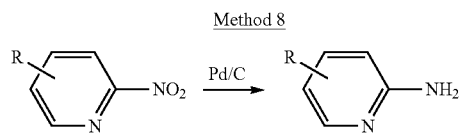

Method 8 is a protocol for the preparation of substituted 2-amino pyridines from 2-nitro pyridines via a palladium-catalyzed hydrogenation reaction that is useful for the synthesis of intermediates en route to the compounds described herein.

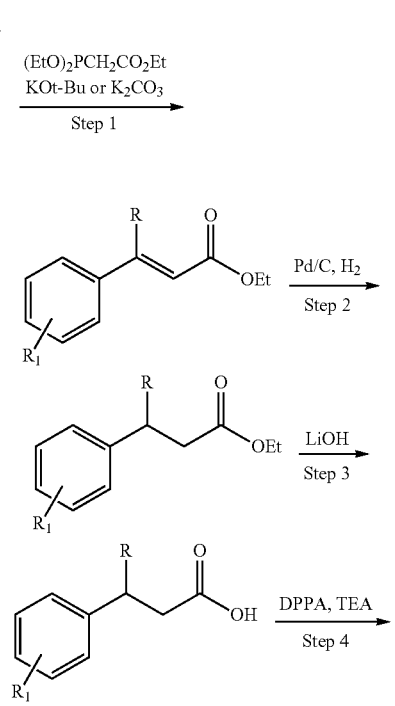

Method 9 is a 5 step-protocol for the preparation of substituted 2-arylethylamines and 2-heteroarylethylamines employing substituted benzaldehydes or ketones that is useful for the synthesis of intermediates en route to the compounds described herein.

Method 10

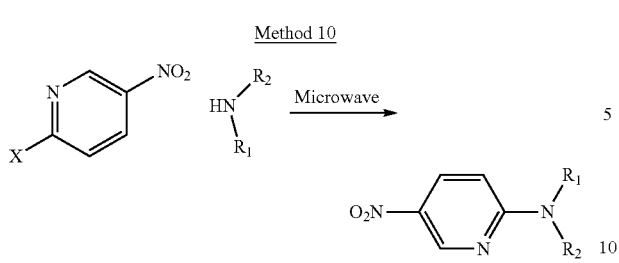

Method 10 is a protocol for the preparation of 2-substituted nitro pyridines from 2-halonitro pyridines and amines that is useful for the synthesis of intermediates en route to the compounds described herein.

Method 11

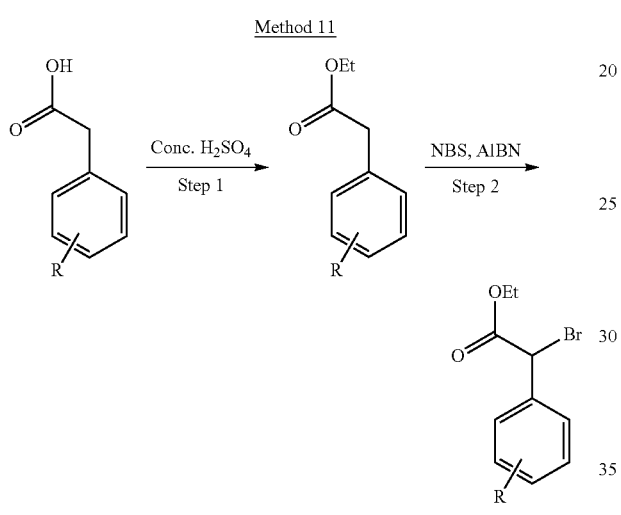

Method 11 is a 2 step-protocol for the preparation of substituted ethyl 2-bromo-2-phenylacetates from substituted phenyl acetic acid derivatives that is useful for the synthesis of intermediates en route to the compounds described herein.

Method 12

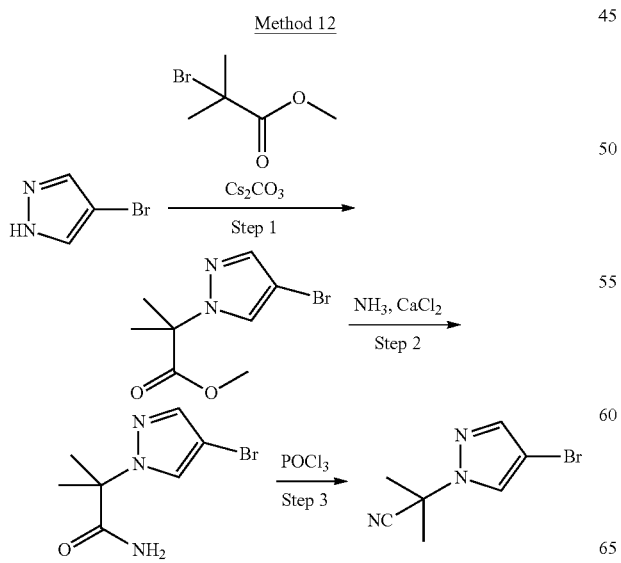

Method 12 is a 3 step-protocol for the synthesis of methyl 2-(4-bromo-1H-pyrazol-1-yl)-2-methylpropanenitrile from 4-bromo-1H-pyrazole that is useful for the synthesis of intermediates en route to the compounds described herein.

Method 13

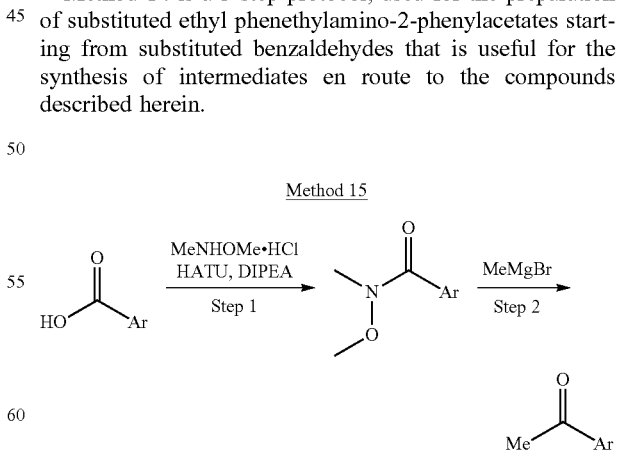

Method 13 is a protocol for the preparation of 5-(4-methyl-1H-1,2,3-triazol-1-yl)pyridin-2-amine from 5-iodopyridin-2-amine that is useful for the synthesis of intermediates en route to the compounds described herein.

Method 14

Method 14 is a 3-step protocol, used for the preparation of substituted ethyl phenethylamino-2-phenylacetates starting from substituted benzaldehydes that is useful for the synthesis of intermediates en route to the compounds described herein.

Method 15

Method 15 is a 2-step protocol, used for the preparation of substituted acetophenones starting from substituted benzoic acids that is useful for the synthesis of intermediates en route to the compounds described herein.

Method 16

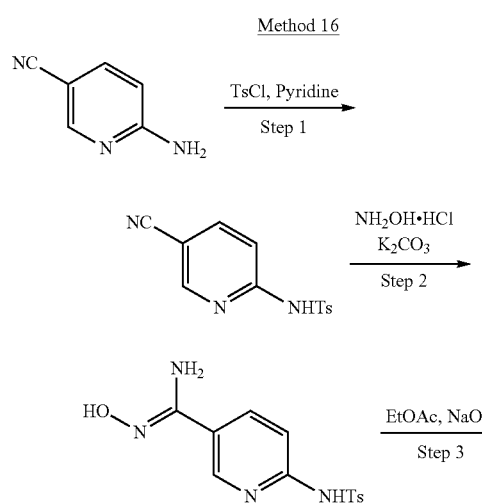

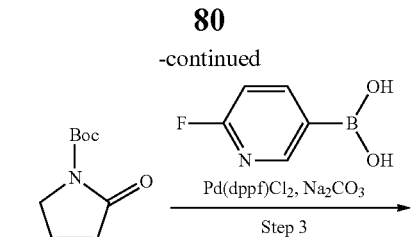

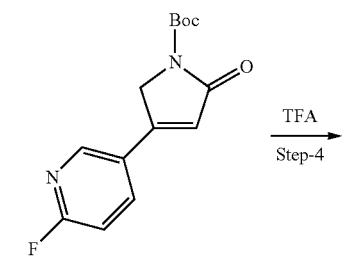

Method 16 is a 4-step protocol, used for the preparation of 5-(5-methyl-1,2,4-oxadiazol-3-yl)pyridin-2-amine starting from substituted 6-aminonicotinonitrile that is useful for the synthesis of intermediates en route to the compounds described herein.

Method 17

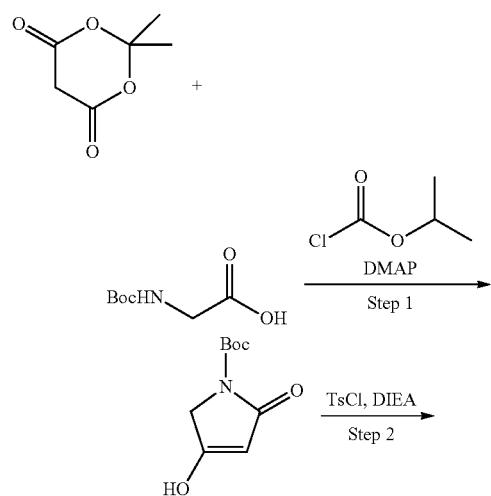

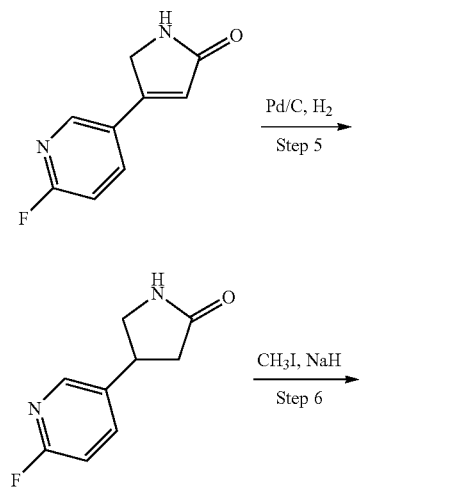

Method 17 is a 7-step protocol, used for the preparation of 4-(6-aminopyridin-3-yl)-1-methylpyrrolidin-2-ones starting from 2,2-dimethyl-1,3-dioxane-4,6-dione that is useful for the synthesis of intermediates en route to the compounds described herein.

Method 18

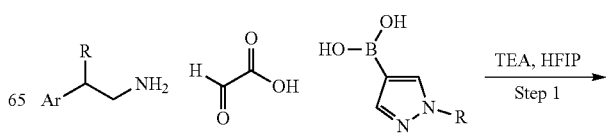

-continued

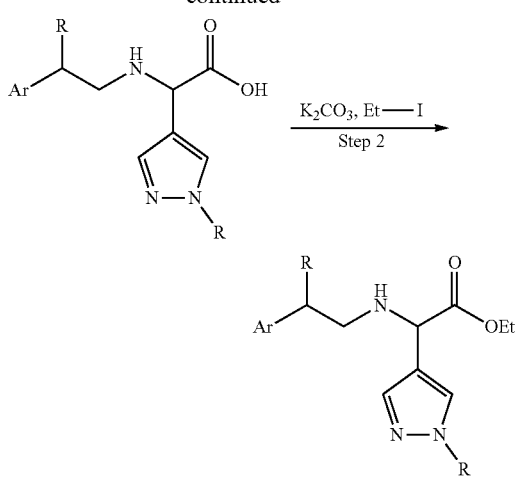

Method 18 is a 2-step protocol, used for the preparation of substituted ethyl 2-(arylethylamino)-2-(1-substituted-1H-pyrazol-4-yl)acetates starting from arylethylamines and substituted boronate (or boronic acid)pyrazoles that is useful for the synthesis of intermediates en route to the compounds described herein.

Method 19

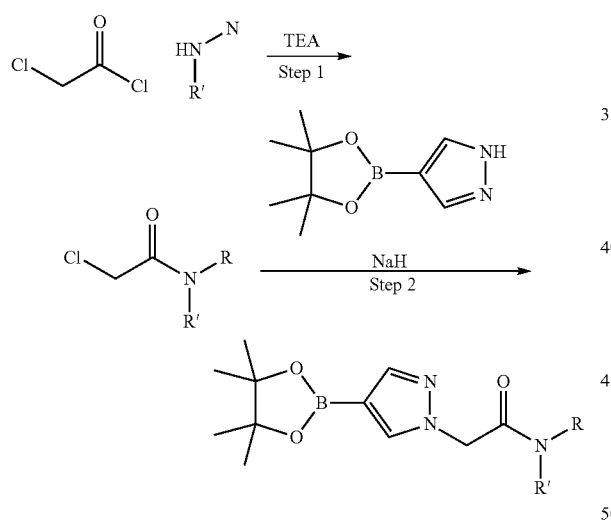

Method 19 is a 2-step protocol, used for the preparation of substituted 1-(amino)-2-(4-(4,4,5,5-tetramethyl-1,3,2-dioxaborolan-2-yl)-1H-pyrazol-1-yl)ethan-1-ones starting from amines that is useful for the synthesis of intermediates en route to the compounds described herein.

Method 20

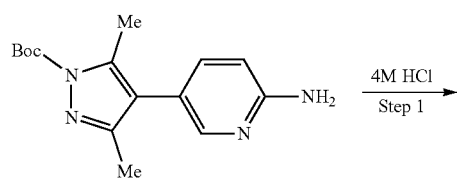

-continued

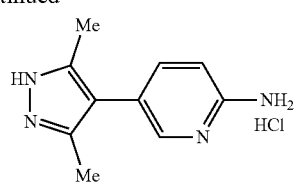

Method 20 is a protocol, used for the preparation of 5-(3,5-dimethyl-1H-pyrazol-4-yl)pyridin-2-amine starting from tert-butyl 4-(6-aminopyridin-3-yl)-3,5-dimethyl-1H-pyrazole-1-carboxylate that is useful for the synthesis of intermediates en route to the compounds described herein.

Method 21

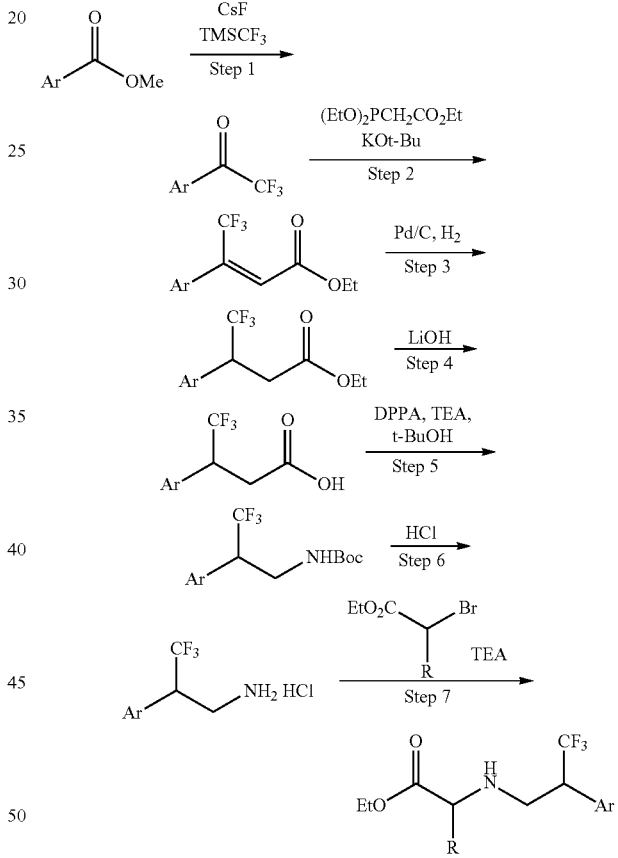

Method 21 is seven-step protocol for the preparation of ethyl trifluoromethyl phenethylalanine derivatives from methyl benzoate derivatives that is useful for the synthesis of intermediates en route to the compounds described herein.

Method 22

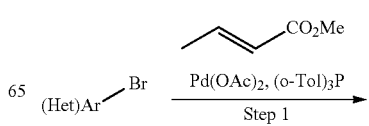

83

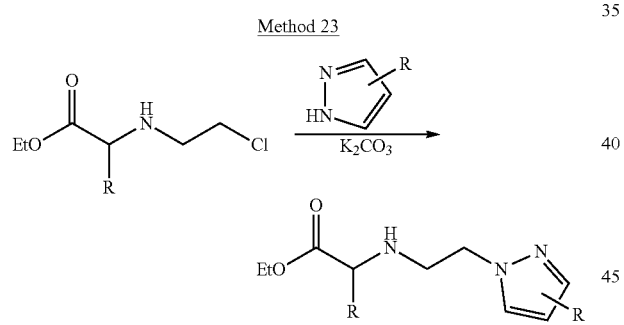

Method 22 is a six-step protocol for the synthesis of ethyl aryl(heteroaryl)propyl alanine derivatives from aryl- and heteroarylbromides that is useful for the synthesis of intermediates en route to the compounds described herein.

Method 23

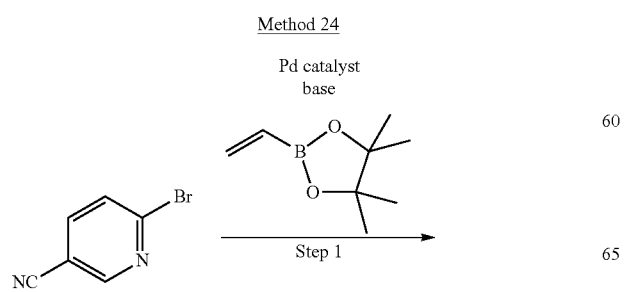

Method 23 is a protocol for the synthesis of ethyl 2-((2-(1H-pyrazol-1-yl)ethyl)amino)-2-acetate derivatives from ethyl 2-((2-chloroethyl)amino)-acetates that is useful for the synthesis of intermediates en route to the compounds described herein.

Method 24

Pd catalyst
base

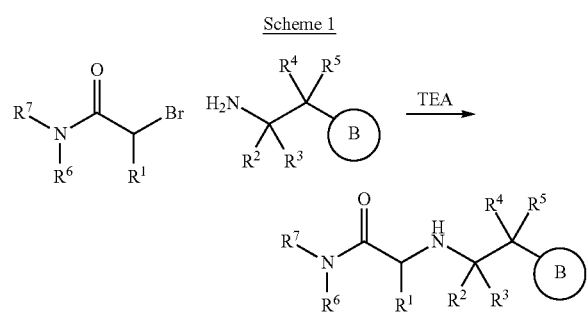

84

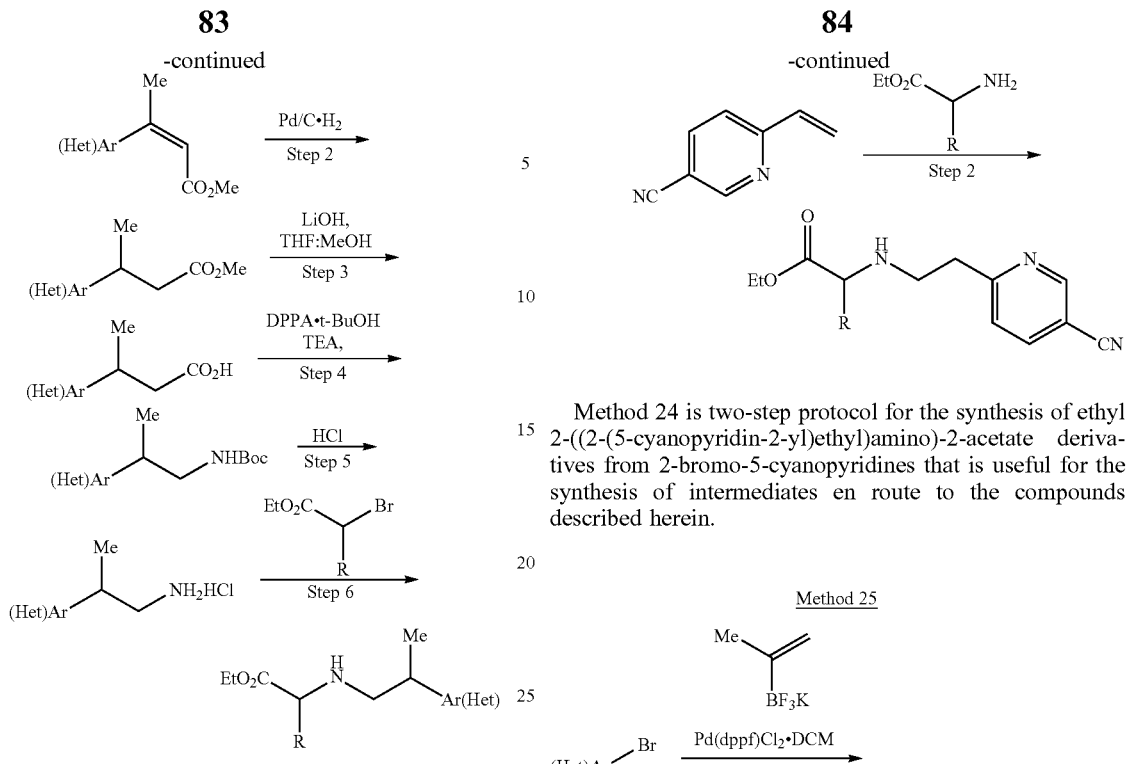

Method 24 is two-step protocol for the synthesis of ethyl 2-((2-(5-cyanopyridin-2-yl)ethyl)amino)-2-acetate derivatives from 2-bromo-5-cyanopyridines that is useful for the synthesis of intermediates en route to the compounds described herein.

Method 25 is a four-step protocol for the synthesis of ethyl aryl(heteroaryl)propyl alanine derivatives from aryl- or heteroarylbromides that is useful for the synthesis of intermediates en route to the compounds described herein.

Scheme 1 illustrates a general method for the synthesis of the compounds of this invention via alkylation of amine with an α-bromoketone or α-bromoamide where B, $R^1$, $R^2$, $R^3$, $R^4$, $R^5$, $R^6$, and $R^7$ are as described herein.

Scheme 2

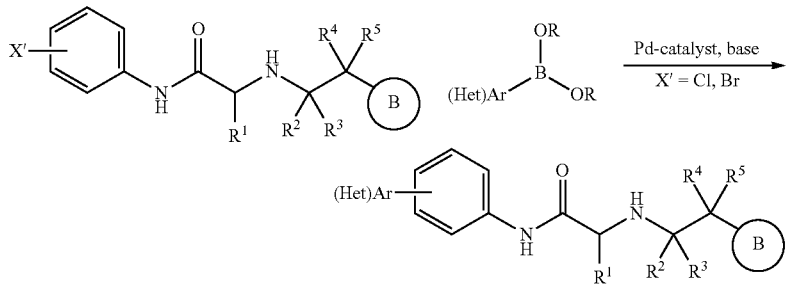

Scheme 2 illustrates a general method for the synthesis of a subset of the compounds described herein via a Suzuki reaction of a variety aryl- or heteroarylboronic esters and acids with a subset substituted compounds of Formula I where B, $R^1$, $R^2$, $R^3$, $R^4$, and $R^5$ are as described herein.

Scheme 3

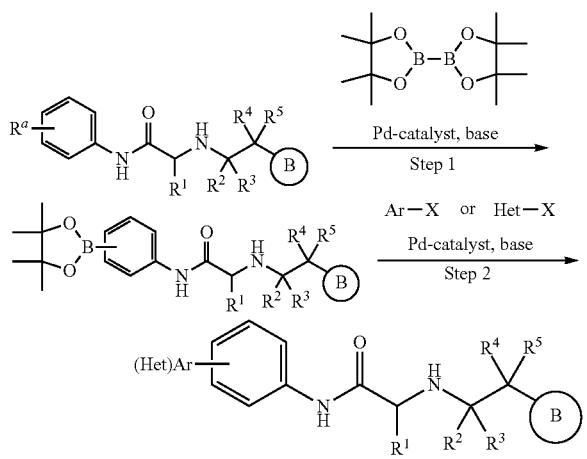

Scheme 3 illustrates a two-step sequence, useful for the synthesis of a subset of the compounds described herein that consists of a palladium-catalyzed borylation reaction of compounds of Formula I where B, $R^1$, $R^2$, $R^3$, $R^4$, and $R^5$ are as described herein.

Scheme 4

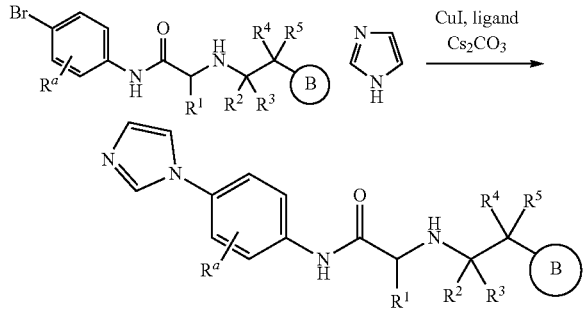

Scheme 4 illustrates a general method for the synthesis of a subset of the compounds described herein via a copper-catalyzed coupling reaction of a variety azoles with a family of substituted compounds of Formula I where B, $R^a$, $R^1$, $R^2$, $R^3$, $R^4$, and $R^5$ are as described herein.

Scheme 5

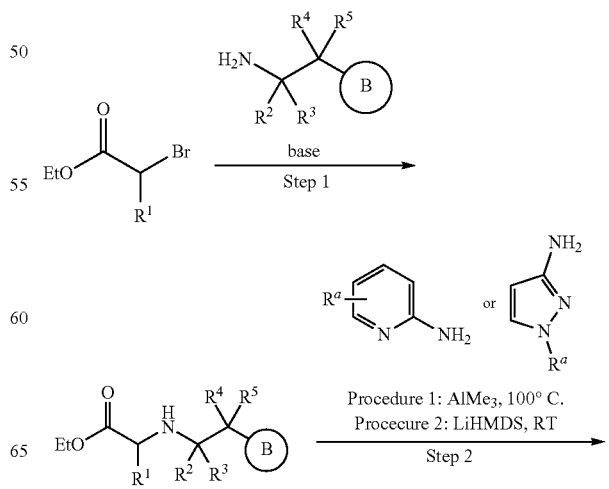

Scheme 5 illustrates a method for the synthesis of a subset of the compounds of this invention via a palladium-catalyzed C—N coupling reaction of amines with a family of substituted compounds of Formula I where B, $R^a$, $R^1$, $R^2$, $R^3$, $R^4$, and $R^5$ are as described herein.

Scheme 6

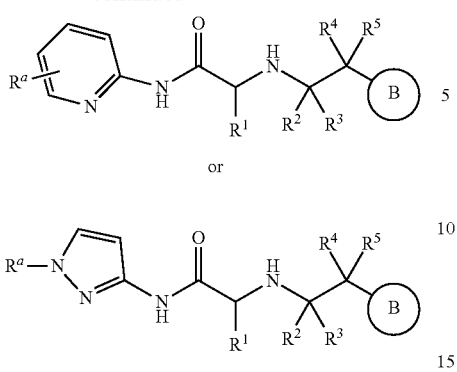

or

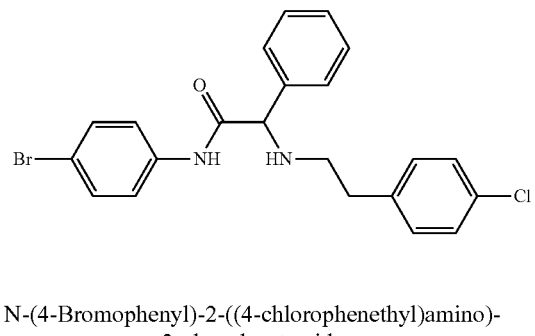

Method 1

N-(4-Bromophenyl)-2-((4-chlorophenethyl)amino)-2-phenylacetamide

Scheme 6 illustrates a 2-step synthetic sequence for the conversion of an α-bromoester to N-aryl-2-(alkylamino) acetamide. The method is useful for the synthesis of a subset of the compounds of Formula I where $R^1$ is a substituted phenyl and B, $R^a$, $R^2$, $R^3$, $R^4$, and $R^5$ are as described herein.

Method 1, Step 1.
2-Bromo-N-(4-bromophenyl)-2-phenylacetamide

To a stirred solution of 2-bromo-2-phenylacetic acid (1 g, 2.32 mmol) in dry DCM (10 ml) was added thionyl chloride (1.1 ml, 3.95 mmol) dropwise at 0° C. and reaction mixture was stirred at 40° C. overnight. After completion of the reaction, excess of thionyl chloride and DCM were evaporated under reduced pressure. Then to this, THF (10 ml) and 4-bromo aniline (0.79 g, 4.64 mmol) were added and resulting reaction mixture was stirred for 4 hours at room temperature. After completion of the reaction, 1 N aqueous HCl solution was added slowly and the DCM layer was separated. The aqueous layer was extracted with DCM (2×30 ml) and the combined organic layers were washed with 2 N aqueous NaOH solution, dried over anhydrous $Na_2SO_4$ and concentrated under reduced pressure to afford the title compound (1 g, 65%). LCMS: m/z=367.98 [M+1].

Scheme 7

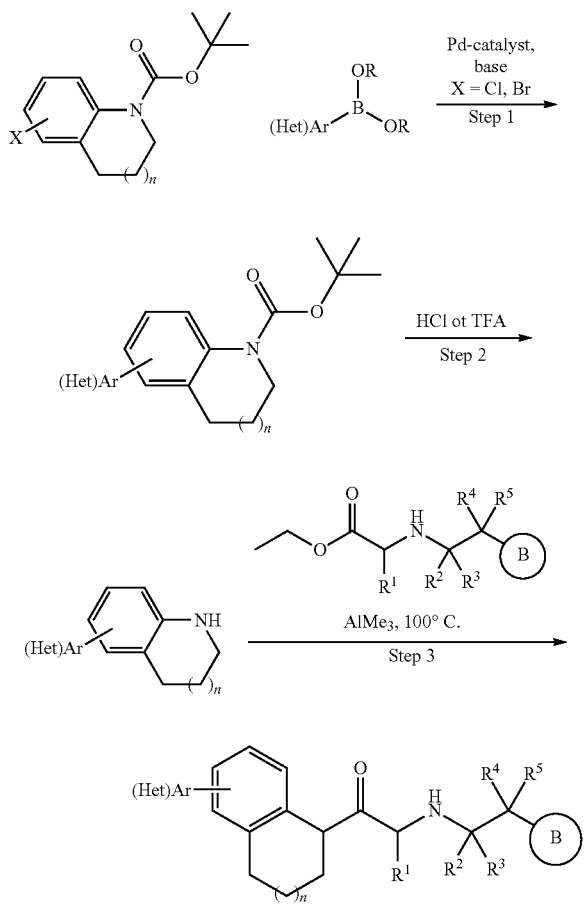

Method 1, Step 2. N-(4-Bromophenyl)-2-((4-chlorophenethyl)amino)-2-phenylacetamide A mixture of 2-bromo-N-(4-bromophenyl)-2-phenylacetamide (0.8 g, 2.17 mmol), 2-(4-chlorophenyl)ethan-1-amine (0.680 g, 4.35 mmol) and TEA (0.7 ml, 4.35 mmol) in DMF (15 ml) were heated for 2 hours at 60° C. After completion of the reaction, the reaction mixture was poured into ice cold water (10 ml) and extracted with ethyl acetate (2×30 ml). The combined organic layers were washed with brine (10 ml), dried over anhydrous $Na_2SO_4$ and concentrated under reduced pressure. The resulting residue was purified by silica gel chromatography to afford the title compound (0.7 g, 67%) as off-white solid. LCMS: m/z=443.5 [M+1] and 445.5 [M+2].

Method 2

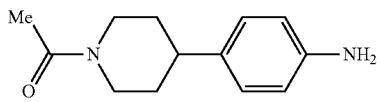

1-(4-(4-Aminophenyl)piperidin-1-yl)ethan-1-one

Scheme 7 illustrates a synthetic sequence used for conversion of a halogenated amine, such as a bromotetrahydroquinoline (n=1) or bromoindoline (n=0), into a subset of compounds of Formula I where $R^1$ is a substituted phenyl and B, $R^2$, $R^3$, $R^4$, and $R^5$ are as described herein.

Method 2, Step 1. 1-(4-(4-Aminophenyl)-3,6-dihydropyridin-1(2H)-yl)ethan-1-one

A mixture of 4-bromoaniline (0.3 g, 1.74 mmol), 1-(4-(4,4,5,5-tetramethyl-1,3,2-dioxaborolan-2-yl)-3,6-dihydropyridin-1(2H)-yl)ethan-1-one (0.525 g, 2.09 mmol) and cesium carbonate (1.70 g, 5.23 mmol) in 4:1 dioxane:water (15 ml) was purged for 20 minutes with argon. Then S-Phos Pd-precatalyst G3 (0.066 g, 0.087 mmol) was added and purging with argon was continue for another 10 minutes. The reaction mixture was heated at 90° C. overnight. After completion of reaction (monitored by TLC), the reaction mixture was treated with water (6 ml) and extracted with ethyl acetate (2×15 ml). The combined organic layers were washed with brine (10 ml), dried over anhydrous Na$_2$SO$_4$ and concentrated under reduced pressure. The resulting residue was purified by silica gel chromatography to afford the title compound as a solid (0.35 g, 92%). LCMS: m/z=217.32 [M+1].

Method 2, Step 2. 1-(4-(4-Aminophenyl)piperidin-1-yl)ethan-1-one 1-(4-(4-aminophenyl)-3,6-dihydropyridin-1(2H)-yl)ethan-1-one (350 mg, 1.62 mmol) was dissolved in 1:1 MeOH:ethyl acetate (3.5 ml) in an autoclave and 10% Pd/C (35 mg, 50% moisture) was added. The reaction was heated at 50° C. for 2 hours under 100 PSI of hydrogen gas pressure. After completion of reaction (monitored by TLC), the reaction mixture was filtered through a pad of celite and the filtrate was concentrated to afford the title compound (300 mg, 85%). LCMS: m/z=219.3 [M+1].

Method 3

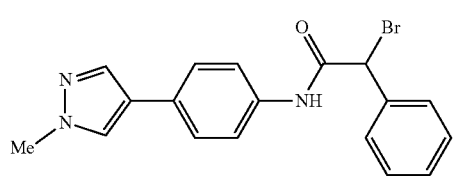

2-Bromo-N-(4-(1-methyl-1H-pyrazol-4-yl)phenyl)-2-phenylacetamide

Method 3, Step 1.
4-(1-Methyl-1H-pyrazol-4-yl)aniline

A mixture of 4-bromoaniline (1.0 g, 5.81 mmol), 1-methyl-4-(4,4,5,5-tetramethyl-1,3,2-dioxaborolan-2-yl)-1H-pyrazole (1.3 g, 6.39 mmol) and cesium carbonate (5.68 g, 17.43 mmol) in 4:1 dioxane:water (20 ml) was purged for 20 minutes with argon. S-Phos Pd-precatalyst G3 (0.213 g, 0.29 mmol) was added and purging was continued for another 10 minutes. The reaction mixture was heated at 100° C. for 2 hours. The reaction mixture was poured into water (15 ml) and extracted with ethyl acetate (2×20 ml). The combined organic layers were washed with brine (10 ml), dried over anhydrous Na$_2$SO$_4$ and concentrated under reduced pressure. The resulting residue was purified by silica gel chromatography to afford the title compound (0.965 g, 95%) as solid. $^1$H NMR (400 MHz, DMSO-d6): 3.81 (s, 3H), 5.01 (s, 2H, —NH$_2$), 6.54 (d, J=8.0 Hz, 2H), 7.20 (d, J=8.4 Hz, 2H), 7.63 (s, 1H), 7.86 (s, 1H). LCMS: m/z=174.2 [M+1].

Method 3, Step 2. 2-Bromo-N-(4-(1-methyl-1H-pyrazol-4-yl)phenyl)-2-phenylacetamide To a stirred solution of 4-(1-methyl-1H-pyrazol-4-yl)aniline (0.95 g, 5.48 mmol) and 2-bromo-2-phenylacetic acid (1.3 g, 6.03 mmol) in ethyl acetate (10 ml) was added T$_3$P (5.22 g, 8.22 mmol; 50% in ethyl acetate). The reaction mixture was stirred for 30 minutes at room temperature. After 30 minutes DIPEA (1.41 g, 10.96 mmol) was added and the reaction mixture was heated at 60° C. for 3 hours. The reaction mixture was poured into water (15 ml) and extracted with ethyl acetate (2×10 ml). The combined organic layers were washed with brine (10 ml), dried over anhydrous Na$_2$SO$_4$ and concentrated under reduced pressure. The resulting residue was purified by silica gel chromatography to afford the title compound (1.2 g, 59%) as a solid. $^1$H NMR (400 MHz, DMSO-d6): 3.85 (s, 3H), 5.79 (s, 1H), 7.38-7.44 (m, 3H), 7.52-7.59 (m, 4H), 7.65 (d, J=6.8 Hz, 2H), 7.82 (s, 1H), 8.09 (s, 1H), 10.54 (s, 1H, —NH). LCMS: m/z=370.1 [M+1] and 372.4 [M+2].

Method 4

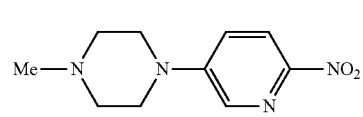

1-Methyl-4-(6-nitropyridin-3-yl)piperazine

Method 4, Step 1.
1-Methyl-4-(6-nitropyridin-3-yl)piperazine

To a stirred solution of 5-bromo-2-nitropyridine (0.5 g, 2.46 mmol) in DMSO (5 ml) was added 1-methylpiperazine (0.369 g, 3.69 mmol), K$_2$CO$_3$ (0.679 g, 4.92 mmol) and TBAB (0.079 g, 0.0246 mmol) at room temperature. The reaction mixture was stirred at 100° C. for 6 hours. After completion of the reaction (monitored by TLC), the reaction was quenched with 1N HCl (15 ml) and extracted with ethyl acetate (2×15 ml). The aqueous layer was treated with 1N NaOH solution and extracted with ethyl acetate (2×25 ml). The combined organic layers were dried over anhydrous Na$_2$SO$_4$ and concentrated under reduced pressure to afford title compound (0.5 g, 91%). $^1$H NMR (400 MHz, DMSO-d6): 2.39 (s, 3H), 2.61 (t, J=5.2 Hz, 4H), 3.50 (t, J=5.2 Hz, 4H), 7.22 (dd, J=8.8 Hz, 2.8 Hz, 1H), 8.15-8.20 (m, 2H).

Method 5

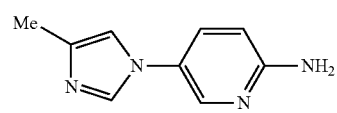

5-(4-Methyl-1H-imidazol-1-yl)pyridin-2-amine

Method 5, Step 1.
5-(4-Methyl-1H-imidazol-1-yl)pyridin-2-amine

To a stirred solution of 5-bromopyridin-2-amine (0.5 g, 2.89 mmol) in DMF (10 ml) was added 4-methyl-1H-imidazole (1.19 g, 14.45 mmol), Cs$_2$CO$_3$ (0.94 g, 2.89 mmol), CuI (0.276 g, 1.45 mmol) and 1-(5,6,7,8-Tetrahydroquinolin-8-yl)ethanone (0.11 g, 0.58 mmol) at room temperature. The reaction mixture was purged with argon gas for 30 minutes and it was heated at 135° C. overnight. After completion of the reaction, water (15 ml) was added and the mixture was extracted with ethyl acetate (2×25 ml). The combined organic layers were dried over anhydrous Na$_2$SO$_4$ and concentrated under reduced pressure. The resulting residue was purified by silica gel chromatography to afford the title compound (0.23 g, 46%). LCMS: m/z=175.3 [M+1].

Method 6

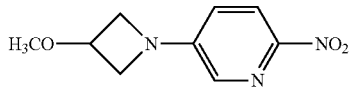

5-(3-Methoxyazetidin-1-yl)-2-nitropyridine

Method 6, Step 1.
5-(3-Methoxyazetidin-1-yl)-2-nitropyridine

To a stirred solution of 5-bromo-2-nitropyridine (0.55 g, 4.44 mmol) in 1,4-dioxane (2.5 ml) was added 3-methoxyazetidine (1.08 g, 5.33 mmol), Cs$_2$CO$_3$ (4.38 g, 13.49 mmol), Pd$_2$(dba)$_3$ (0.162 g, 0.17 mmol) and Xantphos (0.257 g, 0.44 mmol) at room temperature. The reaction mixture was purged with argon gas for 30 minutes and it was heated at 100° C. for 3 hours. After completion of the reaction, water was added (15 ml) and the aqueous layer was extracted with ethyl acetate (2×25 ml). The combined organic layers were dried over anhydrous Na$_2$SO$_4$ and concentrated under reduced pressure. The resulting residue was purified by silica gel chromatography to afford the title compound (0.77 g, 74%). LCMS: m/z=210.1 [M+1].

Method 7

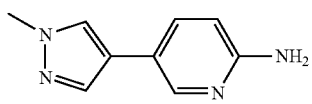

5-(1-Methyl-1H-pyrazol-4-yl)pyridin-2-amine

Method 7.
5-(1-Methyl-1H-pyrazol-4-yl)pyridin-2-amine

A mixture of 5-bromopyridin-2-amine (18.0 g, 104.04 mmol), 1-methyl-4-(4,4,5,5-tetramethyl-1,3,2-dioxaborolan-2-yl)-1H-pyrazole (32.47 g, 156.06 mmol) and cesium carbonate (101.75 g, 312.12 mmol) in dioxane:water (4:1, 360 ml) were purged for 20 minutes with argon gas. To this mixture, Pd(dppf)Cl$_2$ (7.61 g, 10.40 mmol) was added and purging was continued for another 10 minutes. The reaction mixture was heated at 80° C. for 1.5 hours. The reaction mixture was poured into water (200 ml) and extracted with ethyl acetate (2×200 ml). The combined organic layers were washed with brine (150 ml), dried over anhydrous Na$_2$SO$_4$ and concentrated under reduced pressure. The crude product was purified by column chromatography to afford the title compound (15 g, 82%) as a solid, $^1$H NMR (400 MHz, DMSO-d6): 3.83 (s, 3H), 5.86 (s, 2H, —NH$_2$), 6.44 (d, J=8.4 Hz, 1H), 7.20 (dd, J=8.4 Hz, 2.4 Hz, 1H), 7.70 (s, 1H), 7.95 (s, 1H), 8.14 (d, J=2.09 Hz, 1H). LCMS: m/z=175.1 [M+1].

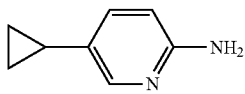

5-Cyclopropylpyridin-2-amine

Method 7. 5-Cyclopropylpyridin-2-amine 5-bromopyridin-2-amine (0.5 g, 2.89 mmol), cyclopropylboronic acid (0.49 g, 5.78 mmol) and K$_3$PO$_4$ (1.84 g, 8.67 mmol) were combined in a mixture of toluene:water (4:1, 10 ml) and the mixture was degassed for 20 minutes with argon gas. To the reaction mixture, palladium acetate (0.032 g, 0.144 mmol) and tricyclohexyl-phosphine (0.081 g, 0.289 mmol) were added and degassing was continued for another 10 minutes. The reaction mixture was heated in a sealed tube at 100° C. for 16 hours. The reaction mixture was diluted with water (15 ml) and extracted with ethyl acetate (2×15 ml). The combined organic layers were washed with brine (15 ml), dried over anhydrous Na$_2$SO$_4$ and concentrated under reduced pressure. The residue was purified by silica gel chromatography to afford the title compound (0.3 g, 77%) as a solid. $^1$H NMR (400 MHz, DMSO-d6): δ 0.49-0.56 (m, 2H), 0.75-0.83 (m, 2H), 1.70-1.77 (m, 1H), 5.65 (s, 2H, —NH2), 6.36 (d, J=8.4 Hz, 1H), 7.04 (dd, J=8.4 Hz, 2.0 Hz, 1H), 7.74 (d, J=1.6 Hz, 1H). LCMS: m/z=135.2 [M+1].

Method 8

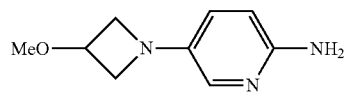

Method 8.
5-(3-Methoxyazetidin-1-yl)pyridin-2-amine

To a stirred solution of 5-((1-methylpiperidin-4-yl)oxy)-2-nitropyridine (1.0 g, 4.78 mmol) in a mixture of Methanol (10 ml) was added 10% Pd/C (0.10 g, 10% w/w, 50% moisture). Then reaction mixture was stirred at room temperature under H2 gas atmosphere for 3 hours. After completion of reaction (monitored by TLC), the reaction mixture was diluted with Ethyl acetate and filtered through celite pad. The celite pad was washed with Ethyl acetate (2×25 ml). The combined filtrate was concentrated under reduced pressure to afford the title compound (0.22 g, 44%) as a solid. LCMS: m/z=180.3 [M+1].

Method 9

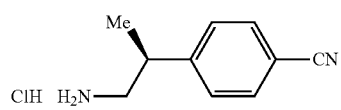

(S)-4-(1-Aminopropan-2-yl)benzonitrile hydrochloride

Method 9, Step 1. Ethyl (E,Z)-3-(4-cyanophenyl)but-2-enoate

To a stirred solution of potassium tert-butoxide (10.09 g, 89.7 mmol) in dry THF (90 ml) was added triethyl phosphonoacetate (20.08 g, 89.7 mmol) at 0° C. under an atmosphere of nitrogen. Then the reaction mixture was stirred for 15 minutes at the same temperature. The reaction was then warmed to room temperature and stirred for 1 hour. Then 4-acetylbenzonitrile (10.0 g, 69.0 mmol) was added as a solution in THF (50 ml) and the reaction was heated to 70° C. for 3 hours. After completion of reaction (monitored by TLC), the pH of the reaction mixture was adjusted to 3-4 with 1N HCl. The THF was removed under reduced pressure and the aqueous layer was extracted with ethyl acetate (2×50 ml). The combined organic layers were washed with brine (50 ml), dried over anhydrous $Na_2SO_4$ and concentrated under reduced pressure. The residue was purified by silica gel chromatography to afford the title compound (8.5 g, 58%). $^1$H NMR (400 MHz, DMSO-d6): 1.15 (t, J=6.8 Hz, 1.5H), 1.36 (t, J=6.8 Hz, 3H), 2.21 (s, 1.5H), 2.60 (s, 3H), 4.05 (q, J=7.1 Hz, 1H), 4.27 (q, J=7.2 Hz, 2H), 6.01 (S, 0.5H), 6.19 (S, 1H), 7.30-7.71 (m, 6H).

Method 9, Step 2. Ethyl 3-(4-cyanophenyl)butanoate

To a stirred solution of ethyl (E, Z) 3-(4-cyanophenyl) but-2-enoate (8.0 g, 37.2 mmol) in methanol:ethyl acetate (1:4, 140 ml) was added Pd/C (0.8 g, 10% w/w, 50% moisture). The reaction was stirred at room temperature under an atmosphere of hydrogen gas for 3 hours. The reaction mixture was diluted with ethyl acetate and filtered through a pad of celite. The combined organic layers were concentrated under reduced pressure to afford the title compound (4.5 g, 56%). $^1$H NMR (400 MHz, $CDCl_3$): 1.23 (t, J=7.2 Hz, 3H), 1.33 (d, J=6.8 Hz, 3H), 2.62 (dd, J=7.6 Hz, 1.2 Hz, 2H), 3.70 (q, J=7.2 Hz, 1H), 4.07-4.15 (m, 2H), 7.37 (d, J=8.0 Hz, 2H), 7.37 (d, J=8.4 Hz, 2H).

Method 9, Step 3. 3-(4-Cyanophenyl)butanoic acid

To a stirred solution of ethyl 3-(4-cyanophenyl)butanoate (4.5 g, 20.71 mmol) in a mixture of MeOH:THF:$H_2O$ (4:2:1, 100 ml) was added LiOH (3.48 g, 82.95 mmol) at 5° C. to 10° C. The resulting reaction mixture was stirred at room temperature for 1.5 hours. After completion of reaction (monitored by TLC), the reaction solvent was evaporated. The residue was dissolved in water (10 ml) and extracted with ethyl acetate (2×15 ml). The pH of the aqueous layer adjusted to 3-4 with concentrated HCl. The precipitate that formed was filtered off to afford title compound (3.8 g, 97%) as a white solid. $^1$H NMR (400 MHz, DMSO-$d_6$): 1.23 (d, J=6.8, 3H), 2.58 (d, J=7.6 Hz, 2H), 3.24 (q, J=7.2, 1H), 7.49 (d, J=8.4 Hz, 2H), 7.77 (d, J=8.4 Hz, 2H), 12.15 (s, 1H).

Method 9, Step 4. tert-Butyl (2-(4-cyanophenyl)propyl)carbamate

To a stirred solution of 3-(4-cyanophenyl)butanoic acid (5.0 g, 26.45 mmol) in tert-butanol (65 ml) was added triethylamine (11.0 ml, 79.36 mmol) at room temperature. Then the reaction mixture was cooled to 5-10° C. and was added DPPA (12.30 g, 44.97 mmol) drop wise. After formation of acylazide, the reaction was stirred at 90° C. overnight. The reaction mixture was diluted with water (40 ml) and extracted with ethyl acetate (2×40 ml). The combined organic layers were washed with brine (25 ml), dried over anhydrous $Na_2SO_4$ and concentrated under reduced pressure. The resulting residue was purified by silica gel chromatography to afford the title compound (4.5 g, 66%) as a solid. $^1$H NMR (400 MHz, DMSO-de): 1.17 (d, J=6.8 Hz, 2H), 1.33 (s, 9H), 2.90-3.00 (m, 1H), 3.04-3.15 (m, 2H), 6.91 (t, J=5.2 Hz, 1H, —NH), 7.42 (d, J=8.4 Hz, 2H), 7.77 (d, J=7.2 Hz, 2H).

Method 9, Step 5. 4-(1-Aminopropan-2-yl)benzonitrile hydrochloride

To a stirred solution of tert-butyl-(2-(4-cyanophenyl)propyl)carbamate (4.5 g, 17.29 mmol) in methanol (9 ml) was added a solution of 4M HCl in dioxane (10.8 ml, 2.4 vol.) drop wise at 0° C. The resulting mixture was stirred at room temperature for 2 hours. The reaction mixture was concentrated under reduced pressure to afford the title compound (2.81 g, 83%) as a solid. $^1$H NMR (400 MHz, DMSO-$d_6$): 1.28 (d, J=6.8 Hz, 2H), 3.03 (d, J=5.6 Hz, 2H), 3.15-3.26 (m, 1H), 7.55 (d, J=8.0 Hz, 2H), 7.83 (d, J=8.0 Hz, 2H), 8.21 (s, 3H). LCMS: m/z=161.6 [M+1].

Method 9, Step 6. 4-(1-Aminopropan-2-yl)benzonitrile 4-(1-aminopropan-2-yl)benzonitrile hydrochloride was treated with an aqueous solution of saturated sodium bicarbonate and extracted with ethyl acetate (3×30 ml) to obtained the crude compound as liquid which was further purified by silica gel chromatography (DCM:MeOH=90:10) to afford the racemic title compound a thick oil (2.29 g, 83%). $^1$H NMR (400 MHz, $CDCl_3$): 1.28 (d, J=6.8 Hz, 3H), 2.85 (d, J=5.6 Hz, 3H), 7.34 (d, J=7.2 Hz, 2H), 7.63 (d, J=7.2 Hz, 2H). LCMS: m/z=161.5 [M+1]. The racemic amine may be resolved in the enantiopure title compound by preparative chiral SFC using a CHIRALPAK AD-H column (250 mm, 50 mm, 5 microns; mobile phase 25% Acetonitrile:Methanol:Dimethylamine (80:20:0.1) in 75% $CO_2$). The early eluting isomer has been unambiguously assigned as (S)-4-(1-aminopropan-2-yl)benzonitrile by obtaining an x-ray co-crystal structures of a truncated form of p300 with both example 22 (isomer 1; (S)-2-((4-cyanophenethyl)amino)-N-(5-(1-methyl-1H-pyrazol-4-yl)pyridin-2-yl)-2-phenylacetamide) and example 33 (isomer 4; (R,S)-2-((2-(4-cyanophenyl)-propyl)amino)-N-(5-(1-methyl-1H-pyrazol-4-yl)pyridin-2-yl)-2-phenylacetamide).

Method 10

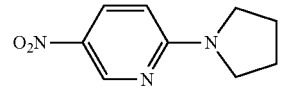

5-Nitro-2-(pyrrolidin-1-yl)pyridine

Method 10. 5-Nitro-2-(pyrrolidin-1-yl)pyridine

To a stirred solution of 2-bromo-5-nitro pyridine (0.5 g, 2.46 mmol) in DMSO (2 ml) was added pyrrolidine (0.262 g, 3.69 mmol) at room temperature. The reaction mixture was heated to 120° C. for 1 hour in the microwave. After completion of the reaction, ice cold water was added (15 ml) and the resulting precipitate was filtered through Buchner funnel to obtain the crude compound. The resulting crude compound was purified by trituration using n-hexanes (10 ml) to afford the title compound (0.370 g, 77%). LCMS: m/z=194.01 [M+1].

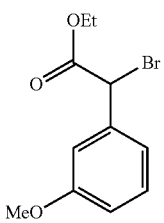

Ethyl 2-bromo-2-(3-methoxyphenyl)acetate

Method 11, Step 1. Ethyl 2-(3-methoxyphenyl)acetate

To a stirred solution of 3-methoxy-2-phenylacetic acid (5 g, 30 mmol) in absolute ethanol (50 ml), sulfuric acid (0.3 ml) was added at 0° C. and reaction mixture was refluxed at 70° C. for 2 hours. Reaction progress was monitored by TLC. After completion of the reaction, ethanol was removed by evaporation under reduced pressure. Then reaction mixture was neutralized with saturated solution of sodium bicarbonate and extracted with DCM (2×15 ml), dried over anhydrous $Na_2SO_4$ and concentrated under reduced pressure to afford the title compound (3.82 g, 81%) as colorless liquid. LCMS: m/z=195.26 [M+1].

Method 11, Step 2. Ethyl 2-bromo-2-(3-methoxyphenyl)acetate

A mixture of ethyl 2-(3-methoxyphenyl)acetate (0.5 g, 2.5 mmol), N-bromosuccinamide (0.50 g, 2.80 mmol) and 2,2'-azobis(2-methylpropionitrile) (0.02, 0.12 mmol) in $CCl_4$ (10 ml) was refluxed for 2 hours. After completion of the reaction (monitored by TLC), the reaction mixture was diluted with n-hexanes and filtered through a pad of celite. The filtrate was dried over anhydrous $Na_2SO_4$ and concentrated under reduced pressure. The resulting compound was purified by silica gel chromatography to afford the title compound (0.8 g, 99%) as a yellowish liquid. LCMS: m/z=273.2 [M+1].

Method 12

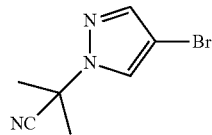

2-(4-Bromo-1H-pyrazol-1-yl)-2-methylpropanenitrile

Method 12, Step 1. Methyl 2-(4-bromo-1H-pyrazol-1-yl)-2-methylpropanoate

To a stirred solution of 4-bromo-1H-pyrazole (3.0 g, 20.41 mmol) in dry DMF (30 ml) was added $Cs_2CO_3$ (19.95 g, 61.23 mmol) and methyl 2-bromo-2-methylpropanoate (3.96 ml, 30.61 mmol) at room temperature under an atmosphere of nitrogen. Then the reaction mixture was stirred at 80° C. for 18 hours. After completion of reaction (monitored by TLC), the reaction mixture was diluted with ice cold water (30 ml) and extracted with ethyl acetate (2×50 ml). The combined organic layers were washed with brine (50 ml), dried over anhydrous $Na_2SO_4$ and concentrated under reduced pressure. The resulting residue was purified by silica gel chromatography to afford the title compound (3.0 g, 60%). $^1$H NMR (400 MHz, DMSO-de): 1.76 (s, 6H), 4.63 (s, 3H), 7.61 (s, 1H), 8.21 (s, 1H).

Method 12, Step 2. 2-(4-Bromo-1H-pyrazol-1-yl)-2-methylpropanamide

An oven dried autoclave was charged with methyl 2-(4-bromo-1H-pyrazol-1-yl)-2-methylpropanoate (1.0 g, 4.05 mmol) and $CaCl_2$ (0.5 g, 4.46 mmol) in methanol (10 ml). The reaction mixture was cooled −78° C. and $NH_3$ gas was purged in to it. Then the reaction was stirred for 20 hours at room temperature. After completion of reaction (monitored by TLC), the reaction mixture was diluted with water and extracted with ethyl acetate (2×30 ml). The combined organic layers were concentrated under reduced pressure and purified by silica gel chromatography to afford the title compound (0.55 g, 59%). $^1$H NMR (400 MHz, DMSO-de): 1.70 (s, 6H), 6.96 (s, NH, 1H), 7.22 (s, NH, 1H), 7.60 (s, 1H), 8.09 (s, 1H).

Method 12, Step 3. 2-(4-Bromo-1H-pyrazol-1-yl)-2-methylpropanenitrile

A solution of 2-(4-bromo-1H-pyrazol-1-yl)-2-methylpropanamide (0.5 g, 2.16 mmol) in $POCl_3$ (5 ml) was heated to 90° C. for 1.5 hours. After completion of reaction (confirmed by the TLC), reaction was quenched with saturated aqueous $NaHCO_3$ solution. The resulting mixture was extracted with ethyl acetate (2×20 ml). The combined organic layers were washed with water (2×20 ml), washed with brine (20 ml), dried over anhydrous $Na_2SO_4$ and concentrated under reduced pressure to afford the title compound (0.35 g, 75%) as a solid. $^1$H NMR (400 MHz, DMSO-$d_6$): 1.98 (s, 6H), 7.78 (s, 1H), 8.34 (s, 1H).

Method 13

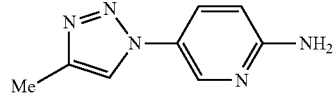

5-(4-Methyl-1H-1, 2, 3-triazol-1-yl)pyridin2-amine

Method 13. 5-(4-Methyl-1H-1, 2, 3-triazol-1-yl)pyridin2-amine

5-Iodo-2-aminopyridine (0.5 g, 2.28 mmol), $NaN_3$ (0.22 g, 3.41 mmol), $K_2CO_3$ (0.38 g, 2.76 mmol), $CuSO_4 \cdot 5H_2O$ (0.06 g, 0.23 mmol), sodium ascorbate (0.09 g, 0.46 mmol), L-Pro line (0.06 g, 0.46 mmol) and 2-butynoic acid (0.28 g, 3.41 mmol) were combined in DMSO (6 ml) at room temperature. Then reaction mixture was heated at 65° C. for 6 hours. After completion of the reaction (monitored by TLC), the reaction was diluted with water (20 ml) and extracted with ethyl acetate (4×25 ml). The combined organic layers were dried over anhydrous $Na_2SO_4$ and concentrated under reduced pressure to give a residue that was was purified by silica gel chromatography to afford the title compound (0.25 g, 71%). LCMS: m/z=176.1 [M+1].

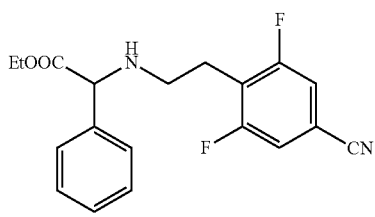

Ethyl 2-((4-cyano-2,6-difluorophenEthyl)amino)-2-phenylacetate

Method 14, Step 1.
(E)-3,5-Difluoro-4-(2-methoxyvinyl)benzonitrile

To a stirred solution of methoxymethyltriphenylphosphonium chloride (1.47 g, 4.31 mmol) in THF (6 ml), potassium carbonate (0.594 g, 4.31 mmol) was added at 0 deg and stirred for 30 minutes at room temperature. To this 3,5-difluoro-4-formylbenzonitrile (0.6 g, 3.59 mmol) was added at room temperature and heated to reflux at 60 deg for 16 hours. The reaction mixture was quenched with water (30 ml) and extracted with ethyl acetate (2×30 ml). The organic layer was dried over sodium sulphate and concentrated under reduced pressure. The crude product was purified by silica gel chromatography to afford the title compound (0.24 g, 34%). $^1$H NMR (400 MHz, DMSO-$d_6$): δ 7.72-7.72 (m, 2H), 6.65 (d, J=6.4 Hz, 1H), 5.20 (d, J=6.4 Hz, 1H), 3.74 (s, 3H).

Method 14, Step 2.
3,5-Difluoro-4-(2-oxoethyl)benzonitrile (E)-3,5-difluoro-4-(2-methoxyvinyl)benzonitrile (0.120 g, 0.614 mmol) was dissolved in THF (3 ml) and 6N HCl (0.6 ml) was added into it. The reaction mixture was heated at 60 □ for 2 hours. The reaction mixture was neutralized with saturated sodium bicarbonate solution (10 ml) and extracted with ethyl acetate (2×20 ml). The organic layer was dried over sodium sulphate and concentrated under reduced pressure to afford the crude title compound which was used in next step without further purification (0.120 g). $^1$H NMR (400 MHz, DMSO-$d_6$): δ 9.71 (s, 1H), 7.84-7.86 (m, 2H), 4.10 (s, 2H).

Method 14, Step 3. Ethyl 2-((4-cyano-2,6-difluorophenethyl)amino)-2-phenylacetate To a solution of 3,5-difluoro-4-(2-oxoethyl)benzonitrile (0.120 g, 0.66 mmol) and ethyl 2-amino-2-phenylacetate (0.171 g, 0.79 mmol) in a mixture of 1:1 methanol:DCE (4 ml), acetic acid (4 drops) was added followed by powdered molecular sieves (0.1 g). The reaction mixture was stirred at room temperature for 1 hour. To this sodium cyanoborohydride (0.061 g, 0.99 mmol) was added and the reaction mixture was stirred at room temperature for 16 hours. The reaction mixture was quenched with sodium bicarbonate solution (5 ml) and extracted with ethyl acetate (3×10 ml). The organic layer was dried over sodium sulphate and concentrated under reduced pressure. The residue was purified by silica gel chromatography to afford the title compound (0.1 g, 44%). LCMS: m/z=345.5 [M+1].

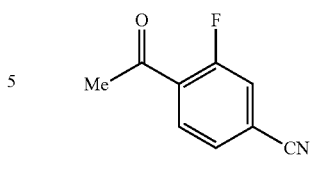

4-Acetyl-3-fluorobenzonitrile

Method 15, Step 1.
4-Cyano-2-fluoro-N-methoxy-N-methylbenzamide

To a stirred solution of 4-cyano-2-fluorobenzoic acid (15 g, 90.84 mmol) in DMF (100 ml), HATU (51.81 g, 136.36 mmol) and DIPEA (58.70 g, 454.21 mmol) were added and the reaction mixture was stirred at room temperature for 1 hour. To this N, O-dimethyl hydroxylamine hydrochloride (26.60 g, 272.7 mmol) was added at 0 deg and the reaction mixture was stirred at room temperature for 5 hours. The reaction mixture was diluted with cold water (200 ml) and extracted with ethyl acetate (2×250 ml). The combined organic layers were washed with brine (100 ml), dried over anhydrous sodium sulfate, and concentrated under reduced pressure. The residue was purified by silica gel chromatography to afford the title compound (12.5 g, 66%). LCMS: m/z=209.1 [M+1].

Method 15, Step 2. 4-Acetyl-3-fluorobenzonitrile

To a stirred solution of 4-cyano-2-fluoro-N-methoxy-N-methylbenzamide (15 g, 72.11 mmol) in THF (150 ml), methylmagnesium bromide (154.53 ml, 1.4M in 3:1 THF:Toluene, 216.34 mmol) was added drop wise at 0 deg and stirred for 30 minutes. The reaction mixture was quenched with ice cold water (150 ml) and extracted with ethyl acetate (2×250 ml). The combined organic layers were washed with brine (100 ml), dried over anhydrous sodium sulfate and concentrated under reduced pressure. The residue was purified by silica gel chromatography to afford the title compound (8.1 g, 69%). $^1$H NMR (400 MHz, DMSO-$d_6$): δ 8.05-8.07 (m, 1H), 7.94-7.96 (m, 1H), 7.82-7.84 (m, 1H), 2.62 (s, 3H).

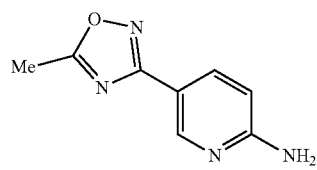

5-(5-Methyl-1,2,4-oxadiazol-5-yl)pyridin-2-amine

Method 16, Step 1.
N-(5-Cyanopyridin-2-yl)-4-methylbenzenesulfonamide

To a stirred solution of 6-aminonicotinonitrile (1 g, 8.39 mmol) in dry pyridine (30 ml) was added para-tosylchloride (3.2 g, 16.7 mmol) at 0° C. The reaction mixture was stirred at room temperature for 30 minutes. After 30 minutes, the reaction mixture was heated to 90° C. overnight. The solvent was removed and the residue was treated with water (25 ml).

The obtained precipitates were collected by filtration and washed with water (25 ml) to afford the pure title compound (1.1 g, 50%). $^1$H NMR (400 MHz, DMSO-d6): δ 2.36 (s, 3H), 7.11 (d, J=8.8 Hz, 1H), 7.39 (d, J=8 Hz, 2H), 7.78-7.88 (m, 2H), 8.10 (dd, J=8.8 Hz, J=6.8 Hz, 1H), 8.62 (s, 1H), 11.89 (s, 1H). LCMS: m/z=274.26 [M+1].

Method 16, Step 2. (Z)—N'-hydroxy-6-((4-methylphenyl)sulfonamido)-nicotinimidamide A mixture of hydroxylamine hydrochloride (0.106 g, 1.53 mmol) and potassium carbonate (0.11 g, 0.80 mmol) in water (2 ml) was added to a solution of N-(5-cyanopyridin-2-yl)-4-methylbenzenesulfonamide (0.2 g, 0.732 mmol) in ethanol (8 ml). The reaction mixture was heated to reflux overnight. The reaction mixture was concentrated and the residue was treated with water (10 ml). The precipitated solid was collected by filtration and washed with water to obtain pure title compound (0.14 g, 62%). LCMS: m/z=307.61 [M+1].

Method 16, Step 3. 4-Methyl-N-(5-(5-methyl-1,2,4-oxadiazol-3-yl)pyridin-2-yl)benzene-sulfonamide To a stirred solution of (Z)—N'-hydroxy-6-((4-methylphenyl)sulfonamido)-nicotinimidamide (0.72 g, 2.35 mmol) in DMSO (15 ml) was added ethyl acetate (0.35 ml, 3.52 mmol) and the reaction mixture was stirred for 15 minutes. To this, NaOH (0.141 g, 3.52 mmol) powder was added in one portion. After completion of reaction, the reaction was quenched with ice cold water (20 ml) and the aqueous layer was extracted with ethyl acetate (2×50 ml). The combined organic layers were washed with brine (25 ml), dried over anhydrous sodium sulfate and concentrated under reduced pressure to afford the title compound (0.25 g, 33%). $^1$H NMR (400 MHz, DMSO-d6): δ 2.36 (s, 3H), 2.65 (s, 3H), 7.24 (d, J=8.8 Hz, 1H), 7.39 (d, J=8 Hz, 2H), 7.85 (d, J=8 Hz, 2H), 8.21 (dd, J=8.8 Hz, J=6.4 Hz, 1H), 8.67 (s, 1H), 11.74 (s, 1H). LCMS: m/z=331.66 [M+1].

Method 16, Step 4. 5-(5-Methyl-1,2,4-oxadiazol-3-yl)pyridin-2-amine 4-methyl-N-(5-(5-methyl-1,2,4-oxadiazol-3-yl)pyridin-2-yl)benzenesulfonamide (0.25 g, 0.75 mmol) was taken in vial and conc. H$_2$SO$_4$ (2.5 ml) was added at 0° C. After completion of reaction, the reaction was poured into a cooled solution of 50% NaOH (aq.). The obtained precipitate was filtered and washed with cooled water (20 ml). The solid was dried over high vacuum to afford the title compound (0.12 g, 90%). $^1$H NMR (400 MHz, DMSO-d6): δ 2.60 (s, 3H), 6.53 (d, J=8.8 Hz, 1H), 6.62 (s, 2H), 7.86 (dd, J=8.4 Hz, 6.4 Hz, 1H), 8.50 (d, J=2 Hz, 1H). LCMS: m/z=177.51 [M+1].

Method 17

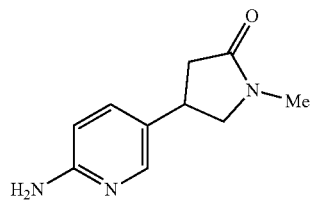

4-(6-Fluoropyridin-3-yl)-1-methylpyrrolidin-2-one

Method 17, Step 1. tert-Butyl 4-hydroxy-2-oxo-2,5-dihydro-1?7-pyrrole-1-carboxylate To a stirred solution of (tert-butoxycarbonyl)glycine (0.5 g, 2.85 mmol) in DCM was added 2,2-dimethyl-1,3-dioxane-4,6-dione (0.62 g, 4.28 mmol) and DMAP (0.52 g, 4.28 mmol) at room temperature. The reaction mixture was stirred for 15 minutes and EDC HCl (0.82 g, 4.28 mmol) was added at 0° C. The reaction mixture was further stirred at room temperature for 5 hours. After completion of reaction, the reaction mixture was diluted with ethyl acetate (100 ml) and the organic layer was washed with brine (50 ml), 20% aqueous citric acid solution (50 ml), and brine (50 ml). The organic layer was dried over sodium sulphate and evaporated to obtain the crude product. The obtained crude product was refluxed in ethyl acetate (50 ml) for 1 hour. After 1 hour, reaction mixture was concentrated to get pure desired compound (0.5 g, 88%). $^1$H NMR (400 MHz, DMSO-d6): δ 1.45-1.47 (m, 9H), 4.16 (s, 2H), 4.89 (s, 1H), 12.17 (s, 1H). LCMS: m/z=144.25 [M−56].

Method 17, Step 2. tert-Butyl 2-oxo-4-(tosyloxy)-2,5-dihydro-1H-pyrrole-1-carboxylate To a stirred solution of tert-butyl 4-hydroxy-2-oxo-2,5-dihydro-1?7-pyrrole-1-carboxylate (0.5 g, 2.51 mmol) in DCM (25 ml) was added DIPEA (0.86 ml, 5.02 mmol) at room temperature. The reaction mixture was stirred for 15 minutes and cooled to 0° C. Then para-tosylchloride (0.47 g, 2.51 mmol) was added portion wise to the reaction mixture and the mixture was stirred at room temperature overnight. After completion of the reaction, the reaction mixture was diluted with saturated sodium bicarbonate (50 ml) and the product was extracted with ethyl acetate (2×50 ml). The combined organic layers were washed with brine (50 ml), dried over anhydrous sodium sulfate and concentrated under reduced pressure. The residue was purified by silica gel chromatography to afford the title compound (0.42 g, 48%). $^1$H NMR (400 MHz, DMSO-d6): δ 1.44 (s, 9H), 2.46 (s, 3H), 4.36 (s, 2H), 5.80 (s, 1H), 7.56-7.58 (m, 2H), 8.01-8.03 (m, 2H). LCMS: m/z=298.36 [M−56].

Method 17, Step 3. tert-Butyl 4-(6-fluoropyridin-3-yl)-2-oxo-2,5-dihydro-1H-pyrrole-1-carboxylate To a mixture of tert-butyl 2-oxo-4-(tosyloxy)-2,5-dihydro-1H-pyrrole-1-carboxylate (1.0 g, 2.83 mmol) and (6-fluoropyridin-3-yl)boronic acid (0.598 g, 4.24 mmol) in 1,2-dimethoxyethane (30 ml) was added Pd(dppf)Cl$_2$-DCM complex (0.41 g, 0.56 mmol) at room temperature. To the reaction mixture 2M Sodium carbonate solution (10 ml) was added and the reaction mixture was purged with argon gas for 30 minutes. The reaction mixture was heated to 90° C. and stirred for 3 hours. The reaction mixture was diluted with water (50 ml) and extracted with ethyl acetate (2×50 ml). The combined organic layers were washed with brine (50 ml), dried over anhydrous sodium sulfate, and concentrated under reduced pressure. The residue was purified by column chromatography to afford the title compound (0.36 g, 57%). $^1$H NMR (400 MHz, DMSO-d6): δ 1.52 (s, 9H), 4.84 (s, 2H), 6.82 (s, 1H), 7.37 (dd, J=8.4 Hz, 6.0 Hz, 1H), 8.37-8.42 (m, 1H), 8.67 (s, 1H). LCMS: m/z=223.07 [M−56].

Method 17, Step 4. 4-(6-Fluoropyridin-3-yl)-1,5-dihydro-2H-pyrrol-2-one

To a stirred solution of tert-butyl 4-(6-fluoropyridin-3-yl)-2-oxo-2,5-dihydro-177-pyrrole-1-carboxylate (1.5 g, 5.39 mmol) in DCM (25 ml) was added TFA (5 ml) drop wise at room temperature. The reaction mixture was further stirred at room temperature for 3 hours. The mixture was concentrated and the residue was co-distilled with toluene twice to afford the title compound, which was directly used in the next step without further purification. LCMS: m/z=179.16 [M+1].

Method 17, Step 5. 4-(6-Fluoropyridin-3-yl)pyrrolidin-2-one

To a stirred solution of 4-(6-fluoropyridin-3-yl)-1,5-dihydro-2H-pyrrol-2-one (0.25 g, 1.40 mmol) in methanol (2.5 ml) was added 10% Pd/C (0.25 g, 50% moisture). Then the reaction was stirred at room temperature under an atmosphere of hydrogen gas for 3 hours. The reaction mixture was diluted with methanol and filtered through a pad of celite. The eluent was concentrated under reduced pressure to afford the title compound (0.16 g, 44%). $^1$H NMR (400 MHz, DMSO-d6): 2.33-2.40 (m, 1H), 3.18-3.27 (m, 2H), 3.60-3.74 (m, 2H), 7.17 (dd, J=8.4 Hz, J=6.0 Hz, 1H), 7.78 (s, 1H), 7.98-8.02 (m, 1H), 8.19 (s, 1H). LCMS: m/z=181.16 [M+1].

Method 17, Step 6. 4-(6-Fluoropyridin-3-yl)-1-methylpyrrolidin-2-one

To a stirred solution of 4-(6-fluoropyridin-3-yl)pyrrolidin-2-one (0.16 g, 0.88 mmol) in DMF (3 ml) was added 60% NaH (0.053 g, 1.32 mmol) at 0° C. The reaction mixture was stirred at same temperature for 30 minutes and iodomethane (0.25 g, 1.77 mmol) was added. The reaction mixture was stirred at room temperature for another 2 hours. The reaction was quenched with cold water (30 ml) and extracted with ethyl acetate (2×50 ml). The combined organic layers were washed with brine (30 ml), dried over sodium sulphate, and concentrated. The residue was purified by silica gel chromatography to afford the title compound (0.12 g, 70%). $^1$H NMR (400 MHz, DMSO-d6): δ 2.38-2.44 (m, 1H), 2.63-2.70 (m, 1H), 2.78 (s, 3H), 3.33-3.37 (m, 1H), 3.61-3.74 (m, 2H), 7.17-7.19 (m, 1H), 7.96-8.01 (m, 1H), 8.19 (s, 1H). LCMS: m/z=195.56 [M$^+$+1].

Method 17, Step 7. 4-(6-Aminopyridin-3-yl)-1-methylpyrrolidin-2-one

A solution of 4-(6-fluoropyridin-3-yl)-1-methylpyrrolidin-2-one (0.30 g, 1.54 mmol) in ammonium hydroxide solution (3 ml) was stirred at 140° C. for 48 hours. The reaction mixture was concentrated under reduced pressure and the residue was purified by reverse phase HPLC to afford the title compound (0.10 g, 34%). $^1$H NMR (400 MHz, DMSO-d6): δ 2.23-2.29 (m, 1H), 2.54-2.56 (m, 1H), 2.74 (s, 3H), 3.19-3.24 (m, 1H), 3.36-3.41 (m, 1H), 3.58-3.62 (m, 1H), 5.79 (s, 2H, —NH$_2$), 6.40 (d, J=8.4 Hz, 1H), 7.33 (dd, J=8.8 Hz, J=2.4 Hz, 1H), 7.79 (d, J=2.4 Hz, 1H). LCMS: m/z=192.20 [M+1].

Method 18

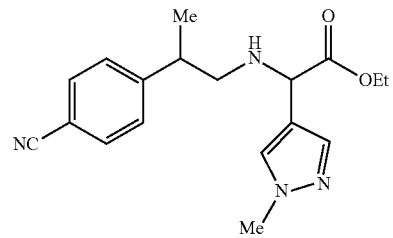

Ethyl 2-((2-(4-cyanophenyl)propyl)amino)-2-(1-methyl-1H-pyrazol-4-yl)acetate

Method 18, Step 1. 2-((2-(4-Cyanophenyl)propyl)amino)-2-(1-methyl-1H-pyrazol-4-yl)acetic acid To a stirred solution of 4-(1-aminopropan-2-yl)benzonitrile hydrochloride (5 g, 30.86 mmol) in DCM (75 ml) were added TEA (3.12 g, 30.86 mmol), 2-oxoacetic acid (2.28 g, 30.86 mmol) and (1-methyl-1H-pyrazol-4-yl)boronic acid (3.80 g, 30.86 mmol) at room temperature. The reaction mixture was stirred at the same temperature for 15 minutes. After that HFIP (13.48 g, 80.24 mmol) was added and the reaction mixture was stirred for 16 hours at room temperature. The reaction was concentrated and the residue was stirred with DCM:pentane (3:7; 150 ml) for 30 minutes. A solid precipitated which was filtered on Buchner funnel and washed with n-pentane to afford title compound (5.5 g, 59%). LCMS: m/z=299 [M+1].

Method 18, Step 2. Ethyl 2-((2-(4-cyanophenyl)propyl)amino)-2-(1-methyl-1H-pyrazol-4-yl)acetate A mixture of 2-((2-(4-cyanophenyl)propyl)amino)-2-(1-methyl-1H-pyrazol-4-yl)acetic acid (5 g, 16.77 mmol) in DMF (100 ml) was heated at 80° C. until the reaction mixture became a clear solution. K$_2$CO$_3$ (5.79 g, 41.94 mmol) and ethyl iodide (2.61 g, 16.77 mmol) were added at the same temperature and the mixture was stirred for 30 minutes. The reaction mixture was then stirred at room temperature for 16 hours. The reaction was quenched with ice cold water (200 ml) and extracted with ethyl acetate (2×75 ml). The combined organic layers were washed with brine (100 ml), dried over anhydrous sodium sulfate, and concentrated under reduced pressure. The residue was purified by silica gel chromatography to afford the title compound (2.5 g, 45%) as a thick liquid. LCMS: m/z=327.7 [M+1].

Method 19

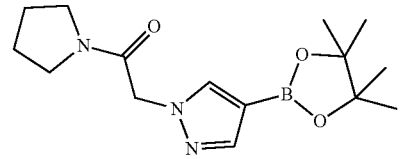

1-(Pyrrolidin-1-yl)-2-(4-(4,4,5,5-tetramethyl-1,3,2-dioxaborolan-2-yl)-1H-pyrazol-1-yl)ethan-1-one

Method 19, Step 1. 2-Chloro-1-(pyrrolidin-1-yl)ethan-1-one

Chloroacetyl chloride (3.4 ml, 42.18 mmol) was added dropwise to a stirred solution of pyrrolidine (2 g, 28.12 mmol) and triethylamine (11.7 ml, 84.36 mmol) in DCM (20 ml) cooled to 0° C. The reaction mixture was stirred at room temperature for 2 hours. The reaction mixture was poured into cold 1N HCl solution (20 ml) and extracted with DCM (2×30 ml). The combined organic layers were washed with brine (20 ml), dried over anhydrous sodium sulfate and concentrated under reduced pressure. The residue was purified by silica gel chromatography to afford the title compound (1.1 g, 26%). $^1$H NMR (400 MHz, DMSO-d6): δ 4.30 (s, 2H), 3.44-3.47 (m, 2H), 3.30-3.35 (m, 2H), 1.86-1.93 (m, 2H), 1.77-1.82 (m, 2H). LCMS: m/z=148.05 [M+1].

Method 19, Step 2. 1-(Pyrrolidin-1-yl)-2-(4-(4,4,5,5-tetramethyl-1,3,2-dioxaborolan-2-yl)-1H-pyrazol-1-yl)ethan-1-one To a stirred solution of 4-(4,4,5,5-tetramethyl-1,3,2-dioxaborolan-2-yl)-1?7-pyrazole (0.943 g, 4.86 mmol) in dry DMF (10 ml) was added NaH (0.213 g, 60%, 5.34 mmol) at 0° C. The reaction mixture was stirred at room temperature for 15 minutes. To this 2-chloro-1-(pyrrolidin-1-yl)ethan-1-one (1.0 g, 7.29 mmol) was added at 0° C. and stirred for 30 minutes at same temperature. The reaction mixture was then stirred at room temperature for another 1 hour. The reaction mixture was poured into ice cold water (20 ml) and extracted with DCM (2×30 ml). The combined organic layers were washed with brine (20 ml), dried over anhydrous sodium sulfate and concentrated under reduced pressure. The crude product was purified by silica gel chromatography to afford the title compound (0.81 g, 58%). LCMS: m/z=306.28 [M+1].

Method 20

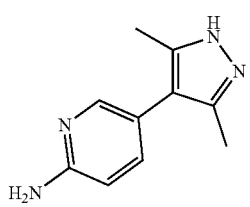

5-(3,5-Dimethyl-1H-pyrazol-4-yl)pyridin-2-amine

Method 24, Step 1.
5-(3,5-Dimethyl-1H-pyrazol-4-yl)pyridin-2-amine

A stirred solution of tert-butyl 4-(6-aminopyridin-3-yl)-3,5-dimethyl-1H-pyrazole-1-carboxylate (0.3 g, 1.04 mmol) in DCM (3 ml) was cooled to 0° C. and HCl (2.2 ml, 8.79 mmol; 4M in 1,4-dioxane) was added drop wise. The reaction mixture was allowed to warm to room temperature and was stirred for 3.5 hours. The reaction mixture was concentrated under reduced pressure to obtain the crude product. The crude product was triturated using n-pentane (3×5 ml) and the solid was filtered off to afford the title compound (175 mg, 75%). LCMS: m/z=189.21 [M+1].

Method 21

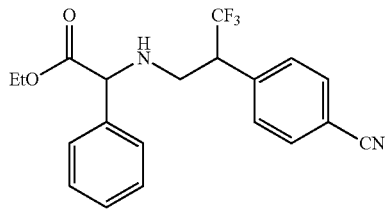

Ethyl 2-((2-(4-cyanophenyl)-3,3,3-trifluoropropyl)amino)-2-phenylacetate

Method 21, Step 1.
4-(2,2,2-Trifluoroacetyl)benzonitrile

To a stirred solution of methyl 4-cyanobenzoate (1.5 g, 9.31 mmol) in dry THF (30 ml) was added trifluoromethyltrimethylsilane (1.98 g, 13.97 mmol) and cesium fluoride (0.14 g, 0.93 mmol) at room temperature and the reaction mixture was stirred for one hour. The pH of the reaction mixture was adjusted to 5-6 with 1N HCl and the aqueous layer was extracted with ethyl acetate (2×50 ml). The combined organic layers were washed with brine (50 ml), dried over anhydrous sodium sulfate and concentrated under reduced pressure. To the resulting residue, TBAF (9.31 ml, 1M in THF, 9.31 mmol) and water (10 ml) was added at room temperature. The reaction mixture was stirred for one hour. Water (50 ml) was added and it the mixture was extracted with ethyl acetate (2×50 ml). The combined organic layers were washed with brine (50 ml), dried over anhydrous sodium sulfate and concentrated under reduced pressure. The residue was purified by silica gel chromatography to afford the title compound (1 g, 51%). $^1$H NMR (400 MHz, DMSO-d6): δ 7.77 (d, J=8.4 Hz, 2H), 7.90 (d, J=8.0 Hz, 2H).

Method 21, Step 2. Ethyl (Z)-3-(4-cyanophenyl)-4,4,4-trifluorobut-2-enoate

To a stirred solution of potassium tert-butoxide (0.12 g, 1.1 mmol) in dry THF (4 ml) was added triethyl phosphonoacetate (0.27 g, 1.1 mmol) at −5 to 0° C. under an atmosphere of nitrogen. Then reaction mixture was stirred for 15 minutes at the same temperature. Then the reaction was warmed to room temperature and stirred for an additional hour. 4-(2,2,2-trifluoroacetyl)benzonitrile (0.2 g, 0.92 mmol) in THF (2 ml) was added to the reaction mixture and reaction was heated to 70° C. for 2 hours. The pH of the reaction mixture was adjusted to 3 to 4 with 1N HCl and THF was then removed under reduced pressure. The aqueous layer was extracted with ethyl acetate (2×50 ml) and the combined organic layers were washed with brine (50 ml), dried over anhydrous sodium sulfate and concentrated under reduced pressure. The resulting residue was purified by silica gel chromatography to afford the title compound (0.1 g, 37%). $^1$H NMR (400 MHz, CDCl$_3$): δ 1.16 (t, J=7.2 Hz, 3H), 4.08-4.14 (m, 2H), 6.71 (s, 1H), 7.45 (d, J=7.6 Hz, 2H), 7.76 (d, J=8.0 Hz, 2H).

Method 21, Step 3. Ethyl 3-(4-cyanophenyl)-4,4,4-trifluorobutanoate

To a stirred solution of ethyl (Z)-3-(4-cyanophenyl)-4,4,4-trifluorobut-2-enoate (0.1 g, 0.37 mmol) in 1:4 methanol:

ethyl acetate (1.5 ml) was carefully added Pd/C (0.02 g, 20% w/w, 50% moisture). The reaction mixture was stirred at room temperature under an atmosphere of hydrogen for 3 hours. Then the reaction mixture was diluted with ethyl acetate (5 ml) and filtered through a pad of celite. The celite pad was washed with ethyl acetate (2×10 ml). The combined filtrate was concentrated under reduced pressure to afford the title compound (0.1 g, Quantitative). $^1$H NMR (400 MHz, CDCl$_3$): δ 1.07 (t, J=6.8 Hz, 3H), 3.13-3.15 (m, 2H), 3.95-4.04 (m, 2H), 4.27-4.33 (m, 1H), 7.71 (d, J=8.0 Hz, 2H), 7.89 (d, J=8.4 Hz, 2H).

Method 21, Step 4.
3-(4-Cyanophenyl)-4,4,4-trifluorobutanoic acid

To a stirred solution of ethyl 3-(4-cyanophenyl)-4,4,4-trifluorobutanoate (0.28 g, 1.03 mmol) in a mixture of MeOH:THF:H$_2$O (4:2:1, 10 ml) was added LiOH H$_2$O (0.08 g, 1.93 mmol) at 5 to 10° C. The resulting reaction mixture was stirred at room temperature for 1.5 hours. Then the organic solvents were removed by evaporation. The crude material was dissolved in water (10 ml) and extracted with ethyl acetate (2×15 ml). The pH of the aqueous layer was adjusted to 3-4 with concentrated HCl. The desired compound precipitated during this process and the solid product was filtered off to afford title compound (0.2 g, 74%) as a white solid. $^1$H NMR (400 MHz, DMSO-d$_6$): δ 3.02 (d, J=7.6 Hz, 2H), 4.21-4.25 (m, 1H), 7.68 (d, J=8.4 Hz, 2H), 7.87 (d, J=8.0 Hz, 2H), 12.52 (s, 1H).

Method 21, Step 5. tert-Butyl (2-(4-cyanophenyl)-3,3,3-trifluoropropyl)carbamate To a stirred solution of 3-(4-cyanophenyl)-4,4,4-trifluorobutanoic acid (0.5 g, 2.05 mmol) in tert-butanol (5 ml) was added triethylamine (0.86 ml, 5.96 mmol) at room temperature. Then the reaction mixture was cooled to 5-10° C. and DPPA (0.96 g, 3.49 mmol) was added drop wise. After formation of the acylazide as confirmed by TLC (after 1 hour), the reaction was stirred at 90° C. overnight. Then the reaction mixture was diluted with water (30 ml) and extracted with ethyl acetate (2×30 ml). The combined organic layers were washed with brine (25 ml), dried over anhydrous sodium sulphate and concentrated under reduced pressure. The resulting residue was purified by silica gel chromatography to afford the title compound (0.3 g, 46%) as solid. $^1$H NMR (400 MHz, DMSO-d$_6$): δ 1.33 (s, 9H), 2.90-3.00 (m, 1H), 3.04-3.15 (m, 2H), 6.91 (t, J=5.2 Hz, 1H, —NH), 7.42 (d, J=8.4 Hz, 2H), 7.77 (d, J=7.2 Hz, 2H).

Method 21, Step 6.
4-(3-Amino-1,1,1-trifluoropropan-2-yl)benzonitrile hydrochloride To a stirred solution of tert-butyl (2-(4-cyanophenyl)-3,3,3-trifluoropropyl)carbamate (0.1 g, 0.31 mmol) in methanol (1 ml) was added a solution of 4M HCl in dioxane (0.24 ml, 2.4 vol.) drop wise at 0° C. The resulting mixture was stirred at room temperature for 2 hours. The reaction mixture was concentrated under reduced pressure to afford the title compound (0.05 g, 63%) as solid. $^1$H NMR (400 MHz, DMSO-d$_6$): δ 3.52-3.57 (m, 2H), 4.33-4.41 (m, 1H), 7.73 (d, J=8.0 Hz, 2H), 7.97 (d, J=8.4 Hz, 2H), 8.36 (s, 3H, —HCl). LCMS: m/z=215.1 [M+1].

Method 21, Step 7. Ethyl 2-((2-(4-cyanophenyl)-3,3,3-trifluoropropyl)amino)-2-phenylacetate A mixture of ethyl 2-bromo-2-phenylacetate (0.40 g, 1.44 mmol), 4-(3-amino-1,1,1-trifluoropropan-2-yl)benzonitrile hydrochloride (0.3 g, 1.20 mmol) and triethylamine (0.58 ml, 4.20 mmol) in DMF (3 ml) was heated at 60° C. for 3 hours. The reaction mixture was poured into ice cold water (50 ml) and extracted with ethyl acetate (2×50 ml). The combined organic layers were washed with brine (25 ml), dried over anhydrous sodium sulphate and concentrated under reduced pressure. The resulting residue was purified by silica gel chromatography to afford the title compound (0.40 g, 76%) as a thick yellow oil. $^1$H NMR (400 MHz, DMSO-d6): δ 1.08-1.11 (m, 3H), 2.59-2.61 (m, 2H), 2.99-3.10 (m, 3H), 4.01-4.11 (m, 3H), 4.40-4.47 (m, 1H), 7.23-7.36 (m, 5H), 7.55-7.61 (m, 2H), 7.88 (t, J=8 Hz, 2H). LCMS: m/z=311.62 [M+1].

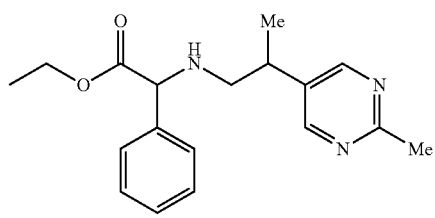

Method 22

Ethyl 2-((2-(2-methylpyrimidin-5-yl)propyl)amino)-2-phenylacetate

Method 22, Step 1. Methyl (Z)-3-(2-methylpyrimidin-5-yl)but-2-enoate

To a stirred solution of 5-bromo-2-methylpyrimidine (5 g, 28.9 mmol) in dry DMF (3 ml) was added methyl crotonate (3.75 g, 37.57 mmol) at room temperature. To this mixture, Pd(OAc)$_2$ (0.64 g, 2.89 mmol), tri(o-tolyl)phosphine (0.88 g, 2.89 mmol) and triethylamine (4.80 ml, 34.68 mmol) were added at room temperature. The reaction mixture was then purged with argon for 20 minutes. Then the mixture was heated to 100° C. overnight. Then the reaction mixture was poured into ice cold water (50 ml) and extracted with ethyl acetate (3×50 ml). The combined organic layers were washed with brine (50 ml), dried over anhydrous sodium sulphate and concentrated under reduced pressure. The resulting residue was purified by silica gel chromatography to afford the title compound (1.8 g, 32%). $^1$H NMR (400 MHz, DMSO-d6): δ 2.61 (s, 3H), 2.80 (s, 3H), 3.82 (s, 3H), 6.20 (s, 1H), 8.77 (s, 2H). LCMS: m/z=193.3 [M+1].

Method 22, Step 2. Methyl 3-(2-methylpyrimidin-5-yl)butanoate

A stirred solution of methyl (Z)-3-(2-methylpyrimidin-5-yl)but-2-enoate (1.8 g, 9.37 mmol) in 1:1 methanol:Ethyl acetate (20 ml) was added 10% Pd/C (0.18 g, 10% w/w, 50% moisture) at room temperature. The reaction mixture was stirred overnight under hydrogen gas pressure (100 psi). The reaction mixture was then filtered through a pad of celite and washed with 1:1 methanol:ethyl acetate (50 ml). The filtrate was concentrated under reduced pressure to afford the title compound (1.2 g, 66%). LCMS: m/z=195.5 [M+1].

Method 22, Step 3.
3-(2-Methylpyrimidin-5-yl)butanoic acid

To a stirred solution of methyl 3-(2-methylpyrimidin-5-yl)butanoate (1.2 g, 6.18 mmol) in a mixture of MeOH:

THF:H₂O (4:2:1, 10 ml) was added LiOH.H₂O (0.38 g, 9.23 mmol) at 5 to 10° C. The resulting reaction mixture was stirred at room temperature for 2 hours. Then the reaction solvent was evaporated and the resulting residue was dissolved in water (10 ml) and extracted with ethyl acetate (2×15 ml). The pH of the aqueous layer was adjusted to 3-4 with concentrated HCl. The desired compound precipitated during this process and the solid filtered off to afford title compound (0.6 g, 54%) as a white solid. LCMS: m/z=181.2 [M+1].

Method 22, Step 4. tert-Butyl (2-(2-methylpyrimidin-5-yl)propyl)carbamate

To a stirred solution of 3-(2-methylpyrimidin-5-yl)butanoic acid (0.6 g, 3.33 mmol) in tert-butanol (6 ml) was added triethylamine (1.37 ml, 9.99 mmol) at room temperature. Then the reaction mixture was cooled to 5-10° C. and DPPA (1.5 g, 5.45 mmol) was added drop wise. After formation of acylazide as confirmed by the TLC, the reaction mixture was stirred at 90° C. overnight. Then the reaction mixture was diluted with water (30 ml) and extracted with ethyl acetate (2×30 ml). The combined organic layers were washed with brine (25 ml), dried over anhydrous sodium sulphate and concentrated under reduced pressure. The resulting residue was purified by silica gel chromatography to afford the title compound (0.4 g, 47%) as thick oil. LCMS: m/z=252.2 [M+1].

Method 22, Step 5. 2-(2-Methylpyrimidin-5-yl)propan-1-amine hydrochloride

To a stirred solution of tert-butyl (2-(2-methylpyrimidin-5-yl)propyl)carbamate (0.4 g, 1.59 mmol) in methanol (4 ml) was added a solution of 4M HCl in dioxane (0.96 ml, 2.4 vol.) drop wise at 0° C. The resulting mixture was stirred at room temperature for 2 hours. The reaction mixture was concentrated under reduced pressure to afford the title compound (0.26 g) as solid. LCMS: m/z=152.1 [M+1].

Method 22, Step 6. Ethyl 2-((2-(2-methylpyrimidin-5-yl)propyl)amino)-2-phenylacetate A mixture of ethyl 2-bromo-2-phenylacetate (0.37 g, 1.52 mmol), 2-(2-methylpyrimidin-5-yl)propan-1-amine hydrochloride (0.26 g, 1.38 mmol) and triethylamine (0.41 ml, 3.04 mmol) in DMF (3 ml) was heated at 60° C. for 3 hours. The reaction mixture was poured into ice cold water (50 ml) and extracted with ethyl acetate (2×50 ml). The combined organic layers were washed with brine (25 ml), dried over anhydrous sodium sulphate and concentrated under reduced pressure to obtain crude product (0.32 g). LCMS: m/z=314.6 [M+1].

Method 23

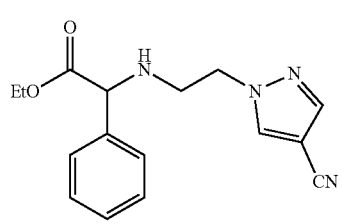

Method 23

Ethyl 2-((2-(4-cyano-1H-pyrazol-1-yl)ethyl)amino)-2-phenylacetate

Method 23. Ethyl 2-((2-(4-cyano-1H-pyrazol-1-yl)ethyl)amino)-2-phenylacetate

To a stirred solution of ethyl 2-((2-chloroethyl)amino)-2-phenylacetate (0.10 g, 0.413 mmol) in DMF (1 ml) was added K₂CO₃ (0.114 g, 0.827 mmol) at 25° C. After stirring for 15 minutes, 1H-pyrazole-4-carbonitrile (0.046 g, 0.496 mmol) was added at 25° C. The reaction mixture was heated at 60° C. for 3 hours. Then the reaction mixture was poured into ice water (15 ml) and the product was extracted with ethyl acetate (2×30 ml). The combined organic layers were washed with brine (20 ml), dried over anhydrous sodium sulphate and concentrated under reduced pressure. The residue was purified by silica gel chromatography to afford the title compound (0.050 g, 40%). LCMS: m/z=299.76 [M+1].

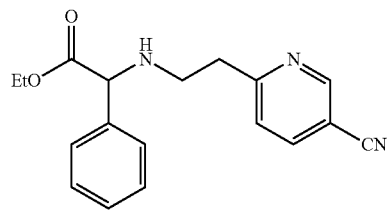

Method 24

Ethyl 2-((2-(5-cyanopyridin-2-yl)ethyl)amino)-2-phenylacetate

Method 24, Step 1. 6-Vinylnicotinonitrile

A mixture of 6-bromonicotinonitrile (2.0 g, 10.92 mmol), 4,4,5,5-tetramethyl-2-vinyl-1,3,2-dioxaborolane (2.5 g, 16.39 mmol) and sodium carbonate (1.4 g, 13.50 mmol) in 4:1 dioxane:water (25 ml) were purged for 20 minutes with argon. To the reaction mixture, Pd(PPh₃)₄ (0.63 g, 0.54 mmol) was added and purging with argon was continued for another 10 minutes. The reaction mixture was heated at 90° C. for 12 hours. The reaction mixture was poured into water (50 ml) and extracted with ethyl acetate (2×100 ml). The combined organic layers were washed with brine (50 ml), dried over anhydrous sodium sulphate and concentrated under reduced pressure. The crude product was purified by silica gel chromatography to afford the title compound (0.7 g, 49%) as solid. ¹H NMR (400 MHz, DMSO-d6): δ 5.72 (d, J=10.8 Hz, 1H), 6.42 (d, J=17.2 Hz, 1H), 6.82-6.89 (m, 1H), 7.44 (d, J=8.0 Hz, 1H), 7.93 (dd, J=8.0 Hz, 2.0 Hz, 1H), 8.85 (s, 1H). LCMS: m/z=131.3 [M+1].

Method 24, Step 2. Ethyl 2-((2-(5-cyanopyridin-2-yl)ethyl)amino)-2-phenylacetate To a stirred solution of 6-vinylnicotinonitrile (0.20 g, 15.0 mmol) in ethanol (2 ml) was added triethylamine (2.0 ml, 15.0 mmol) and ethyl 2-amino-2-phenylacetate (0.30 g, 16.7 mmol) at 25° C. The reaction mixture was heated at 90° C. for 5 hours. The reaction mixture was concentrated under reduced pressure and to the residue, water (25 ml) was added. The aqueous layer was extracted with ethyl acetate (2×30 ml). The combined organic layers were washed with brine (20 ml), dried over anhydrous sodium sulphate and concentrated under reduced pressure. The crude product was purified by silica gel chromatography to afford the title compound (0.3 g, 40%). $^1$H NMR (400 MHz, DMSO-d6): δ 1.23 (t, J=7.2 Hz, 3H), 2.93-2.98 (m, 1H), 3.03-3.11 (m, 3H), 4.12-4.26 (m, 2H), 4.40 (s, 1H), 7.30-7.43 (m, 7H), 7.89 (dd, J=8.0 Hz, 2.0 Hz, 1H), LCMS: m/z=310.36 [M+1].

Method 25

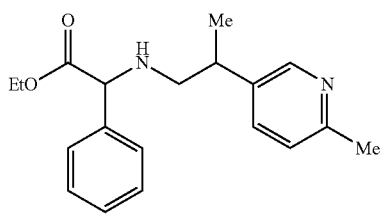

Ethyl 2-((2-(6-methylpyridin-3-yl)propyl)amino)-2-phenylacetate

Method 25, Step 1.
2-Methyl-5-(prop-1-en-2-yl)pyridine

A mixture of 5-bromo-2-methylpyridine (2.0 g, 11.62 mmol), potassium isopropenyl trifluoroborate (2.5 g, 17.43 mmol) and cesium carbonate (11.3 g, 34.88 mmol) in 4:1 isopropanol:water (50 ml) were purged for 20 minutes with argon. To the reaction mixture, Pd(dppf)Cl$_2$.DCM (0.84 g, 1.16 mmol) was added and purging with argon was continued for another 10 minutes. The reaction mixture was heated at 100° C. for 2-3 hours. The reaction mixture was poured into water (50 ml) and extracted with ethyl acetate (2×100 ml). The combined organic layers were washed with brine (50 ml), dried over anhydrous sodium sulphate and concentrated under reduced pressure. The residue was purified by silica gel chromatography to afford the title compound (1.03 g, 49%) as solid. LCMS: m/z=134.5 [M+1].

Method 25, Step 2. (E)-2-Methyl-5-(1-nitroprop-1-en-2-yl)pyridine

To a stirred solution of 1-chloro-4-(prop-1-en-2-yl)benzene (0.5 g, 3.73 mmol) in dry DCE (5.0 ml) under an atmosphere of nitrogen was added AgNO$_2$ (1.72 g, 11.19 mmol), TEMPO (0.23 g, 1.49 mmol), 4 Å molecular sieves (1.5 g) at room temperature. The resulting reaction mixture was stirred for 10 minutes at room temperature and then it was heated to 70° C. overnight. The reaction mixture was cooled to room temperature and it was diluted with dichloromethane (50 ml). The mixture was then filtered through a pad of celite pad and the pad was washed with dichloromethane (50 ml). The eluent was then concentrated under reduced pressure. The residue was purified by silica gel column chromatography to afford the title compound (0.4 g, 30%) as light yellow solid. LCMS: m/z=179.5 [M+1].

Method 25, Step 3.
2-(6-Methylpyridin-3-yl)propan-1-amine

To a solution of (E)-1-chloro-4-(1-nitroprop-1-en-2-yl) benzene (0.45 g, 2.52 mmol) in dry THF (5 ml) under an atmosphere of nitrogen atmosphere was added LAH (5.0 ml, 1M in THF, 5.05 mmol) drop wise at 0° C. The reaction mixture was stirred overnight at room temperature. Saturated aqueous sodium bicarbonate solution (50 ml) was added and reaction mixture was extracted with ethyl acetate (3×50 ml). The combined organic layers were washed with brine, dried over anhydrous sodium sulphate and concentrated under reduced pressure to afford the title compound (0.35 g) as yellow oil. This was used in the next step without further purification.

Method 25, Step 4. Ethyl 2-((2-(6-methylpyridin-3-yl)propyl)amino)-2-phenylacetate A mixture of ethyl 2-bromo-2-phenylacetate (0.37 g, 1.55 mmol), 2-(6-methylpyridin-3-yl)propan-1-amine (0.35 g, 2.32 mmol) and triethylamine (0.58 ml, 3.10 mmol) in DMF (5 ml) was heated at 60° C. for 3 hours. The reaction mixture was poured into ice cold water (50 ml) and extracted with ethyl acetate (2×50 ml). The combined organic layers were washed with brine (25 ml), dried over anhydrous sodium sulphate and concentrated under reduced pressure to give the crude product which was purified by silica gel column chromatography to afford the title compound (0.15 g, 20%). LCMS: m/z=313.1 [M+1].

Scheme 1

The starting materials required for the synthesis of examples prepared using Scheme 1 were either commercially available or prepared using methods 1 through 3.

Example 1

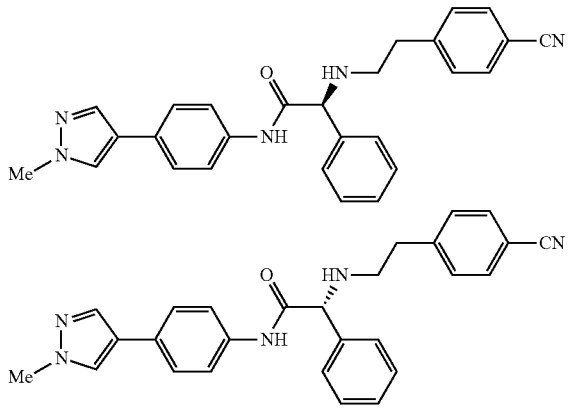

(S)- and (R)-2-((4-Cyanophenethyl)amino)-N-(4-(1-methyl-1H-pyrazol-4-yl)phenyl)-2-phenylacetamide Scheme 1. (S)- and (R)-2-((4-Cyanophenethyl) amino)-N-(4-(1-methyl-1H-pyrazol-4-yl)phenyl)-2-phenylacetamide A mixture of 2-bromo-N-(4-(1-methyl-1H-pyrazol-4-yl) phenyl)-2-phenylacetamide (0.5 g, 1.35 mmol), 4-(2-aminoethyl)benzonitrile hydrochloride (0.296 g, 2.7 mmol) and TEA (0.6 ml, 4.05 mmol) in DMF (5 ml) was heated for 2 hours at 60° C. After completion of the reaction, the reaction mixture was poured into ice cold water (15 ml) and extracted with ethyl acetate (2×30 ml). The combined organic layers were washed with brine (15 ml), dried over anhydrous Na₂SO₄ and concentrated under reduced pressure. The resulting residue was purified by silica gel chromatography to afford the title compound as solid (0.35 g, 59%) in racemic form.

The racemic title compound was resolved by chiral HPLC (CHIRALPAK AD-H; 30% (50:50 ACN:IPA in liquid $CO_2$ + 0.1% DEA) to furnish the enantiopure compounds. The faster-eluting enantiomer of the title compound was obtained as a solid (Isomer 1): $^1$H NMR (400 MHz, DMSO-d6): δ 2.76-2.78 (m, 2H), 2.86-2.88 (m, 2H), 3.85 (s, 3H), 4.38 (s, 1H), 7.28-7.37 (m, 3H), 7.45-7.49 (m, 6H), 7.53 (d, J=8.8 Hz, 2H), 7.75 (d, J=8.4 Hz, 2H), 7.79 (s, 1H), 8.06 (s, 1H), 10.04 (s, 1H). LCMS: m/z=436.5 [M+1]. The slower-eluting enantiomer of the title compound was obtained as a solid (Isomer 2: $^1$H NMR (400 MHz, DMSO-d6): δ 2.76-2.79 (m, 2H), 2.86-2.89 (m, 2H), 3.85 (s, 3H), 4.38 (s, 1H), 7.28-7.37 (m, 3H), 7.44-7.49 (m, 6H), 7.53 (d, J=8.8 Hz, 2H), 7.75 (d, J=8.0 Hz, 2H), 7.79 (s, 1H), 8.06 (s, 1H), 10.03 (s, 1H). LCMS: m/z=436.5 [M+1].

The following compounds were prepared using similar procedures to those described for Example 1 using the appropriate starting materials. The separated isomers for each compound are listed in the order to which they elute. For example, in instances where there are two isomers, isomer 1 is the faster eluting isomer and isomer 2 is the slower-eluting isomer. In instances where there are four isomers, isomer 1 is the fastest eluting isomer followed by isomer 2, then isomer 3, and then isomer 4. Additionally, when more than one chiral column is listed the columns are used in sequential order as listed. For example, if three columns are listed for the purification of a compound with 2 stereocenters, the first was used to separate the mixture into two mixtures, of stereoisomers 1 and 2 and stereoisomers 3 and 4. The mixture of stereoisomers 1 and 2 were then further separated into the pure stereoisomer by the second column listed and the mixture of stereoisomers 3 and 4 were separated into the pure stereoisomers by the third column listed. In some instances, a single chiral column may resolve all four stereoisomers. Additionally, one column may resolve the mixture into pure stereoisomer 1, pure stereoisomer 2, and a mixture of stereoisomers 3 and 4 and a second chiral column is used to resolve the mixture. The stereochemical representation (i.e., R or S) of each isomer of a compound is not drawn in the table and rather named to make clear that support for both is intended. Chiral carbon atom(s) are designated by the asterisk (*). In some instances, chiral building blocks are used to prepare compounds with multiple stereocenters and certain stereoisomers have not been prepared. In these instances where the stereochemistry of one stereocenter is known it will be drawn as such and the other stereocenters that have not been unambiguously assigned will be designated by an asterisk (*). In instances where a compound is racemic, it has been noted as such. In one aspect, the present disclosure relates to the racemic form of any compound described herein. These conventions are followed throughout the entirety of the application.

TABLE 1

| Example Nos. | Structure (Methods and Schemes for Preparation) | IUPAC Name | Exact Mass [M + 1] | Chiral Column; Mobile Phase |
|---|---|---|---|---|
| 2 Isomer 1 Isomer 2 Isomer 3 Isomer 4 | | (S, S)-, (S, R)-, (R, R)-, and (R, S)-2-((2-(4-chlorophenyl)propyl)amino)-N-(4-(1-methyl-1H-pyrazol-4-yl)phenyl)-2-phenylacetamide | Calc'd 459.2, Found 459.4, 459.2, 459.5 and 459.5 | CHIRALPAK AD-H; 30% (50:50 MeOH:IPA) in hexanes + 0.1% DEA |
| 3 Isomer 1 Isomer 2 Isomer 3 Isomer 4 | | (S, S)-, (S, R)-, (R, R)-, and (R, S)-2-((1-(4-chlorophenyl)propan-2-yl)amino)-N-(4-(1-methyl-1H-pyrazol-4-yl)phenyl)-2-phenylacetamide | Calc'd 459.2, Found 459.5, 459.5, 459.5 and 459.5 | 1- CHIRALCEL IC; 25% MeOH in Liquid $CO_2$ + 0.1% DEA 2- CHIRALPAK AD-H; 40% (50:50 MeOH:IPA) in hexanes + 0.1% DEA |
| 4 Isomer 1 Isomer 2 | | (S)- and (R)-N-(4-(1-methyl-1H-pyrazol-4-yl)phenyl)-2-phenyl-2-((4-sulfamoylphenethyl)amino)acetamide | Calc'd 490.6, Found 490.5 and 490.5 | CHIRALPAK AD-H; 50% (50:50 MeOH:IPA) in hexanes + 0.1% DEA |

Scheme 2

The starting materials required for the synthesis of examples prepared using Scheme 2 were either commercially available or prepared using methods 1 through 3.

Example 5

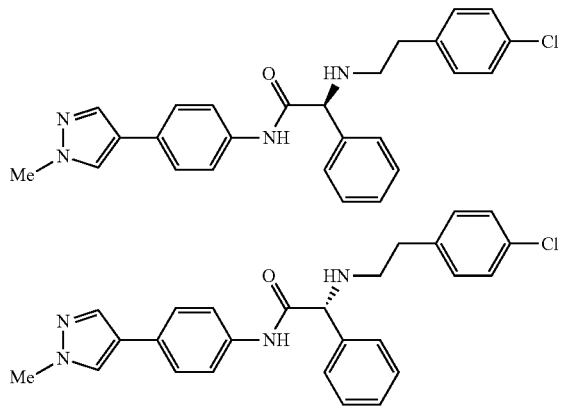

(S)- and (R)-2-((4-Chlorophenethyl)amino)-N-(4-(1-methyl-1H-pyrazol-4-yl)phenyl)-2-phenylacetamide Scheme 2. (S)- and (R)-2-((4-Chlorophenethyl)amino)-N-(4-(1-methyl-1H-pyrazol-4-yl)phenyl)-2-phenylacetamide A mixture of N-(4-bromophenyl)-2-((4-chlorophenethyl)amino)-2-phenylacetamide (0.2 g, 0.90 mmol), 1-methyl-4-(4,4,5,5-tetramethyl-1,3,2-dioxaborolan-2-yl)-1H-pyrazole (0.205 g, 0.99 mmol) and cesium carbonate (0.9 g, 2.69 mmol) in 4:1 dioxane:water (5 ml) was purged for 20 minutes with argon. S-Phos Pd-precatalyst G3 (0.070 g, 0.089 mmol) was added and purging was continued for another 10 minutes. The reaction mixture was heated in a sealed tube at 100° C. for 2 hours. After completion of reaction (monitored by TLC), the reaction mixture was treated with water (10 ml) and extracted with ethyl acetate (2×15 ml). The combined organic layers were washed with brine (20 ml), dried over anhydrous $Na_2SO_4$ and concentrated under reduced pressure. The resulting residue was purified by silica gel chromatography to afford the title compound as solid (0.090 g, 55%) in racemic form.

The racemic title compound was resolved by chiral HPLC (CHIRALPAK IB; 30% (50:50 MeOH:IPA) in hexanes+ 0.1% DEA) to furnish the enantiopure compounds. The faster-eluting enantiomer of the title compound was obtained as a solid (Isomer 1): $^1$H NMR (400 MHz, DMSO-d6): δ 2.68-2.78 (m, 4H), 3.85 (s, 3H), 4.37 (s, 1H), 7.25-7.30 (m, 3H), 7.33-7.37 (m, 4H), 7.44-7.49 (m, 4H), 7.53 (d, J=8.4 Hz, 2H), 7.80 (s, 1H), 8.06 (s, 1H), 10.01 (s, 1H). LCMS: m/z=445.57 [M+1]. The slower-eluting enantiomer of the title compound was obtained as a solid (Isomer 2): $^1$H NMR (400 MHz, DMSO-d6): δ 2.72-2.78 (m, 4H), 3.85 (s, 3H), 4.37 (s, 1H), 7.25-7.30 (m, 3H), 7.33-7.37 (m, 4H), 7.44-7.54 (m, 6H), 7.80 (s, 1H), 8.06 (s, 1H), 10.01 (s, 1H). LCMS: m/z=445.62 [M+1].

Example 6

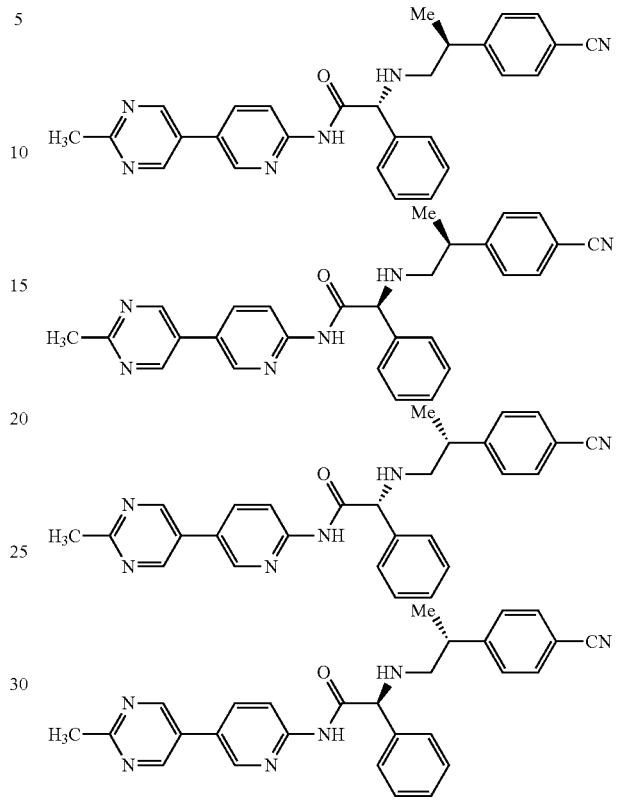

(S,S)-, (R,R)-, (S,R)- and (R,S)-2-((2-(4-Cyanophenyl)propyl)amino)-N-(5-(2-methylpyrimidin-5-yl)pyridin-2-yl)-2-phenylacetamide Scheme 3, Step 1. 2-((2-(4-Cyanophenyl)propyl)amino)-N-(5-(2-methylpyrimidin-5-yl)pyridin-2-yl)-2-phenylacetamide A mixture of N-(5-bromopyridin-2-yl)-2-((2-(4-cyanophenyl)propyl)amino)-2-phenylacetamide (0.300 g, 0.66 mmol), 2-methyl-5-(4,4,5,5-tetramethyl-1,3,2-dioxaborolan-2-yl)pyrimidine (0.293 g, 1.33 mmol) and cesium carbonate (0.650 g, 2.0 mmol) in dioxane:water (4:1, 7.5 ml) was degassed with argon gas for 20 minutes. $PdCl_2$(dppf) (0.049 g, 0.066 mmol) was added and degassing was continued for another 10 minutes. The reaction mixture was heated at 100° C. for 1 hour. After completion of reaction (monitored by TLC), the reaction mixture was diluted with water (20 ml) and extracted with ethyl acetate (2×30 ml). The combined organic layers were washed with brine, dried over anhydrous $Na_2SO_4$ and concentrated under reduced pressure. The crude product was purified by silica gel chromatography to give title compound (0.270 g, 78%) as off-white solid in racemic form.

The racemic title compound was resolved by chiral HPLC (CHIRALCEL OX-H; 30% (30:70 ACN:IPA) in hexanes+ 0.1% DEA) then (CHIRALCEL OJ-H; 25% (MeOH) in liquid $CO_2$+0.1% DEA) to furnish the enantiopure compounds. The first-eluting enantiomer of the title compound was obtained as a solid (Isomer 1): $^1$H NMR (400 MHz, DMSO-d6) δ 1.21 (d, J=7.2 Hz, 3H), 2.66 (s, 3H), 2.69-2.71 (m, 3H), 3.03-3.05 (m, 1H), 4.50 (d, J=7.6 Hz, 1H), 7.25-7.41 (m, 7H), 7.76 (d, J=8 Hz, 2H), 8.12-8.30 (m, 2H), 8.74 (d, J=2 Hz 1H), 9.05 (s, 2H), 10.52 (s, 1H). LCMS: m/z=463.4 [M+1]; The second-eluting enantiomer of the title compound was obtained as a solid (Isomer 2): $^1$H NMR (400 MHz, DMSO-d6) δ 1.22 (d, J=6.8 Hz, 3H), 2.68 (s, 3H), 2.69-2.73 (m, 3H), 3.04-3.06 (m, 1H), 4.52 (d, J=6.0 Hz, 1H), 7.25-7.49 (m, 7H), 7.77 (d, J=8 Hz, 2H), 8.12-8.30 (m, 2H), 8.74 (s, 1H), 9.06 (s, 2H), 10.54 (s, 1H). LCMS: m/z=463.6 [M+1]. The third-eluting enantiomer of the title compound was obtained as a solid (Isomer 3): $^1$H NMR (400 MHz, DMSO-d6) δ 1.23 (d, J=6.8 Hz, 3H), 2.68 (s, 3H), 2.70-2.72 (m, 2H), 3.04-3.06 (m, 1H), 4.51 (d, J=6.0 Hz, 1H), 7.25-7.49 (m, 7H), 7.77 (d, J=8 Hz, 2H), 8.12-8.30 (m, 2H), 8.74 (s, 1H), 9.06 (s, 2H), 10.55 (s, 1H). LCMS: m/z=463.5 [M+1]; The forth-eluting enantiomer of the title compound was obtained as a solid (Isomer 4): $^1$H NMR (400 MHz, DMSO-d6) δ 1.23 (d, J=6.8 Hz, 3H), 2.68 (s, 3H), 2.70-2.72 (m, 2H), 3.04-3.06 (m, 1H), 4.51 (d, J=6.4 Hz, 1H), 7.25-7.49 (m, 7H), 7.77 (d, J=8.4 Hz, 2H), 8.14-8.24 (m, 2H), 8.76 (s, 1H), 9.07 (s, 2H), 10.55 (s, 1H). LCMS: m/z=463.4 [M+1].

The compounds in Table 2 were prepared using similar procedures to those described for Examples 5 and 6 using the appropriate starting materials.

Example 9

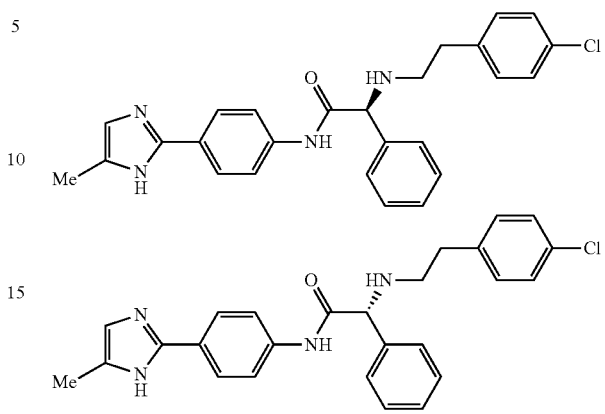

(S)- and (R)-2-((4-Chlorophenethyl)amino)-N-(4-(5-methyl-1H-imidazol-2-yl)phenyl)-2-phenylacetamide Scheme 3, Step 1. 2-((4-Chlorophenethyl)amino)-2-phenyl-N-(4-(4,4,5,5-tetramethyl-1,3,2-dioxaborolan-2-yl)phenyl) acetamide A mixture of N-(4-bromophenyl)-2-((4-chlorophenethyl)amino)-2-phenyl acetamide (1.5 g, 3.39 mmol), bis(pinacolato)diboran (1.2 g, 5.09 mmol) and KOAc (0.83 g, 8.47 mmol) in 1,4-dioxane (30 ml) was purged for 20 minutes with argon. To this mixture, 1,1'-bis(diphenylphosphino)ferrocene-palladium(II)dichloride (0.248 g, 0.33 mmol) was added and purging was continued for another 10 minutes. The reaction mixture was heated in a sealed tube at 90° C.

TABLE 2

| Example No. | Structure (Methods and Schemes for Preparation) | IUPAC Name | Exact Mass [M + 1] | Chiral Column and Mobile Phase |
|---|---|---|---|---|
| 7 Isomer 1 Isomer 2 | | (S)- and (R)-N-(5-(1H-pyrazol-4-yl)pyridin-2-yl)-2-((4-cyanophenethyl)amino)-2-phenylacetamide | Calc'd 423.5, Found 423.6 and 423.5 | CHIRALCEL OJ-H; 15% MeOH in Liquid $CO_2$ + 0.1% DEA |
| 8 Isomer 1 Isomer 2 Isomer 3 Isomer 4 | | (S, S), (S, R), (R, R), and (R, S)-2-((2-(4-cyanophenyl)propyl)amino)-N-(5-(1-(1-hydroxy-2-methylpropan-2-yl)-1H-pyrazol-4-yl)pyridin-2-yl)-2-phenylacetamide | Calc'd 509.6, Found 509.5, 509.5, 509.9 and 509.9 | 1-CHIRALPAK IC; 30% (50:50 MeOH:IPA) in hexanes + 0.1% DEA 2-CHIRALPAK IC; 20% (30:70 ACN:IPA) in hexanes + 0.1% DEA |

Scheme 3

The starting materials required for the synthesis of examples prepared using Scheme 3 were either commercially available or prepared using methods 1 through 3.

for 6 hours. After completion of the reaction (monitored by TLC), the reaction mixture was treated with water (20 ml) and extracted with ethyl acetate (3×20 ml). The combined organic layers were washed with brine (20 ml), dried over anhydrous $Na_2SO_4$ and concentrated under reduced pressure. The crude residue was purified by silica gel chromatography to afford the title compound as a solid (1.2 g, 72%). $^1$H NMR (400 MHz, DMSO-d6): δ 1.28 (s, 12H), 2.69-2.76 (m, 4H), 4.38 (s, 1H), 7.25-7.30 (m, 3H), 7.33-7.36 (m, 4H), 7.44 (d, J=6.8 Hz, 2H), 7.54 (d, J=8.4 Hz, 2H), 7.60 (d, J=8.4 Hz, 2H), 10.09 (s, —NH). LCMS: m/z=491.5 [M+1].

Scheme 3, Step 2. (S)- and (R)-2-((4-chlorophenethyl)amino)-N-(4-(5-methyl-1H-imidazol-2-yl)phenyl)-2-phenylacetamide A mixture of 2-((4-chlorophenethyl)amino)-2-phenyl-N-(4-(4,4,5,5-tetramethyl-1,3,2-dioxaborolan-2-yl)phenyl)acetamide (0.2 g, 0.40 mmol), 2-bromo-5-methyl-1H-imidazole (0.131 g, 0.81 mmol) and cesium carbonate (0.332 g, 1.02 mmol) in 4:1 dioxane:water (10 ml) was purged with argon for 20 minutes. 1,1'-bis(diphenylphosphino)-ferrocene-palladium(II)dichloride (0.029 g, 0.04 mmol) was added and purging was continued for another 10 minutes. The reaction mixture was heated in a sealed tube with microwave irradiation at 135° C. for 2 hours. After completion of the reaction (monitored by TLC), the reaction mixture was treated with water (20 ml) and extracted with ethyl acetate (2×20 ml). The combined organic layers were washed with brine (20 ml), dried over anhydrous $Na_2SO_4$ and concentrated under reduced pressure. The crude residue was purified by silica gel chromatography to afford the title compound as solid (0.080 g, 44%) in racemic form.

The racemic title compound was resolved by chiral HPLC (CHIRALPAK AD-H; (50:50 ACN:IPA) in liquid $CO_2$+ 0.1% DEA) to furnish the enantiopure compounds. The faster-eluting enantiomer of the title compound was obtained as a solid (Isomer 1): $^1$H NMR (400 MHz, DMSO-d6): δ 2.13-2.21 (m, 3H), 2.67-2.77 (m, 4H), 4.37 (s, 1H), 6.64-6.88 (m, 1H), 7.25-7.29 (m, 3H), 7.33-7.36 (m, 4H), 7.44 (d, J=7.6 Hz, 2H), 7.55 (d, J=8.4 Hz, 2H), 7.78 (t, J=5.6 Hz, 2H), 10.08 (s, 1H, —NH), 12.06-12.12 (m, 1H, —NH). LCMS: m/z=445.4 [M+1]. The slower-eluting enantiomer of the title compound was obtained as a solid (Isomer 2): $^1$H NMR (400 MHz, DMSO-d6): δ 2.13-2.21 (m, 3H), 2.73-2.77 (m, 4H), 4.37 (s, 1H), 6.64-6.88 (m, 1H), 7.25-7.29 (m, 3H), 7.33-7.36 (m, 4H), 7.44 (d, J=7.2 Hz, 2H), 7.55 (d, J=8.4 Hz, 2H), 7.78-7.80 (m, 2H), 10.08 (s, 1H, —NH), 12.06-12.13 (m, 1H, —NH). LCMS: m/z=445.5 [M+1].

The following compounds were prepared using similar procedures to those described for Example 9 using the appropriate starting materials.

TABLE 3

| Example No. | Structure (Methods and Schemes for Preparation) | IUPAC Name | Exact Mass [M + 1] | Chiral Column and Mobile Phase |
|---|---|---|---|---|
| 10 Isomer 1 Isomer 2 | | (S)- and (R)-2-((4-chlorophenethyl)amino)-2-phenyl-N-(4-(pyridazin-3-yl)phenyl)acetamide | Calc'd 443.2, Found 443.3 and 443.4 | CHIRALPAK IC; 45% (50:50 MeOH:IPA) in hexanes + 0.1% DEA |
| 11 Isomer 1 Isomer 2 | | (S)- and (R)-2-((4-cyanophenethyl)amino)-N-(4-(5-methyl-1H-imidazol-2-yl)phenyl)-2-phenylacetamide | Calc'd 436.3, Found 436.3 and 436.2 | CHIRALPAK AD-H; 35% (50:50 ACN:IPA) in Liquid $CO_2$ + 0.1% DEA |
| 12 Isomer 1 Isomer 2 | | (S)- and (R)-2-((4-cyanophenethyl)amino)-2-phenyl-N-(4-(pyridazin-3-yl)phenyl)acetamide | Calc'd 434.2, Found 434.3 and 434.3 | CHIRALPAK IC; 40% (70:30 MeOH:IPA) in hexanes + 0.1% DEA |

TABLE 3-continued

| Example No. | Structure (Methods and Schemes for Preparation) | IUPAC Name | Exact Mass [M + 1] | Chiral Column and Mobile Phase |
|---|---|---|---|---|
| 13 Isomer 1 Isomer 2 | | (S)- and (R)-2-((4-cyanophenethyl)amino)-N-(5-(1-methyl-1H-imidazol-4-yl)pyridin-2-yl)-2-phenylacetamide | Calc'd 437.2, Found 437.6 and 437.6 | CHIRALPAK IB; 35% (25:75 MeOH:IPA) in hexanes + 0.1% DEA |
| 14 Isomer 1 Isomer 2 | | (S)- and (R)-2-((4-cyanophenethyl)amino)-N-(5-(1-methyl-1H-pyrazol-3-yl)pyridin-2-yl)-2-phenylacetamide | Calc'd 437.2, Found 437.5 and 437.4 | CHIRALPAK IB; 15% (50:50 MeOH:IPA) in Liquid $CO_2$ + 0.1% DEA |
| 15 Isomer 1 Isomer 2 Isomer 3 Isomer 4 | | (S, S)-, (S, R)-, (R, R)- and (R, S)-2-((2-(4-cyanophenyl)propyl)amino)-N-(5-(6-methylpyridazin-3-yl)pyridin-2-yl)-2-phenylacetamide | Calc'd 463.6, Found 463.8, 463.8, 463.8 and 463.8 | 1-CHIRALCEL OX-H; 20% (70:30 IPA:ACN) in hexanes + 0.1% DEA 2-CHIRALPAK IC; 37% MeOH in Liquid $CO_2$ + 0.1% DEA |

Scheme 4

The starting materials required for the synthesis of examples prepared using Scheme 4 were either commercially available or prepared using methods 1 through 3.

Example 16

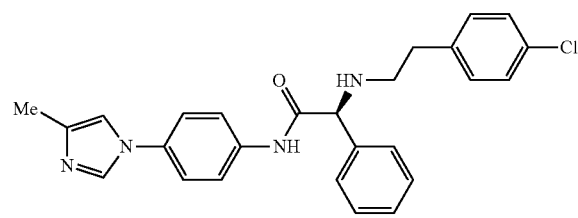 [SMILES: Cn1cc(-c2ccc(NC(=O)C(NCCc3ccc(Cl)cc3)c3ccccc3)nc2)cn1]

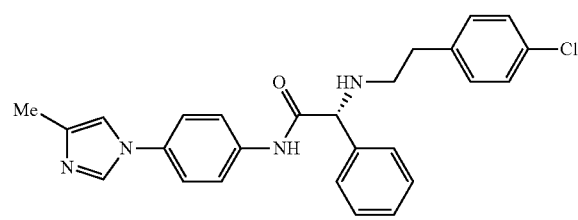

(S)- and (R)-2-((4-Chlorophenethyl)amino)-N-(4-(4-methyl-1H-imidazol-1-yl)phenyl)-2-phenylacetamide Scheme 4. (S)- and (R)-2-((4-Chlorophenethyl)amino)-N-(4-(4-methyl-1H-imidazol-1-yl)phenyl)-2-phenylacetamide A mixture of N-(4-bromophenyl)-2-((4-chlorophenethyl)amino)-2-phenylacetamide (0.15 g, 0.33 mmol), 4-methyl-1H-imidazole (0.14 g, 1.69 mmol), CuI (0.032 g, 0.16 mmol) and cesium carbonate (0.11 g, 0.33 mmol) in DMF (3 ml) was purged for 20 minutes with argon. 1-(5,6,7,8-tetrahydroquinolin-8-yl)ethanone (0.011 g, 0.06 mmol) was added and purging was continued for another 10 minutes. The reaction mixture was heated in a sealed tube at 135° C. for 16 hours. After completion of the reaction (monitored by TLC), the mixture was treated with water (10 ml) and extracted with ethyl acetate (2×10 ml). The combined organic layers were washed with brine (10 ml), dried over anhydrous $Na_2SO_4$ and concentrated under reduced pressure. The resulting residue was purified by silica gel chromatography to afford the title compound as solid (0.1 g, 66%) in racemic form.

The racemic title compound was resolved by chiral HPLC (CHIRALPAK OJ-H; 20% MeOH in Liquid $CO_2$+0.1% DEA) to furnish the enantiopure compounds. The faster-eluting enantiomer of the title compound was obtained as a solid (Isomer 1): ¹H NMR (400 MHz, DMSO-d6): δ 2.15 (s, 3H), 2.68-2.78 (m, 4H), 4.39 (d, J=7.6 Hz, 1H), 7.25-7.31 (m, 3H), 7.33-7.37 (m, 4H), 7.45-7.47 (m, 2H), 7.52 (d, J=8.0 Hz, 2H), 7.66-7.77 (m, 3H), 8.05 (s, 1H), 10.21 (s, —NH). LCMS: m/z=445.4 [M+1]. The slower-eluting enantiomer of the title compound was obtained as a solid (Isomer 2): ¹H NMR (400 MHz, DMSO-d6): 2.15 (s, 3H), 2.72-2.82 (m, 4H), 4.40 (s, 1H), 7.25-7.30 (m, 3H), 7.33-7.37 (m, 4H), 7.46 (d, J=7.2 Hz, 2H), 7.52 (d, J=8.8 Hz, 2H), 7.66-7.70 (m, 3H), 8.05 (s, 1H), 10.26 (s, —NH). LCMS: m/z=445.4 [M+1].

Scheme 5

The starting materials required for the synthesis of examples prepared using Scheme 5 were either commercially available or prepared using methods 1 through 3.

Example 17

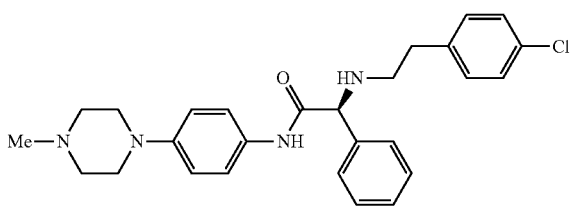

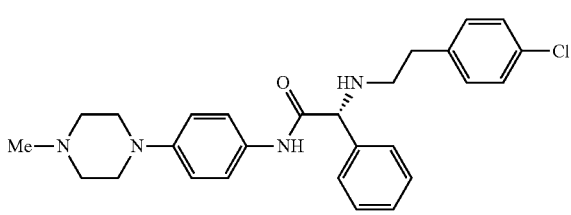

(S)- and (R)-2-((4-Chlorophenethyl)amino)-N-(4-(4-methylpiperazin-1-yl)phenyl)-2-phenylacetamide Scheme 6. (S)- and (R)-2-((4-Chlorophenethyl) amino)-N-(4-(4-methylpiperazin-1-yl)phenyl)-2-phenylacetamide A mixture of N-(4-bromophenyl)-2-((4-chlorophenethyl) amino)-2-phenylacetamide (0.4 g, 0.79 mmol), 1-methylpiperazine (0.1 g, 1.01 mmol) and cesium carbonate (0.55 g, 1.69 mmol) in dioxane (4 ml) was purged for 20 minutes with argon. Brett-Phos Pd-precatalyst G3 (0.061 g, 0.067 mmol) was added and purging was continued for another 10 minutes. The reaction mixture was heated in a sealed tube with microwave irradiation at 135° C. for 2 hours. After completion of the reaction (monitored by TLC), the mixture was treated with water (15 ml) and extracted with ethyl acetate (2×15 ml). The combined organic layers were washed with brine (15 ml), dried over anhydrous $Na_2SO_4$ and concentrated under reduced pressure. The resulting residue was purified by silica gel chromatography to give afford the title compound as solid (0.08 g, 25%) in racemic form.

The racemic title compound was resolved by chiral HPLC (CHIRALCEL OX-H; 35% (50:50 MeOH:IPA) in hexanes+ 0.1% DEA) to furnish the enantiopure compounds. The faster-eluting enantiomer of the title compound was obtained as a solid (Isomer 1): ¹H NMR (400 MHz, DMSO-d6): δ 2.21 (s, 3H), 2.42-2.45 (m, 4H), 2.68-2.77 (m, 5H), 3.04-3.06 (m, 4H), 4.32 (d, J=7.2 Hz, 1H), 6.86 (d, J=8.8 Hz, 2H), 7.24-7.44 (m, 11H), 9.83 (s, 1H). LCMS: m/z=463.1 [M+1]. The slower-eluting enantiomer of the title compound was obtained as a solid (Isomer 2): ¹H NMR (400 MHz, DMSO-d6): δ 2.23 (s, 3H), 2.46-2.51 (m, 4H), 2.69-2.77 (m, 5H), 3.04-3.06 (m, 4H), 4.33 (s, 1H), 6.86 (d, J=8.8 Hz, 2H), 7.24-7.44 (m, 11H), 9.83 (s, 1H). LCMS: m/z=463.5 [M+1].

The following compounds were prepared using similar procedures to those described for Example 17 using the appropriate starting materials.

TABLE 4

| Example No. | Structure (Methods and Schemes for Preparation) | IUPAC Name | Exact Mass [M + 1] | Chiral Column and Mobile Phase |
| --- | --- | --- | --- | --- |
| 18 Isomer 1 Isomer 2 | | (S)- and (R)-2-((4-cyanophenethyl)amino)-N-(4-(4-methylpiperazin-1-yl)phenyl)-2-phenylacetamide | Calc'd 454.3, Found 454.5 and 454.5 | CHIRALCEL OX-H; MeOH in Liquid $CO_2$ + 0.1% DEA |

Scheme 6

The starting materials required for the synthesis of examples prepared using Scheme 7 were generally prepared using methods 1 through 3 or were commercially available.

Example 19

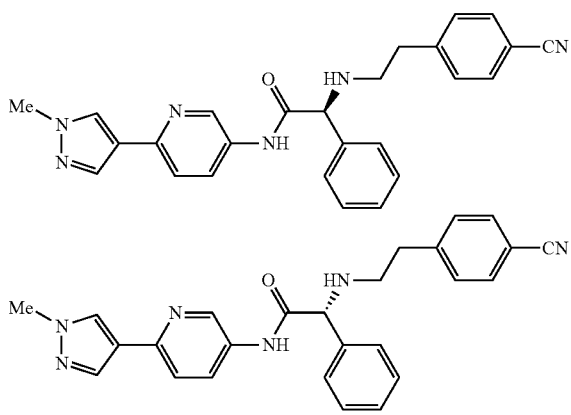

(S)- and (R)-2-((4-cyanophenethyl)amino)-N-(6-(1-methyl-1H-pyrazol-4-yl)pyridin-3-yl)-2-phenylacetamide

Scheme 6, Step 1. Ethyl 2-((4-cyanophenethyl)amino)-2-phenylacetate

A mixture of ethyl 2-bromo-2-phenylacetate (2.0 g, 8.22 mmol), 4-(2-aminoethyl)benzonitrile hydrochloride (2.25 g, 12.33 mmol) and TEA (2.50 g, 24.66 mmol) in DMF (20 ml) was heated for 3 hours at 60° C. The reaction mixture was poured into ice cold water (50 ml) and extracted with ethyl acetate (2×50 ml). The combined organic layers were washed with brine (25 ml), dried over anhydrous $Na_2SO_4$ and concentrated under reduced pressure. The resulting residue was purified by silica gel chromatography to afford the title compound (2.2 g, 86%) as a thick liquid. $^1$H NMR (400 MHz, DMSO-d6): δ 1.10 (t, J=7.2 Hz, 3H), 2.62-2.82 (m, 4H), 4.02-4.09 (m, 2H), 4.39 (d, J=8.4 Hz, 1H), 7.28-7.35 (m, 5H), 7.40 (d, J=8.4 Hz, 2H), 7.72 (d, J=8.4 Hz, 2H). LCMS: m/z=309.28 [M+1].

Scheme 6, Step 2, Procedure 1. (S)- and (R)-2-((4-Cyanophenethyl)amino)-N-(6-(1-methyl-1H-pyrazol-4-yl)pyridin-3-yl)-2-phenylacetamide To a mixture of 6-(1-methyl-1H-pyrazol-4-yl)pyridin-3-amine (250 mg, 1.44 mmol) and ethyl 2-((4-cyanophenethyl)amino)-2-phenylacetate (531 mg, 1.72 mmol) in toluene, trimethyl aluminium (2.9 ml, 2.870 mmol; 1 M in toluene) was added under an atmosphere of nitrogen at room temperature. The resulting reaction mixture was heated to 100° C. for 2 hours. After completion of the reaction (monitored by TLC), the mixture was diluted with ethyl acetate (20 ml) and slowly quenched with water (20 ml) at room temperature. The aqueous layer was extracted with ethyl acetate (2×20 ml). The combined organic layers were washed with brine (20 ml), dried over anhydrous $Na_2SO_4$ and concentrated under reduced pressure. The resulting residue was purified by silica gel chromatography to afford the title compound (150 mg, 30%) in racemic form.

The racemic title compound was resolved by chiral HPLC (CHIRALPAK IB; 55% (50:50 MeOH:IPA) in hexanes+ 0.1% DEA) to furnish the enantiopure compounds. The faster-eluting enantiomer of the title compound was obtained as a solid (Isomer 1): $^1$H NMR (400 MHz, DMSO-d6): δ 2.61-2.82 (m, 2H), 2.87-2.89 (m, 2H), 3.87 (s, 3H), 4.43 (s, 1H), 7.27-7.31 (m, 1H), 7.34-7.39 (m, 2H), 7.44-7.48 (m, 4H), 7.57-7.59 (d, J=8.8 Hz, 1H), 7.74-7.76 (d, J=8.0 Hz, 2H), 7.92 (s, 1H), 8.01 (dd, J=8.8 Hz, 2.4 Hz, 1H), 8.20 (s, 1H), 8.66 (d, J=2.4 Hz, 1H), 10.34 (s, 1H, —NH). LCMS: m/z=437.24 [M+1]. The slower-eluting enantiomer of the title compound was obtained as a solid (Isomer 2): $^1$H NMR (400 MHz, DMSO-d6): δ 2.77-2.78 (m, 2H), 2.87-2.89 (m, 2H), 3.87 (s, 3H), 4.42 (s, 1H), 7.27-7.31 (m, 1H), 7.34-7.39 (m, 2H), 7.44-7.48 (m, 4H), 7.59 (d, J=8.4 Hz, 1H), 7.75 (d, J=8.0 Hz, 2H), 7.92 (s, 1H), 8.01 (dd, J=8.4 Hz, 2.4 Hz, 1H), 8.20 (s, 1H), 8.66 (d, J=2.0 Hz, 1H), 10.34 (s, 1H, —NH). LCMS: m/z=437.24 [M+1].

Example 22

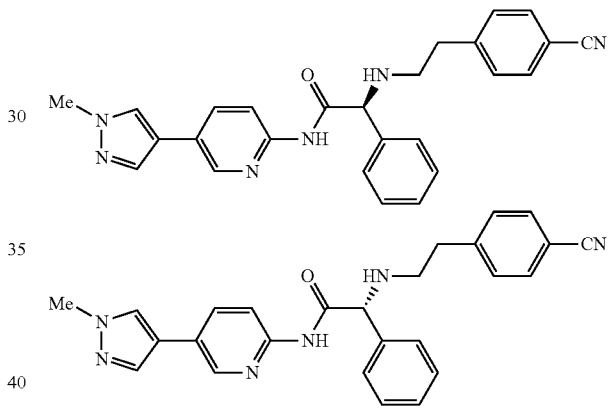

(S)- and (R)-2-((4-cyanophenethyl)amino)-N-(5-(1-methyl-1H-pyrazol-4-yl)pyridin-2-yl)-2-phenylacetamide

Scheme 6, Step 2, Procedure 1. (S)- and (R)-2-((4-cyanophenethyl)amino)-N-(5-(1-methyl-1H-pyrazol-4-yl)pyridin-2-yl)-2-phenylacetamide To a stirred solution of 5-(1-methyl-1H-pyrazol-4-yl)pyridin-2-amine (1.0 g, 5.74 mmol), ethyl 2-((4-cyanophenethyl)amino)-2-phenylacetate (2.12 g, 6.88 mmol) in dry toluene (10 ml) was added trimethylaluminium (5.8 ml, 2M in toluene, 11.48 mmol) at 0° C. The reaction mixture was stirred at 100° C. for 2 hours. After completion of the reaction, the reaction mixture was poured into ice cold water (50 ml) and extracted with ethyl acetate (2×100 ml). The combined organic layers were washed with brine (50 ml), dried over anhydrous sodium sulphate and concentrated under reduced pressure. The resulting residue was purified by silica gel chromatography to afford the title compound (0.30 g, 12%) as racemic mixture.

The racemic title compound was resolved by chiral HPLC (CHIRALCEL OJ-H; 14% MeOH in liquid $CO_2$+0 0.1% DEA) to furnish the enantiopure compounds. The faster-eluting enantiomer (example 22, isomer 1 in tables 5 and 8 below) of the title compound was obtained as a solid. ¹H NMR (400 MHz, DMSO-d6): δ 2.73-2.80 (m, 2H), 2.85-2.88 (m, 3H), 3.86 (s, 3H), 4.53 (d, J=8.8 Hz, 1H), 7.25-7.29 (m, 1H), 7.32-7.35 (m, 2H), 7.44 (d, J=8.0 Hz, 4H), 7.73 (d, J=8.0 Hz, 2H), 7.89 (s, 1H), 7.92-7.95 (m, 1H), 8.02 (d, J=8.4 Hz, 1H), 8.17 (s, 1H), 8.55 (d, J=1.6 Hz, 1H), 10.48 (s, 1H). LCMS: m/z=437.22 [M+1].

Example 100

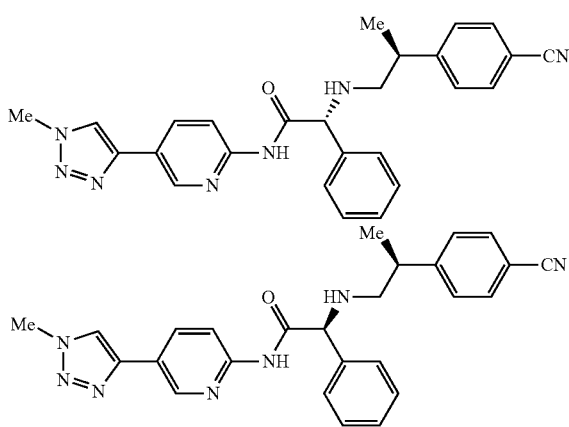

Scheme 6, Step 2, Procedure 1. (R,S)-, (S,S)-2-((2-(4-cyanophenyl)propyl)amino)-N-(5-(1-methyl-1H-1,2,3-triazol-4-yl)pyridin-2-yl)-2-phenylacetamide To a stirred solution of 5-(1-methyl-1H-1,2,3-triazol-4-yl)pyridin-2-amine (0.1 g, 0.56 mmol), a 1:1 mixture of (S,R)- and (S,S)-ethyl 2-((4-cyanophenethyl)amino)-2-phenylacetate (0.27 g, 0.85 mmol) in dry toluene (2 ml) was added trimethylaluminium (0.6 ml, 2M in toluene, 1.13 mmol) at 0° C. The reaction mixture was stirred at 100° C. for 2 hours. After completion of the reaction, the reaction mixture was poured into ice cold water (25 ml) and extracted with ethyl acetate (2×50 ml). The combined organic layers were washed with brine (25 ml), dried over anhydrous sodium sulphate and concentrated under reduced pressure. The resulting residue was purified by silica gel chromatography to afford the title compounds (0.078 g, 31%) as mixture.

The title compounds were resolved by chiral HPLC (CHIRALPAKIC; 10% (70:30 IPA:ACN) in n-hexanes+0.1% DEA). The slower-eluting enantiomer (example 100, isomer 2 in tables 5 and 8 below) of the title compound was obtained as a solid. ¹H NMR (400 MHz, DMSO-d6): δ 1.24 (d, J=5.6 Hz, 1H), 2.51-2.66 (m, 3H), 3.04 (d, J=7.2 Hz, 1H), 4.10 (s, 3H), 4.50 (d, J=7.6 Hz, 1H), 7.28-7.47 (m, 7H), 7.76 (d, J=7.2 Hz, 2H), 8.12-8.18 (m, 2H), 8.57 (s, 1H), 8.79 (s, 1H), 10.64 (s, 1H). LCMS: m/z=452.52=[M+1].

Example 20

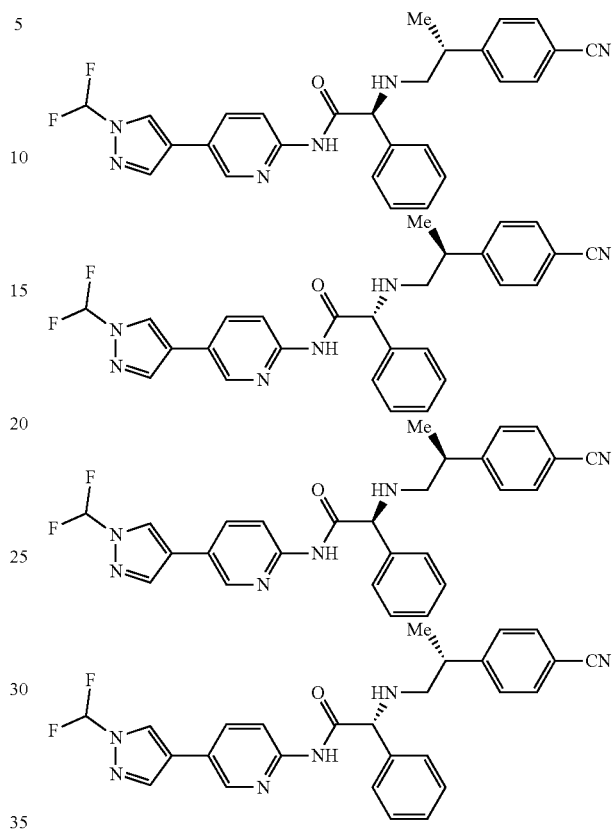

(S,R)-, (R,S)-, (S,S)-, (R,R)-(2-((2-(4-cyanophenyl)propyl)amino)-N-(5-(1-(difluoromethyl)-1H-pyrazol-4-yl)pyridin-2-yl)-2-phenylacetamide Scheme 6, Step 2, Procedure 2. (S,R)-, (R,S)-, (S,S)-, (R,R)-(2-((2-(4-Cyanophenyl)propyl)amino)-N-(5-(1-(difluoromethyl)-1H-pyrazol-4-yl)pyridin-2-yl)-2-phenylacetamide To a stirred solution of 5-(1-(difluoromethyl)-1H-pyrazol-4-yl)pyridin-2-amine (0.35 g, 1.67 mmol), ethyl 2-((4-cyanophenethyl)amino)-2-phenylacetate (0.59 g, 1.83 mmol) in dry THF (4 ml) was added LiHMDS (2 ml, 1M in THF, 3.34 mmol) at 0° C. The reaction mixture was stirred at room temperature for 1 hour. After completion of the reaction (monitored by TFC), the reaction mixture was poured into ice cold water (15 ml) and extracted with ethyl acetate (2×25 ml). The combined organic layers were washed with brine (15 ml), dried over anhydrous Na₂SO₄ and concentrated under reduced pressure. The resulting residue was purified by silica gel chromatography to afford a mixture of the title compounds (0.5 g, 61%).

The mixture was resolved by chiral HPLC (CHIRALCEL OX-H; 45% (50:50 MeOH:IPA) in hexanes+0.1% DEA) then (CHIRALPAKIC; 30% (50:50 MeOH:IPA) in hexanes+0.1% DEA) to furnish the enantiopure compounds. The first-eluting enantiomer of the title compound was obtained as a solid (Isomer 1): ¹H NMR (400 MHz, DMSO-d6) δ 1.22 (d, J=6.8 Hz, 3H), 2.69-2.71 (m, 3H), 3.03-3.07 (m, 1H), 4.49 (d, J=6.8 Hz, 1H), 7.26-7.49 (m, 7H), 7.72-

7.78 (m, 2H), 7.87 (s, 1H), 8.02-8.12 (m, 2H), 8.33 (s, 1H), 8.71 (d, J=1.2 Hz, 1H), 8.79 (s, 1H), 10.46 (s, 1H). LCMS: m/z=487.7 [M+1]; The second-eluting enantiomer of the title compound was obtained as a solid (Isomer 2): $^1$H NMR (400 MHz, DMSO-d6) δ 1.24 (d, J=6.8 Hz, 3H), 2.60-2.71 (m, 3H), 3.01-3.07 (m, 1H), 4.50 (d, J=8.4 Hz, 1H), 7.21-7.49 (m, 7H), 7.72-7.80 (m, 2H), 7.87 (s, 1H), 8.02-8.12 (m, 2H), 8.33 (s, 1H), 8.72 (s, 1H), 8.79 (s, 1H), 10.61 (s, 1H). LCMS: m/z=487.7 [M+1]; The third-eluting enantiomer of the title compound was obtained as a solid (Isomer 3): $^1$H NMR (400 MHz, DMSO-d6) δ 1.22 (d, J=6.8 Hz, 3H), 2.69-2.71 (m, 3H), 3.04-3.07 (m, 1H), 4.49 (d, J=7.6 Hz, 1H), 7.26-7.49 (m, 7H), 7.72-7.78 (m, 2H), 7.87 (s, 1H), 8.02-8.12 (m, 2H), 8.33 (s, 1H), 8.71 (s, 1H), 8.79 (s, 1H), 10.46 (s, 1H). LCMS: m/z=487.7 [M+1]; The forth-eluting enantiomer of the title compound was obtained as a solid (Isomer 4): $^1$H NMR (400 MHz, DMSO-d6) δ 1.24 (d, J=6.4 Hz, 3H), 2.62-2.70 (m, 3H), 3.01-3.07 (m, 1H), 4.50 (d, J=8.8 Hz, 1H), 7.22-7.49 (m, 7H), 7.72-7.78 (m, 2H), 7.87 (s, 1H), 8.02-8.13 (m, 2H), 8.33 (s, 1H), 8.72 (s, 1H), 8.79 (s, 1H), 10.61 (s, 1H). LCMS: m/z=487.7 [M+1].

Example 33

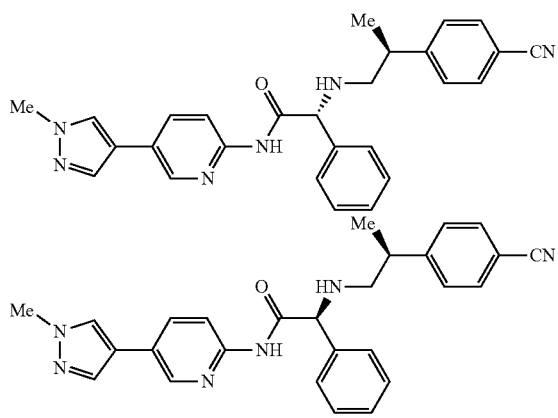

(R,S)-, (S,S)-2-(4-cyanophenyl)propyl)amino)-N-(5-(1-methyl-1H-pyrazol-4-yl)pyridin-2-yl)-2-phenylacetamide Scheme 6, Step 1. (R,S)-, (S,S)-ethyl 2-((2-(4-cyanophenyl)propyl)amino)-2-phenylacetate A mixture of ethyl 2-bromo-2-phenylacetate (9.11 g, 37.5 mmol), (S)-4-(1-aminopropan-2-yl)benzonitrile (5.0 g, 31.2 mmol) and TEA (13.1 ml, 93.7 mmol) in DMF (50 ml) was heated at 60° C. for 3 hours. The reaction mixture was poured into ice cold water (150 ml) and extracted with ethyl acetate (2×150 ml). The combined organic layers were washed with brine (150 ml), dried over anhydrous Na$_2$SO$_4$ and concentrated under reduced pressure. The resulting residue was purified by silica gel chromatography to afford a mixture of the title compounds (7.0 g, 70%) as a thick liquid. $^1$H NMR (400 MHz, DMSO-d$_6$): 1.08 (t, J=6.8 Hz, 3H), 1.16 (d, J=6.8 Hz, 3H), 2.35-2.44 (m, 1H), 2.49-2.66 (m, 1H), 2.96 (q, J=6.8 Hz, 1H), 3.96-4.06 (m, 2H), 4.32 (s, 1H), 7.26-7.42 (m, 7H), 7.74 (t, J=7.6 Hz, 2H). LCMS: m/z=323.6 [M+1].

Scheme 6, Step 2, Procedure 2. (R,S)-, (S,S)-2-(4-cyanophenyl)propyl)amino)-N-(5-(1-methyl-1H-pyrazol-4-yl)pyridin-2-yl)-2-phenylacetamide To a stirred solution of 5-(1-methyl-1H-pyrazol-4-yl)pyridin-2-amine (2.5 g, 14.4 mmol), a 1:1 mixture of (S,R)- and (S, S)-ethyl 2-((2-(4-cyanophenyl)propyl)amino)-2-phenylacetate (7.0 g, 21.7 mmol) in dry THF (50 ml) was added LiHMDS (37 ml, 1M in THF, 36.2 mmol) at 0° C. The reaction mixture was stirred at room temperature for 1 hour. After completion of the reaction, the reaction mixture was poured into ice cold water (100 ml) and extracted with ethyl acetate (2×75 ml).

The combined organic layers were washed with brine (100 ml), dried over anhydrous Na$_2$SO$_4$ and concentrated under reduced pressure. The resulting residue was purified by silica gel chromatography to afford a mixture of the title compounds (5.0 g, 51%).

The title compounds were resolved by chiral HPLC (CHIRALCEL OJ-H; 15% MeOH in liquid CO$_2$+0.1% DEA) to obtain the slower-eluting isomer (example 33, isomer 4 in tables 5 and 8 below). $^1$H NMR (400 MHz, DMSO-d6): 1.23 (d, J=6.8 Hz, 3H), 2.64-2.69 (m, 3H), 3.02 (q, J=6.8 Hz, 1H), 3.86 (s, 3H), 4.47 (d, J=7.6 Hz, 1H), 7.24-7.45 (m, 7H), 7.75 (d, J=8.4 Hz, 2H); 7.90 (s, 1H), 7.92-8.03 (m, 2H), 8.18 (s, 1H), 8.56 (d, J=1.6 Hz, 1H), 10.52 (s, —NH, 1H). LCMS: m/z=451.5 [M+1].

Example 84

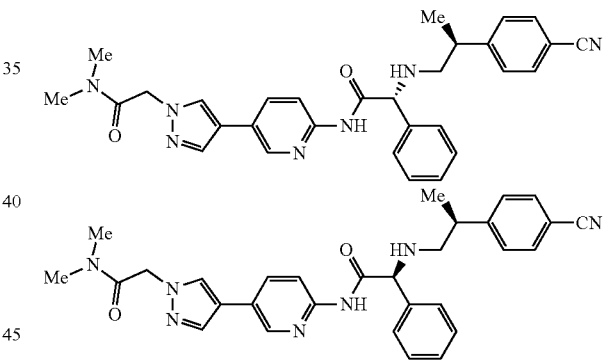

(S,S)-, (R,S)-2-((2-(4-cyanophenyl)propyl)amino)-N-(5-(1-(2-(dimethylamino)-2-oxoethyl)-1H-pyrazol-4-yl)pyridin-2-yl)-2-phenylacetamide Scheme 6, Step 2, Procedure 2. (S,S)-, (R,S)-2-((2-(4-cyanophenyl)propyl)amino)-N-(5-(1-(2-(dimethylamino)-2-oxoethyl)-1H-pyrazol-4-yl)pyridin-2-yl)-2-phenylacetamide To a stirred solution of 2-(4-(6-aminopyridin-3-yl)-1H-pyrazol-1-yl)-N,N-dimethylacetamide (2.0 g, 8.15 mmol), a 1:1 mixture of (S,R)- and (S,S)-ethyl 2-((2-(4-cyanophenyl)propyl)amino)-2-phenylacetate (3.94 g, 12.23 mmol) in dry THF (30 ml) was added LiHMDS (16.3 ml, 1M in THF, 16.30 mmol) at 0° C. The reaction mixture was stirred at room temperature for 1 hour. After completion of the reaction, the reaction mixture was poured into ice cold water (50 ml) and extracted with ethyl acetate (2×100 ml). The combined organic layers were washed with brine (50 ml), dried over anhydrous sodium sulphate and concentrated under reduced pressure. The resulting residue was purified by silica gel chromatography to afford a mixture of the title compounds (2.5 g, 59%).

The mixture was resolved by Chiral HPLC (CHIRALCEL OJ-H; 15% MeOH in Liquid $CO_2$+0.1% DEA) to furnish the enantiopure compounds. The slower-eluting enantiomer (example 84, isomer 2 in tables 5 and 8 below) of the title compound was obtained as a solid. $^1$H NMR (400 MHz, DMSO-d6) δ 1.24 (d, J=6.8 Hz, 3H), 2.67 (d, J=6.4 Hz, 3H), 2.87 (s, 3H), 3.01-3.05 (m, 4H), 4.48 (d, J=7.2 Hz, 1H), 5.14 (s, 2H), 7.25-7.46 (m, 7H), 7.76 (d, J=8.0 Hz, 2H), 7.93-8.05 (m, 3H), 8.12 (s, 1H), 8.59 (d, J=1.6 Hz, 1H), 10.50 (s, 1H). LCMS: m/z=522.61 [M+1].

Example 104

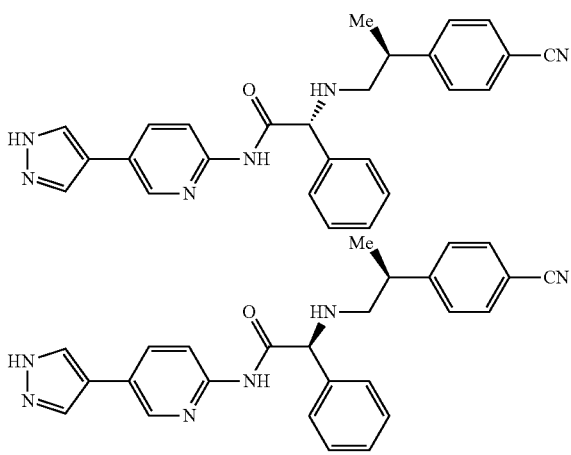

(R,S)-, (S,S)—N-(5-(1H-pyrazol-4-yl)pyridin-2-yl)-2-((2-(4-cyanophenyl)propyl)amino)-2-phenylacetamide Scheme 6, Step 2, Procedure 2. (R,S)-, (S,S)—N-(5-(1H-pyrazol-4-yl)pyridin-2-yl)-2-((2-(4-cyanophenyl)propyl)amino)-2-phenylacetamide To a stirred solution of tert-butyl 4-(6-aminopyridin-3-yl)-1H-pyrazole-1-carboxylate (0.8 g, 3.07 mmol), a 1:1 mixture of (S,R)- and (S,S)-ethyl 2-((4-cyanophenethyl)amino)-2-phenylacetate (1.38 g, 4.30 mmol) in dry THF (20 ml) was added LiHMDS (7.6 ml, 1M in THF, 7.69 mmol) at 0° C. The reaction mixture was stirred at room temperature for 1 hour. After completion of the reaction, the reaction mixture was poured into ice cold water (50 ml) and extracted with ethyl acetate (2×50 ml). The combined organic layers were washed with brine (50 ml), dried over anhydrous sodium sulphate and concentrated under reduced pressure. The resulting residue was purified by silica gel chromatography to afford a mixture of the title compounds (0.52 g, 40%).

The mixture was resolved by Chiral HPLC (CHIRALPAK IG; 100% (70:30 MeOH:ACN) to furnish the enantiopure compounds. The slower-eluting enantiomer (example 104, isomer 2 in tables 5 and 8 below) of the title compound was obtained as a solid. $^1$H NMR (400 MHz, DMSO-d6) δ 1.24 (d, J=8.0 Hz, 3H), 2.66 (s, 3H), 3.01-3.06 (s, 1H), 4.49 (s, 1H), 7.25-7.46 (m, 7H), 7.76 (d, J=8.0 Hz, 2H), 7.97-8.04 (m, 3H), 8.25 (s, 1H), 8.62 (s, 1H), 10.51 (s, 1H), 13.02 (s, 1H). LCMS: m/z=437.46 [M+1].

Example 127

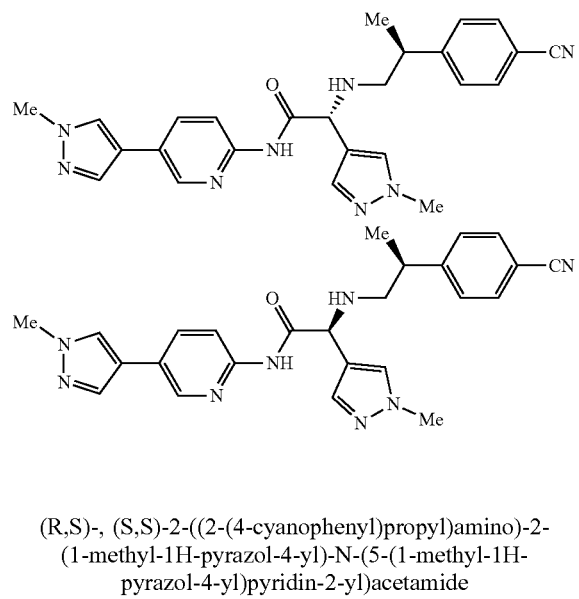

(R,S)-, (S,S)-2-((2-(4-cyanophenyl)propyl)amino)-2-(1-methyl-1H-pyrazol-4-yl)-N-(5-(1-methyl-1H-pyrazol-4-yl)pyridin-2-yl)acetamide Scheme 6, Step 2, Procedure 2. (R,S)-, (S,S)-((2-(4-cyanophenyl)propyl)amino)-2-(1-methyl-1H-pyrazol-4-yl)-N-(5-(1-methyl-1H-pyrazol-4-yl)pyridin-2-yl)acetamide To a stirred solution of 5-(1-methyl-1H-pyrazol-4-yl)pyridin-2-amine (1.5 g, 8.61 mmol), a 1:1 mixture of (S,R)- and (S,S)-ethyl 2-((2-(4-cyanophenyl)propyl)amino)-2-(1-methyl-1H-pyrazol-4-yl)acetate (3.37 g, 10.33 mmol) in dry THF (30 ml) was added LiHMDS (22.0 ml, 1M in THF, 21.52 mmol) at 0° C. The reaction mixture was stirred at room temperature for 1 hour. After completion of the reaction, the reaction mixture was poured into ice cold water (50 ml) and extracted with ethyl acetate (2×100 ml). The combined organic layers were washed with brine (50 ml), dried over anhydrous sodium sulphate and concentrated under reduced pressure. The resulting residue was purified by silica gel chromatography to afford a mixture of the title compounds (2.9 g, 74%).

The mixture was resolved by Chiral HPLC (CHIRALCEL OJ-H; 10% MeOH in Liquid $CO_2$+0.1% DEA) to furnish the enantiopure compounds. The slower-eluting enantiomer (example 127, isomer 4 in tables 5 and 8 below) of the title compound was obtained as a solid. $^1$H NMR (400 MHz, DMSO-d6) δ 1.24 (d, J=6.8 Hz, 3H), 2.68 (s, 2H), 2.97-3.03 (s, 1H), 3.57 (s, 1H), 3.77 (s, 3H), 3.87 (s, 3H), 4.36 (s, 1H), 7.34 (s, 1H), 7.45 (d, J=8.4 Hz, 2H), 7.59 (s, 1H), 7.75 (d, J=8.4 Hz, 2H), 7.91 (s, 1H), 7.95 (dd, J=2.0 Hz, 8.4 Hz, 2H), 8.18 (s, 1H), 8.57 (d, J=1.6 Hz, 1H), 10.36 (s, 1H). LCMS: m/z=455.51 [M+1].

The following compounds were prepared using similar procedures to those described for Examples 19, 22, 100, 20, 33, 84, 104, and 127 using the appropriate starting materials.

TABLE 5

| Example No. | Structure (Methods and Schemes for Preparation) | IUPAC Name | Exact Mass [M + 1] | Chiral Column and Mobile Phase |
|---|---|---|---|---|
| 21 Isomer 1 Isomer 2 | | (S)- and (R)-N-(4-(1-acetylpiperidin-4-yl)phenyl)-2-((4-chlorophenethyl)amino)-2-phenylacetamide | Calc'd 490.2, Found 490.5 and 490.5 | CHIRALCEL OJ-H; 18% MeOH in Liquid $CO_2$ + 0.1% DEA |
| 22 Isomer 1 Isomer 2 | | (S)- and (R)-2-((4-cyanophenethyl)amino)-N-(5-(1-methyl-1H-pyrazol-4-yl)pyridin-2-yl)-2-phenylacetamide | Calc'd 437.2, Found 437.3 and 437.3 | CHIRALCEL OJ-H; 15% (50:50 ACN:IPA) in Liquid $CO_2$ + 0.1% DEA |
| 23 Isomer 1 Isomer 2 | | (S)- and (R)-2-((4-cyanophenethyl)amino)-N-(2-(1-methyl-1H-pyrazol-4-yl)pyrimidin-5-yl)-2-phenylacetamide | Calc'd 438.2, Found 438.3 and 438.3 | CHIRALCEL OJ-H; 20% MeOH in Liquid $CO_2$ + 0.1% DEA |
| 24 Isomer 1 Isomer 2 | | (S)- and (R)-2-((4-cyanophenethyl)amino)-N-(2-methoxy-4-(1-methyl-1H-pyrazol-4-yl)phenyl)-2-phenylacetamide | Calc'd 466.2, Found 466.2 and 466.2 | CHIRALPAK AD-H; 35% MeOH in Liquid $CO_2$ + 0.1% DEA |
| 25 Isomer 1 Isomer 2 | | (S)- and (R)-2-((4-cyanophenethyl)amino)-N-(3-methoxy-4-(1-methyl-1H-pyrazol-4-yl)phenyl)-2-phenylacetamide | Calc'd 466.2, Found 466.5 and 466.5 | CHIRALPAK AD-H; 25% MeOH in Liquid $CO_2$ + 0.1% DEA |
| 26 Isomer 1 Isomer 2 | | (S)- and (R)-N-(2-chloro-4-(1-methyl-1H-pyrazol-4-yl)phenyl)-2-((4-cyano-phenethyl)amino)-2-phenylacetamide | Calc'd 470.2, Found 470.2 and 470.2 | CHIRALPAK IB; 20% MeOH in Liquid $CO_2$ + 0.1% DEA |

TABLE 5-continued

| Example No. | Structure (Methods and Schemes for Preparation) | IUPAC Name | Exact Mass [M + 1] | Chiral Column and Mobile Phase |
|---|---|---|---|---|
| 27 Isomer 1 Isomer 2 | | (S)- and (R)-N-(3-chloro-4-(1-methyl-1H-pyrazol-4-yl)phenyl)-2-((4-cyano-phenethyl)amino)-2-phenylacetamide | Calc'd 470.2, Found 470.5 and 470.5 | CHIRALPAK AD-H; 38% MeOH in Liquid CO$_2$ + 0.1% DEA |
| 28 Isomer 1 Isomer 2 | | (S)- and (R)-2-((4-cyanophenethyl)amino)-N-(5-(4-methyl-1H-imidazol-1-yl)pyridin-2-yl)-2-phenylacetamide | Calc'd 437.2, Found 437.6 and 437.6 | CHIRALCEL OJ-H; 20% MeOH in liquid CO$_2$ + 0.1% DEA |
| 29 Isomer 1 Isomer 2 | | (S)- and (R)-2-((4-cyano-2-fluorophenethyl)amino)-N-(5-(1-methyl-1H-pyrazol-4-yl)pyridin-2-yl)-2-phenylacetamide | Calc'd 455.2, Found 455.4 and 455.4 | CHIRALCEL OX-H; 40% (50:50 MeOH:IPA) in hexanes + 0.1% DEA |
| 30 Isomer 1 Isomer 2 | | (S)- and (R)-2-((4-cyanophenethyl)amino)-2-phenyl-N-(1-(tetrahydro-2H-pyran-4-yl)-1H-pyrazol-3-yl)acetamide | Calc'd 430.2, Found 430.3 and 430.2 | CHIRALCEL OX-H; 18% (50:50 ACN:MeOH) in Liquid CO$_2$ + 0.1% DEA |
| 31 Isomer 1 Isomer 2 | | (S)- and (R)-2-((4-cyanophenethyl)amino)-N-(5-(3-methoxyazetidin-1-yl)pyridin-2-yl)-2-phenylacetamide | Calc'd 442.5, Found 442.4 and 442.4 | CHIRALCEL OX-H; 60% (50:50 MeOH:IPA) in hexanes + 0.1% DEA |
| 32 Isomer 1 Isomer 2 Isomer 3 Isomer 4 | | (S, S)-, (S, R)-, (R, R)- and (R, S)-2-((2-(4-cyanophenyl)propyl)amino)-N-(5-(3-methoxyazetidin-1-yl)pyridin-2-yl)-2-phenylacetamide | Calc'd 456.3, Found 456.3, 456.3, 456.7 and 456.7 | 1-CHIRALCEL OX-H; 25% (70:30 IPA:ACN) in hexanes + 0.1% DEA 2-CHIRALCEL OX-H; 50% (50:50 MeOH:IPA) in hexanes + 0.1% DEA |

TABLE 5-continued

| Example No. | Structure (Methods and Schemes for Preparation) | IUPAC Name | Exact Mass [M + 1] | Chiral Column and Mobile Phase |
|---|---|---|---|---|
| 33 Isomer 1 Isomer 2 Isomer 3 Isomer 4 | | (S, S)-, (S, R)-, (R, R)- and (R, S)-2-((2-(4-cyanophenyl)propyl)amino)-N-(5-(1-methyl-1H-pyrazol-4-yl)pyridin-2-yl)-2-phenylacetamide | Calc'd 451.2, Found 451.3, 451.3, 449.1 and 451.2 | 1-CHIRALPAK IC; 40% (50:50 IPA:MeOH) in hexanes + 0.1% DEA 2-CHIRALCEL OJ-H; 15% MeOH in Liquid CO2 + 0.1% DEA |
| 34 Isomer 1 Isomer 2 | | (S)- and (R)-2-((4-cyanophenethyl)amino)-2-phenyl-N-(5-phenylpyridin-2-yl)acetamide | Calc'd 433.2, Found 433.2 and 433.2 | CHIRALPAK IC; 25% MeOH in Liquid CO$_2$ + 0.1% DEA |
| 35 Isomer 1 Isomer 2 | | (S)- and (R)-2-((4-cyanophenethyl)amino)-2-phenyl-N-(6-(pyrrolidin-1-yl)pyridin-3-yl)acetamide | Calc'd 426.2, Found 426.2 and 426.2 | CHIRALPAK IB; 30% MeOH in Liquid CO$_2$ + 0.1% DEA |
| 36 Isomer 1 Isomer 2 | | (S)- and (R)-2-((4-cyanophenethyl)amino)-N-(6-(4-methylpiperazin-1-yl)pyridin-3-yl)-2-phenylacetamide | Calc'd 455.3, Found 455.5 and 455.5 | CHIRALCEL OX-H; 20% (50:50 ACN:IPA) in Liquid CO$_2$ + 0.1% DEA |
| 37 Isomer 1 Isomer 2 | | (S)- and (R)-2-((4-cyanophenethyl)amino)-2-phenyl-N-(5-(pyrrolidin-1-yl)pyridin-2-yl)acetamide | Calc'd 426.2, Found 426.3 and 426.3 | CHIRALCEL OJ-H; 15% MeOH in Liquid CO$_2$ + 0.1% DEA |
| 38 Isomer 1 Isomer 2 | | (S)- and (R)-2-((4-cyanophenethyl)amino)-N-(5-(4,4-difluoropiperidin-1-yl)pyridin-2-yl)-2-phenylacetamide | Calc'd 476.2, Found 476.5 and 476.3 | CHIRALCEL OX-H; 25% (30:70 ACN:IPA) in hexanes + 0.1% DEA |

TABLE 5-continued

| Example No. | Structure (Methods and Schemes for Preparation) | IUPAC Name | Exact Mass [M + 1] | Chiral Column and Mobile Phase |
|---|---|---|---|---|
| 39 Isomer 1 Isomer 2 Isomer 3 Isomer 4 | | (S, S)-, (S, R)-, (R, R)- and (R, S)-2-((2-(4-cyanophenyl)propyl)amino)-N-(6-methyl-5-(1-methyl-1H-pyrazol-4-yl)pyridin-2-yl)-2-phenylacetamide | Calc'd 465.3, Found 465.4, 465.4, 465.6 and 465.7 | 1-CHIRALPAK IC; 40% (50:50 MeOH:IPA) in hexanes + 0.1% DEA 2-CHIRALCEL OX-H; 30% (30:70 ACN:IPA) in hexanes + 0.1% DEA 3-CHIRALPAK AD-H; 20% MeOH in Liquid $CO_2$ + 0.1% DEA |
| 40 Isomer 1 Isomer 2 | | (S)- and (R)-2-((4-cyanophenethyl)amino)-2-phenyl-N-(5-(4-(2,2,2-trifluoroethyl)piperazin-1-yl)pyridin-2-yl)acetamide | Calc'd 523.2, Found 523.4 and 523.4 | CHIRALCEL OX-H; 15% (50:50 ACN:IPA) in Liquid $CO_2$ + 0.1% DEA |
| 41 Isomer 1 Isomer 2 | | (S)- and (R)-2-((4-cyano-2-methylphenethyl)amino)-N-(5-(1-methyl-1H-pyrazol-4-yl)pyridin-2-yl)-2-phenylacetamide | Calc'd 451.2, Found 451.5 and 451.4 | CHIRALCEL OX-H; 55% (50:50 MeOH:IPA) in hexanes + 0.1% DEA |
| 42 Isomer 1 Isomer 2 | | (S)- and (R)-2-((4-cyanophenethyl)amino)-N-(5-cyclopropylpyridin-2-yl)-2-phenylacetamide | Calc'd 397.2, Found 397.4 and 397.4 | CHIRALCEL OJ-H; 10% (50:50 ACN:IPA) in Liquid $CO_2$ + 0.1% DEA |
| 43 Isomer 1 Isomer 2 | | (S)- and (R)-N-(3-chloro-5-(1-methyl-1H-pyrazol-4-yl)pyridin-2-yl)-2-((4-cyanophenethyl)amino)-2-phenylacetamide | Calc'd 471.2, Found 471.5 and 471.5 | CHIRALCEL OX-H; 70% (25:75 MeOH:IPA) in hexanes + 0.1% DEA |
| 44 Isomer 1 Isomer 2 | | (S)- and (R)-2-((4-cyanophenethyl)amino)-N-(5-(4-methyl-3-oxopiperazin-1-yl)pyridin-2-yl)-2-phenylacetamide | Calc'd 469.6, Found 469.7 and 469.8 | CHIRALPAK IC; 45% (30:70 ACN:IPA) in hexanes + 0.1% DEA |

TABLE 5-continued

| Example No. | Structure (Methods and Schemes for Preparation) | IUPAC Name | Exact Mass [M + 1] | Chiral Column and Mobile Phase |
|---|---|---|---|---|
| 45 Isomer 1 Isomer 2 | | (S)- and (R)-2-((4-chlorophenethyl)amino)-N-(5-(4-methyl-3-oxopiperazin-1-yl)pyridin-2-yl)-2-phenylacetamide | Calc'd 479.2, Found 478.8 and 478.7 | CHIRALCEL OX-H; 60% (50:50 MeOH:IPA) in hexanes + 0.1% DEA |
| 46 Isomer 1 Isomer 2 | | (S)- and (R)-2-((4-cyanophenethyl)amino)-N-(5-cyclobutylpyridin-2-yl)-2-phenylacetamide | Calc'd 411.2, Found 411.3 and 411.3 | CHIRALPAK IB; 10% MeOH in Liquid $CO_2$ + 0.1% DEA |
| 47 Isomer 1 Isomer 2 Isomer 3 Isomer 4 | | (S, S)-, (S, R)-, (R, R)- and (R, S)-2-((2-(4-cyanophenyl)propyl)amino)-N-(5-(1-(2-cyanopropan-2-yl)-1H-pyrazol-4-yl)pyridin-2-yl)-2-phenylacetamide | Calc'd 504.2, Found 504.4, 504.7, 504.7 and 504.6 | 1-CHIRALPAK IC;20% MeOH in Liquid $CO_2$ + 0.1% DEA 2-CHIRALPAK AD-H; 35% MeOH in Liquid $CO_2$ + 0.1% DEA |
| 48 Isomer 1 Isomer 2 | | (S)- and (R)-N-(5-(1-methyl-1H-pyrazol-4-yl)pyridin-2-yl)-2-((4-methylphenethyl)amino)-2-phenylacetamide | Calc'd 426.2, Found 426.4 and 426.4 | CHIRALCEL OJ-H; 30% MeOH in Liquid $CO_2$ + 0.1% DEA |
| 49 Isomer 1 Isomer 2 | | (S)- and (R)-2-((4-cyanophenethyl)amino)-N-(5-(4-methylpiperazin-1-yl)pyridin-2-yl)-2-phenylacetamide | Calc'd 455.3, Found 455.6 and 455.5 | CHIRALCEL OJ-H; 18% MeOH in Liquid $CO_2$ + 0.1% DEA |
| 50 Isomer 1 Isomer 2 | | (S)- and (R)-2-((4-cyanophenethyl)amino)-2-phenyl-N-(1-phenyl-1H-pyrazol-3-yl)acetamide | Calc'd 422.3, Found 422.6 and 422.3 | CHIRALCEL OJ-H; 30% MeOH in Liquid $CO_2$ + 0.1% DEA |

TABLE 5-continued

| Example No. | Structure (Methods and Schemes for Preparation) | IUPAC Name | Exact Mass [M + 1] | Chiral Column and Mobile Phase |
|---|---|---|---|---|
| 51 Isomer 1 Isomer 2 | | (S)- and (R)-2-((2-chloro-4-cyanophenethyl)amino)-N-(5-(1-methyl-1H-pyrazol-4-yl)pyridin-2-yl)-2-phenylacetamide | Calc'd 471.2, Found 471.3 and 471.3 | CHIRALCEL OX-H; 50% (50:50 WA:MeOH) in hexanes + 0.1% DEA |
| 52 Isomer 1 Isomer 2 Isomer 3 Isomer 4 | | (S, S)-, (S, R)-, (R, R)- and (R, S)-2-((2-(4-cyanophenyl)propyl)amino)-N-(5-(1-cyclobutyl-1H-pyrazol-4-yl)pyridin-2-yl)-2-phenylacetamide | Calc'd 491.3, Found 491.6, 491.5, 491.6 and 491.6 | 1-CHIRALCEL OX-H; 20% (50:50; ACN:IPA) in Liquid $CO_2$ + 0.1% DEA 2-CHIRALCEL OX-H; 45% (50:50 MeOH:IPA) in hexanes + 0.1% DEA |
| 53 Isomer 1 Isomer 2 | | (S)- and (R)-2-((4-cyanophenethyl)amino)-N-(5-(4-methoxy-4-methylpiperidin-1-yl)pyridin-2-yl)-2-phenylacetamide | Calc'd 484.3, Found 484.5 and 484.6 | CHIRALCEL OX-H; 55% (50:50 MeOH:IPA) in hexanes + 0.1% DEA |
| 54 Isomer 1 Isomer 2 Isomer 3 Isomer 4 | | (S, S)-, (S, R)-, (R, R)- and (R, S)-N-(5-(1-(tert-butyl)-1H-pyrazol-4-yl)pyridin-2-yl)-2-((2-(4-cyanophenyl)propyl)amino)-2-phenylacetamide | Calc'd 493.3, Found 493.6, 493.4, 493.7 and 493.7 | 1-CHIRALCEL OX-H; 35% (50:50 IPA:MeOH) in hexanes + 0.1% DEA 2-CHIRALPAK IC; 30% (50:50 IPA:MeOH) in hexanes + 0.1% DEA |
| 55 Isomer 1 Isomer 2 | | (S)- and (R)-2-((4-chlorophenethyl)amino)-N-(5-(1-methyl-1H-pyrazol-4-yl)pyridin-2-yl)-2-phenylacetamide | Calc'd 446.2, Found 446.5 and 446.5 | CHIRALCEL OJ-H; 30% MeOH in Liquid $CO_2$ + 0.1% DEA |
| 56 Isomer 1 Isomer 2 | | (S)- and (R)-2-((4-cyanophenethyl)amino)-N-(5-(1-methyl-1H-pyrazol-4-yl)pyrazin-2-yl)-2-phenylacetamide | Calc'd 438.2, Found 438.5 and 438.5 | CHIRALPAK IB; 45% (50:50 MeOH:IPA) in hexanes + 0.1% DEA |

TABLE 5-continued

| Example No. | Structure (Methods and Schemes for Preparation) | IUPAC Name | Exact Mass [M + 1] | Chiral Column and Mobile Phase |
|---|---|---|---|---|
| 57 Isomer 1 Isomer 2 | | (S)- and (R)-2-((4-cyanophenethyl)amino)-N-(6-(1-methyl-1H-pyrazol-4-yl)pyridazin-3-yl)-2-phenylacetamide | Calc'd 438.2, Found 438.3 and 438.3 | CHIRALPAK IC; 35% (50:50 ACN:IPA) in hexanes + 0.1% DEA |
| 58 Isomer 1 Isomer 2 | | (S)- and (R)-2-((4-fluorophenethyl)amino)-N-(5-(1-methyl-1H-pyrazol-4-yl)pyridin-2-yl)-2-phenylacetamide | Calc'd 430.2, Found 430.3 and 430.5 | CHIRALCEL OJ-H; 20% MeOH in Liquid $CO_2$ + 0.1% DEA |
| 59 Isomer 1 Isomer 2 Isomer 3 Isomer 4 | | (S, S)-, (S, R)-, (R, R)- and (R, S)-N-(5-(4-(tert-butyl)-1H-imidazol-1-yl)pyridin-2-yl)-2-((2-(4-cyanophenyl)propyl)amino)-2-phenylacetamide | Calc'd 493.3, Found 493.7, 493.6, 493.7 and 493.8 | 1-CHIRALCEL OJ-H; 10% MeOH in Liquid $CO_2$ + 0.1% DEA 2-CHIRALCEL OX-H; 25% (70:30 IPA:ACN) in hexanes + 0.1% DEA |
| 60 Isomer 1 Isomer 2 | | (S)- and (R)-2-((4-cyanophenethyl)amino)-N-(5-(3-methyl-5,6-dihydro-[1,2,4]triazolo[4,3-a]pyrazin-7(8H)-yl)pyridin-2-yl)-2-phenylacetamide | Calc'd 493.2, Found 493.2 and 493.4 | CHIRALCEL OX-H; 100% (50:50 MeOH:IPA) + 0.1% DEA |
| 61 Isomer 1 Isomer 2 Isomer 3 Isomer 4 | | (S, S)-, (S, R)-, (R, R)- and (R, S)-2-((2-(4-cyanophenyl)propyl)amino)-N-(5-(3-methyl-1H-pyrazol-1-yl)pyridin-2-yl)-2-phenylacetamide | Calc'd 451.2, Found 451.2, 451.2, 451.2 and 451.2 | 1-CHIRALCEL OX-H; 35% (50:50 MeOH:IPA) in hexanes + 0.1% DEA 2-CHIRALCEL OX-H; 15% (50:50 MeOH:IPA) in hexanes + 0.1% DEA |
| 62 Isomer 1 Isomer 2 Isomer 3 Isomer 4 | | (S, S)-, (S, R)-, (R, R)- and (R, S)-2-((2-(4-cyanophenyl)propyl)amino)-N-(5-(4-methyl-1H-pyrazol-1-yl)pyridin-2-yl)-2-phenylacetamide | Calc'd 451.2, Found 451.4, 451.2, 451.3 and 451.3 | 1-CHIRALCEL OX-H; 20% MeOH in Liquid $CO_2$ + 0.1% DEA 2-CHIRALPAK IC; 15% (30:70 ACN:IPA) in hexanes + 0.1% DEA |

TABLE 5-continued

| Example No. | Structure (Methods and Schemes for Preparation) | IUPAC Name | Exact Mass [M + 1] | Chiral Column and Mobile Phase |
|---|---|---|---|---|
| 63 Isomer 1 Isomer 2 | 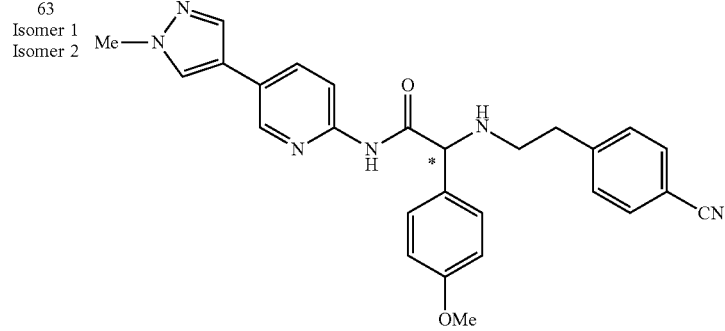 | (S)- and (R)-2-((4-cyanophenethyl)amino)-2-(4-methoxyphenyl)-N-(5-(1-methyl-1H-pyrazol-4-yl)pyridin-2-yl)acetamide | Calc'd 467.2, Found 467.5 and 467.6 | CHIRALPAK IC; 37% MeOH in Liquid $CO_2$ + 0.1% DEA |
| 64 Isomer 1 Isomer 2 | 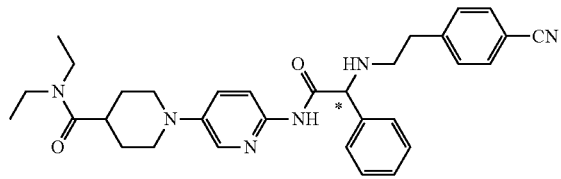 [SMILES: CCN(CC)C(=O)C1CCN(c2ccc(NC(=O)C(NCCc3ccc(C#N)cc3)c3ccccc3)nc2)CC1] | (S)- and (R)-1-(6-(2-((4-cyanophenethyl)amino)-2-phenylacetamido)pyridin-3-yl)-N,N-diethylpiperidine-4-carboxamide | Calc'd 539.3, Found 539.9 and 539.9 | CHIRALPAK AD-H; 35% (50:50 ACN:IPA) in Liquid $CO_2$ + 0.3% DEA |
| 65 Isomer 1 Isomer 2 | 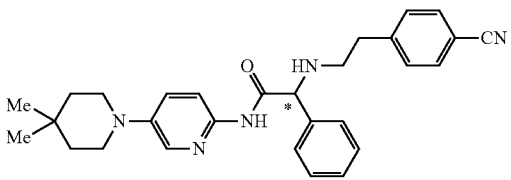 [SMILES: CC1(C)CCN(c2ccc(NC(=O)C(NCCc3ccc(C#N)cc3)c3ccccc3)nc2)CC1] | (S)- and (R)-2-((4-cyanophenethyl)amino)-N-(5-(4,4-dimethylpiperidin-1-yl)pyridin-2-yl)-2-phenylacetamide | Calc'd 468.3, Found 468.5 and 468.6 | CHIRALCEL OX-H; 35% (50:50 MeOH:IPA) in hexanes + 0.1% DEA |
| 66 Isomer 1 Isomer 2 | 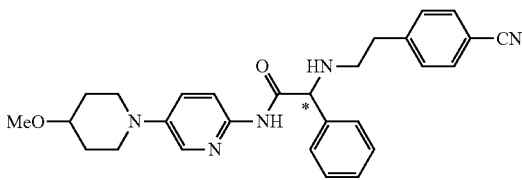 [SMILES: COC1CCN(c2ccc(NC(=O)C(NCCc3ccc(C#N)cc3)c3ccccc3)nc2)CC1] | (S)- and (R)-2-((4-cyanophenethyl)amino)-N-(5-(4-methoxypiperidin-1-yl)pyridin-2-yl)-2-phenylacetamide | Calc'd 470.3, Found 470.5 and 470.5 | CHIRALCEL OX-H; 45% (50:50 MeOH:IPA) in hexanes + 0.1% DEA |
| 67 Isomer 1 Isomer 2 | 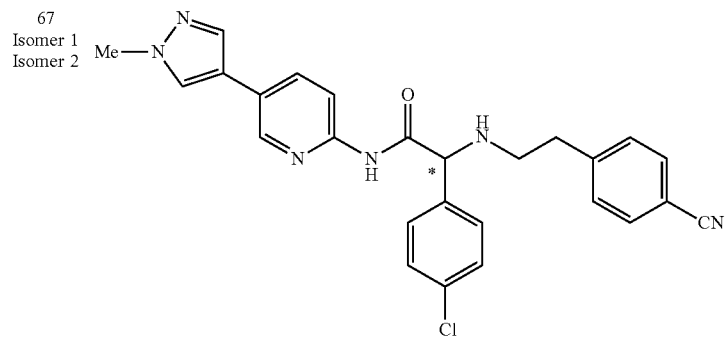 | (S)- and (R)-2-(4-chlorophenyl)-2-((4-cyanophenethyl)amino)-N-(5-(1-methyl-1H-pyrazol-4-yl)pyridin-2-yl)acetamide | Calc'd 471.2, Found 471.5 and 471.3 | CHIRALCEL OX-H; 35% (30:70 ACN:IPA) in hexanes + 0.1% DEA |
| 68 Isomer 1 Isomer 2 | 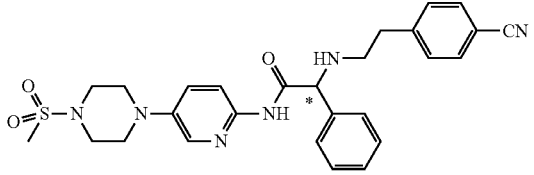 [SMILES: CS(=O)(=O)N1CCN(c2ccc(NC(=O)C(NCCc3ccc(C#N)cc3)c3ccccc3)nc2)CC1] | (S)- and (R)-2-((4-cyanophenethyl)amino)-N-(5-(4-(methylsulfonyl)piperazin-1-yl)pyridin-2-yl)-2-phenylacetamide | Calc'd 519.2, Found 519.5 and 519.6 | CHIRALPAK IC; 35% (70:30 IPA:ACN) in hexanes + 0.1% DEA |

TABLE 5-continued

| Example No. | Structure (Methods and Schemes for Preparation) | IUPAC Name | Exact Mass [M + 1] | Chiral Column and Mobile Phase |
|---|---|---|---|---|
| 69 Isomer 1 Isomer 2 | | (S)- and (R)-2-((4-chlorophenethyl)amino)-N-(5-(4-methylpiperazin-1-yl)pyridin-2-yl)-2-phenylacetamide | Calc'd 464.2, Found 464.5 and 464.5 | CHIRALCEL OX-H; 35% (50:50 MeOH:IPA) in hexanes + 0.1% DEA |
| 70 Isomer 1 Isomer 2 | | (S)- and (R)-2-((4-cyanophenethyl)amino)-2-(3-methoxyphenyl)-N-(5-(1-methyl-1H-pyrazol-4-yl)pyridin-2-yl)acetamide | Calc'd 467.2, Found 467.3 and 467.3 | CHIRALCEL OJ-H; 20% MeOH in Liquid $CO_2$ + 0.1% DEA |
| 71 Isomer 1 Isomer 2 | | (S)- and (R)-2-((4-cyanophenethyl)amino)-N-(5-(4-methyl-5-oxo-1,4-diazepan-1-yl)pyridin-2-yl)-2-phenylacetamide | Calc'd 483.2, Found 483.6 and 483.6 | CHIRALCEL OJ-H; 35% MeOH in Liquid $CO_2$ + 0.1% DEA |
| 72 Isomer 1 Isomer 2 | | (S)- and (R)-N-(5-(4-acetylpiperazin-1-yl)pyridin-2-yl)-2-((4-cyanophenethyl)amino)-2-phenylacetamide | Calc'd 483.2, Found 483.4 and 483.6 | CHIRALCEL OX-H; 55% (50:50 MeOH:IPA) in hexanes + 0.1% DEA |
| 73 Isomer 1 Isomer 2 | | (S)- and (R)-2-((4-cyanophenethyl)amino)-N-(5-(2-methoxyethoxy)pyridin-2-yl)-2-phenylacetamide | Calc'd 438.2, Found 438.4 and 438.5 | CHIRALCEL OX-H; 25% MeOH in Liquid $CO_2$ + 0.1% DEA |
| 74 Isomer 1 Isomer 2 | | (S)- and (R)-2-((4-cyanophenethyl)amino)-N-(4-fluoro-5-(1-methyl-1H-pyrazol-4-yl)pyridin-2-yl)-2-phenylacetamide | Calc'd 455.2, Found 455.7 and 455.3 | CHIRALCEL OJ-H; 10% (50:50 MeOH:IPA) in Liquid $CO_2$ + 0.1% DEA |

TABLE 5-continued

| Example No. | Structure (Methods and Schemes for Preparation) | IUPAC Name | Exact Mass [M + 1] | Chiral Column and Mobile Phase |
|---|---|---|---|---|
| 75 Isomer 1 Isomer 2 | 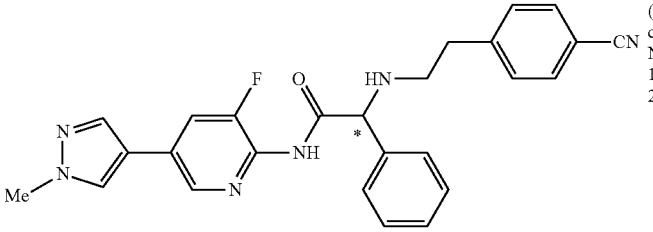 | (S)- and (R)-2-((4-cyanophenethyl)amino)-N-(3-fluoro-5-(1-methyl-1H-pyrazol-4-yl)pyridin-2-yl)-2-phenylacetamide | Calc'd 455.2, Found 455.7 and 455.3 | CHIRALCEL OX-H; 60% (30:70 ACN:IPA) in hexanes + 0.1% DEA |
| 76 Isomer 1 Isomer 2 | 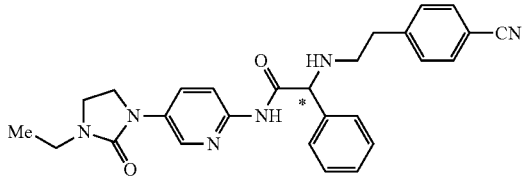 [SMILES: CCN1CCN(c2ccc(NC(=O)C(NCCc3ccc(C#N)cc3)c3ccccc3)nc2)C1=O] | (S)- and (R)-2-((4-cyanophenethyl)amino)-N-(5-(3-ethyl-2-oxoimidazolidin-1-yl)pyridin-2-yl)-2-phenylacetamide | Calc'd 469.2, Found 469.6 and 469.6 | CHIRALCEL OJ-H; 20% MeOH in Liquid $CO_2$ + 0.1% DEA |
| 77 Isomer 1 Isomer 2 | 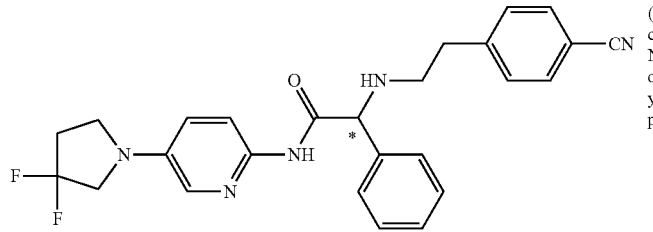 | (S)- and (R)-2-((4-cyanophenethyl)amino)-N-(5-(3,3-difluoropyrrolidin-1-yl)pyridin-2-yl)-2-phenylacetamide | Calc'd 462.2, Found 462.7 and 462.7 | CHIRALCEL OX-H; 25% (70:30 IPA:ACN) in hexanes + 0.1% DEA |
| 78 Isomer 1 Isomer 2 | 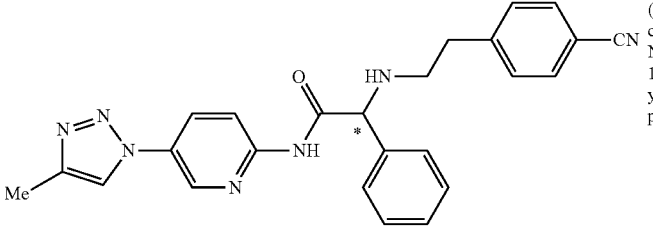 | (S)- and (R)-2-((4-cyanophenethyl)amino)-N-(5-(4-methyl-1H-1,2,3-triazol-1-yl)pyridin-2-yl)-2-phenylacetamide | Calc'd 438.2, Found 438.5 and 438.4 | CHIRALCEL OX-H; 15% MeOH in Liquid $CO_2$ + 0.1% DEA |
| 79 Isomer 1 Isomer 2 | 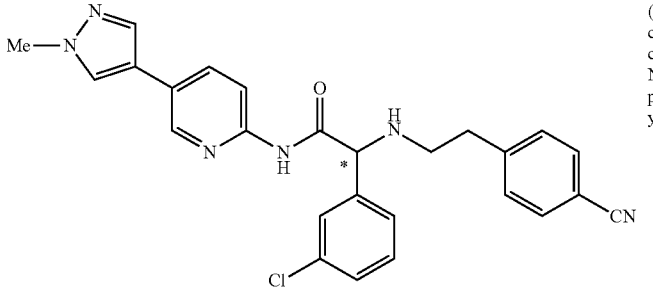 | (S)- and (R)-2-(3-chlorophenyl)-2((4-cyanophenethyl)amino)-N-(5-(1-methyl-1H-pyrazol-4-yl)pyridin-2-yl)acetamide | Calc'd 471.2, Found 471.4 and 471.5 | CHIRALCEL OX-H; 20% (70:30 IPA:ACN) in hexanes + 0.1% DEA |
| 80 Isomer 1 Isomer 2 | 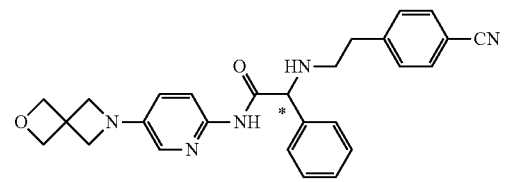 [SMILES: N#Cc1ccc(CCNC(C(=O)Nc2ccc(N3CC4(COC4)C3)cn2)c2ccccc2)cc1] | (S)- and (R)-N-(5-(2-oxa-6-azaspiro[3.3]heptan-6-yl)pyridin-2-yl)-2-((4-cyanophenethyl)amino)-2-phenylacetamide | Calc'd 454.2, Found 454.7 and 454.7 | CHIRALCEL OX-H; 28% MeOH in Liquid $CO_2$ + 0.1% DEA |

TABLE 5-continued

| Example No. | Structure (Methods and Schemes for Preparation) | IUPAC Name | Exact Mass [M + 1] | Chiral Column and Mobile Phase |
|---|---|---|---|---|
| 81 Isomer 1 Isomer 2 | | (S)- and (R)-2-((4-cyanophenethyl)amino)-N-(5-morpholinopyridin-2-yl)-2-phenylacetamide | Calc'd 442.2, Found 442.6 and 442.6 | CHIRALCEL OJ-H; 13% MeOH in Liquid CO$_2$ + 0.1% DEA |
| 82 Isomer 1 Isomer 2 Isomer 3 Isomer 4 | | (S, S)-, (S, R)-, (R, R)- and (R, S)-2-((2-(4-cyanophenyl)propyl)amino)-N-(4-(1-methyl-1H-pyrazol-4-yl)phenyl)-2-phenylacetamide | Calc'd 450.2, Found 450.5, 450.3, 450.3 and 450.4 | 1-CHIRALPAK IC; 20% (30:70 ACN:IPA) in hexanes + 0.1% DEA 2-CHIRALCEL OJ-H; 15% (50:50 IPA:ACN) in Liquid CO$_2$ + 0.1% DEA |
| 83 Isomer 1 Isomer 2 Isomer 3 Isomer 4 | | (S, S)-, (S, R)-, (R, R)- and (R, S)-2-((2-(4-cyanophenyl)propyl)amino)-2-phenyl-N-(5-(1-(2,2,2-trifluoroEthyl)-1H-pyrazol-4-yl)pyridin-2-yl)acetamide | Calc'd 519.2, Found 519.4, 519.4, 519.3 and 519.4 | 1-CHIRALCEL OX-H; 8% MeOH in Liquid CO$_2$ + 0.1% DEA 2-CHIRALCEL OX-H; 40% (70:30 IPA:ACN) in hexanes + 0.1% DEA |
| 84 Isomer 1 Isomer 2 | | (R, S)- and (S, S)-((2-(4-cyanophenyl)propyl)amino)-N-(5-(1-(2-(dimethylamino)-2-oxoethyl)-1H-pyrazol-4-yl)pyridin-2-yl)-2-phenylacetamide | Calc'd 522.3, Found 522.8 and 522.6 | CHIRALCEL OJ-H; 15% MeOH in Liquid CO$_2$ + 0.1% DEA |
| 85 Isomer 1 Isomer 2 | | (S)- and (R)-2-((4-cyano-3-fluorophenEthyl)amino)-N-(5-(1-methyl-1H-pyrazol-4-yl)pyridin-2-yl)-2-phenylacetamide | Calc'd 455.2, Found 455.3 and 455.3 | CHIRALCEL OX-H; 30% (70:30 IPA:ACN) in hexanes + 0.1% DEA |
| 86 Racemic | | (S)- and (R)- 2-((4-cyano-2,6-difluorophenEthyl)amino)-N-(5-(1-methyl-1H-pyrazol-4-yl)pyridin-2-yl)-2-phenylacetamide | Calc'd 473.2, Found 473.3 | Racemic |

TABLE 5-continued

| Example No. | Structure (Methods and Schemes for Preparation) | IUPAC Name | Exact Mass [M + 1] | Chiral Column and Mobile Phase |
|---|---|---|---|---|
| 87 Isomer 1 Isomer 2 | | (S)- and (R)- 2-((4-cyanophenEthyl)amino)-2-(2-methoxyphenyl)-N-(5-(1-methyl-1H-pyrazol-4-yl)pyridin-2-yl)acetamide | Calc'd 467.2, Found 467.4 and 467.4 | CHIRALCEL OX-H; 20% (50:50 IPA:MeOH) in hexanes + 0.1% DEA |
| 88 Isomer 1 Isomer 2 | | (S)- and (R)- 2-(2-chlorophenyl)-2-((4-cyanophenEthyl)amino)-N-(5-(1-methyl-1H-pyrazol-4-yl)pyridin-2-yl)acetamide | Calc'd 471.2, Found 471.3 and 471.3 | CHIRALCEL OJ-H; 20% MeOH in Liquid $CO_2$ + 0.1% DEA |
| 89 Isomer 1 Isomer 2 | | (S)- and (R)- 2-((4-cyanophenEthyl)amino)-2-cyclohexyl-N-(5-(1-methyl-1H-pyrazol-4-yl)pyridin-2-yl)acetamide | Calc'd 443.3, Found 443.6 and 443.5 | CHIRALCEL OX-H; 25% (70:30 IPA:ACN) in hexanes + 0.1% DEA |
| 90 Isomer 1 Isomer 2 Isomer 3 Isomer 4 | | (S, S)-, (S, R)-, (R, R)- and (R, S)-2-((2-(4-cyano-2-fluorophenyl)propyl)amino)-N-(5-(1-methyl-1H-pyrazol-4-yl)pyridin-2-yl)-2-phenylacetamide | Calc'd 469.2, Found 469.6, 469.7, 469.7 and 469.7 | 1-CHIRALCEL OX-H; 40% (50:50 IPA:MeOH) in hexanes + 0.1% DEA 2-CHIRALCEL OJ-H; 18% MeOH in Liquid $CO_2$ + 0.1% DEA |
| 91 Isomer 1 Isomer 2 Isomer 3 Isomer 4 | | (S, S)-, (S, R)-, (R, R)- and (R, S)-2-((2-(4-cyano-3-fluorophenyl)propyl)amino)-N-(5-(1-methyl-1H-pyrazol-4-yl)pyridin-2-yl)-2-phenylacetamide | Calc'd 469.2, Found 469.5, 469.5, 469.5 and 469.4 | 1-CHIRALCEL OX-H; 35% (50:50 IPA:MeOH) in hexanes + 0.1% DEA 2-CHIRALCEL OX-H; 45% (50:50 IPA:MeOH) in hexanes + 0.1% DEA |
| 92 Isomer 1 Isomer 2 Isomer 3 Isomer 4 | | (S, S, R)-, (S, R, R)-, (R, R, R)- and (R, S, R)-2-((2-(4-cyanophenyl)propyl)amino)-N-(5-((R)-3-methoxypyrrolidin-1-yl)pyridin-2-yl)-2-phenylacetamide | Calc'd 470.3, Found 470.3, 470.4, 470.8 and 470.8 | 1-CHIRALCEL OX-H; 28% MeOH in Liquid $CO_2$ + 0.1% DEA 2-CHIRALPAK AD-H; 100% (80:20 ACN:MeOH) + 0.1% DEA |

TABLE 5-continued

| Example No. | Structure (Methods and Schemes for Preparation) | IUPAC Name | Exact Mass [M + 1] | Chiral Column and Mobile Phase |
|---|---|---|---|---|
| 93 Isomer 1 Isomer 2 Isomer 3 Isomer 4 | | (S, S, S)-, (S, R, S)-, (R, R, S)- and (R, S, S)-2-((2-(4-cyanophenyl)propyl)amino)-N-(5-((S)-3-methoxypyrrolidin-1-yl)pyridin-2-yl)-2-phenylacetamide | Calc'd 470.3, Found 470.7, 470.7, 470.7 and 470.7 | 1-CHIRALCEL OX-H; 35% (50:50 MeOH:IPA) in Liquid $CO_2$ + 0.1% DEA 2-CHIRALCEL OS-H; 35% (50:50 MeOH:IPA) in Liquid $CO_2$ + 0.1% DEA |
| 94 Isomer 1 Isomer 2 | | (S)- and (R)-2-((4-chloro-2-cyanophenEthyl)amino)-N-(5-(1-methyl-1H-pyrazol-4-yl)pyridin-2-yl)-2-phenylacetamide | Calc'd 471.2, Found 471.4 and 471.4 | CHIRALCEL OX-H; 45% (50:50 MeOH:IPA) in hexanes + 0.1% DEA |
| 95 Isomer 1 Isomer 2 | | (S)- and (R)-2-((4-cyano-2-(trifluoromethyl)-phenethyl)amino)-N-(5-(1-methyl-1H-pyrazol-4-yl)pyridin-2-yl)-2-phenylacetamide | Calc'd 505.2, Found 505.7 and 505.7 | CHIRALCEL OX-H; 25% (70:30 IPA:ACN) in hexanes + 0.1% DEA |
| 96 Isomer 1 Isomer 2 | | (S)- and (R)-N-(5-(2-oxa-6-azaspiro[3.4]octan-6-yl)pyridin-2-yl)-2-((4-cyanophenEthyl)amino)-2-phenylacetamide | Calc'd 468.2, Found 468.5 and 468.4 | CHIRALCEL OJ-H; 35% MeOH in Liquid $CO_2$ + 0.1% DEA |
| 97 Isomer 1 Isomer 2 | | (S)- and (R)-2-(((1-(4-chlorophenyl)cyclopropyl)methyl)amino)-N-(5-(1-methyl-1H-pyrazol-4-yl)pyridin-2-yl)-2-phenylacetamide | Calc'd 472.2, Found 472.3 and 472.3 | CHIRALCEL OX-H; 65% (50:50 IPA:MeOH) in hexanes + 0.1% DEA |
| 98 Isomer 1 Isomer 2 Isomer 3 Isomer 4 | | (S, S)-, (S, R)-, (R, R)- and (R, S)-2-((2-(4-cyanophenyl)propyl)amino)-N-(5-(2-methyl-2H-1,2,3-triazol-4-yl)pyridin-2-yl)-2-phenylacetamide | Calc'd 452.2, Found 452.3, 452.3, 452.6 and 452.6 | 1-CHIRALCEL OJ-H; 18% MeOH in Liquid $CO_2$ + 0.1% DEA 2-CHIRALPAK IC; 35% (50:50 IPA:MeOH) in hexanes + 0.1% DEA |

TABLE 5-continued

| Example No. | Structure (Methods and Schemes for Preparation) | IUPAC Name | Exact Mass [M + 1] | Chiral Column and Mobile Phase |
|---|---|---|---|---|
| 99 Isomer 1 Isomer 2 Isomer 3 Isomer 4 | | (S, S)-, (S, R)-, (R, R)- and (R, S)-N-(5-(1-methyl-1H-pyrazol-4-yl)pyridin-2-yl)-2-phenyl-2-((2-(4-(trifluoromethyl)phenyl)propyl)amino)acetamide | Calc'd 494.2, Found 494.4, 494.3, 494.5 and 494.5 | 1-CHIRALCEL OX-H; 35% (50:50 IPA:MeOH) in hexanes + 0.1% DEA 2-CHIRALCEL OJ-H; 15% MeOH in Liquid CO$_2$ + 0.1% DEA |
| 100 Isomer 1 Isomer 2 Isomer 3 Isomer 4 | | (S, S)-, (S, R)-, (R, R)- and (R, S)-2-((2-(4-cyanophenyl)propyl)amino)-N-(5-(1-methyl-1H-1,2,3-triazol-4-yl)pyridin-2-yl)-2-phenylacetamide | Calc'd 452.2, Found 452.5, 452.5, 452.5 and 452.5 | 1-CHIRALPAK IC; 10% (70:30 IPA:ACN) in hexanes + 0.1% DEA 2-CHIRALPAK IC; 28% MeOH in Liquid CO$_2$ + 0.1% DEA |
| 101 Isomer 1 Isomer 2 Isomer 3 Isomer 4 | | (S, S)-, (S, R)-, (R, R)- and (R, S)-2-((2-(4-cyanophenyl)propyl)amino)-N-(5-(4-methyl-3-oxopiperazin-1-yl)pyridin-2-yl)-2-phenylacetamide | Calc'd 483.2, Found 483.5, 483.4, 483.8 and 483.8 | 1-CHIRALCEL OJ-H; 20% MeOH in Liquid CO$_2$ + 0.1% DEA 2-CHIRALCEL OJ-H; 20% (50:50 IPA:MeOH) in Liquid CO$_2$ + 0.1% DEA |
| 102 Isomer 1 Isomer 2 | | (S, S)- and (R, S)-2-((2-(4-cyanophenyl)propyl)amino)-N-(5-(4-Ethyl-3-oxopiperazin-1-yl)pyridin-2-yl)-2-phenylacetamide | Calc'd 497.3, Found 497.5 and 497.9 | CHIRALCEL OJ-H; 20% (50:50 IPA:MeOH) in Liquid CO$_2$ + 0.1% DEA |
| 103 Isomer 1 Isomer 2 Isomer 3 Isomer 4 | | (S, S)-, (S, R)-, (R, R)- and (R, S)-2-((2-(4-cyanophenyl)propyl)amino)-N-(5-(3-oxo-4-(2,2,2-trifluoroEthyl)piperazin-1-yl)pyridin-2-yl)-2-phenylacetamide | Calc'd 551.2, Found 551.9, 551.6, 551.8 and 551.7 | 1-CHIRALPAK IB; 40% (50:50 IPA:MeOH) in hexanes + 0.1% DEA 2-CHIRALCEL OX-H; 80% (50:50 IPA:MeOH) in hexanes + 0.1% DEA |
| 104 Isomer 1 Isomer 2 Isomer 3 Isomer 4 | | (S, S)-, (S, R)-, (R, R)- and (R, S)-N-(5-(1H-pyrazol-4-yl)pyridin-2-yl)-2-((2-(4-cyanophenyl)propyl)amino)-2-phenylacetamide | Calc'd 437.2, Found 437.6, 437.6, 437.4 and 437.4 | 1-CHIRALPAK AD-H; 25% (70:30 IPA:ACN) in hexanes + 0.1% DEA 2-CHIRALCEL OX-H; 25% (70:30 IPA:ACN) in hexanes + 0.1% DEA |

| Example No. | Structure (Methods and Schemes for Preparation) | IUPAC Name | Exact Mass [M + 1] | Chiral Column and Mobile Phase |
|---|---|---|---|---|
| 105 Isomer 1 Isomer 2 | | (R, S)- and (S, S)-2-((2-(4-cyanophenyl)propyl)amino)-N-(1'-methyl-2'-oxo-1',2'-dihydro-[3,4'-bipyridin]-6-yl)-2-phenylacetamide | Calc'd 478.2, Found 478.8 and 478.8 | CHIRALCEL OX-H; 50% (70:30 IPA:ACN) in hexanes + 0.1% DEA |
| 106 Isomer 1 Isomer 2 | | (R, S)- and (S, S)-2-((2-(4-cyanophenyl)propyl)amino)-N-(5-(1-methyl-6-oxo-1,6-dihydropyrimidin-4-yl)pyridin-2-yl)-2-phenylacetamide | Calc'd 479.2, Found 479.7 and 479.7 | CHIRALPAK IC; 35% (70:30 IPA:ACN) in hexanes + 0.1% DEA |
| 107 Isomer 1 Isomer 2 | | (R, S)- and (S, S)-2-((2-(4-cyanophenyl)propyl)amino)-N-(5-(5-methyl-1,2,4-oxadiazol-3-yl)pyridin-2-yl)-2-phenylacetamide | Calc'd 453.2, Found 453.7 and 453.4 | CHIRALCEL OJ-H; 35% (50:50 IPA:MeOH) in hexanes + 0.1% DEA |
| 108 Isomer 1 Isomer 2 Isomer 3 Isomer 4 | | (S, S)-, (S, R)-, (R, R)- and (R, S)-2-((2-(4-cyanophenyl)propyl)amino)-N-(5-(5-methyl-1,1-dioxido-1,2,5-thiadiazolidin-2-yl)pyridin-2-yl)-2-phenylacetamide | Calc'd 505.2, Found 505.5, 505.5, 506.2 and 505.5 | 1-CHIRALCEL OJ-H; 20% MeOH in Liquid CO$_2$ + 0.1% DEA 2-CHIRALCEL OJ-H; 15% MeOH in Liquid CO$_2$ + 0.1% DEA |
| 109 Isomer 1 Isomer 2 Isomer 3 Isomer 4 | | (R, S, S)-, (R, S, R), (S, S, S)- and (S, S, R)-2-((2-(4-cyanophenyl)propyl)amino)-N-(5-(1-methyl-5-oxopyrrolidin-3-yl)pyridin-2-yl)-2-phenylacetamide | Calc'd 468.3, Found 468.9, 468.9, 468.8 and 468.8 | CHIRALPAK IC; 35% (70:30 IPA:ACN) in hexanes + 0.1% DEA |
| 110 Isomer 1 Isomer 2 | | (S)- and (R)-2-((4-cyanophenEthyl)amino)-2-(2-fluorophenyl)-N-(5-(1-methyl-1H-pyrazol-4-yl)pyridin-2-yl)acetamide | Calc'd 455.2, Found 455.4 and 455.5 | CHIRALCEL OX-H; 40% (70:30 IPA:ACN) in hexanes + 0.1% DEA |

TABLE 5-continued

| Example No. | Structure (Methods and Schemes for Preparation) | IUPAC Name | Exact Mass [M + 1] | Chiral Column and Mobile Phase |
|---|---|---|---|---|
| 111 Isomer 1 Isomer 2 | | (S)- and (R)-2-((4-cyanophenEthyl)amino)-2-(3-fluorophenyl)-N-(5-(1-methyl-1H-pyrazol-4-yl)pyridin-2-yl)acetamide | Calc'd 455.2, Found 455.4 and 455.7 | CHIRALCEL OX-H; 25% (70:30 IPA:ACN) in hexanes + 0.1% DEA |
| 112 Isomer 1 Isomer 2 | | (S)- and (R)-2-((4-cyanophenEthyl)amino)-2-(4-fluorophenyl)-N-(5-(1-methyl-1H-pyrazol-4-yl)pyridin-2-yl)acetamide | Calc'd 455.2, Found 455.8 and 455.4 | CHIRALCEL OJ-H; 50% (50:50 IPA:MeOH) in hexanes + 0.1% DEA |
| 113 Isomer 1 Isomer 2 | | (R, S)- and (S, S)-2-((2-(4-cyanophenyl)propyl)amino)-N-(5-(1,3-dimethyl-1H-pyrazol-4-yl)pyridin-2-yl)-2-phenylacetamide | Calc'd 465.2, Found 465.6 and 465.9 | CHIRALCEL OJ-H; 18% MeOH in Liquid CO$_2$ + 0.1% DEA |
| 114 Isomer 1 Isomer 2 | | (R, S)- and (S, S)-2-((2-(4-cyanophenyl)propyl)amino)-N-(5-(1,5-dimethyl-1H-pyrazol-4-yl)pyridin-2-yl)-2-phenylacetamide | Calc'd 465.2, Found 465.8 and 465.6 | CHIRALPAK IB; 18% (50:50 IPA:MeOH) in hexanes + 0.1% DEA |
| 115 Isomer 1 Isomer 2 | | (R, S)- and (S, S)-2-((2-(4-cyanophenyl)propyl)amino)-N-(4-methyl-5-(1-methyl-1H-pyrazol-4-yl)pyridin-2-yl)-2-phenylacetamide | Calc'd 465.2, Found 465.4 and 465.4 | CHIRALCEL OJ-H; 35% MeOH in Liquid CO$_2$ + 0.1% DEA |
| 116 Isomer 1 Isomer 2 | | (S)- and (R)-2-((4-cyanophenEthyl)amino)-2-(3-cyanophenyl)-N-(5-(1-methyl-1H-pyrazol-4-yl)pyridin-2-yl)acetamide | Calc'd 462.2, Found 462.7 and 462.7 | CHIRALCEL OX-H; 60% (50:50 IPA:MeOH) in hexanes + 0.1% DEA |

TABLE 5-continued

| Example No. | Structure (Methods and Schemes for Preparation) | IUPAC Name | Exact Mass [M + 1] | Chiral Column and Mobile Phase |
|---|---|---|---|---|
| 117 Isomer 1 Isomer 2 | | (S)- and (R)-2-((4-cyanophenEthyl)amino)-N-(5-(1-methyl-1H-pyrazol-4-yl)pyridin-2-yl)-2-(3-(trifluoromethyl)phenyl)acetamide | Calc'd 505.2, Found 505.7 and 505.2 | CHIRALCEL OX-H; 15% MeOH in Liquid CO$_2$ + 0.1% DEA |
| 118 Isomer 1 Isomer 2 | | (S)- and (R)-2-((4-cyanophenEthyl)amino)-2-(3-hexylphenyl)-N-(5-(1-methyl-1H-pyrazol-4-yl)pyridin-2-yl)acetamide | Calc'd 521.3, Found 521.8 and 521.8 | CHIRALCEL OX-H; 20% (70:30 IPA:ACN) in hexanes + 0.1% DEA |
| 119 Isomer 1 Isomer 2 | | (S)- and (R)-2-((4-cyanophenEthyl)amino)-2-(4-cyanophenyl)-N-(5-(1-methyl-1H-pyrazol-4-yl)pyridin-2-yl)acetamide | Calc'd 462.2, Found 462.7 and 462.6 | CHIRALCEL OX-H; 55% (50:50 IPA:MeOH) in hexanes + 0.1% DEA |
| 120 Isomer 1 Isomer 2 | | (S)- and (R)-2-((4-cyanophenEthyl)amino)-N-(5-(1-methyl-1H-pyrazol-4-yl)pyridin-2-yl)-2-(4-(trifluoromethyl)phenyl)acetamide | Calc'd 505.2, Found 505.2 and 505.2 | CHIRALCEL OX-H; 20% (50:50 IPA:ACN) in Liquid CO$_2$ + 0.1% DEA |
| 121 Isomer 1 Isomer 2 | | (S)- and (R)-2-((4-cyanophenEthyl)amino)-2-(4-hexylphenyl)-N-(5-(1-methyl-1H-pyrazol-4-yl)pyridin-2-yl)acetamide | Calc'd 521.3, Found 521.7 and 522.0 | CHIRALPAK IC; 28% (50:50 MeOH:ACN) in Liquid CO$_2$ + 0.1% DEA |

TABLE 5-continued

| Example No. | Structure (Methods and Schemes for Preparation) | IUPAC Name | Exact Mass [M + 1] | Chiral Column and Mobile Phase |
|---|---|---|---|---|
| 122 Isomer 1 Isomer 2 | | (S)- and (R)-2-((4-cyanophenEthyl)amino)-N-(4-(1-methyl-1H-pyrazol-4-yl)pyridin-2-yl)-2-phenylacetamide | Calc'd 437.2, Found 437.7 and 437.7 | CHIRALCEL OX-H; 20% (70:30 IPA:ACN) in hexanes + 0.1% DEA |
| 123 Isomer 1 Isomer 2 | | (S)- and (R)-2-((4-cyanophenEthyl)amino)-N-(6-(1-methyl-1H-pyrazol-4-yl)pyridin-2-yl)-2-phenylacetamide | Calc'd 437.2, Found 437.6 and 437.5 | CHIRALCEL OJ-H; 15% MeOH in Liquid $CO_2$ + 0.1% DEA |
| 124 Isomer 1 Isomer 2 | | (R, S, rac)- and (S, S, rac)-2-((2-(4-cyanophenyl)propyl)amino)-N-(5-(3,4-dimethyl-5-oxopiperazin-1-yl)pyridin-2-yl)-2-phenylacetamide | Calc'd 497.3, Found 497.7 and 497.7 | CHIRALCEL OJ-H; 25% MeOH in Liquid $CO_2$ + 0.1% DEA |
| 125 Isomer 1 Isomer 2 Isomer 3 Isomer 4 | | (R, S, S)-, (R, S, R), (S, S, S)- and (S, S, R)-2-((2-(4-cyanophenyl)propyl)amino)-N-(5-(2,4-dimethyl-5-oxopiperazin-1-yl)pyridin-2-yl)-2-phenylacetamide | Calc'd 497.3, Found 497.7, 497.7, 497.7 and 497.5 | 1-CHIRALCEL OX-H; 40% (70:30 IPA:ACN) in hexanes + 0.1% DEA 2-CHIRALCEL OJ-H; 20% MeOH in Liquid $CO_2$ + 0.1% DEA |
| 126 Isomer 1 Isomer 2 Isomer 3 Isomer 4 | | (R, S, S)-, (R, S, R), (S, S, S)- and (S, S, R)-2-((2-(4-cyanophenyl)propyl)amino)-N-(5-(2,4-dimethyl-3-oxopiperazin-1-yl)pyridin-2-yl)-2-phenylacetamide | Calc'd 497.3, Found 497.2, 497.2, 497.2 and 497.2 | 1-CHIRALCEL OJ-H; 30% MeOH in Liquid $CO_2$ + 0.1% DEA 2-CHIRALCEL OX-H; 35% (70:30 IPA:ACN) in hexanes + 0.1% DEA |
| 127 Isomer 1 Isomer 2 Isomer 3 Isomer 4 | | (S, S)-, (S, R)-, (R, R)- and (R, S)-2-((2-(4-cyanophenyl)propyl)amino)-2-(1-methyl-1H-pyrazol-4-yl)-N-(5-(1-methyl-1H-pyrazol-4-yl)pyridin-2-yl)acetamide | Calc'd 455.2, Found 455.5, 455.5, 455.7 and 455.7 | 1-CHIRALCEL OJ-H; 15% MeOH in Liquid $CO_2$ + 0.1% DEA 2-CHIRALPAK IC; 32% (50:50 MeOH:ACN) in Liquid $CO_2$ + 0.1% DEA |

TABLE 5-continued

| Example No. | Structure (Methods and Schemes for Preparation) | IUPAC Name | Exact Mass [M + 1] | Chiral Column and Mobile Phase |
|---|---|---|---|---|
| 128 Isomer 1 Isomer 2 Isomer 3 Isomer 4 | | (S, S)-, (S, R)-, (R, R)- and (R, S)-2-((2-(4-cyanophenyl)propyl)amino)-N-(5-(1-(difluoromethyl)-1H-pyrazol-4-yl)pyridin-2-yl)-2-(1-methyl-1H-pyrazol-4-yl)acetamide | Calc'd 491.2, Found 491.6, 491.7, 491.7 and 491.8 | 1-CHIRALCEL OJ-H; 15% MeOH in Liquid CO$_2$ + 0.1% DEA 2-CHIRALPAK AD-H; 22% (50:50 MeOH:ACN) in Liquid CO$_2$ + 0.1% DEA |
| 129 Isomer 1 Isomer 2 | | (R, S)- and (S, S)-2-((2-(4-cyanophenyl)propyl)amino)-2-(5-fluoropyridin-3-yl)-N-(5-(1-methyl-1H-pyrazol-4-yl)pyridin-2-yl)acetamide | Calc'd 470.2, Found 470.5 and 470.5 | CHIRALCEL OX-H; 45% (70:30 IPA:ACN) in hexanes + 0.1% DEA |
| 130 Isomer 1 Isomer 2 | | (R, S)- and (S, S)-2-((2-(4-cyanophenyl)propyl)amino)-2-phenyl-N-(5-(1,3,5-trimethyl-1H-pyrazol-4-yl)pyridin-2-yl)acetamide | Calc'd 479.3, Found 479.9 and 479.9 | CHIRALPAK IC; 24% (50:50 MeOH:ACN) in Liquid CO$_2$ + 0.1% DEA |
| 131 Isomer 1 Isomer 2 | | (R, S)- and (S, S)-2-((2-(4-cyanophenyl)propyl)amino)-N-(5-(3,5-dimethylisoxazol-4-yl)pyridin-2-yl)-2-phenylacetamide | Calc'd 466.2, Found 466.6 and 466.6 | CHIRALPAK AD-H; 100% MeOH + 0.1% DEA |
| 132 Isomer 1 Isomer 2 | | (R, S)- and (S, S)-2-((2-(4-cyanophenyl)propyl)amino)-N-(5-(1-(2-oxo-2-(pyrrolidin-1-yl)Ethyl)-1H-pyrazol-4-yl)pyridin-2-yl)-2-phenylacetamide | Calc'd 548.3, Found 549.0 and 548.9 | CHIRALCEL OJ-H; 15% MeOH in Liquid CO$_2$ + 0.1% DEA |
| 133 Isomer 1 Isomer 2 | | (R, S)- and (S, S)-2-((2-(4-cyanophenyl)propyl)amino)-N-(5-(3,5-dimethyl-1H-pyrazol-4-yl)pyridin-2-yl)-2-phenylacetamide | Calc'd 465.2, Found 465.7 and 465.8 | CHIRALCEL OJ-H; 15% MeOH in Liquid CO$_2$ + 0.1% DEA |

TABLE 5-continued

| Example No. | Structure (Methods and Schemes for Preparation) | IUPAC Name | Exact Mass [M + 1] | Chiral Column and Mobile Phase |
|---|---|---|---|---|
| 134 Isomer 1 Isomer 2 | | (R, S)- and (S, S)-2-((2-(4-cyanophenyl)propyl)amino)-N-(5-(1-methyl-6-oxo-1,6-dihydropyridazin-3-yl)pyridin-2-yl)-2-phenylacetamide | Calc'd 479.2, Found 479.7 and 479.6 | CHIRALCEL OJ-H; 18% MeOH in Liquid CO$_2$ + 0.1% DEA |
| 135 Isomer 1 Isomer 2 | | (R, S)- and (S, S)-N-(5-(4-acetylpiperazin-1-yl)pyridin-2-yl)-2-((2-(4-cyanophenyl)propyl)amino)-2-(3-fluorophenyl)acetamide | Calc'd 515.3, Found 515.6 and 515.6 | CHIRALCEL OJ-H; 20% MeOH in Liquid CO$_2$ + 0.1% DEA |
| 136 Isomer 1 Isomer 2 Isomer 3 Isomer 4 | | (S, S)-, (S, R)-, (R, R)- and (R, S)-2-((2-(4-cyanophenyl)propyl)amino)-2-(1-methyl-1H-pyrazol-4-yl)-N-(5-(4-methyl-3-oxopiperazin-1-yl)pyridin-2-yl)acetamide | Calc'd 487.3, Found 487.6, 487.7, 487.6 and 487.6 | 1-CHIRALPAK IG; 100% (30:70 MeOH:ACN) + 0.1% DEA 2-CHIRALPAK AD-H; 35% (50:50 MeOH:ACN) in Liquid CO$_2$ + 0.1% DEA |
| 137 Isomer 1 Isomer 2 | | (R, S)- and (S, S)-2-((2-(4-cyanophenyl)propyl)amino)-2-(3-fluorophenyl)-N-(5-(4-methyl-3-oxopiperazin-1-yl)pyridin-2-yl)acetamide | Calc'd 501.3, Found 501.7 and 501.7 | CHIRALCEL OJ-H; 15% MeOH in Liquid CO$_2$ + 0.1% DEA |
| 138 Isomer 1 Isomer 2 | | (R, S)- and (S, S)-2-((2-(4-cyanophenyl)propyl)amino)-N-(5-(1-(2-(dimethylamino)-2-oxoEthyl)-1H-pyrazol-4-yl)pyridin-2-yl)-2-(3-fluorophenyl)acetamide | Calc'd 540.2, Found 540.8 and 540.8 | CHIRALCEL OJ-H; 20% MeOH in Liquid CO$_2$ + 0.1% DEA |
| 139 Isomer 1 Isomer 2 | | (R, S)- and (S, S)-2-(2-(4-cyanophenyl)propyl)amino)-N-(5-(1-methyl-6-oxo-1,6-dihydropyridazin-4-yl)pyridin-2-yl)-2-phenylacetamide | Calc'd 479.2, Found 479.5 and 479.5 | CHIRALCEL OJ-H; 50:50 ACN:IPA in Liquid CO$_2$ + 0.1% DEA |
| 140 Isomer 1 Isomer 2 | | (S)- and (R)-N-(5-(1-methyl-1H-pyrazol-4-yl)pyridin-2-yl)-2-phenyl-2-((2-(6-(trifluoromethyl)pyridin-3-yl)ethyl)amino)acetamide | Calc'd 481.2, Found 481.8 and 481.8 | CHIRALCEL OJ-H; MeOH in Liquid CO$_2$ + 0.1% DEA |

TABLE 5-continued

| Example No. | Structure (Methods and Schemes for Preparation) | IUPAC Name | Exact Mass [M + 1] | Chiral Column and Mobile Phase |
|---|---|---|---|---|
| 141 Isomer 1 Isomer 2 | | (S)- and (R)-(5-(1-methyl-1H-pyrazol-4-yl)pyridin-2-yl)-2-((2-(6-methylpyridin-3-yl)ethyl)amino)-2-phenylacetamide | Calc'd 427.2, Found 427.8 and 427.6 | CHIRALCEL OJ-H; 50:50 MeOH:IPA in Liquid CO$_2$ + 0.1% DEA |
| 142 Isomer 1 Isomer 2 | | (S)- and (R)-2-((2-(5-cyanopyridin-2-yl)ethyl)amino)-N-(5-(1-methyl-1H-pyrazol-4-yl)pyridin-2-yl)-2-phenylacetamide | Calc'd 438.2, Found 438.8 and 438.7 | CHIRALCEL OX-H; 35% (70:30 IPA:ACN) in Hexanes + 0.1% DEA |
| 143 Isomer 1 Isomer 2 Isomer 3 Isomer 4 | | (S, S)-, (S, R)-, (R, R)- and (R, S)-N-(5-(1-methyl-1H-pyrazol-4-yl)pyridin-2-yl)-2-((2-(6-methylpyridin-3-yl)propyl)amino)-2-phenylacetamide | Calc'd 441.2, Found 441.8, 441.8, 441.9, and 441.9 | 1-CHIRALCEL OX-H; 40% (70:30 IPA:ACN) in hexanes + 0.1% DEA then 2-CHIRALCEL AD-H; 35% IPA in Liquid CO$_2$ + 0.1% DEA |
| 144 Isomer 1 Isomer 2 | | (S)- and (R)-2-((2-(4-cyano-1H-pyrazol-1-yl)ethyl)amino)-N-(5-(1-methyl-1H-pyrazol-4-yl)pyridin-2-yl)-2-phenylacetamide | Calc'd 427.2, Found 427.8 and 427.8 | CHIRALPAK IG; 90:10 ACN:MeOH in Liquid CO$_2$ + 0.1% DEA |
| 145 Isomer 1 Isomer 2 | | (S)- and (R)-2-((2-(3-cyano-5-methyl-1H-pyrazol-1-yl)ethyl)amino)-N-(5-(1-methyl-1H-pyrazol-4-yl)pyridin-2-yl)-2-phenylacetamide | Calc'd 441.2, Found 441.7 and 441.7 | CHIRALCEL OX-H; 50:50 MeOH:IPA in Hexane + 0.1% DEA |
| 146 Isomer 1 Isomer 2 | | (R, S)- and (S, S)-2-((2-(4-cyanophenyl)propyl)amino)-N-(5-(1-(2-(methylamino)-2-oxoethyl)-1H-pyrazol-4-yl)pyridin-2-yl)-2-phenylacetamide | Calc'd 508.2, Found 508.4 and 508.4 | CHIRALCEL OJ-H; MEOH in Liquid CO$_2$ + 0.1% DEA |

TABLE 5-continued

| Example No. | Structure (Methods and Schemes for Preparation) | IUPAC Name | Exact Mass [M + 1] | Chiral Column and Mobile Phase |
|---|---|---|---|---|
| 147 Isomer 1 Isomer 2 | | (R, S)- and (S, S)-N-(5-(1-(2-amino-2-oxoethyl)-1H-pyrazol-4-yl)pyridin-2-yl)-2-((2-(4-cyanophenyl)propyl)amino)-2-phenylacetamide | Calc'd 494.2, Found 494.2 and 494.2 | CHIRALCEL OJ-H; MeOH in Liquid $CO_2$ + 0.1% DEA |
| 148 Isomer 1 Isomer 2 | | (S)- and (R)-2-((4-chlorophenethyl)amino)-2-(1-methyl-1H-pyrazol-4-yl)-N-(5-(1-methyl-1H-pyrazol-4-yl)pyridin-2-yl)acetamide | Calc'd 450.2, Found 450.2 and 450.2 | Regis (S,S)-Whelk O-1 ; 35% MeOH in LIQUID $CO_2$ + 0.1% isopropylamine |
| 149 Isomer 1 Isomer 2 Isomer 3 Isomer 4 | | (S, S, (S, R)-, (R, R)- and (R, S)-2-((2-(4-cyanophenyl)-3,3,3-trifluoropropyl)amino)-N-(5-(1-methyl-1H-pyrazol-4-yl)pyridin-2-yl)-2-phenylacetamide | Calc'd 505.5, Found 505.7, 505.7, 505.7, and 505.7 | 1-CHIRALCEL OX-H; 33% (50:50 MeOH: IPA) in hexanes + 0.1% DEA then 2-CHIRALCEL OJ-H; 10% MeOH in LIQUID $CO_2$ + 0.1% DEA) |
| 150 Isomer 1 Isomer 2 Isomer 3 Isomer 4 | | (S, S)-, (S, R)-, (R, R)- and (R, S)-N-(5-(1-methyl-1H-pyrazol-4-yl)pyridin-2-yl)-2-((2-(2-methylpyrimidin-5-yl)propyl)amino)-2-phenylacetamide | Calc'd 442.5, Found 442.8, 442.8, 442.8, and 442.8 | CHIRALPAK IG; 100% (70:30 MeOH: ACN) + 0.1% Diethyl amine |

Scheme 7

The starting materials required for the synthesis of examples prepared using Scheme 8. The examples were generally prepared using methods 1 through 16 or were commercially available.

Example 151

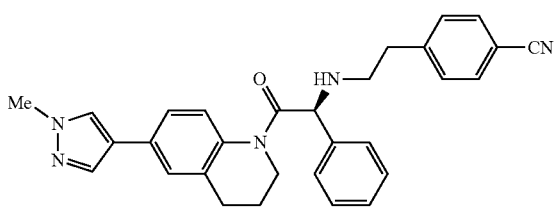

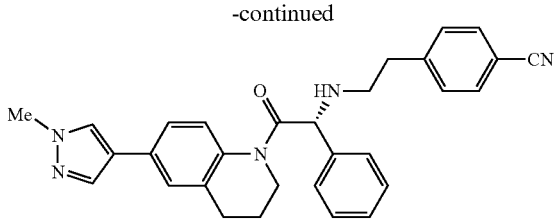

(S)- and (R)-4-(2-((2-(6-(1-Methyl-1H-pyrazol-4-yl)-3,4-dihydroquinolin-1(2H)-yl)-2-oxo-1-phenylethyl)amino)ethyl)benzonitrile Scheme 7, Step 1. tert-Butyl 6-(1-methyl-1H-pyrazol-4-yl)-3,4-dihydroquinoline-1(2H)-carboxylate A mixture of tert-butyl 6-bromo-3,4-dihydroquinoline-1 (2H)-carboxylate (0.55 g, 1.76 mmol), 1-methyl-4-(4,4,5,5-tetramethyl-1,3,2-dioxaborolan-2-yl)-1H-pyrazole (0.439 g, 2.11 mmol) and cesium carbonate (1.43 g, 4.40 mmol) in mixture of 4:1 Dioxane:water (10 ml) was purged for 20 minutes with argon gas. S-Phos Pd-G3-precatalyst (0.066 g, 0.08 mmol) was added and purging was continued for another 10 minutes. The reaction mixture was heated at 100° C. for 2 hours. The reaction mixture was poured into water (25 ml) and extracted with ethyl acetate (2×30 ml). The combined organic layers were washed with brine (20 ml), dried over anhydrous $Na_2SO_4$ and concentrated under reduced pressure. The resulting residue was purified by silica gel chromatography to afford the title compound (0.55 g, 99%) as a solid. $^1$H NMR (400 MHz, DMSO-d6): 1.08 (s, 9H), 1.81-1.87 (m, 2H), 2.74 (t, J=6.4 Hz, 2H), 3.63 (t, J=6.0 Hz, 2H), 3.85 (s, 3H), 7.29-7.31 (m, 2H), 7.54 (d, J=9.2 Hz, 1H), 7.80 (s, 1H), 8.07 (s, 1H); LCMS: m/z=314.2 [M+1].

Scheme 7, Step 2. 6-(1-Methyl-1H-pyrazol-4-yl)-1,2,3,4-tetrahydroquinoline

To a stirred solution of tert-butyl 6-(1-methyl-1H-pyrazol-4-yl)-3,4-dihydroquinoline-1(2H)-carboxylate (0.1 g, 0.31 mmol) in dry 1,4-dioxane (1 ml) was added 4M HCl in dioxane (1 ml) dropwise at 0° C. The reaction mixture was stirred at room temperature for 2 hours. The reaction mixture was concentrated and neutralized with saturated sodium bicarbonate and extracted with ethyl acetate (3×10 ml). The combined organic layer was washed with brine (10 ml), dried over anhydrous $Na_2SO_4$ and concentrated under reduced pressure to afford the title compound (0.050 g, 73%). LCMS: m/z=214.2 [M+1].

Method 7, Step 3. (S)- and (R)-4-(2-((2-(6-(1-Methyl-1H-pyrazol-4-yl)-3,4-dihydroquinolin-1(2H)-yl)-2-oxo-1-phenylethyl)amino)ethyl)benzonitrile To a mixture of 6-(1-methyl-1H-pyrazol-4-yl)-1,2,3,4-tetrahydroquinoline (0.05 g, 0.23 mmol) and ethyl 2-((4-cyanophenethyl)amino)-2-phenylacetate (0.060 g, 0.19 mmol) in toluene (0.6 ml) was added TMA (0.19 ml, 2M in Toluene, 0.39 mmol) under an atmosphere of nitrogen at 0° C. The resulting reaction mixture was heated at 100° C. for 2 hours. After completion of the reaction (monitored by TLC), the mixture was slowly quenched with saturated sodium bicarbonate (10 ml) and aqueous layer was extracted with ethyl acetate (2×10 ml). The combined organic layers were washed with brine (10 ml), dried over anhydrous $Na_2SO_4$ and concentrated under reduced pressure. The resulting residue was purified by silica gel chromatography to afford the title compound (0.03 g, 32%) as a racemic mixture. The racemic compound was resolved by chiral HPLC (CHIRALCEL OJ-H; 15% (50:50 ACN:IPA) in Liq-uid $CO_2$+0.1% DEA) to furnish the enantiopure compounds. The faster-eluting enantiomer of the title compound was obtained as a solid (Isomer 1): $^1$H NMR (400 MHz, DMSO-d6): δ 1.71-1.77 (m, 2H), 2.58-2.79 (m, 6H), 3.36-3.52 (m, 1H), 3.79-3.85 (m, 1H), 3.86 (s, 3H), 4.86 (s, 1H), 6.85-7.19 (m, 2H), 7.25-7.35 (m, 6H), 7.41 (d, J=7.6 Hz, 2H), 7.75 (d, J=8.0 Hz, 2H), 7.85 (s, 1H), 8.12 (s, 1H). LCMS: m/z=476.3 [M+1]. The slower-eluting enantiomer of the title compound was obtained as a solid (Isomer 2): $^1$H NMR (400 MHz, DMSO-d6): δ 1.71-1.77 (m, 2H), 2.65-2.79 (m, 6H), 3.36-3.46 (m, 1H), 3.79-3.81 (m, 1H), 3.86 (s, 3H), 4.86 (s, 1H), 6.85-7.15 (m, 2H), 7.25-7.35 (m, 6H), 7.41 (d, J=8.0 Hz, 2H), 7.75 (d, J=8.0 Hz, 2H), 7.85 (s, 1H), 8.12 (s, 1H). LCMS: m/z=476.3 [M+1].

The following compounds were prepared using similar procedures to those described for Example 151 using the appropriate starting materials.

TABLE 6

| Example No. | Structure (Methods and Schemes for Preparation) | IUPAC Name | Exact Mass [M + 1] | Chiral Column and Mobile Phase |
|---|---|---|---|---|
| 152 Isomer 1 Isomer 2 | | (S)- and (R)-4-(2-((2-(5-(1-methyl-1H-pyrazol-4-yl)indolin-1-yl)-2-oxo-1-phenylethyl)amino)ethyl)benzonitrile | Calc'd 462.2, Found 462.4 and 462.4 | CHIRALPAK IB; 40% (50:50 IPA:MeOH) in hexanes + 0.1% DEA |

Example 153

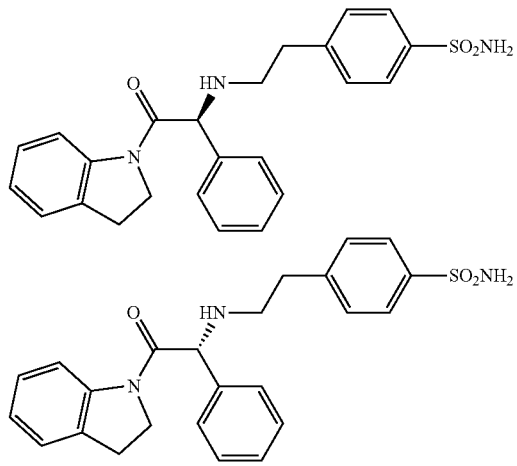

(S)- and (R)-4-(2-((2-(indolin-1-yl)-2-oxo-1-phenylethyl)amino)ethyl)benzenesulfonamide To a solution of indoline (0.5 g, 4.19 mmol) and TEA (0.849 g, 8.39 mmol) in DMF (10 ml) was added 2-chloro-2-phenylacetyl chloride (0.79 g, 4.19 mmol) drop wise at 0° C. and the reaction mixture was stirred at room temperature for 2 hours. The above reaction mixture was added dropwise to a stirred solution of 4-(2-aminoethyl)benzenesulfonamide (1.67 g, 8.38 mmol) in DMF (5 ml) at room temperature over a period of 10 minutes. The resulting reaction mixture was stirred at room temperature for 2 hours. The reaction mixture was poured into ice cold water (15 ml) and extracted with ethyl acetate (2×15 ml). The combined organic layers were washed with brine (15 ml), dried over anhydrous $Na_2SO_4$ and concentrated under reduced pressure. The resulting reside was purified by silica gel chromatography to afford the title compound as solid (0.25 g, 14%) in racemic form.

The racemic title compound was resolved by chiral HPLC (CHIRALPAK IB; 40%(50:50 MeOH:IPA) in hexanes+ 0.1% DEA) to furnish the enantiopure compounds. The faster-eluting enantiomer of the title compound was obtained as a solid (Isomer 1): $^1$H NMR (400 MHz, DMSO-d6): δ 2.61-2.84 (m, 4H), 2.99-3.15 (m, 2H), 3.68-3.75 (m, 1H), 4.31-4.38 (m, 1H), 4.69 (s, 1H), 7.01 (t, J=8.0 Hz, 1H), 7.12-7.25 (m, 2H), 7.28-7.44 (m, 8H), 7.73 (d, J=8.0 Hz, 2H), 8.15 (d, J=8.0 Hz, 1H). LCMS: (Method C-3): $R_T$ 1.54 min; m/z 436.5 [M+1]. The slower-eluting enantiomer of the title compound was obtained as a solid (Isomer 2): $^1$H NMR (400 MHz, DMSO-d6): δ 2.64-2.83 (m, 4H), 2.99-3.18 (m, 2H), 3.68-3.75 (m, 1H), 4.31-4.38 (m, 1H), 4.69 (s, 1H), 7.01 (t, J=8.0 Hz, 1H), 7.14-7.22 (m, 2H), 7.28-7.41 (m, 8H), 7.73 (d, J=8.0 Hz, 2H), 8.15 (d, J=8.0 Hz, 1H). LCMS: m/z=436.5 [M+1].

The following compounds were prepared using similar procedures to those described for Example 153 using the appropriate starting materials.

*Escherichia coli* cells. The expressed protein was purified by Ni2+ affinity, followed by anion exchange chromatography. Appropriate fractions were pooled and buffer exchanged into 20 mM Hepes pH 7.5, 150 mM NaCl, and 1 mM TCEP.

Compounds of interest solubilized in DMSO were stamped in a Greiner black 384-well plate in a 10-point duplicate dose response using an Echo 550 (Labcyte). p300-HAT domain purified in-house (aa 1287-1666) was diluted to 6 nM in reaction buffer (50 mM Tris pH 8.0, 100 mM NaCl, 1 mM DTT, 0.069 mM Brij-35, 0.1 mM EDTA, 0.1 mg/mL BSA), combined with 4.14 μM AcCoA (Sigma-Aldrich) and 0.46 μM $^3$H-AcCoA (PerkinElmer), and 12.5 μL added to each well and incubated for 30 min at RT. Reactions were initiated with 12.5 μL 2 μM biotinylated H3(1-21) peptide (New England Peptide) and run for 1 hr at RT, then quenched with 20 μL stop solution (200 mM Tris pH 8.0, 200 mM EDTA, 2M NaCl, 160 μM anacardic acid). 35 μL of the reaction volume was transferred to a 384-well streptavidin FlashPlate (PerkinElmer) using a Bravo liquid handler (Velocity 11) and incubated for 1.5 hr at RT. Plates were aspirated, washed with 95 μL wash buffer (15 mM Tris pH 8.5, 0.069 μM Brij-35), aspirated, sealed, and scintillation counts read on a Topcount (PerkinElmer). Data were analyzed in Genedata to determine inhibitor $IC_{50}$ values.

The full length p300 SPA assay was run following the same protocol as p300 HAT SPA assay, but used 6 nM purified full length p300 (purchased from Active Motif) in place of the purified p300-HAT domain.

TABLE 7

| Example No. | Structure (Methods and Schemes for Preparation) | IUPAC Name | Exact Mass [M + 1] | Chiral Column and Mobile Phase |
|---|---|---|---|---|
| 154 | | 4-(2-((2-(3,4-dihydroquinolin-1(2H)-yl)-2-oxo-1-phenylethyl)amino)ethyl)benzenesulfonamide | Calc'd 450.6, Found 450.3 | racemic |

Biochemical and Cellular Assays

The activity of the compounds described herein as p300/CBP HAT inhibitors may be readily determined using a scintillation proximity assay (SPA) methodology (Udenfriend, S.; Gerber, L.; Nelson, N. Scintillation Proximity Assay: A Sensitive and Continuous Isotopic Method for Monitoring Ligand/Receptor and Antigen/Antibody Interactions. *Anal. Biochem.* 1987, 16f 494-500). In particular, the compounds of the following examples had activity in reference assays by exhibiting the ability to inhibit the acetylation of histone peptide by a truncated form of the p300 enzyme (p300 HAT). Any compound exhibiting a $IC_{50}$ of about 100 μM or below would be considered a p300/CBP-HAT inhibitor as defined herein.

In a typical experiment the p300 HAT inhibitory activity of the compounds described herein was determined in accordance with the following experimental method.

The p300 HAT domain (residues 1287-1666) was expressed and purified with an N-terminal His tag from Select compounds were also evaluated in a H3K18Ac MSD cellular assay that measures the ability of compounds to inhibit the the acetylation of chromatin at H3K18, a process catalyzed by p300 and CBP. In a typical experiment the p300 HAT inhibitory activity inside cells of the compounds described herein was determined in accordance with the following experimental method. 20 k HCT-116 cells per well are plated in 75 μL RPMI+10% FBS media the night before treatment. Compounds plated in DMSO at 4× final concentration are resuspended in 30 μL RPMI+10% FBS, then 25 μL is combined with corresponding wells containing cells. Treated cells are incubated for 2 hr at 37° C., then lysed in 500 μL final volume and frozen at −80° C. MSD plates (Meso Scale Discovery) are coated overnight at 4° C. with 60 μL 1:500 α-total histone antibody (Millipore MAB3422) in PBS. Plates are then blocked with 5% BSA in TBST shaking at RT for 1 hr, washed, and 30 μL lysate added to each well for 2 hr shaking at RT. Plates are washed and 25 μL 1:216 α-H3K18ac antibody (CST 9675) in PBS added, then incubated for 1 hr shaking at RT. Plates are washed again, then 25 μL 1:1000 Sulfo-Tag goat α-rabbit antibody (Meso Scale Discovery R32Ab-1) in PBS is added for 1 hr shaking at RT. Plates are washed once more, then 150 μL 1× Read Buffer (MSD #R92TD-3) is added to all wells and read on MSD SECTOR Imager 2400 using the conventional read setup.

The compounds of the following examples had activity in inhibiting the HAT domain of the p300 enzyme in the aforementioned assays with a $IC_{50}$ of less than about 100 μM. Many of compounds described herein had activity in inhibiting the HAT domain of the p300 enzyme in the aforementioned assays, with an $IC_{50}$ of less than about 10 μM, preferably less than or about 0.1 μM. Additional data is provided in the following Examples. Such a result is indicative of the intrinsic activity of the compounds in use as inhibitors of the histone acetyl transferase domain of the p300 enzyme. In general, one of ordinary skill in the art would appreciate that a substance is considered to effectively inhibit p300 HAT activity if it has a $IC_{50}$ of less than or about 1 μM, preferably less than or about 0.1 μM. The present disclosure also includes compounds which possess activity as inhibitors of other histone acetyl transferase enzymes, such as CBP-HAT. The p300 HAT $IC_{50}$ is a measure of the ability of the test compound to inhibit the action of the p300 enzyme.

P300 inhibitory activity of compounds described herein estimated from a P300 HAT SPA assay are shown by Table 8. All activities are the average of at least 2 replicate titrations.

TABLE 8

| Example number | Isomer | P300 HAT SPA $IC_{50}$ (μM) | FL P300 $IC_{50}$ (μM) | H3K18Ac MSD $EC_{50}$ (μM) |
|---|---|---|---|---|
| 1 | Isomer 1 | 4.99 | | |
|   | Isomer 2 | 0.130 | 0.004 | 0.107 |
| 2 | Isomer 1 | >5 | | |
|   | Isomer 2 | 0.119 | | 0.324 |
|   | Isomer 3 | 2.74 | | |
|   | Isomer 4 | >5 | | |
| 3 | Isomer 1 | 0.196 | | |
|   | Isomer 2 | >5 | | |
|   | Isomer 3 | >5 | | |
|   | Isomer 4 | 3.89 | | |
| 4 | Isomer 1 | 4.99 | | |
|   | Isomer 2 | 1.37 | | |
| 5 | Isomer 1 | 0.239 | 0.009 | 0.059 |
|   | Isomer 2 | >5 | | |
| 6 | Isomer 1 | 1.68 | | |
|   | Isomer 2 | >2 | | |
|   | Isomer 3 | >2 | | |
|   | Isomer 4 | 0.0209 | | |
| 7 | Isomer 1 | 0.026 | <0.002 | 0.0193 |
|   | Isomer 2 | 0.376 | 0.0134 | |
| 8 | Isomer 1 | 0.309 | | |
|   | Isomer 2 | 1.35 | | |
|   | Isomer 3 | 1.23 | | |
|   | Isomer 4 | 0.0196 | | |
| 9 | Isomer 1 | >5 | | |
|   | Isomer 2 | 0.133 | | |
| 10 | Isomer 1 | >5 | | |
|   | Isomer 2 | 0.580 | | |
| 11 | Isomer 1 | 0.279 | | |
|   | Isomer 2 | >5 | | |
| 12 | Isomer 1 | >5 | | |
|   | Isomer 2 | 0.479 | | 1.80 |
| 13 | Isomer 1 | >5 | 0.273 | |
|   | Isomer 2 | 0.066 | <0.002 | 0.0923 |
| 14 | Isomer 1 | >5 | 0.176 | |
|   | Isomer 2 | 0.191 | | 0.479 |
| 15 | Isomer 1 | >2 | | |
|   | Isomer 2 | >2 | | |
|   | Isomer 3 | >2 | | |
|   | Isomer 4 | 0.0413 | 0.0015 | |
| 16 | Isomer 1 | 0.614 | | 1.13 |
|   | Isomer 2 | >5 | | |
| 17 | Isomer 1 | 0.655 | | 0.998 |
|   | Isomer 2 | >5 | | |
| 18 | Isomer 1 | 0.576 | | 0.230 |
|   | Isomer 2 | >5 | | |
| 19 | Isomer 1 | 3.07 | 0.104 | |
|   | Isomer 2 | >5 | | |
| 20 | Isomer 1 | 0.925 | | |
|   | Isomer 2 | 0.0137 | 0.00164 | 0.0226 |
|   | Isomer 3 | 1.63 | | |
|   | Isomer 4 | >2 | | |
| 21 | Isomer 1 | 3.48 | | |
|   | Isomer 2 | >5 | | |
| 22 | Isomer 1 | 0.0194 | <0.0005 | 0.0246 |
|   | Isomer 2 | 0.421 | | 0.0668 |
| 23 | Isomer 1 | >5 | | |
|   | Isomer 2 | >5 | | |
| 24 | Isomer 1 | >5 | | |
|   | Isomer 2 | 0.607 | | |
| 25 | Isomer 1 | 1.59 | 0.0401 | |
|   | Isomer 2 | >5 | | |
| 26 | Isomer 1 | 0.0889 | 0.003 | 0.265 |
|   | Isomer 2 | 1.85 | | |
| 27 | Isomer 1 | 0.576 | | 2.02 |
|   | Isomer 2 | >5 | | |
| 28 | Isomer 1 | 0.046 | <0.002 | 0.0596 |
|   | Isomer 2 | 2.83 | 0.024 | |
| 29 | Isomer 1 | 0.0229 | | |
|   | Isomer 2 | 2.76 | | |
| 30 | Isomer 1 | >5 | | |
|   | Isomer 2 | >5 | | |
| 31 | Isomer 1 | 0.0714 | 0.00257 | |
|   | Isomer 2 | >5 | 0.167 | |
| 32 | Isomer 1 | >2 | | |
|   | Isomer 2 | 0.0188 | | |
|   | Isomer 3 | >2 | | |
|   | Isomer 4 | >2 | | |
| 33 | Isomer 1 | 0.330 | 0.0127 | 0.936 |
|   | Isomer 2 | 1.8 | 0.078 | >2 |
|   | Isomer 3 | 0.455 | 0.169 | >2 |
|   | Isomer 4 | 0.0083 | <0.0005 | 0.014 |
| 34 | Isomer 1 | >5 | 7.25 | |
|   | Isomer 2 | 0.361 | 0.011 | |
| 35 | Isomer 1 | >5 | | |
|   | Isomer 2 | >5 | | |
| 36 | Isomer 1 | 3.27 | | |
|   | Isomer 2 | >5 | | |
| 37 | Isomer 1 | 0.0654 | | 0.118 |
|   | Isomer 2 | 3.73 | | |
| 38 | Isomer 1 | 0.206 | | |
|   | Isomer 2 | >2 | | |
| 39 | Isomer 1 | >2 | | |
|   | Isomer 2 | >2 | | |
|   | Isomer 3 | 0.0177 | | |
|   | Isomer 4 | 0.304 | | |
| 40 | Isomer 1 | 0.190 | | |
|   | Isomer 2 | >5 | | |
| 41 | Isomer 1 | 0.0103 | | |
|   | Isomer 2 | 1.79 | | |
| 42 | Isomer 1 | 0.0536 | | 0.333 |
|   | Isomer 2 | 3.0 | | |
| 43 | Isomer 1 | 0.185 | | |
|   | Isomer 2 | >5 | | |
| 44 | Isomer 1 | >2 | 0.278 | |
|   | Isomer 2 | 0.0416 | 0.00266 | |
| 45 | Isomer 1 | 0.026 | 0.00146 | |
|   | Isomer 2 | 1.02 | 0.0431 | |
| 46 | Isomer 1 | >5 | | |
|   | Isomer 2 | 0.486 | | |
| 47 | Isomer 1 | 0.448 | | |
|   | Isomer 2 | 0.0242 | | |
|   | Isomer 3 | >2 | | |
|   | Isomer 4 | 0.425 | | |
| 48 | Isomer 1 | 0.042 | <0.002 | 0.046 |
|   | Isomer 2 | 1.56 | 0.0318 | |

TABLE 8-continued

| Example number | Isomer | P300 HAT SPA IC$_{50}$ (μM) | FL P300 IC$_{50}$ (μM) | H3K18Ac MSD EC$_{50}$ (μM) |
|---|---|---|---|---|
| 49 | Isomer 1 | 0.0793 | | 0.0484 |
| | Isomer 2 | >5 | | |
| 50 | Isomer 1 | 0.279 | | |
| | Isomer 2 | >5 | | |
| 51 | Isomer 1 | 0.015 | | 0.0229 |
| | Isomer 2 | 0.237 | | |
| 52 | Isomer 1 | 0.612 | | |
| | Isomer 2 | >2 | | |
| | Isomer 3 | 0.0311 | | |
| | Isomer 4 | >2 | | |
| 53 | Isomer 1 | 0.121 | 0.00516 | |
| | Isomer 2 | >2 | >1 | |
| 54 | Isomer 1 | 0.383 | | |
| | Isomer 2 | 0.0239 | | |
| | Isomer 3 | >2 | | |
| | Isomer 4 | 1.97 | | |
| 55 | Isomer 1 | 0.019 | | 0.0315 |
| | Isomer 2 | >5 | | |
| 56 | Isomer 1 | 0.416 | | 0.444 |
| | Isomer 2 | >5 | | |
| 57 | Isomer 1 | 0.815 | | |
| | Isomer 2 | >5 | | |
| 58 | Isomer 1 | 0.0407 | | 0.082 |
| | Isomer 2 | >5 | | |
| 59 | Isomer 1 | 1.5 | | |
| | Isomer 2 | >2 | | |
| | Isomer 3 | >2 | | |
| | Isomer 4 | 0.0393 | | |
| 60 | Isomer 1 | 0.0325 | | |
| | Isomer 2 | >2 | | |
| 61 | Isomer 1 | 2.41 | 0.120 | |
| | Isomer 2 | >5 | 0.123 | |
| | Isomer 3 | 0.0315 | <0.002 | |
| | Isomer 4 | 1.34 | 0.0685 | |
| 62 | Isomer 1 | >2 | 0.224 | |
| | Isomer 2 | 0.565 | 0.0167 | |
| | Isomer 3 | >2 | 0.618 | |
| | Isomer 4 | 0.0526 | <0.002 | |
| 63 | Isomer 1 | 0.086 | | |
| | Isomer 2 | >2 | | |
| 64 | Isomer 1 | >2 | | |
| | Isomer 2 | 0.568 | | |
| 65 | Isomer 1 | 0.477 | | |
| | Isomer 2 | >5 | | |
| 66 | Isomer 1 | 0.144 | | |
| | Isomer 2 | >5 | | |
| 67 | Isomer 1 | >2 | | |
| | Isomer 2 | 0.216 | | |
| 68 | Isomer 1 | >2 | | |
| | Isomer 2 | 0.070 | 0.0019 | |
| 69 | Isomer 1 | 0.0358 | | |
| | Isomer 2 | >2 | | |
| 70 | Isomer 1 | >2 | | |
| | Isomer 2 | 0.243 | | |
| 71 | Isomer 1 | 0.0869 | | |
| | Isomer 2 | >2 | | |
| 72 | Isomer 1 | 0.0852 | 0.00413 | |
| | Isomer 2 | >2 | 0.0469 | |
| 73 | Isomer 1 | >2 | | |
| | Isomer 2 | 0.197 | | |
| 74 | Isomer 1 | >2 | 0.214 | |
| | Isomer 2 | 0.146 | 0.005 | |
| 75 | Isomer 1 | 0.149 | 0.0042 | |
| | Isomer 2 | >2 | 0.387 | |
| 76 | Isomer 1 | 0.088 | | |
| | Isomer 2 | >2 | | |
| 77 | Isomer 1 | 0.0394 | | |
| | Isomer 2 | 1.98 | | |
| 78 | Isomer 1 | 0.296 | | |
| | Isomer 2 | >2 | | |
| 79 | Isomer 1 | >2 | | |
| | Isomer 2 | 0.0977 | | |
| 80 | Isomer 1 | 0.201 | | |
| | Isomer 2 | >2 | | |
| 81 | Isomer 1 | 0.139 | | |
| | Isomer 2 | >2 | | |
| 82 | Isomer 1 | >5 | | |
| | Isomer 2 | >5 | | |
| | Isomer 3 | 0.604 | | |
| | Isomer 4 | 0.0116 | | 0.0236 |
| 83 | Isomer 1 | >2 | | |
| | Isomer 2 | >2 | | |
| | Isomer 3 | 0.503 | | |
| | Isomer 4 | 0.0206 | | |
| 84 | Isomer 1 | 0.395 | | |
| | Isomer 2 | 0.0162 | 0.00215 | 0.0347 |
| 85 | Isomer 1 | 0.0319 | | |
| | Isomer 2 | 0.470 | | |
| 86 | racemic | 0.169 | | |
| 87 | Isomer 1 | 0.264 | | |
| | Isomer 2 | >2 | | |
| 88 | Isomer 1 | 0.0654 | | |
| | Isomer 2 | >2 | | |
| 89 | Isomer 1 | >2 | | |
| | Isomer 2 | 1.43 | | |
| 90 | Isomer 1 | 0.210 | | |
| | Isomer 2 | 0.0096 | | 0.0151 |
| | Isomer 3 | 1.6 | | |
| | Isomer 4 | >2 | | |
| 91 | Isomer 1 | 0.473 | | |
| | Isomer 2 | 0.0064 | 0.00075 | |
| | Isomer 3 | 1.02 | | |
| | Isomer 4 | 0.401 | | |
| 92 | Isomer 1 | 0.881 | | |
| | Isomer 2 | 0.0115 | | |
| | Isomer 3 | 0.599 | | |
| | Isomer 4 | >2 | | |
| 93 | Isomer 1 | 0.412 | | |
| | Isomer 2 | >2 | | |
| | Isomer 3 | 0.036 | | |
| | Isomer 4 | >2 | | |
| 94 | Isomer 1 | 0.0851 | | |
| | Isomer 2 | >2 | | |
| 95 | Isomer 1 | 0.0414 | | |
| | Isomer 2 | 1.01 | | |
| 96 | Isomer 1 | 0.0674 | | |
| | Isomer 2 | >2 | | |
| 97 | Isomer 1 | 0.191 | | |
| | Isomer 2 | >2 | | |
| 98 | Isomer 1 | 0.571 | | |
| | Isomer 2 | 0.00659 | 0.001 | |
| | Isomer 3 | >2 | | |
| | Isomer 4 | 1.46 | | |
| 99 | Isomer 1 | 0.869 | | |
| | Isomer 2 | 1.02 | | |
| | Isomer 3 | >2 | | |
| | Isomer 4 | 0.0283 | | |
| 100 | Isomer 1 | 0.668 | | |
| | Isomer 2 | 0.0169 | 0.000565 | 0.0297 |
| | Isomer 3 | >2 | | |
| | Isomer 4 | >2 | | |
| 101 | Isomer 1 | 0.0169 | 0.00114 | 0.0307 |
| | Isomer 2 | 0.245 | | |
| | Isomer 3 | 0.355 | | |
| | Isomer 4 | >2 | | |
| 102 | Isomer 1 | 0.0308 | | |
| | Isomer 2 | 1.55 | | |
| 103 | Isomer 1 | >2 | | |
| | Isomer 2 | 0.0143 | | |
| | Isomer 3 | 1.0 | | |
| | Isomer 4 | >2 | | |
| 104 | Isomer 1 | 1.37 | | |
| | Isomer 2 | 0.0091 | <0.0005 | 0.014 |
| | Isomer 3 | 0.415 | | |
| | Isomer 4 | 1.02 | | |
| 105 | Isomer 1 | >2 | | |
| | Isomer 2 | 0.0164 | 0.0007 | |
| 106 | Isomer 1 | >2 | | |
| | Isomer 2 | 0.0255 | | |
| 107 | Isomer 1 | >2 | | |
| | Isomer 2 | 0.0723 | | |

TABLE 8-continued

| Example number | Isomer | P300 HAT SPA IC$_{50}$ (µM) | FL P300 IC$_{50}$ (µM) | H3K18Ac MSD EC$_{50}$ (µM) |
|---|---|---|---|---|
| 108 | Isomer 1 | >2 | | |
| | Isomer 2 | 0.0237 | | |
| | Isomer 3 | >2 | | |
| | Isomer 4 | >2 | | |
| 109 | Isomer 1 | >2 | | |
| | Isomer 2 | >2 | | |
| | Isomer 3 | 0.0613 | | |
| | Isomer 4 | 0.0261 | 0.0033 | |
| 110 | Isomer 1 | >2 | | |
| | Isomer 2 | 0.036 | | |
| 111 | Isomer 1 | 0.257 | | |
| | Isomer 2 | 0.0094 | 0.000917 | 0.0239 |
| 112 | Isomer 1 | 0.0385 | | |
| | Isomer 2 | 1.53 | | |
| 113 | Isomer 1 | 1.80 | | |
| | Isomer 2 | 0.0102 | 0.00074 | |
| 114 | Isomer 1 | 0.528 | | |
| | Isomer 2 | 0.0105 | 0.00073 | |
| 115 | Isomer 1 | >2 | | |
| | Isomer 2 | 0.0327 | 0.0012 | |
| 116 | Isomer 1 | 0.443 | | |
| | Isomer 2 | >2 | | |
| 117 | Isomer 1 | >2 | | |
| | Isomer 2 | >2 | | |
| 118 | Isomer 1 | >2 | | |
| | Isomer 2 | 1.9 | | |
| 119 | Isomer 1 | 0.374 | | |
| | Isomer 2 | 1.59 | | |
| 120 | Isomer 1 | >2 | | |
| | Isomer 2 | >2 | | |
| 121 | racemic | >2 | | |
| 122 | Isomer 1 | >60 | | |
| | Isomer 2 | 48.9 | | |
| 123 | Isomer 1 | >2 | 2.02 | |
| | Isomer 2 | >2 | 13.5 | |
| 124 | Isomer 1 | 0.011 | 0.00178 | |
| | Isomer 2 | 0.768 | | |
| 125 | Isomer 1 | 1.65 | | |
| | Isomer 2 | >2 | | |
| | Isomer 3 | 0.0174 | | |
| | Isomer 4 | 0.0196 | | |
| 126 | Isomer 1 | 0.0211 | | |
| | Isomer 2 | >2 | | |
| | Isomer 3 | >2 | | |
| | Isomer 4 | 0.022 | | |
| 127 | Isomer 1 | >2 | | |
| | Isomer 2 | >2 | | |
| | Isomer 3 | >2 | | |
| | Isomer 4 | 0.0219 | <0.00324 | 0.0188 |
| 128 | Isomer 1 | 0.572 | | |
| | Isomer 2 | >2 | | |
| | Isomer 3 | >2 | | |
| | Isomer 4 | 0.0249 | <0.00324 | 0.0296 |
| 129 | Isomer 1 | 0.0754 | | |
| | Isomer 2 | 0.0202 | | |
| 130 | Isomer 1 | <2 | | |
| | Isomer 2 | 0.014 | <0.00324 | |
| 131 | Isomer 1 | 0.367 | | |
| | Isomer 2 | 0.038 | | |
| 132 | Isomer 1 | 0.932 | | |
| | Isomer 2 | 0.0133 | | 0.0291 |
| 133 | Isomer 1 | 1.23 | | |
| | Isomer 2 | 0.0144 | <0.00324 | 0.0406 |
| 134 | Isomer 1 | >2 | | |
| | Isomer 2 | 0.0321 | <0.00324 | 0.0777 |
| 135 | Isomer 1 | 0.855 | | |
| | Isomer 2 | 0.0093 | <0.00324 | 0.056 |
| 136 | Isomer 1 | >2 | | |
| | Isomer 2 | >2 | | |
| | Isomer 3 | 0.0264 | <0.00324 | 0.0701 |
| | Isomer 4 | >2 | | |
| 137 | Isomer 1 | 0.783 | | |
| | Isomer 2 | 0.00862 | <0.00324 | 0.0273 |
| 138 | Isomer 1 | 0.435 | | |
| | Isomer 2 | 0.00608 | <0.00324 | 0.0482 |
| 139 | Isomer 1 | 0.026 | <0.00324 | |
| | Isomer 2 | >2 | | |
| 140 | Isomer 1 | 0.153 | | |
| | Isomer 2 | >2 | | |
| 141 | Isomer 1 | 0.0951 | | |
| | Isomer 2 | >2 | | |
| 142 | Isomer 1 | >2 | | |
| | Isomer 2 | 0.210 | | |
| 143 | Isomer 1 | >2 | | |
| | Isomer 2 | 0.0212 | <0.00324 | 0.0248 |
| | Isomer 3 | >2 | | |
| | Isomer 4 | 0.171 | | |
| 144 | Isomer 1 | >2 | | |
| | Isomer 2 | 1.07 | | |
| 145 | Isomer 1 | 0.783 | | |
| | Isomer 2 | >2 | | |
| 146 | Isomer 1 | 0.993 | | |
| | Isomer 2 | 0.00776 | | |
| 147 | Isomer 1 | 1.88 | | |
| | Isomer 2 | 0.00616 | | |
| 148 | Isomer 1 | 0.0508 | 0.00235 | 0.0845 |
| | Isomer 2 | 0.140 | | |
| 149 | Isomer 1 | >2 | | |
| | Isomer 2 | 0.019 | <0.00324 | |
| | Isomer 3 | 0.647 | | |
| | Isomer 4 | >2 | | |
| 150 | Isomer 1 | >2 | | |
| | Isomer 2 | >2 | | |
| | Isomer 3 | >2 | | |
| | Isomer 4 | 0.622 | | |
| 151 | Isomer 1 | >5 | | |
| | Isomer 2 | >5 | | |
| 152 | Isomer 1 | 0.966 | 0.0406 | |
| | Isomer 2 | 0.0318 | <0.002 | |
| 153 | Isomer 1 | >60 | | |
| | Isomer 2 | 1.93 | | |
| 154 | racemic | >60 | | |

While we have described a number of embodiments, it is apparent that our basic examples may be altered to provide other embodiments that utilize the compounds and methods of this invention. Therefore, it will be appreciated that the scope of this invention is to be defined by the appended claims rather than by the specific embodiments that have been represented by way of example.

The contents of all references (including literature references, issued patents, published patent applications, and co-pending patent applications) cited throughout this application are hereby expressly incorporated herein in their entireties by reference. Unless otherwise defined, all technical and scientific terms used herein are accorded the meaning commonly known to one with ordinary skill in the art.

The invention claimed is:

1. A compound having the Formula I:

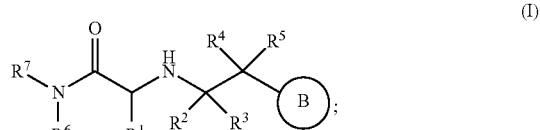

(I)

or a pharmaceutically acceptable salt thereof, wherein
Ring B is aryl, heterocyclyl, or heteroaryl each of which may be optionally substituted with 1 to 4 groups selected from $R^b$;
$R^6$ is a hydrogen or $C_{1-6}$alkyl;
$R^7$ is phenyl or monocyclic heteroaryl, each of which is substituted with one group selected from $R^f$, and wherein said phenyl and monocyclic heteroaryl for R$^7$ may also be optionally substituted with 1 to 4 groups selected from R$^a$; or R$^6$ and R$^7$ taken together with the nitrogen ring to which they are attached form a fused bicyclic heterocyclyl optionally substituted with 1 to 4 groups selected from R$^a$;

R$^1$ is phenyl optionally substituted with 1 to 3 groups selected from R$^c$;

each of R$^2$, R$^3$, R$^4$, and R$^5$ are independently hydrogen or C$_{1-6}$ alkyl, wherein said C$_{1-6}$alkyl is optionally substituted with 1 or 2 groups selected from halo, —C(O)OR$^d$, —OC$_{1-6}$alkylN(R$^d$)$_2$, —C$_{1-6}$alkylN(R$^d$)$_2$, —N(R$^d$)$_2$, —NR$^d$C$_{1-6}$alkylOR$^d$, —SOR$^d$, —S(O)$_2$R$^d$, —SON(R$^d$)$_2$, —SO$_2$N(R$^d$)$_2$, C$_{3-10}$cycloalkyl, C$_{5-10}$heterocyclyl, C$_{5-10}$heteroaryl, and C$_{6-10}$aryl;

each of R$^a$, R$^b$, and R$^c$ are each independently halo, CN, oxo, NO$_2$, C$_{1-6}$alkyl, C$_{2-6}$alkenyl, C$_{1-6}$alkoxy, C$_{1-6}$haloalkoxy, C$_{1-6}$haloalkyl, —C$_{1-6}$alkylOR$^d$, —C(O)R$^d$, —C(O)OR$^d$, —C$_{1-6}$alkylC(O)OR$^d$, —C(O)N(R$^d$)$_2$, —C(O)NR$^d$C$_{1-6}$alkylOR$^d$, —OC$_{1-6}$alkylN(R$^d$)$_2$, —C$_{1-6}$alkylC(O)N(R$^d$)$_2$, —C$_{1-6}$alkylN(R$^d$)$_2$, —N(R$^d$)$_2$, —C(O)NR$^d$C$_{1-6}$ alkylN(R$^d$)$_2$, —NR$^d$C$_{1-6}$alkylN(R$^d$)$_2$, —NR$^d$C$_{1-6}$alkylOR$^d$, —SOR$^d$, —S(O)$_2$R$^d$, —SON(R$^d$)$_2$, —SO$_2$N(R$^d$)$_2$, SF$_5$, -Ocycloalkyl, —O—C$_{1-4}$alkylaryl, —C$_{1-6}$alkylcycloalkyl, —C$_{1-6}$alkylaryl, —C$_{1-6}$alkylheteroaryl, —C$_{1-6}$alkylheterocyclyl, cycloalkyl, heterocyclyl, heteroaryl, or aryl, wherein each of said cycloalkyl, heterocyclyl, aryl, and heteroaryl alone and in connection with -Ocycloalkyl, —C$_{1-6}$alkylcycloalkyl, —C$_{1-6}$alkylaryl, —C$_{1-6}$alkylheteroaryl, and —C$_{1-6}$alkylheterocyclyl are optionally substituted with 1 to 3 groups selected from halo, C$_{1-6}$alkyl, C$_{1-6}$haloalkyl, C$_{1-6}$alkoxy, C$_{1-6}$haloalkoxy, —N(R$^d$)$_2$, —C(O)R$^d$, and —C$_{1-6}$alkyl OR$^d$;

each R$^d$ is independently hydrogen, C$_{1-6}$haloalkyl, or C$_{1-6}$alkyl; and each R$^f$ is independently cycloalkyl, heterocyclyl, heteroaryl, or aryl, wherein each of said cycloalkyl, heterocyclyl, aryl, and heteroaryl are optionally substituted with 1 to 3 groups selected from halo, CN, oxo, NO$_2$, C$_{1-6}$alkyl, C$_{2-6}$alkenyl, C$_{1-6}$alkoxy, C$_{1-6}$haloalkoxy, C$_{1-6}$haloalkyl, —C$_{1-6}$alkylOR$^d$, —C(O)R$^d$, —C(O)OR$^d$, —C$_{1-6}$alkylC(O)OR$^d$, —C(O)N(R$^d$)$_2$, —C(O)NR$^d$C$_{1-6}$alkylOR$^d$, —OC$_{1-6}$alkylN(R$^d$)$_2$, —C$_{1-6}$alkylC(O)N(R$^d$)$_2$, —C$_{1-6}$alkylN(R$^d$)$_2$, —N(R$^d$)$_2$, —C(O)NR$^d$C$_{1-6}$ alkylN(R$^d$)$_2$, —NR$^d$C$_{1-6}$alkylN(R$^d$)$_2$, —NR$^d$C$_{1-6}$ alkylOR$^d$, —SOR$^d$, —S(O)$_2$R$^d$, —SON(R$^d$)$_2$, —SO$_2$N(R$^d$)$_2$, SF$_5$, -Ocycloalkyl;

provided the compound is not N—[1,1'-biphenyl]-2-yl-2[[2-(3,4-dimethoxyphenyl)ethyl]amino]-propanamide, or 2-[(2-phenylpropyl)amino]-N-[4-(1H-1,2,4-triazol-1-yl)phenyl]-propanamide, or a salt thereof.

2. The compound of claim 1, wherein Ring B is phenyl optionally substituted with 1 to 3 groups selected from R$^b$.

3. The compound of claim 1, wherein R$^3$ is hydrogen.

4. The compound of claim 1, wherein R$^5$ is hydrogen.

5. The compound of claim 1, wherein R$^2$ is hydrogen or C$_{1-4}$alkyl.

6. The compound of claim 1, wherein R$^4$ is hydrogen or C$_{1-4}$alkyl.

7. The compound of claim 1, wherein the compound is of the Formula IV or V:

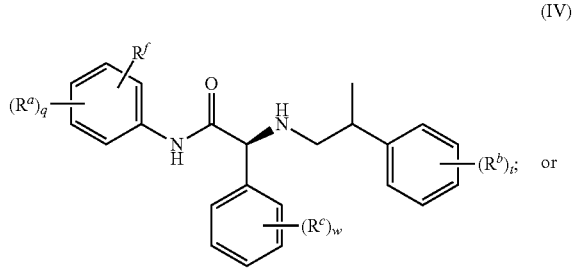

(IV)

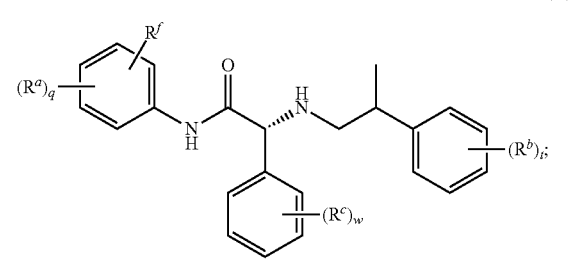

(V)

or a pharmaceutically acceptable salt thereof, wherein w, q, and t are each independently 0, 1, or 2.

8. The compound of claim 1, wherein the compound is of the Formula VI or VII:

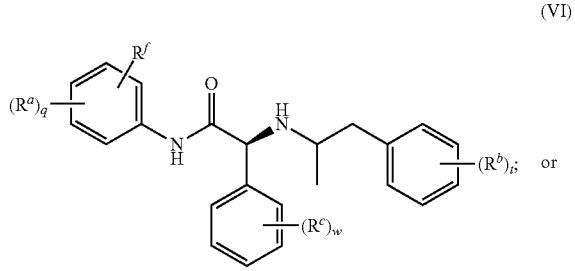

(VI)

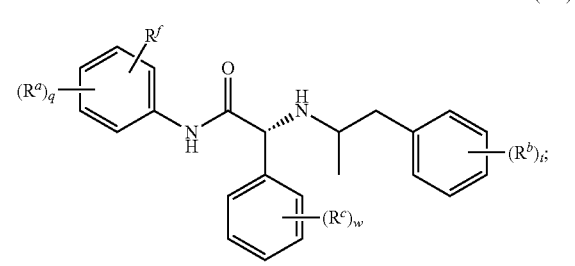

(VII)

or a pharmaceutically acceptable salt thereof, wherein w, q, and t are each independently 0, 1, or 2.

9. The compound of claim 1, wherein the compound is of the Formula VIII or IX:

(VIII)

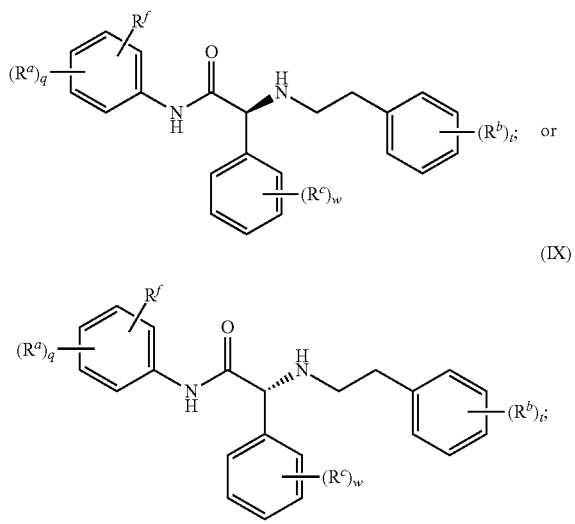

or (IX)

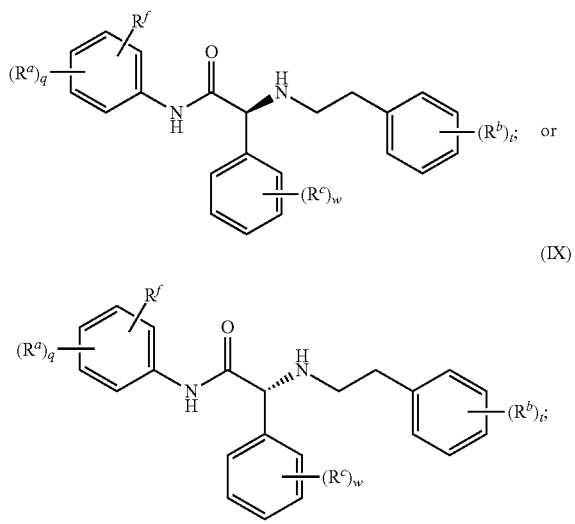

or a pharmaceutically acceptable salt thereof, wherein w, q, and t are each independently 0, 1, or 2.

10. The compound of claim 1, wherein $R^c$, if present, is $C^{1-6}$alkyl, $C^{1-6}$alkoxy, $C_{1-6}$haloalkoxy, or $C_{1-6}$haloalkyl.

11. The compound of claim 1, wherein $R^a$ is $C_{1-4}$alkoxy or halo.

12. The compound of claim 1, wherein $R^f$ is heteroaryl or heterocyclyl, each of which may be optionally substituted with 1 to 3 groups selected from selected from halo, CN, oxo, $NO_2$, $C_{1-6}$alkyl, $C_{2-6}$alkenyl, $C_{1-6}$alkoxy, $C_{1-6}$haloalkoxy, $C_{1-6}$haloalkyl, —$C_{1-6}$alkyl$OR^d$, —$C(O)R^d$, —$C(O)OR^d$, —$C_{1-6}$alkylC(O)$OR^d$, —$C(O)N(R^d)_2$, —$C(O)NR^dC_{1-6}$alkyl$OR^d$, —$OC_{1-6}$alkyl$N(R^d)_2$, —$C_{1-6}$alkylC(O)N$(R^d)_2$, —$C_{1-6}$alkylN$(R^d)_2$, —$N(R^d)_2$, —$C(O)NR^dC_{1-6}$alkylN$(R^d)_2$, —$NR^dC_{1-6}$alkylN$(R^d)_2$, —$NR^dC_{1-6}$alkyl$OR^d$, —$SOR^d$, —$S(O)_2R^d$, —$SON(R^d)_2$, —$SO_2N(R^d)_2$, $SF_5$, -Ocycloalkyl.

13. The compound of claim 1, wherein the compound is of the Formula XII or XIII:

(XII)

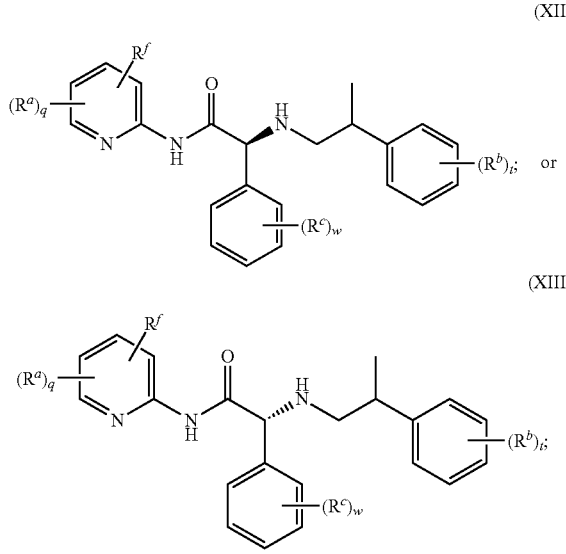

or (XIII)

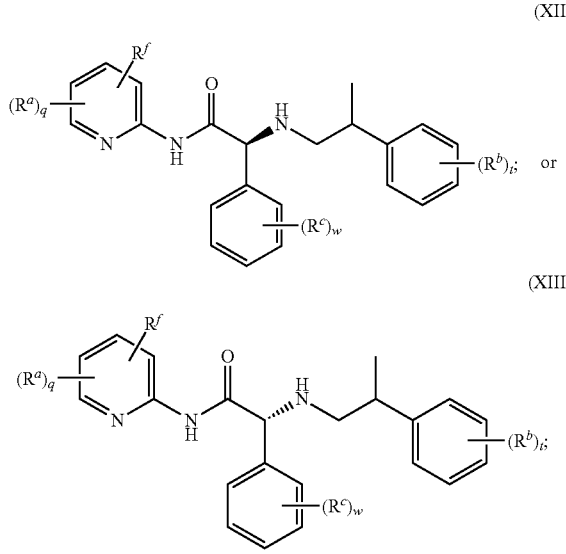

or a pharmaceutically acceptable salt thereof, wherein w, q, and t are each independently 0, 1, or 2.

14. The compound of claim 1, wherein the compound is of the Formula XVI or XVII:

(XVI)

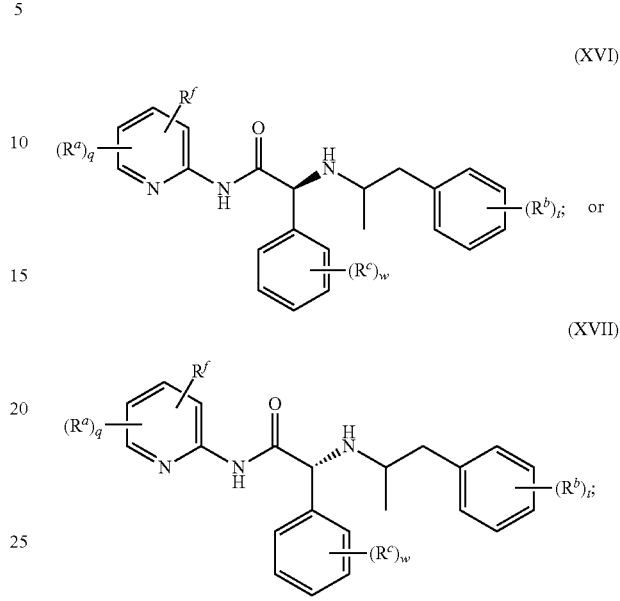

or (XVII)

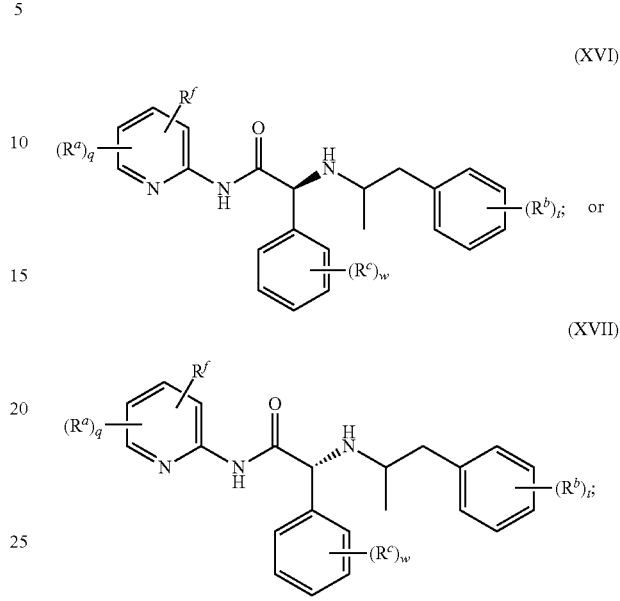

or a pharmaceutically acceptable salt thereof, wherein w, q, and t are each independently 0, 1, or 2.

15. The compound of claim 13, wherein $R^c$, if present, is independently $C_{1-6}$alkyl, halo, or CN.

16. The compound of claim 13, wherein w is 0 or 1.

17. The compound of claim 13, wherein $R^b$ is halo, cyano, or —$SO_2NH_2$.

18. The compound of claim 13, wherein t is 1.

19. The compound of claim 13, wherein q is 1.

20. The compound of claim 13, wherein $R^f$ is cycloalkyl, phenyl, heteroaryl, or heterocyclyl, each of which may be optionally substituted with 1 to 3 groups selected from halo, CN, oxo, $NO_2$, $C_{1-6}$alkyl, $C_{2-6}$ alkenyl, $C_{1-6}$alkoxy, $C_{1-6}$haloalkoxy, $C_{1-6}$haloalkyl, —$C_{1-6}$alkyl$OR^d$, —$C(O)R^d$, —$C(O)OR^d$, —$C_{1-6}$alkylC(O)$OR^d$, —$C(O)N(R^d)_2$, —$C(O)NR^dC_{1-6}$alkyl$OR^d$, —$OC_{1-6}$alkyl$N(R^d)_2$, —$C_{1-6}$alkylC(O)N$(R^d)_2$, —$C_{1-6}$alkylN$(R^d)_2$, —$N(R^d)_2$, —$C(O)NR^dC_{1-6}$alkylN$(R^d)_2$, —$NR^dC_{1-6}$alkylN$(R^d)_2$, —$NR^dC_{1-6}$alkyl$OR^d$, —$SOR^d$, —$S(O)_2R^d$, —$SON(R^d)_2$, —$SO_2N(R^d)_2$, $SF_5$, -Ocycloalkyl.

21. A compound selected from

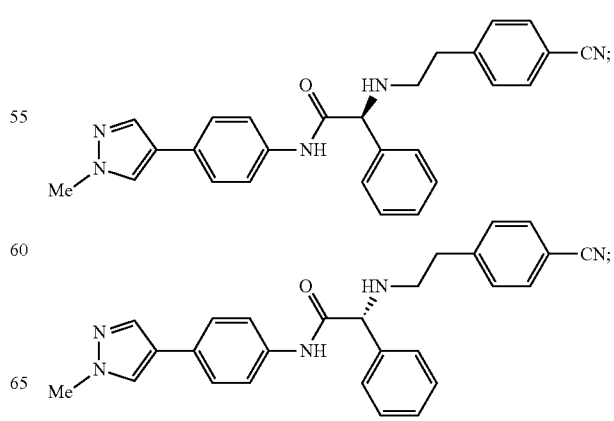

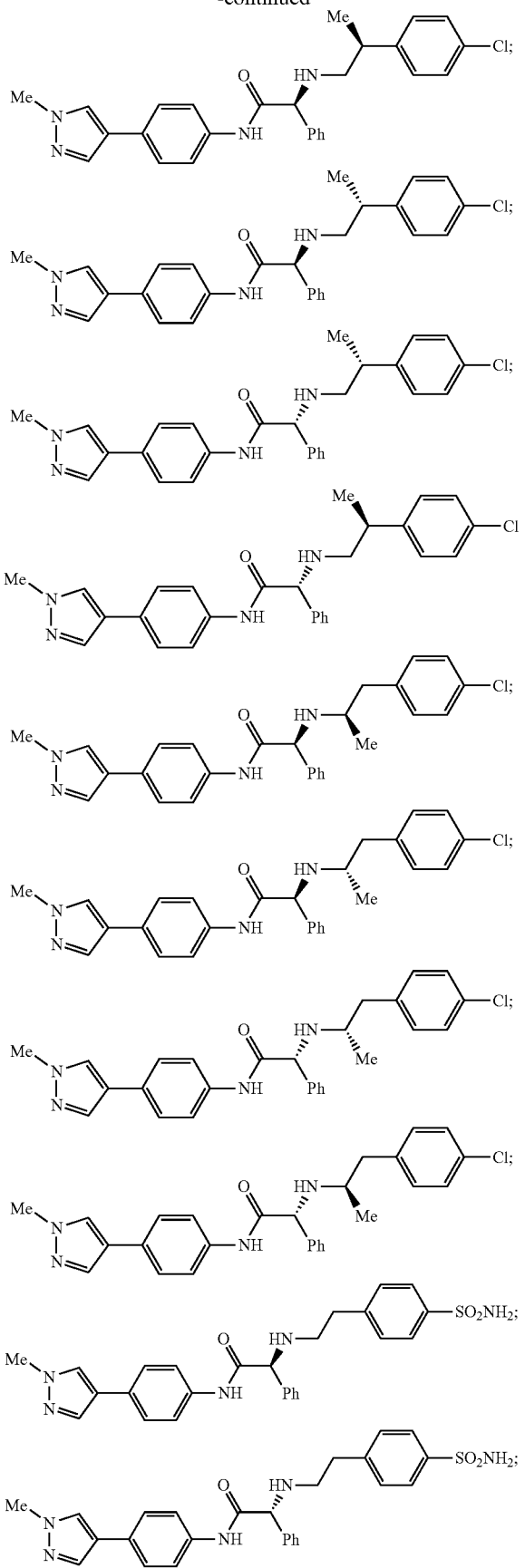
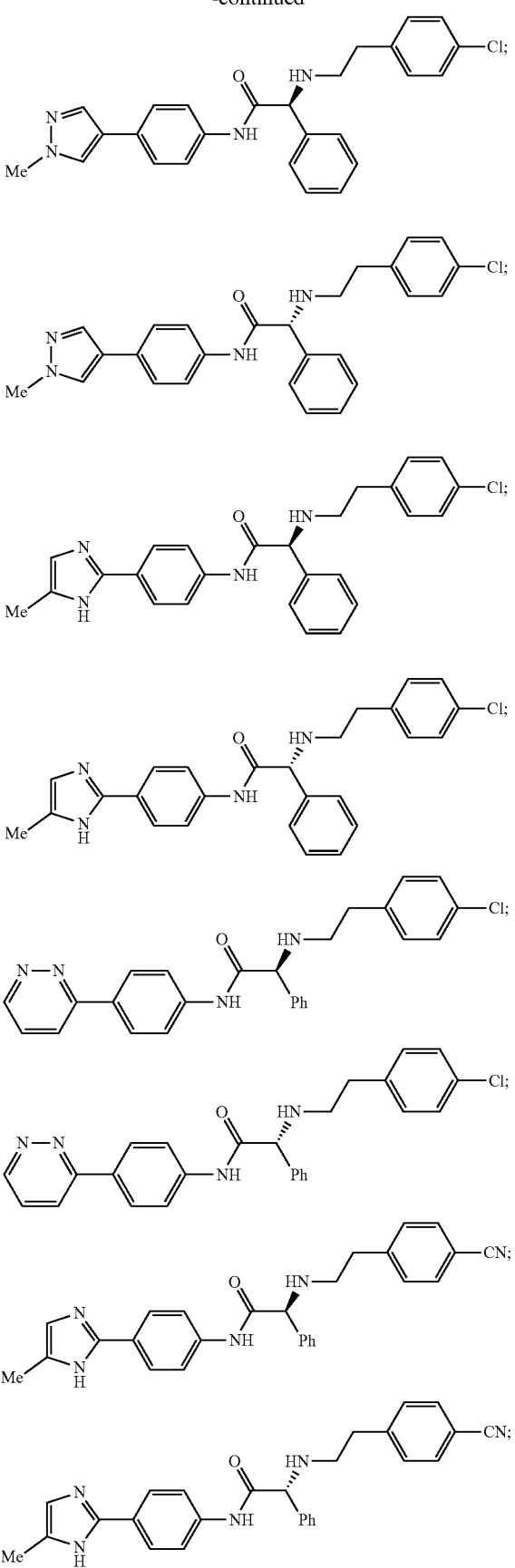

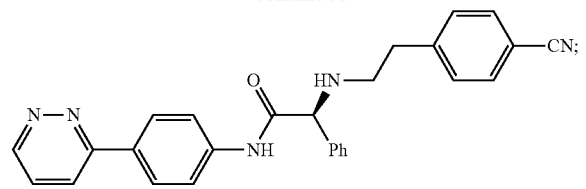
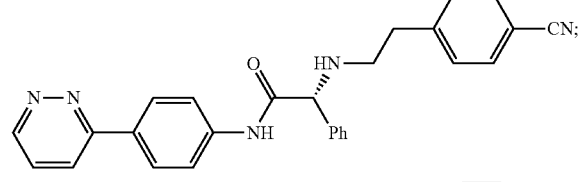
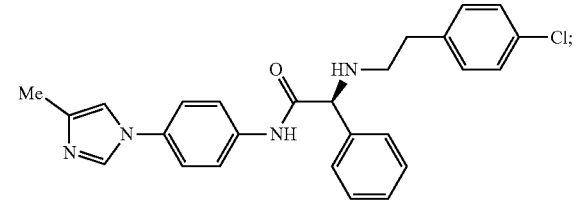
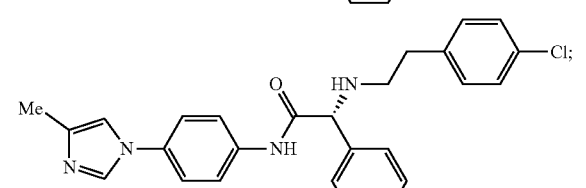
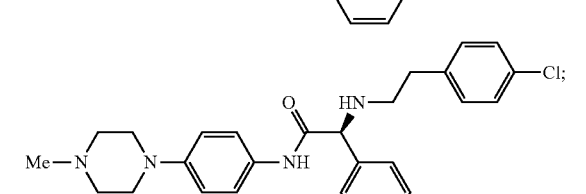
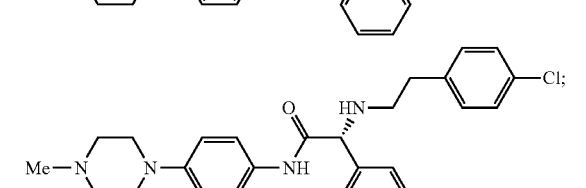
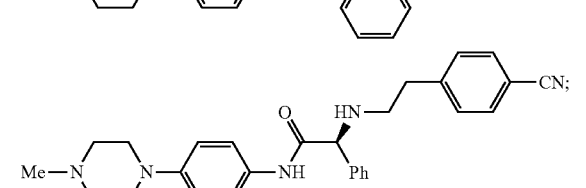
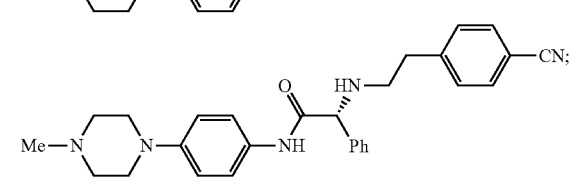
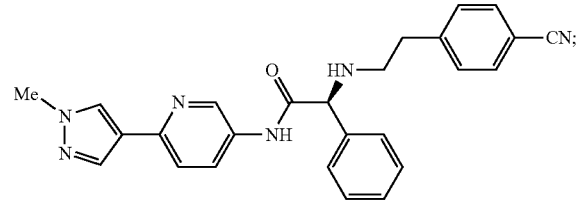
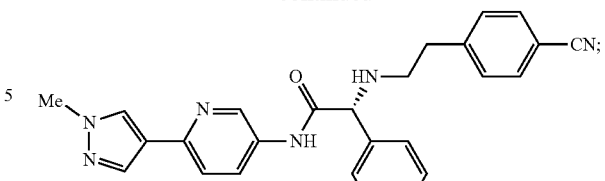
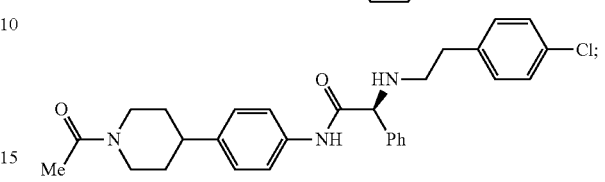
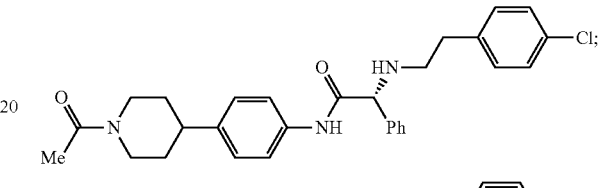
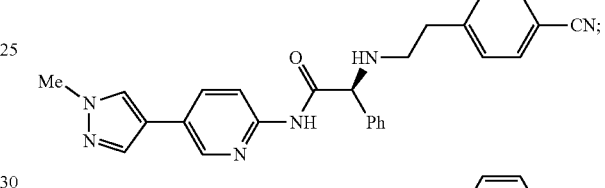
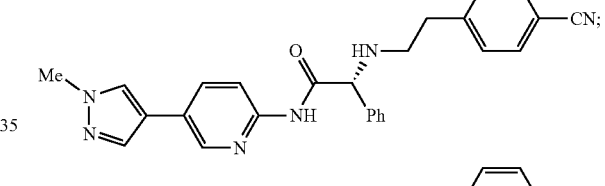
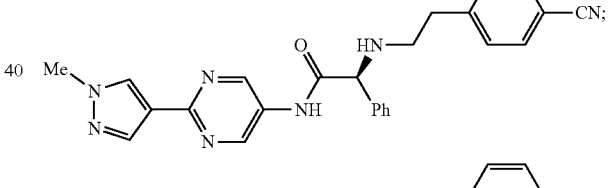
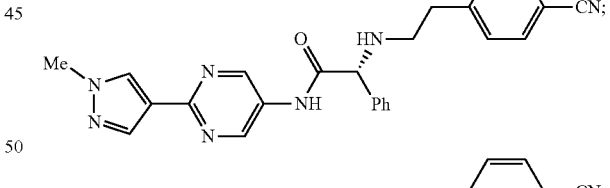
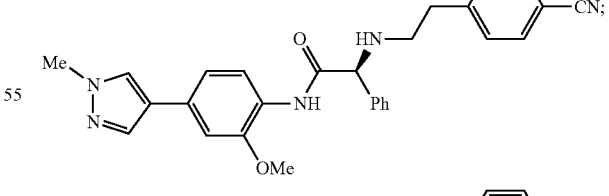
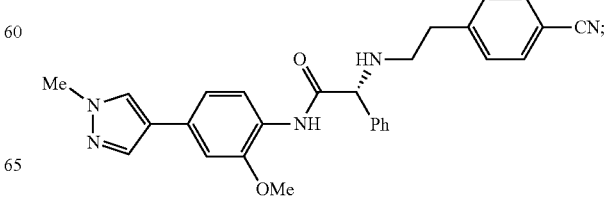

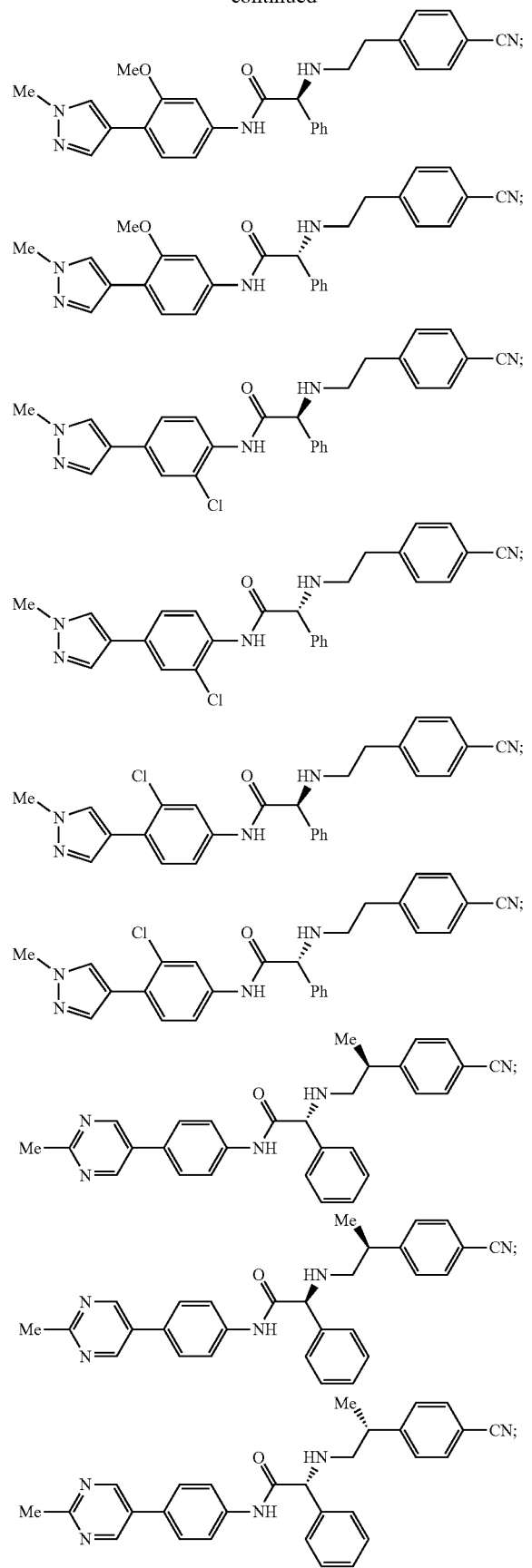
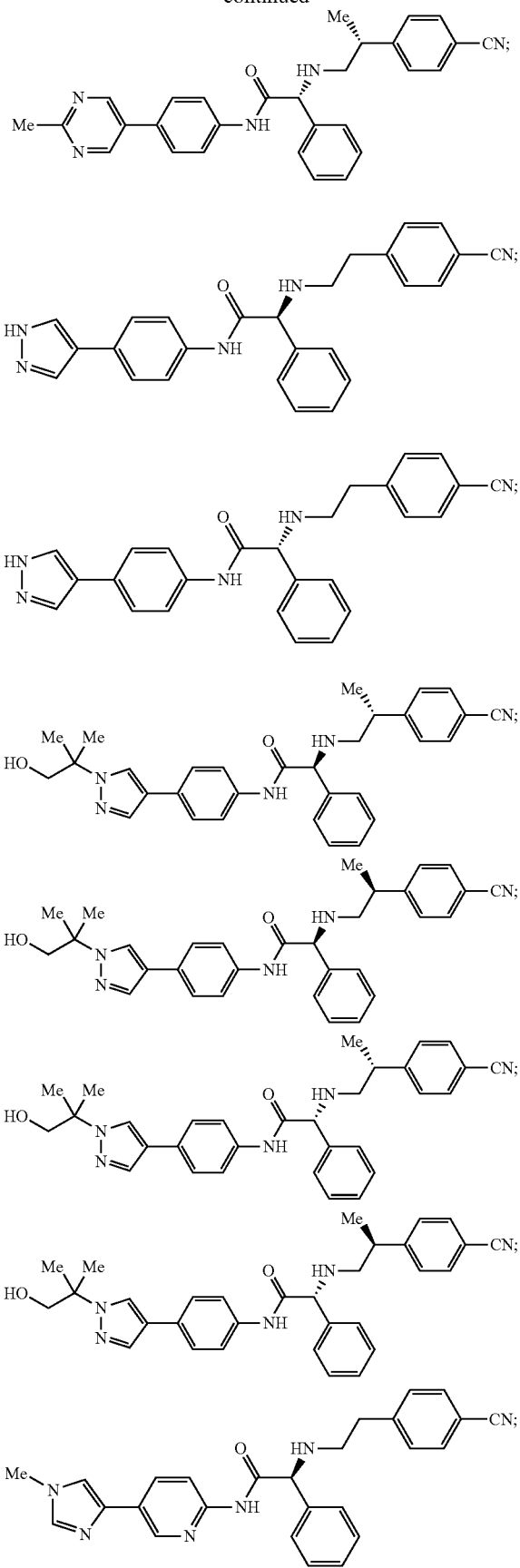

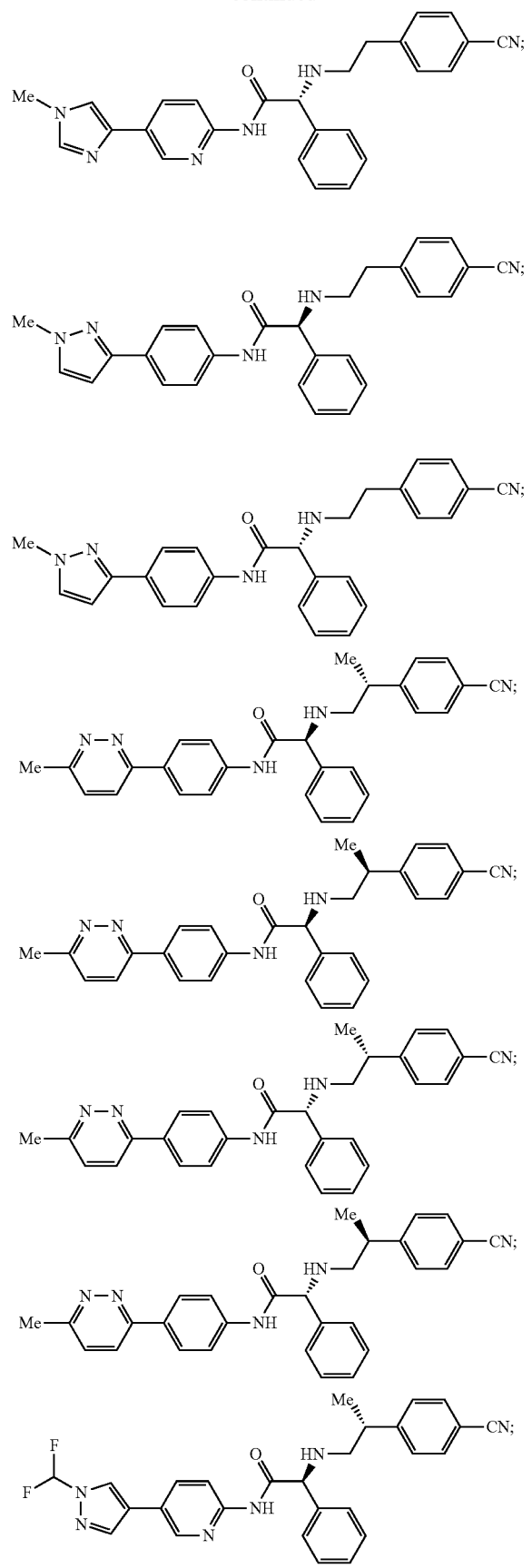
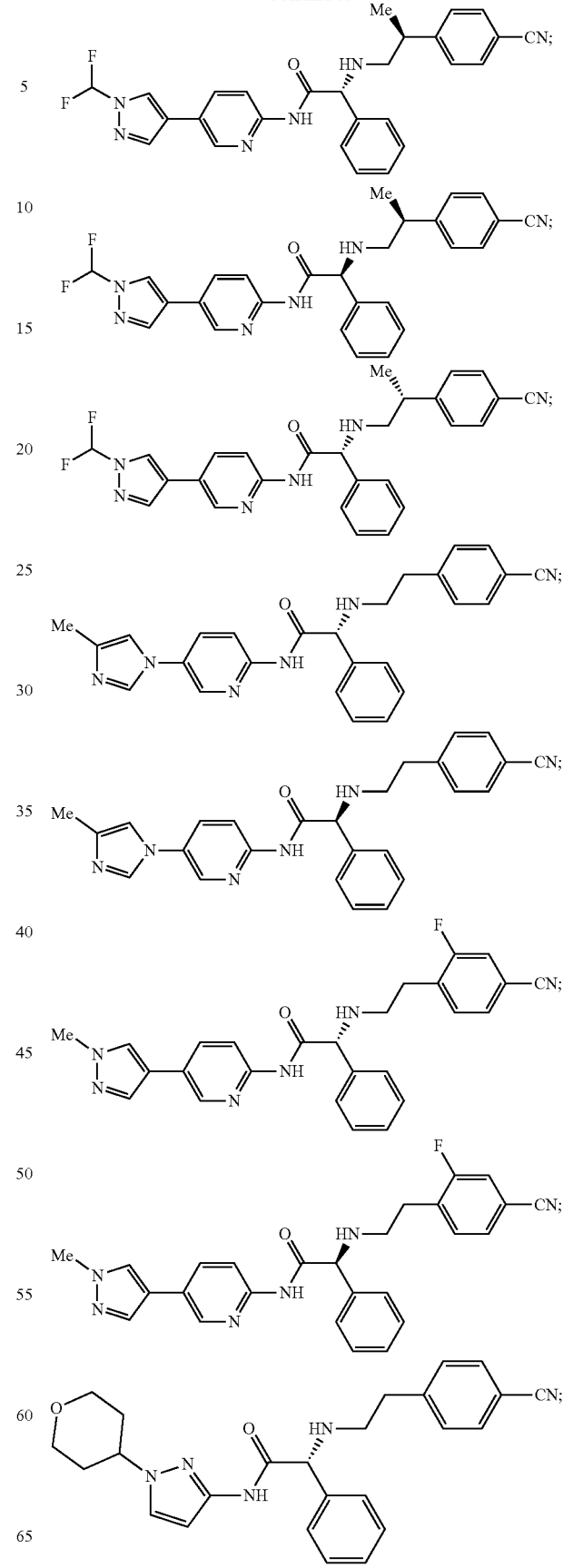

197
-continued
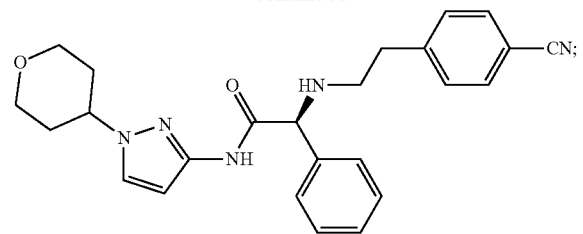
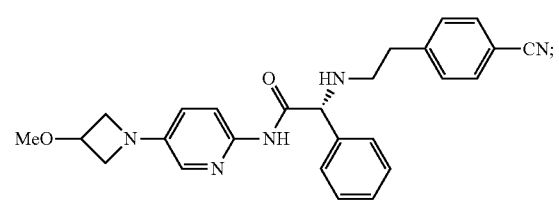
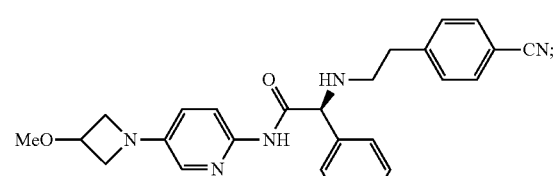
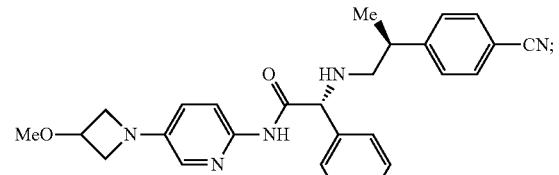
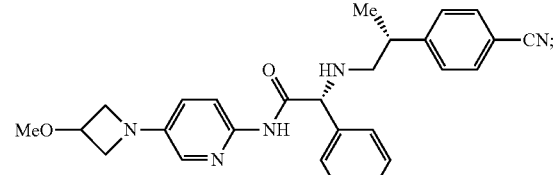
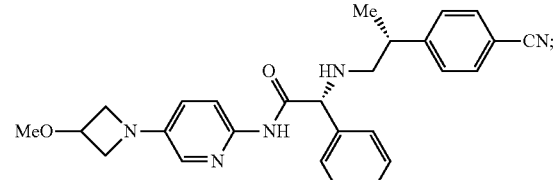
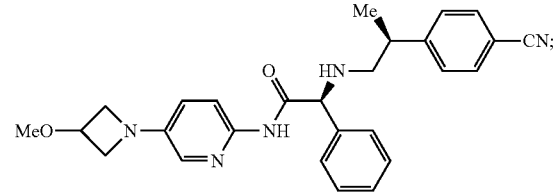
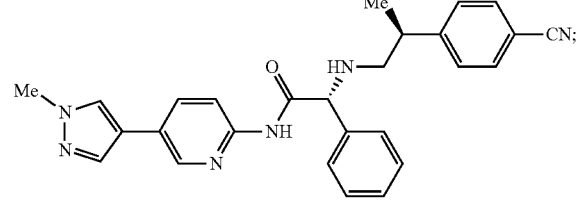
198
-continued
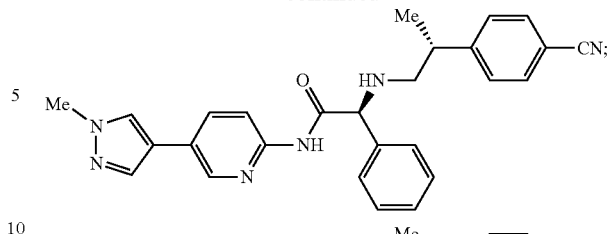
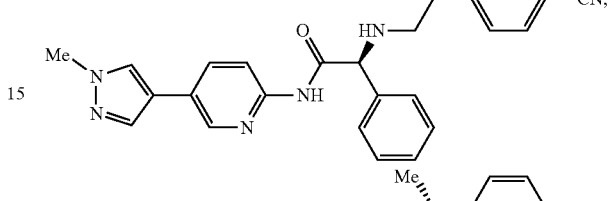
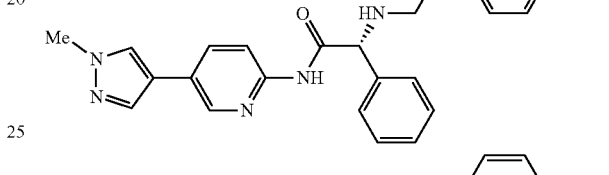
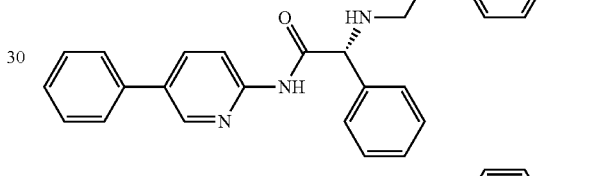
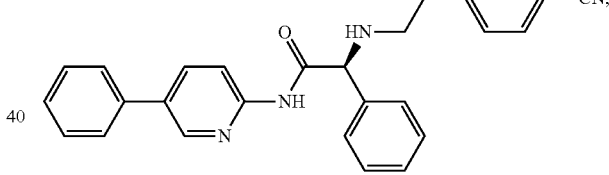
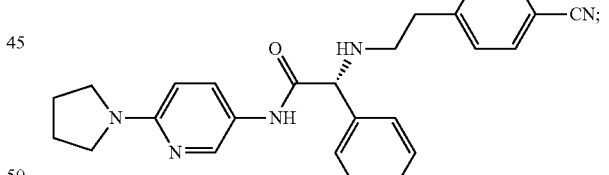
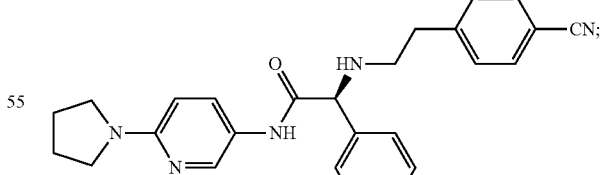
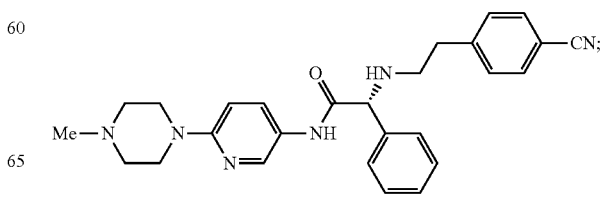

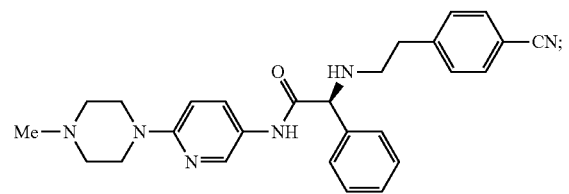
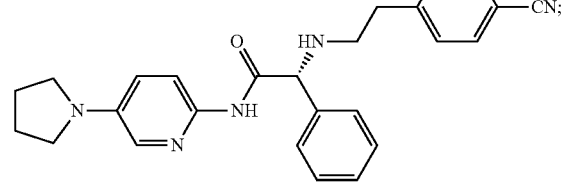
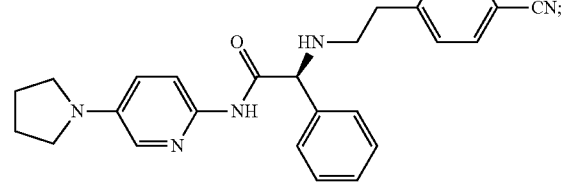
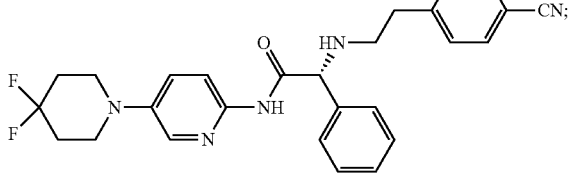
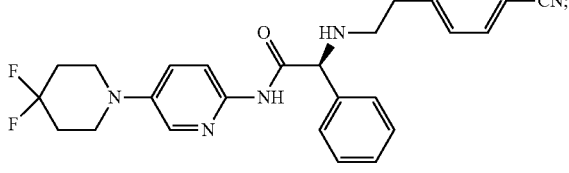
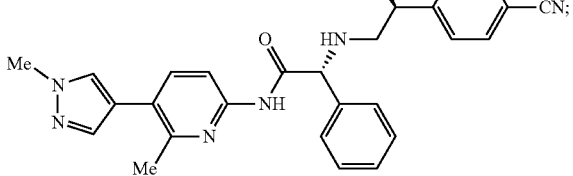
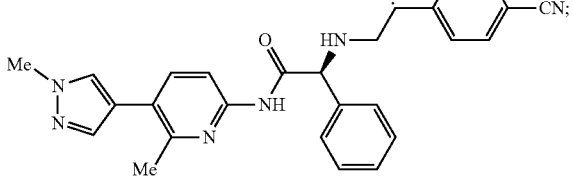
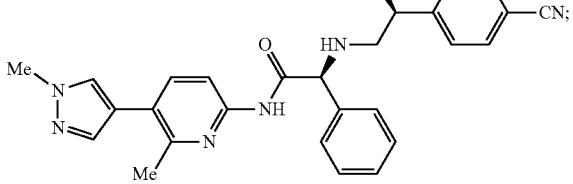
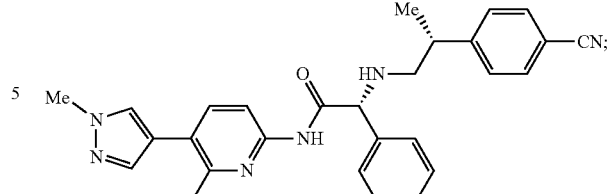
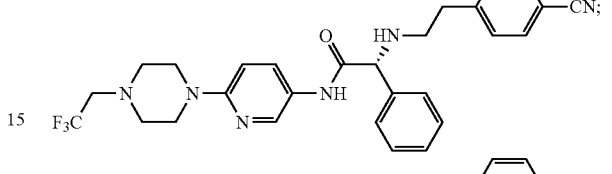
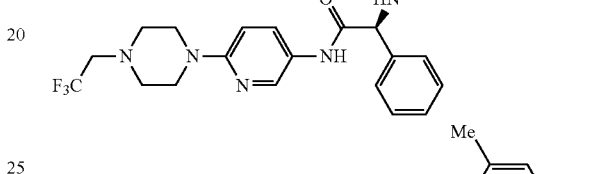
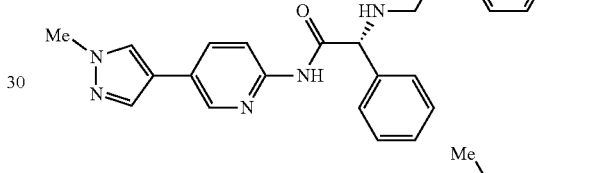
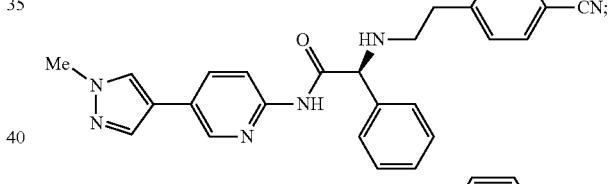
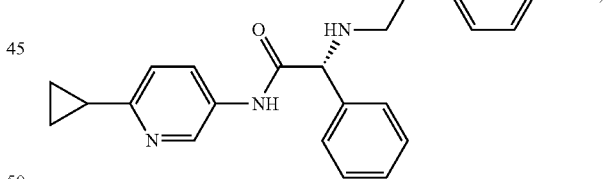
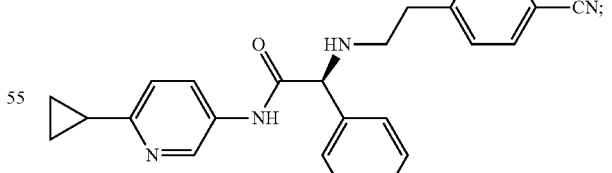
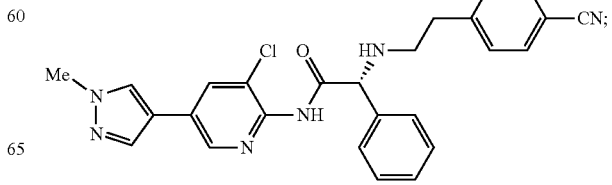

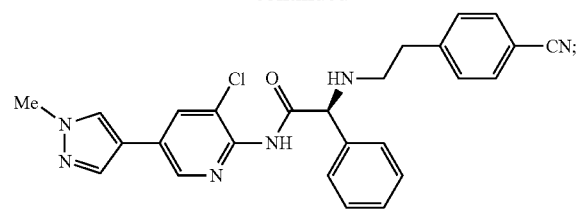
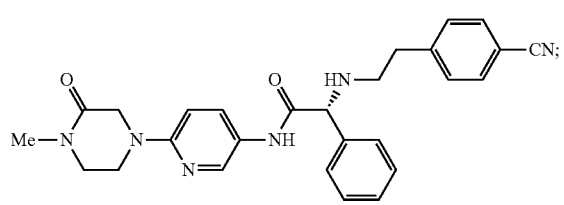
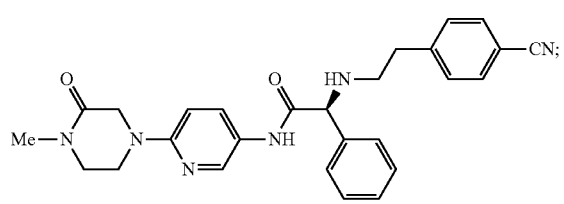
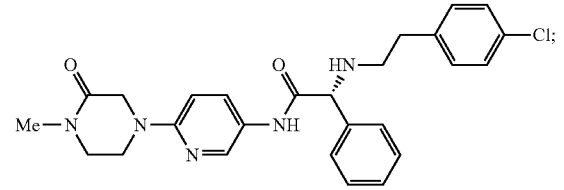
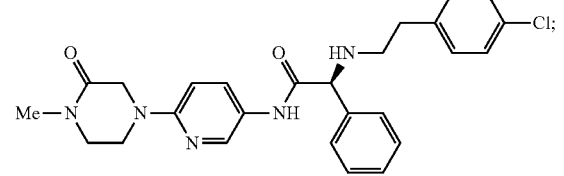
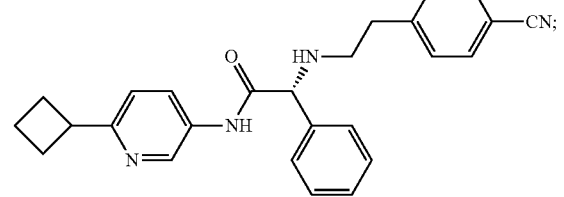
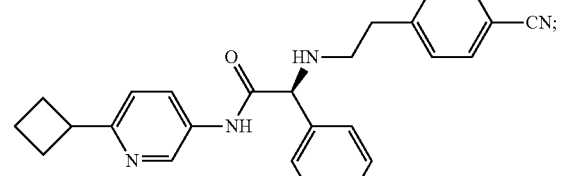
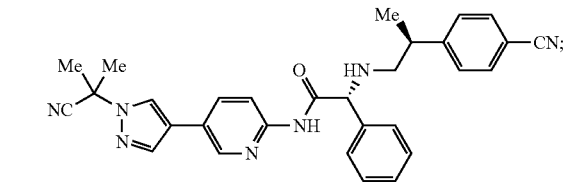
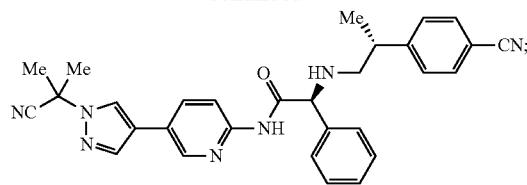
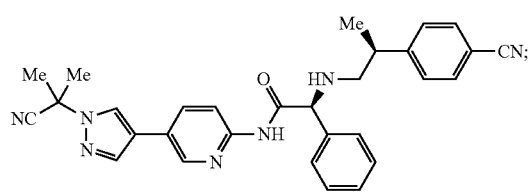
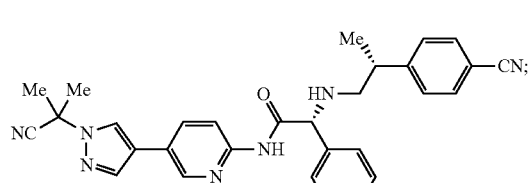
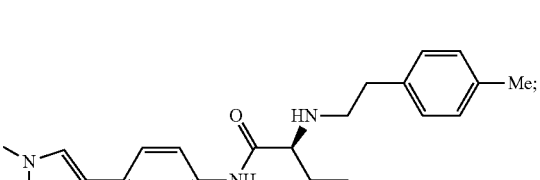
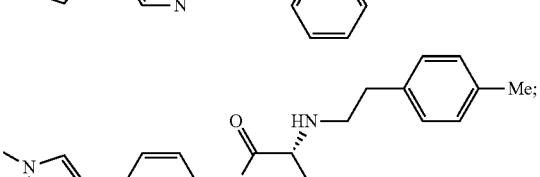
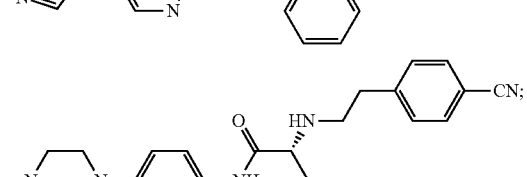
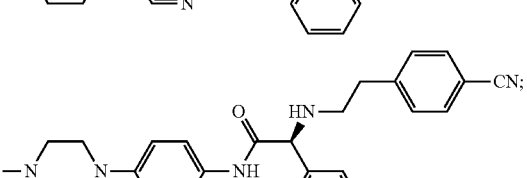
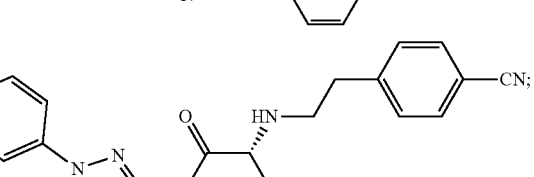

203
-continued
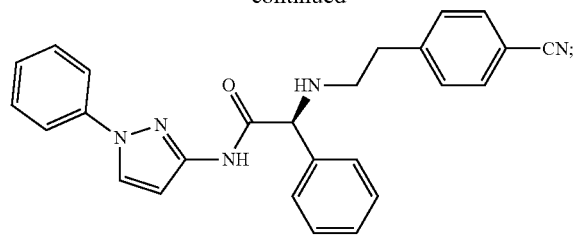
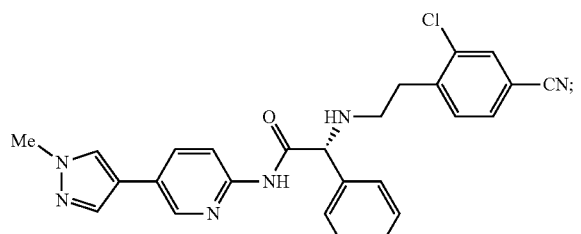
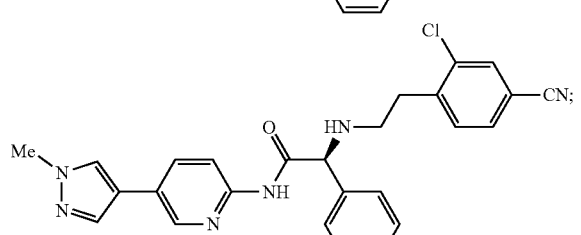
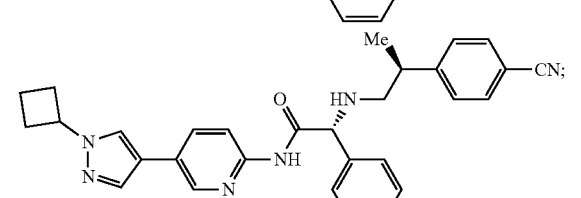
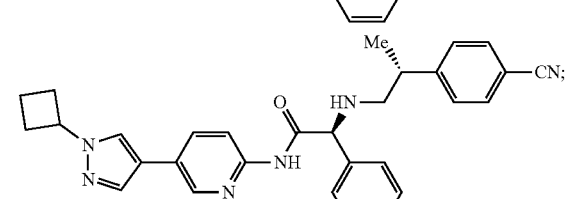
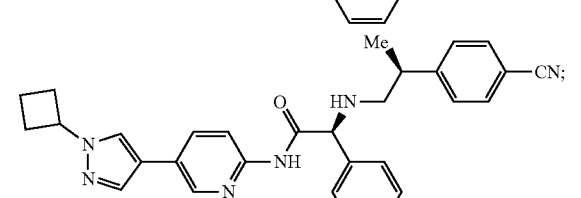
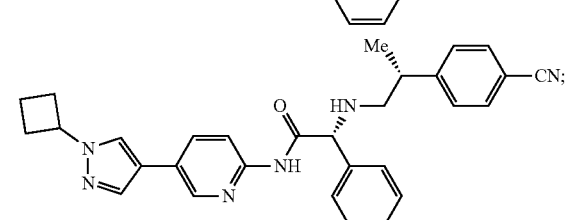
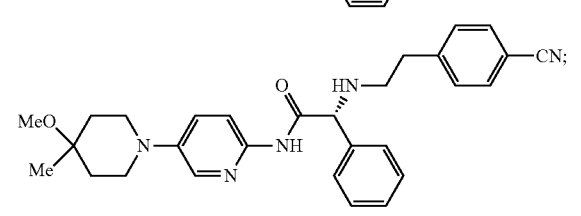
204
-continued
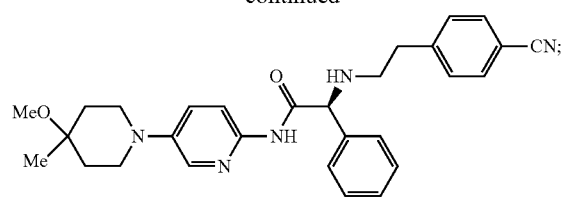
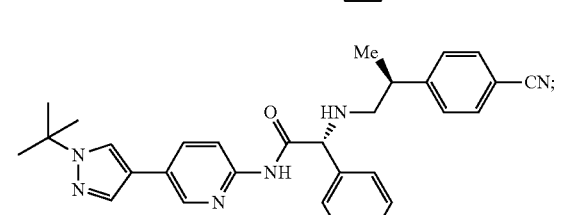
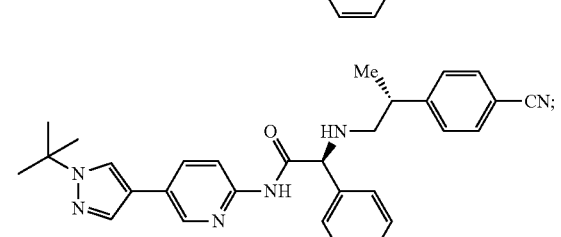
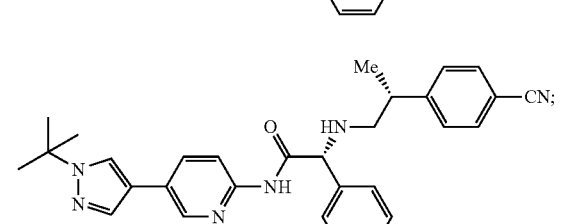
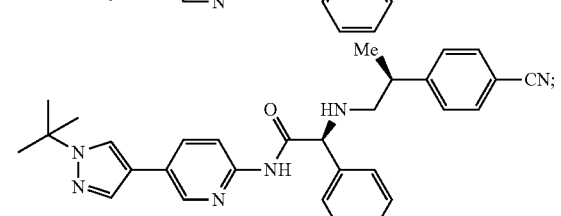
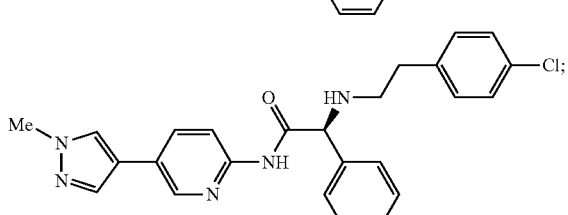
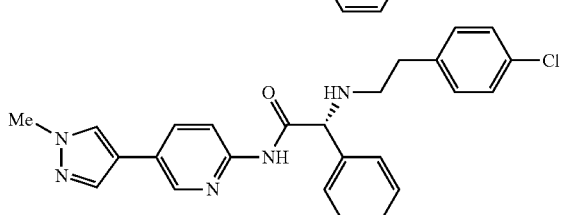
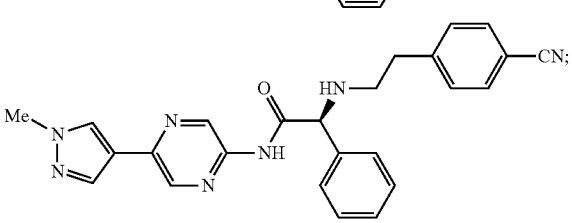

205
-continued
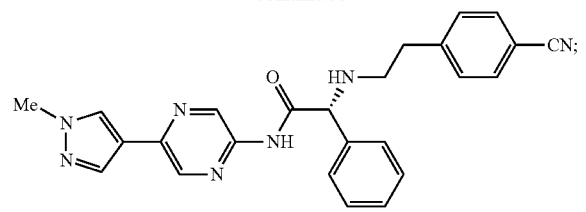
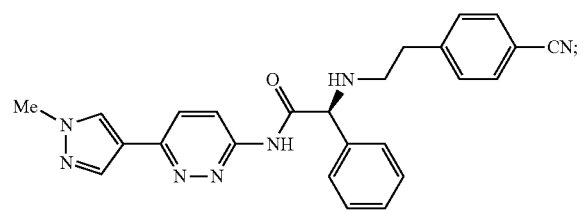
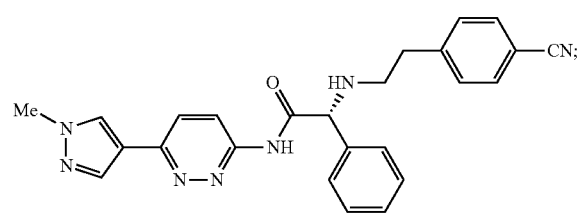
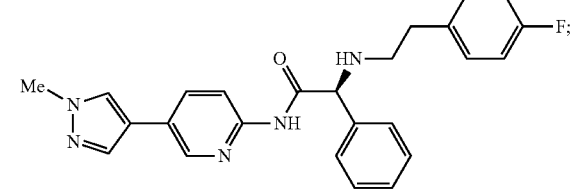
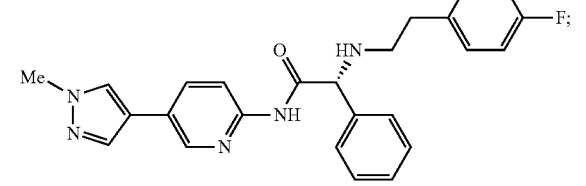
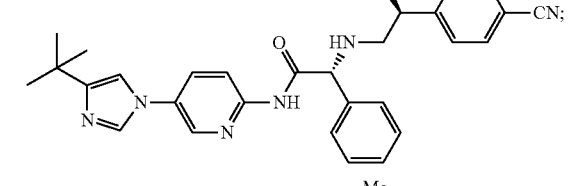
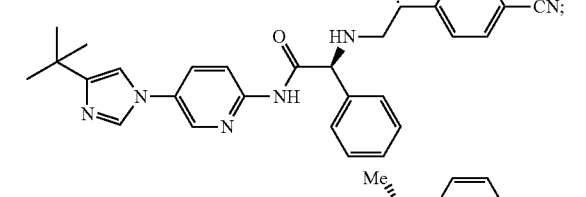
206
-continued
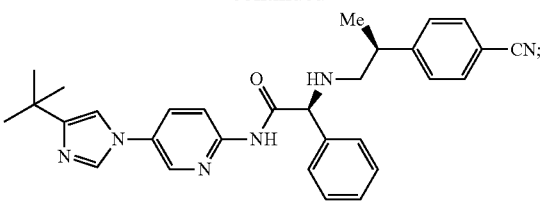
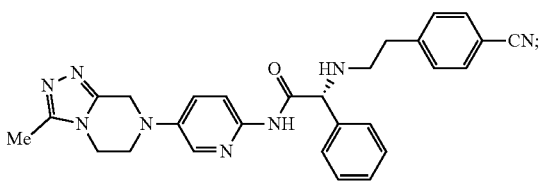
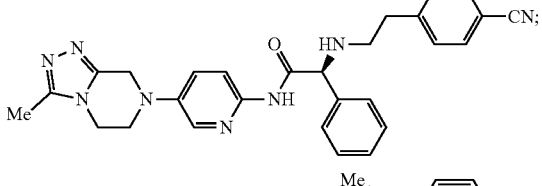
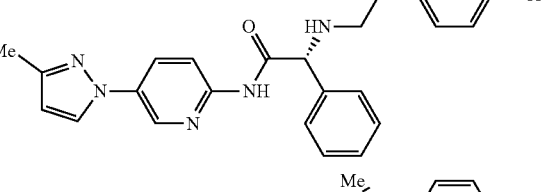
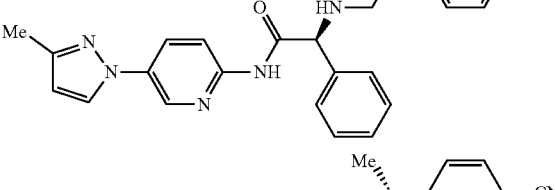
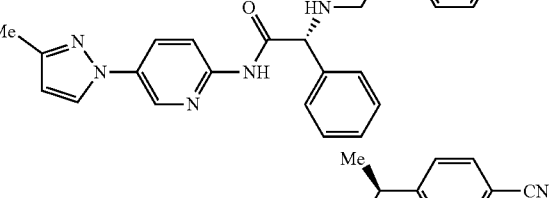
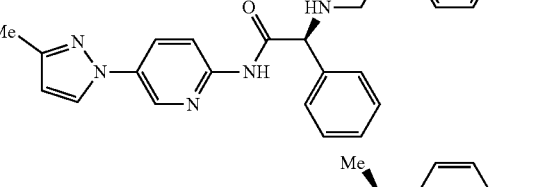

209
-continued
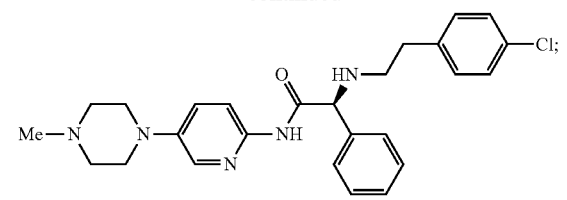
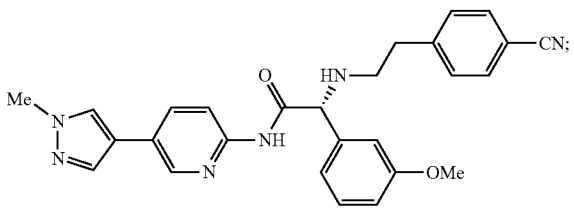
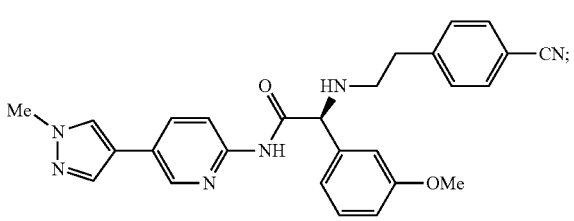
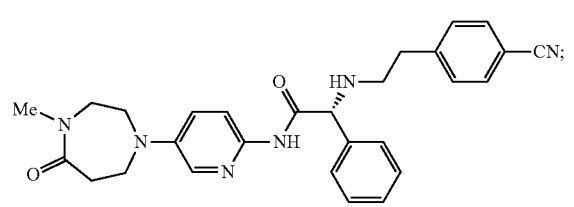
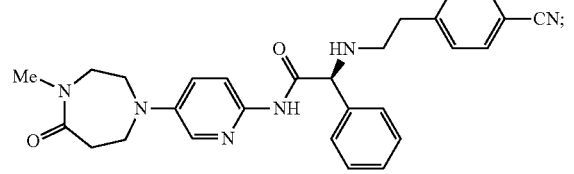
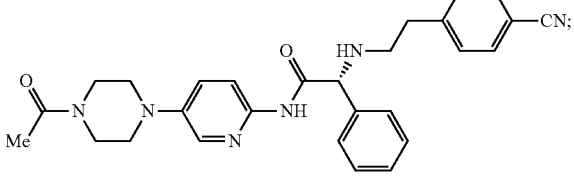
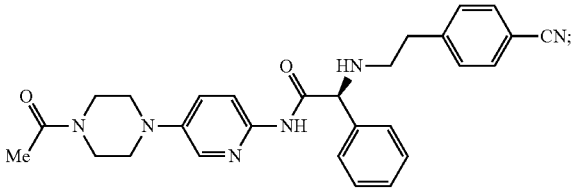
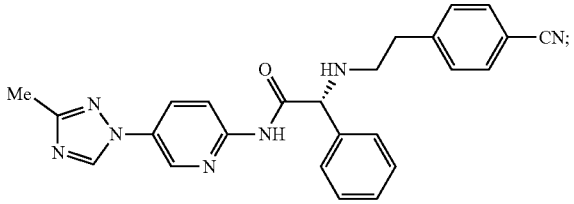
210
-continued
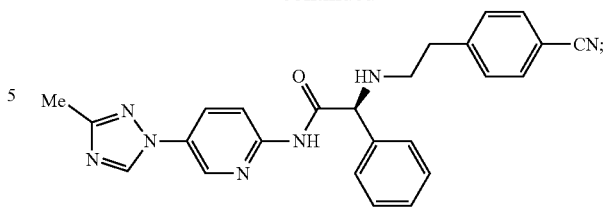
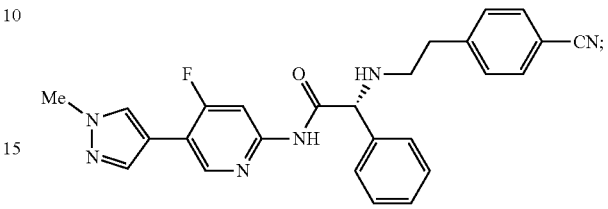
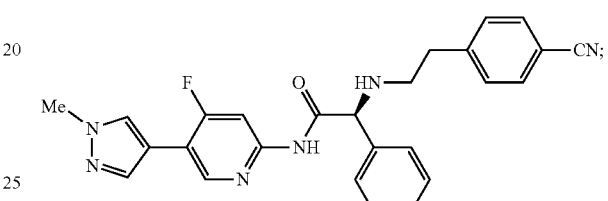
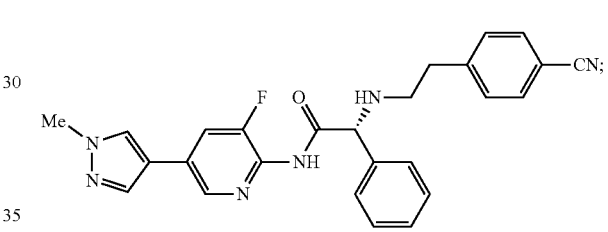
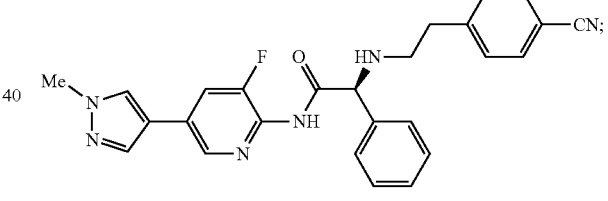
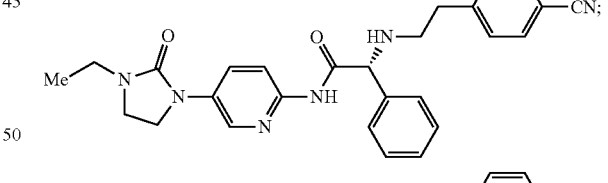
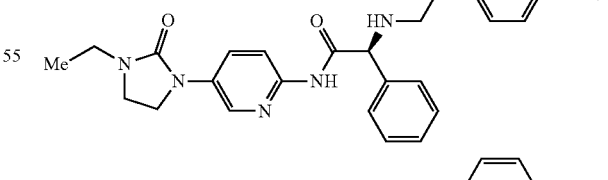
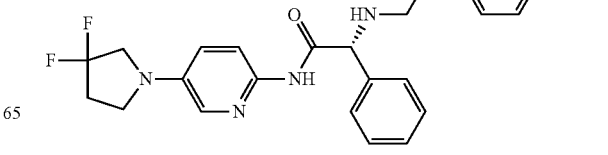

211
-continued
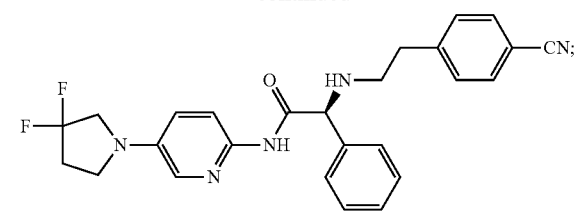
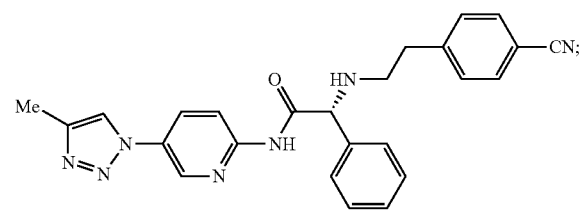
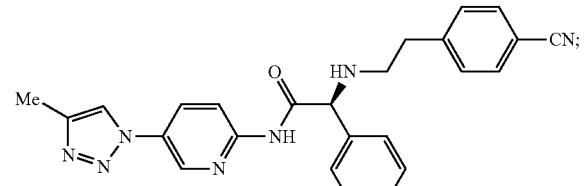
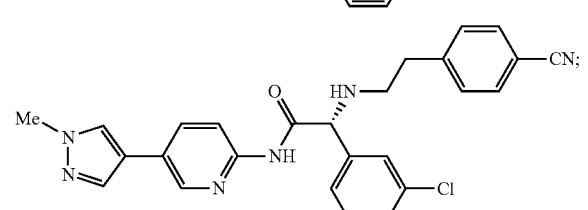
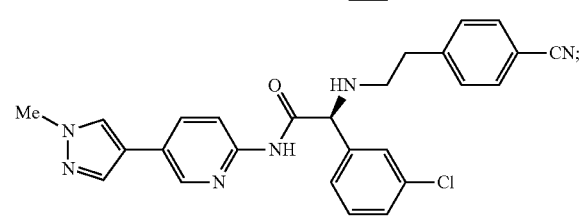
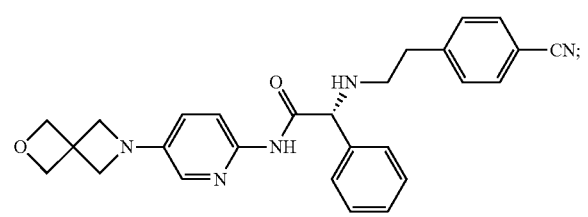
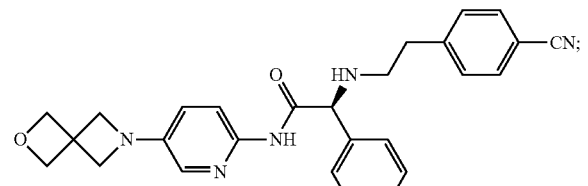
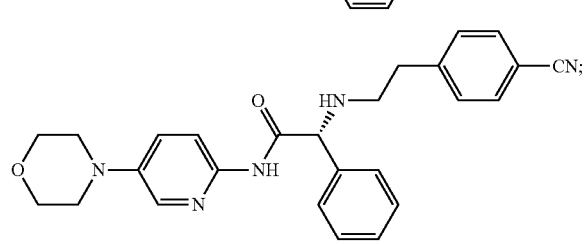
212
-continued
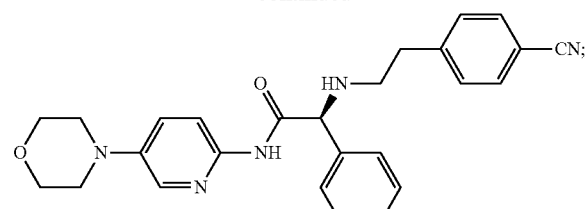
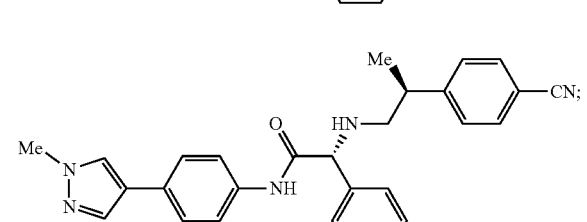
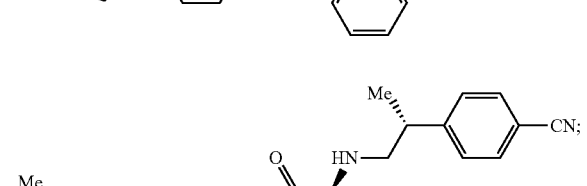
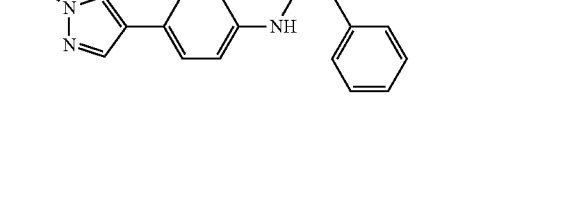
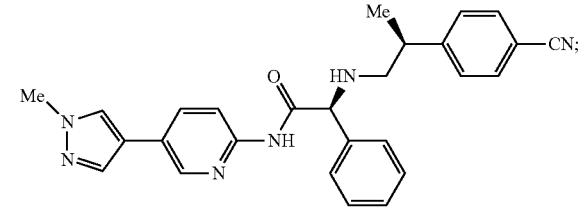
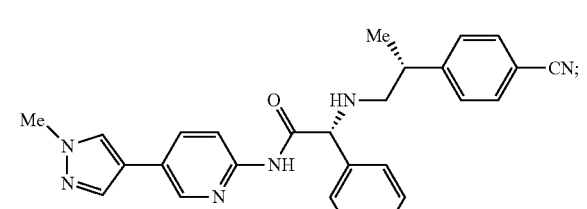
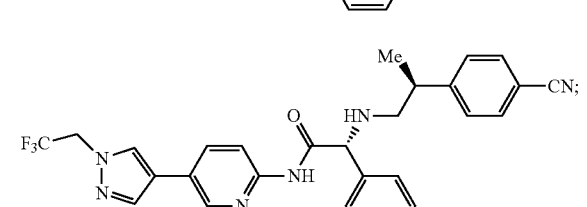
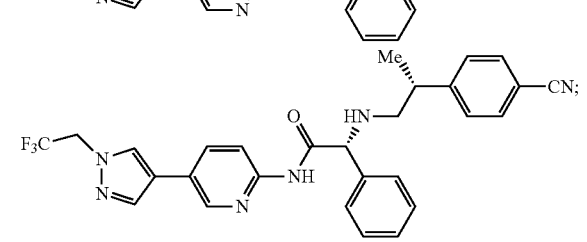

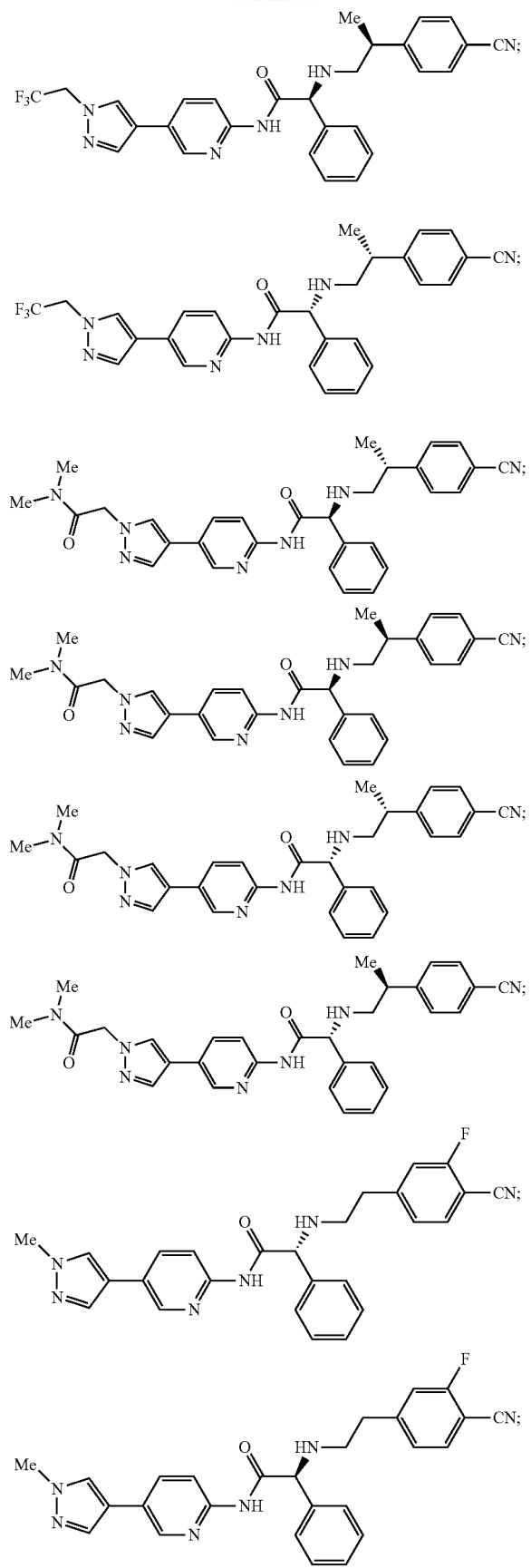
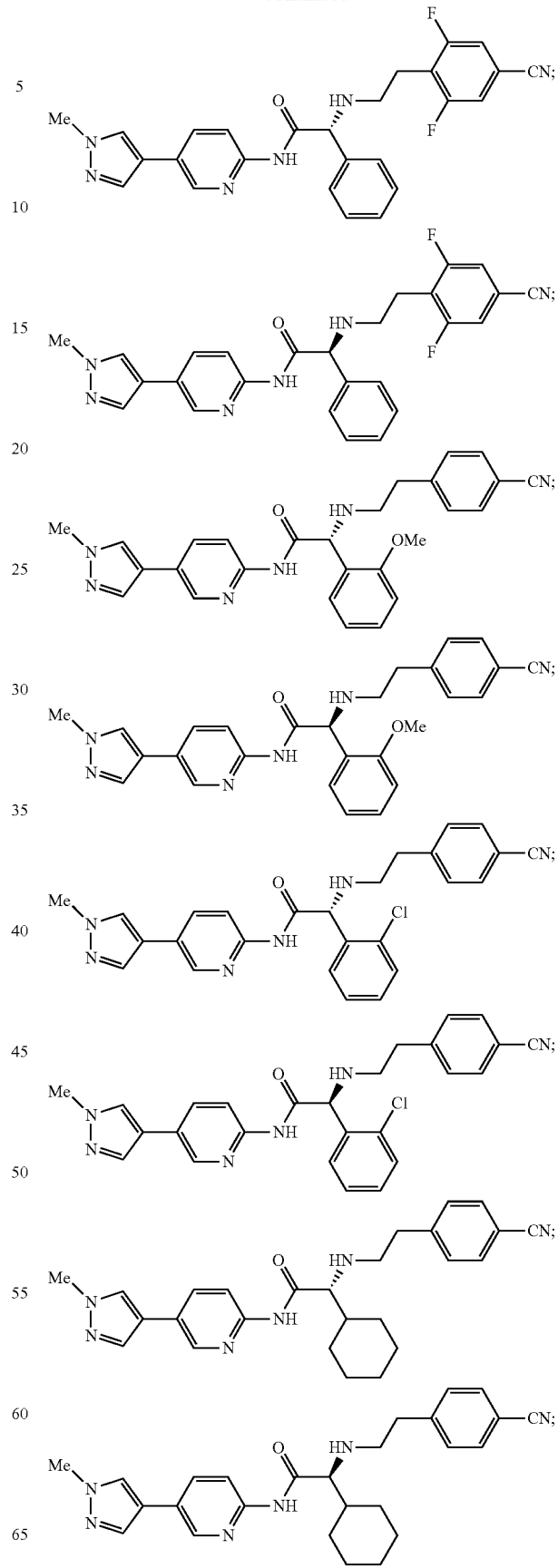

215
-continued
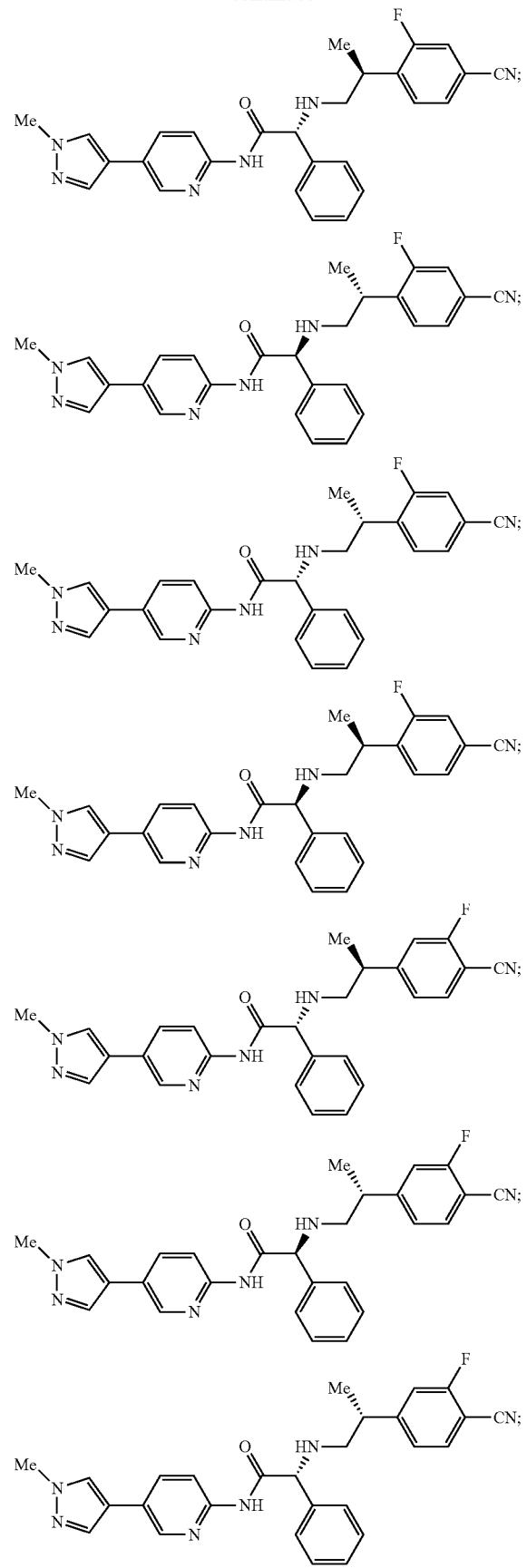
216
-continued
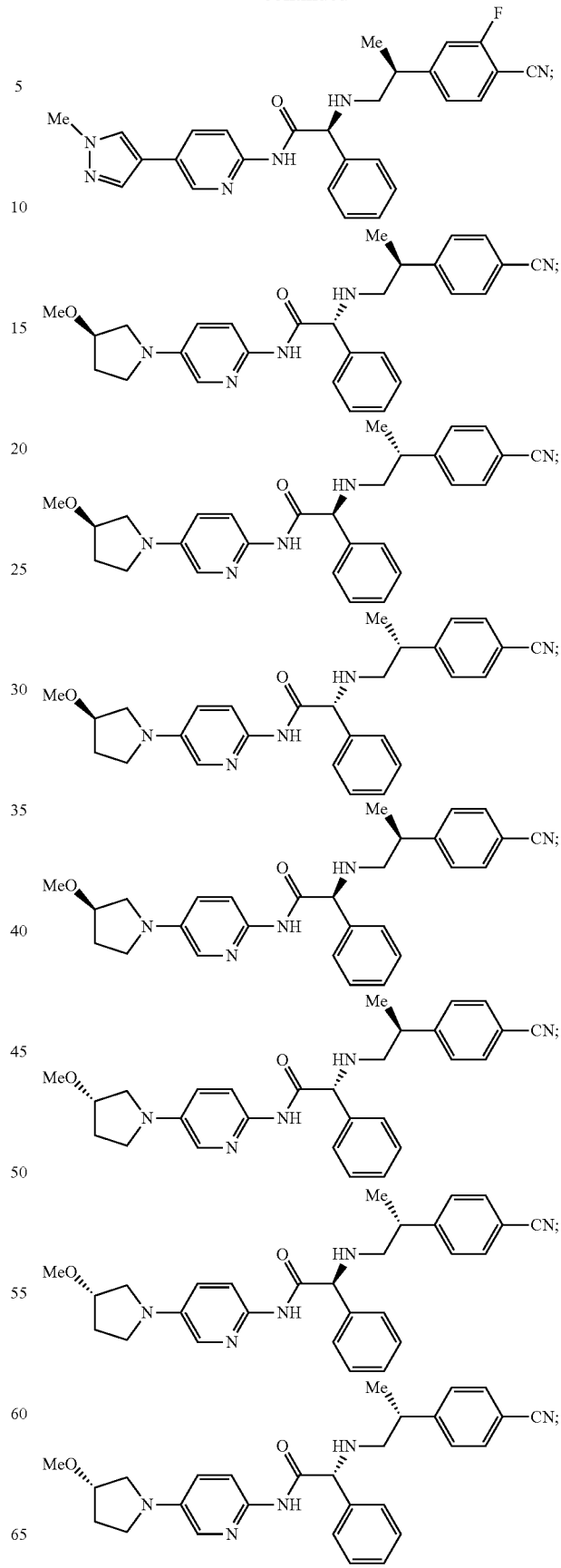

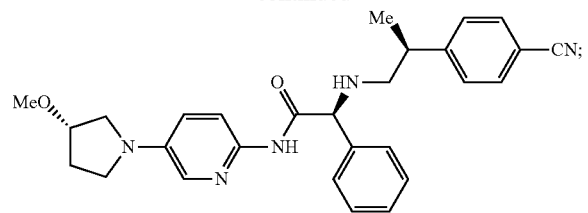
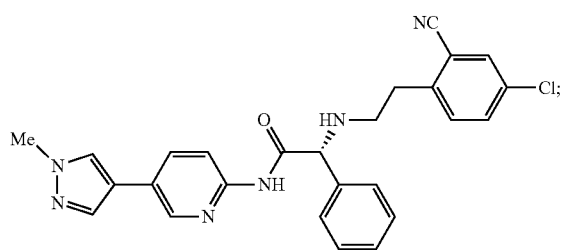
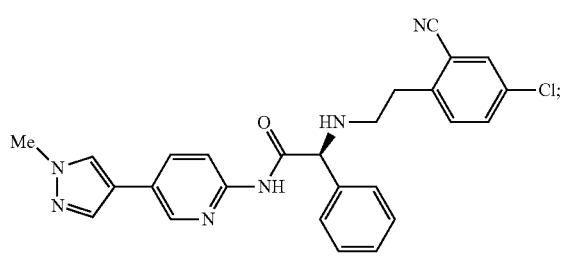
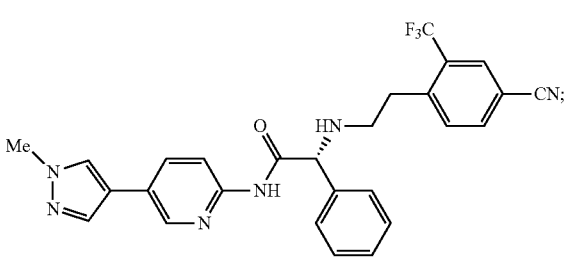
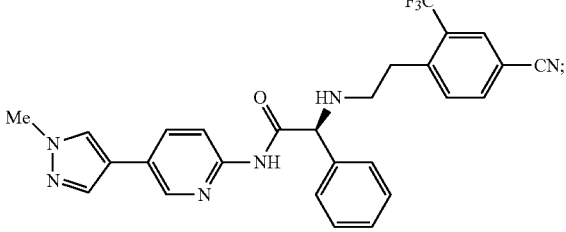
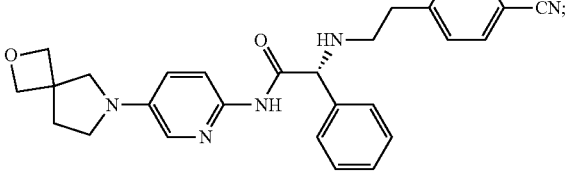
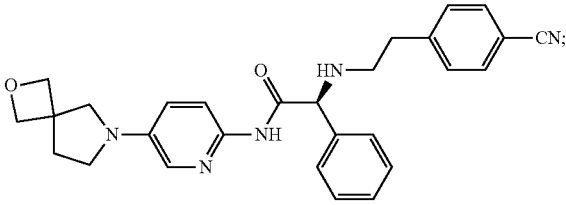
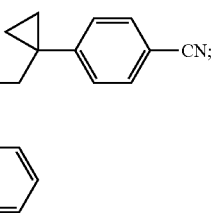
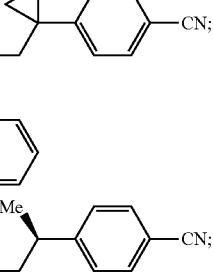
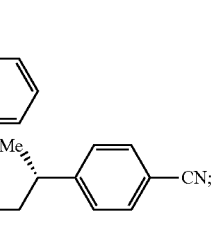
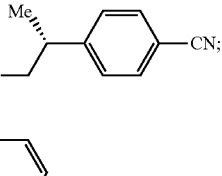
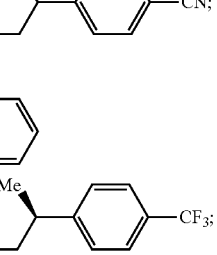
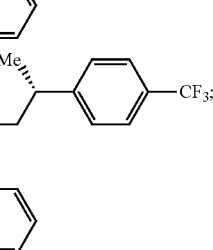

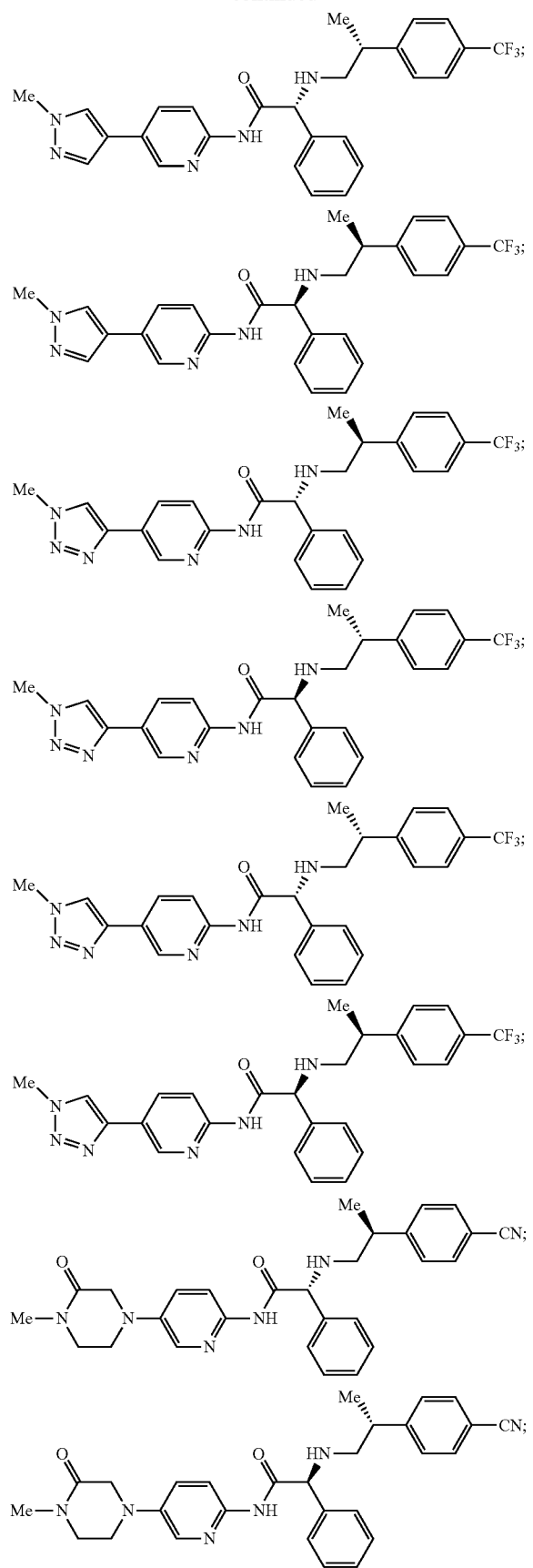
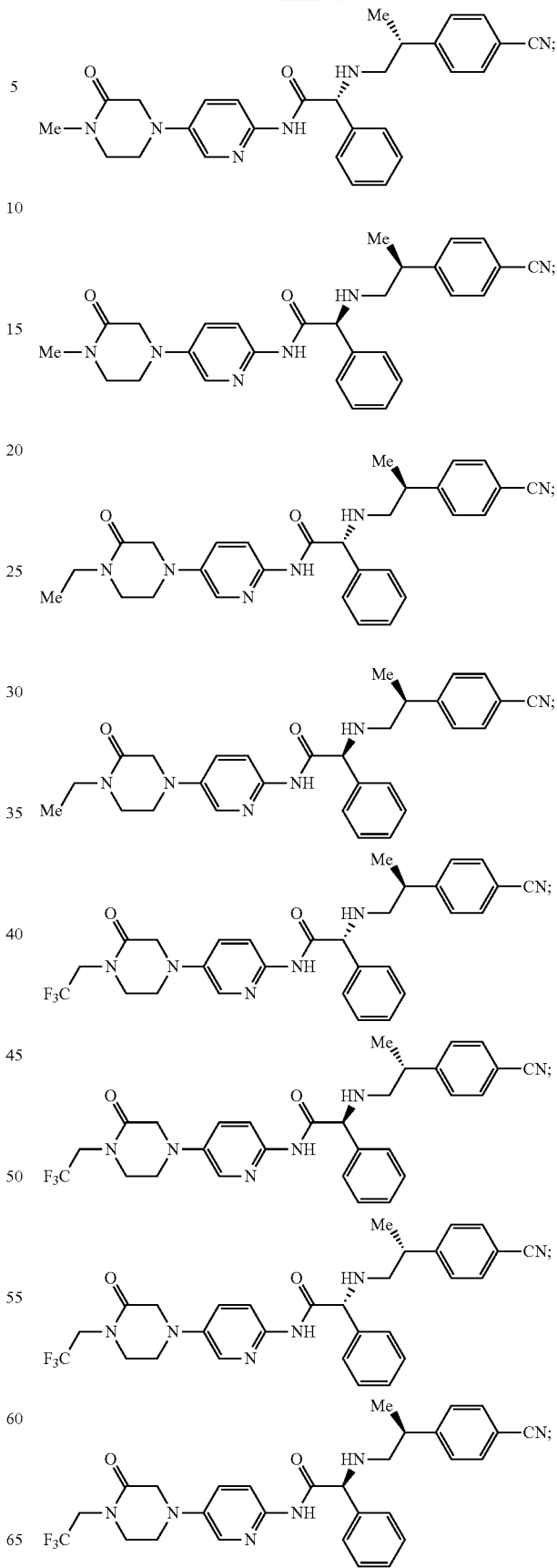

221
-continued
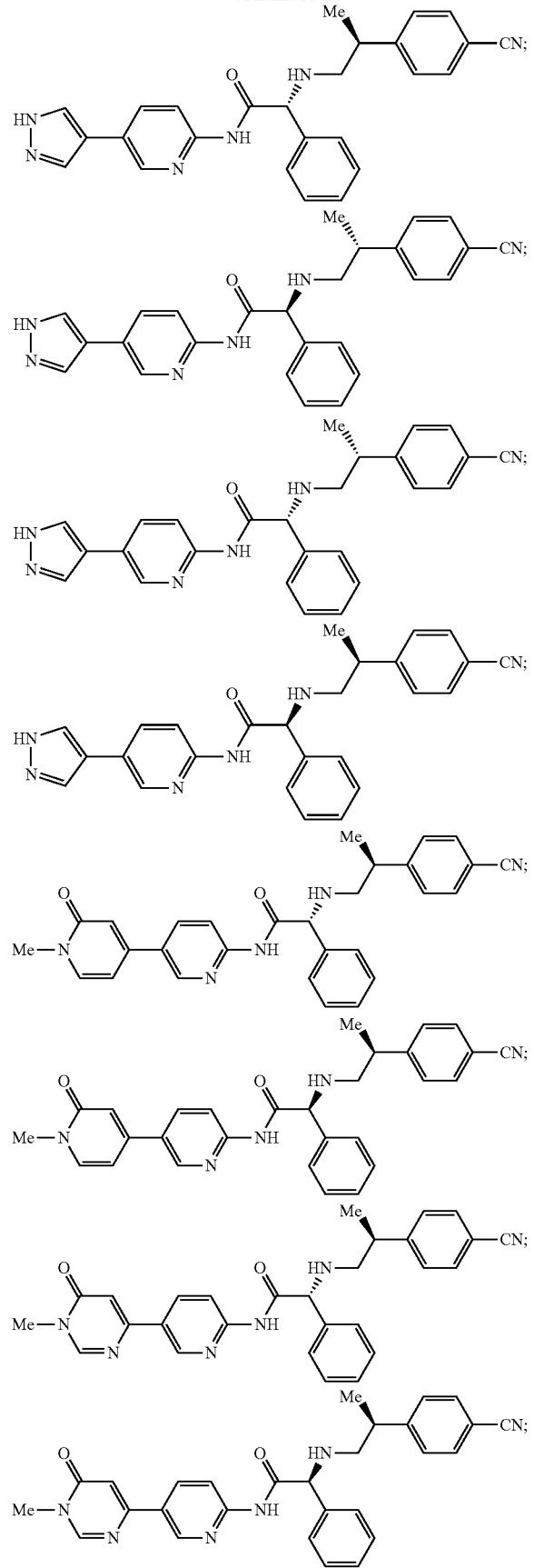
222
-continued
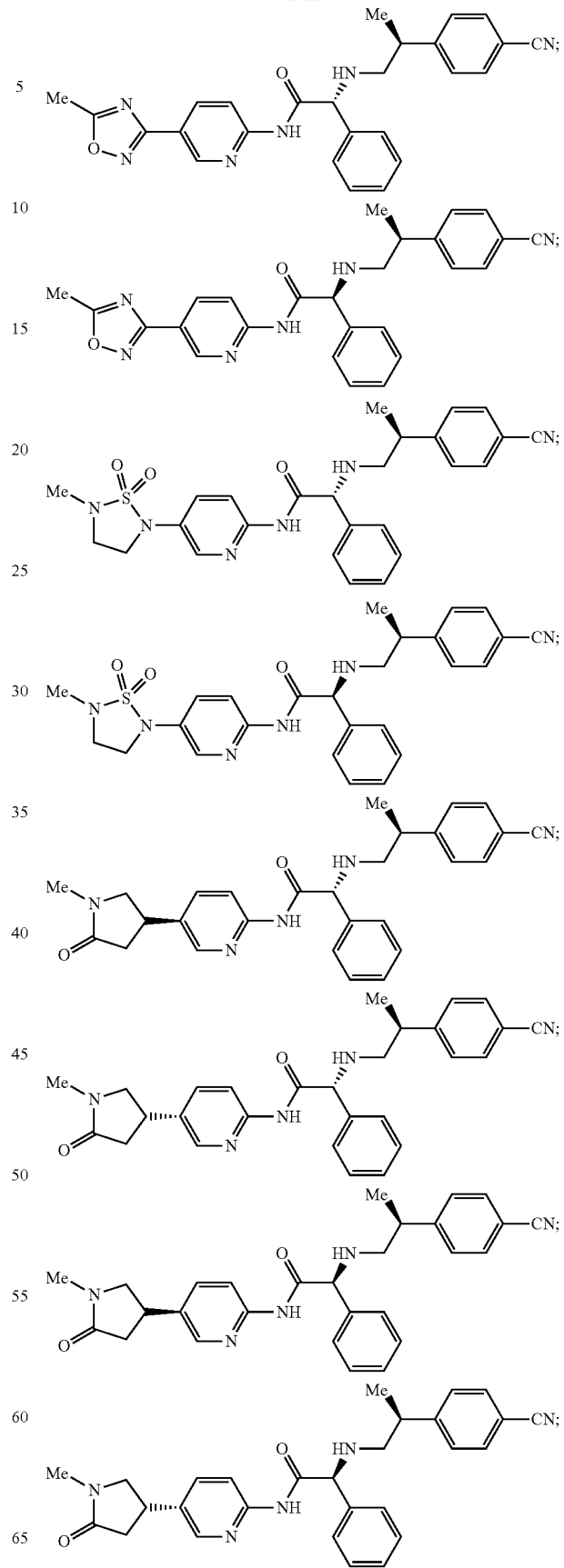

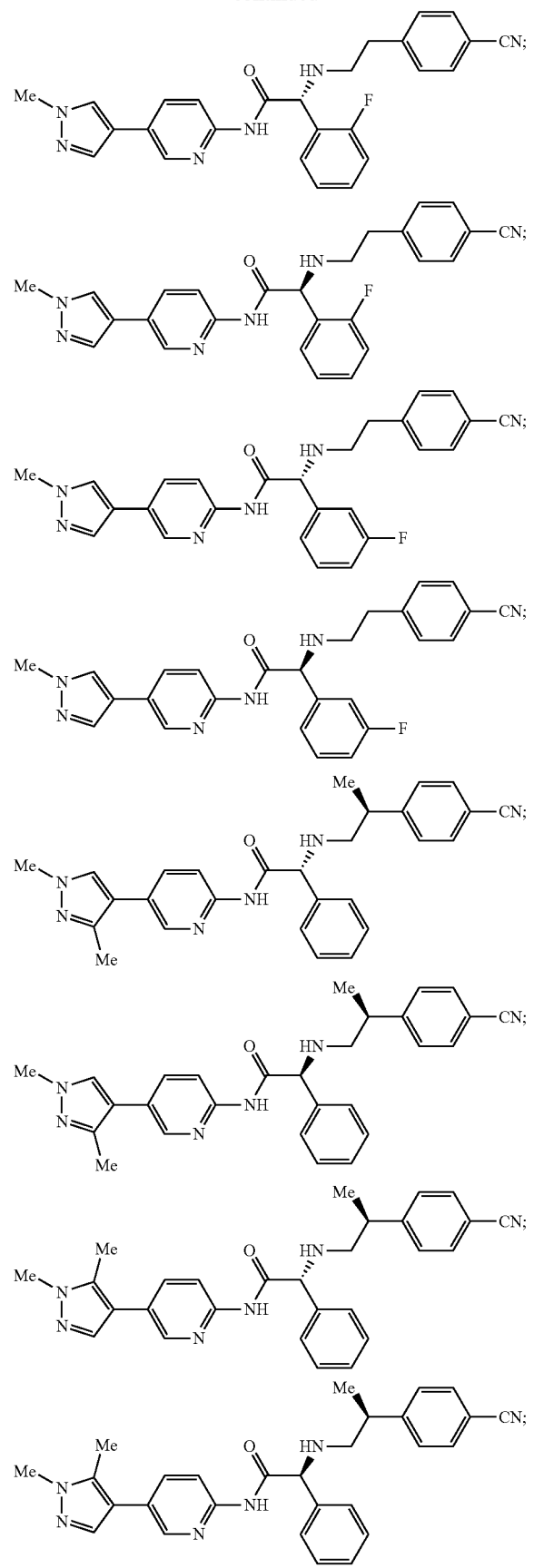
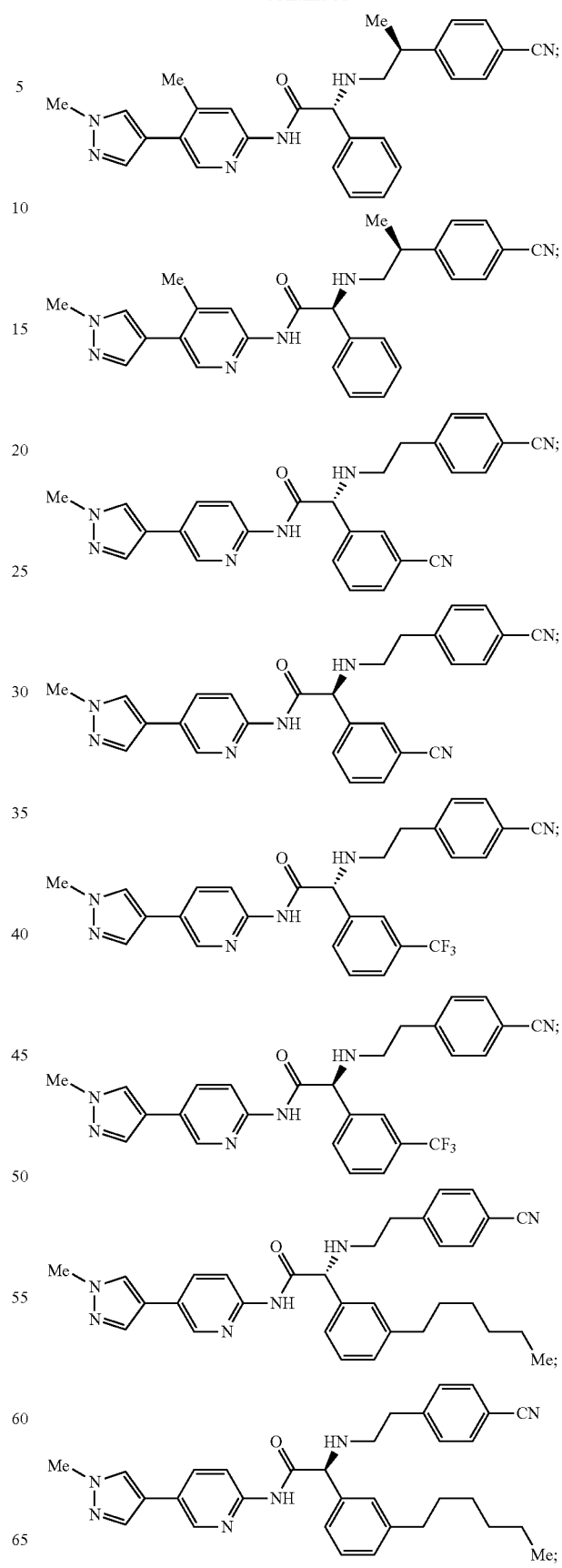

-continued
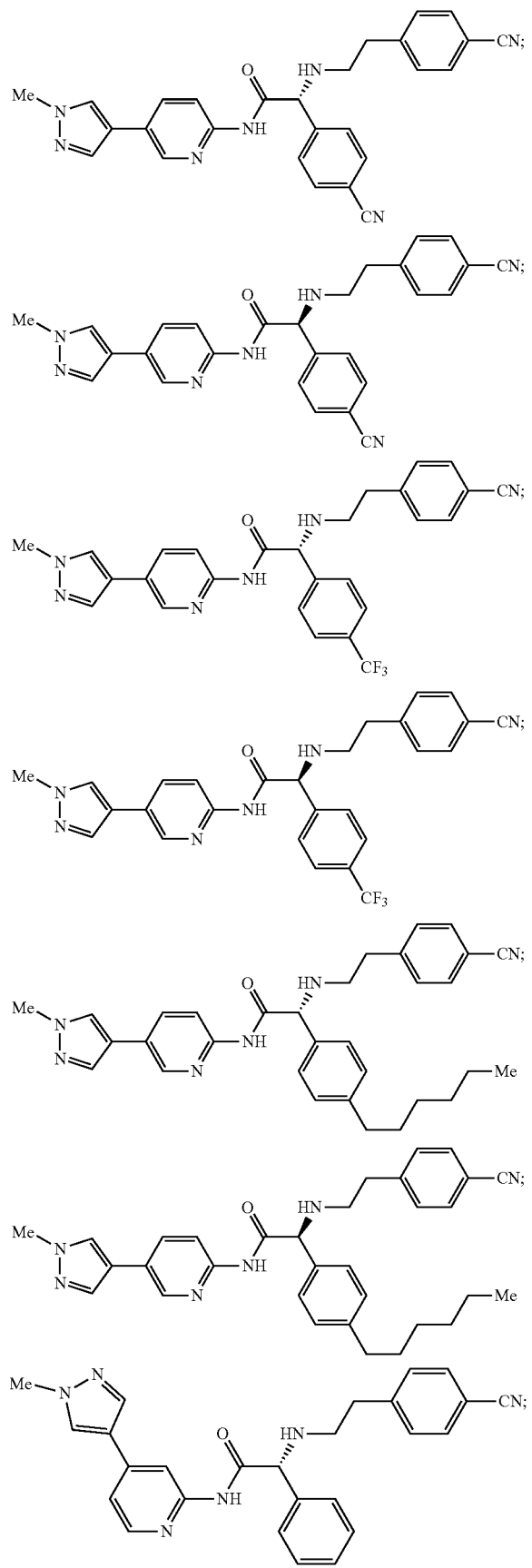
-continued
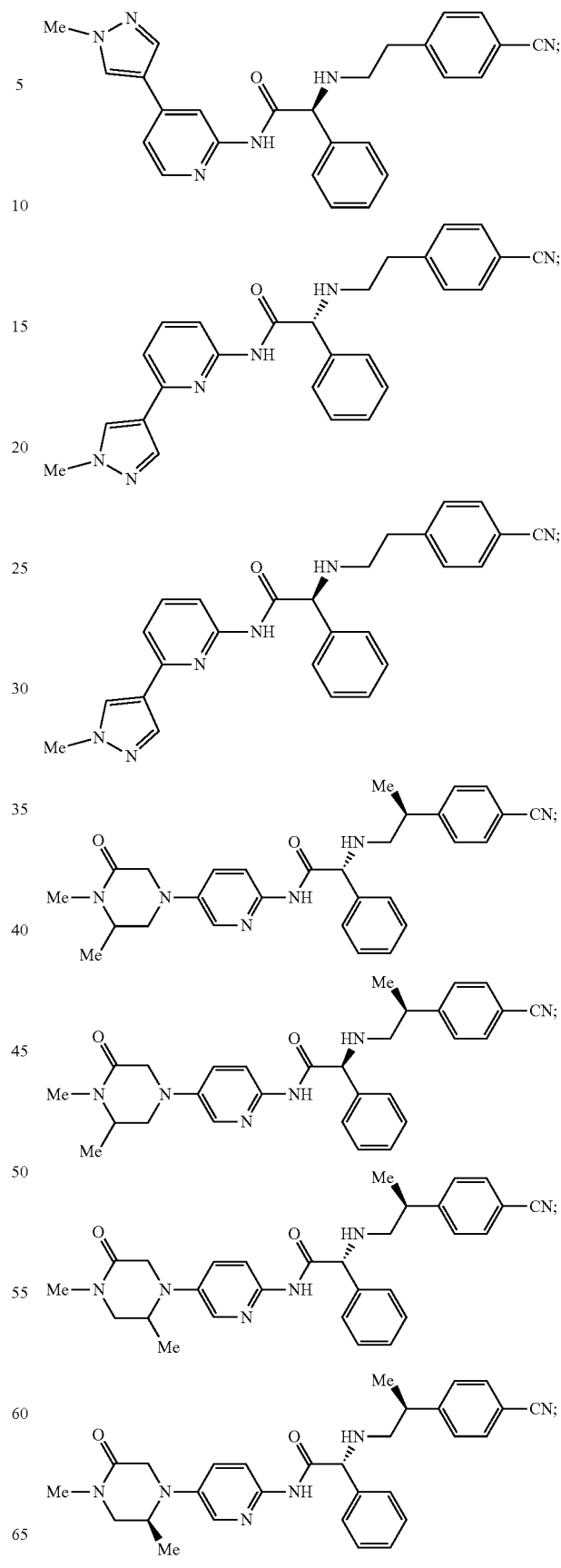

227
-continued
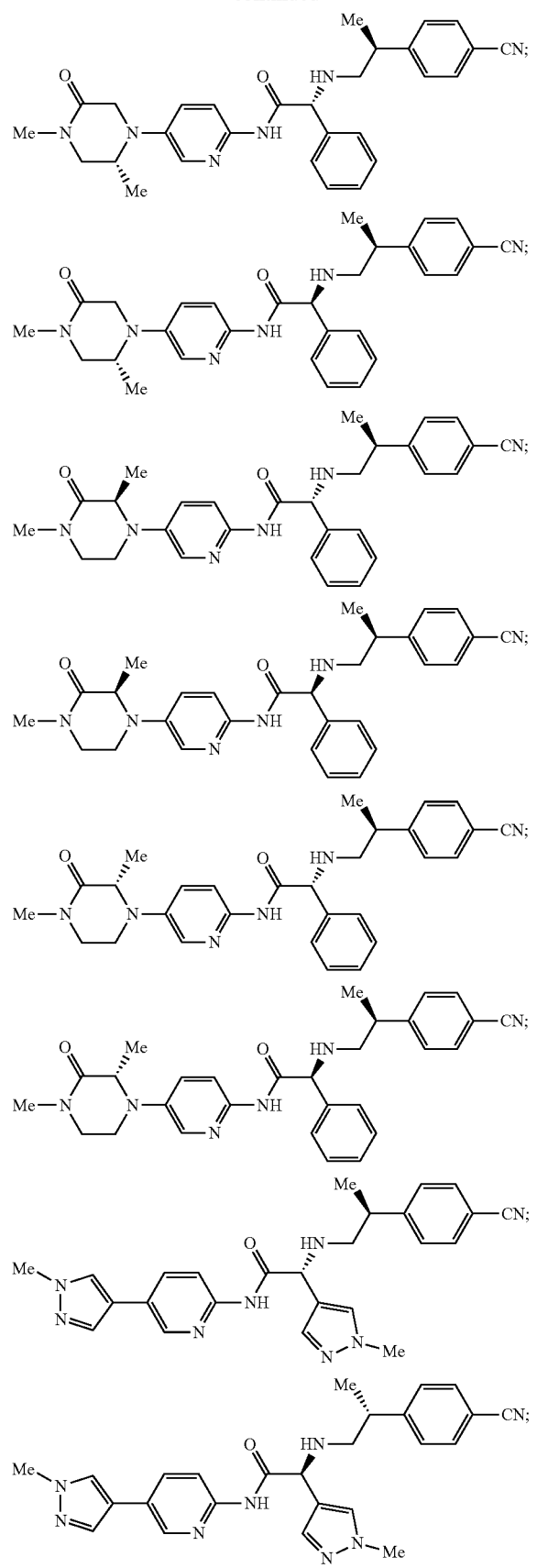
228
-continued
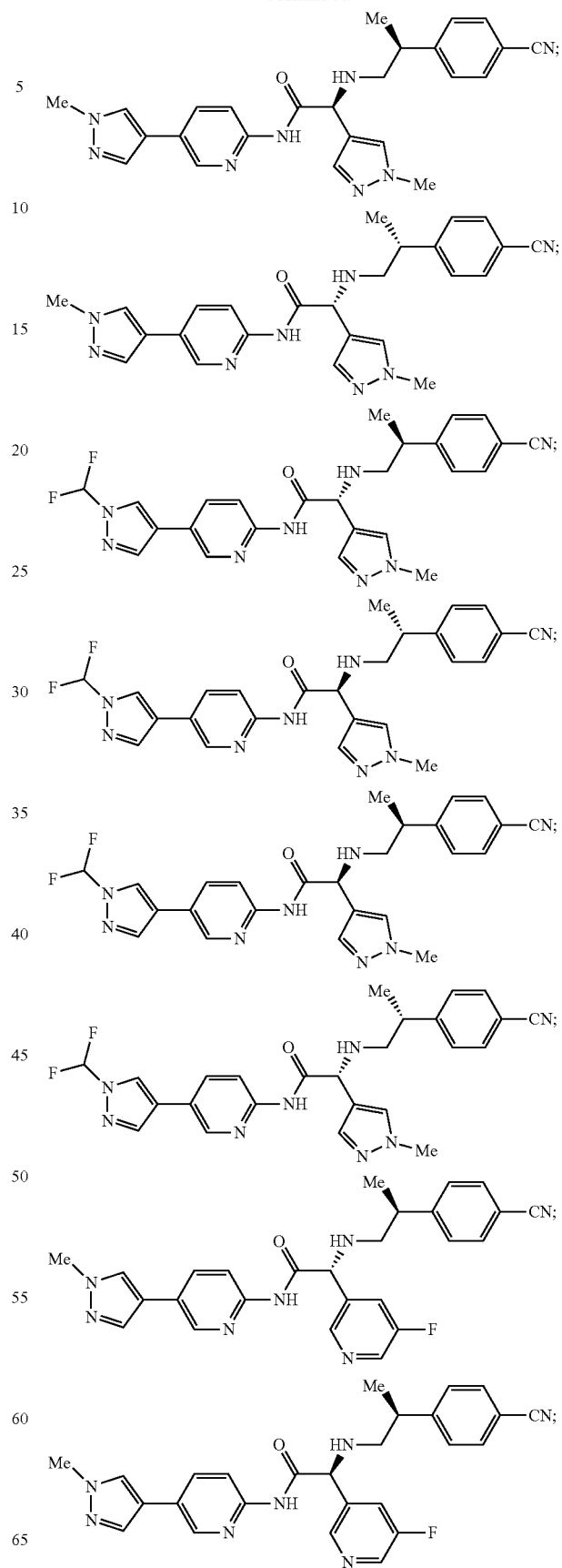

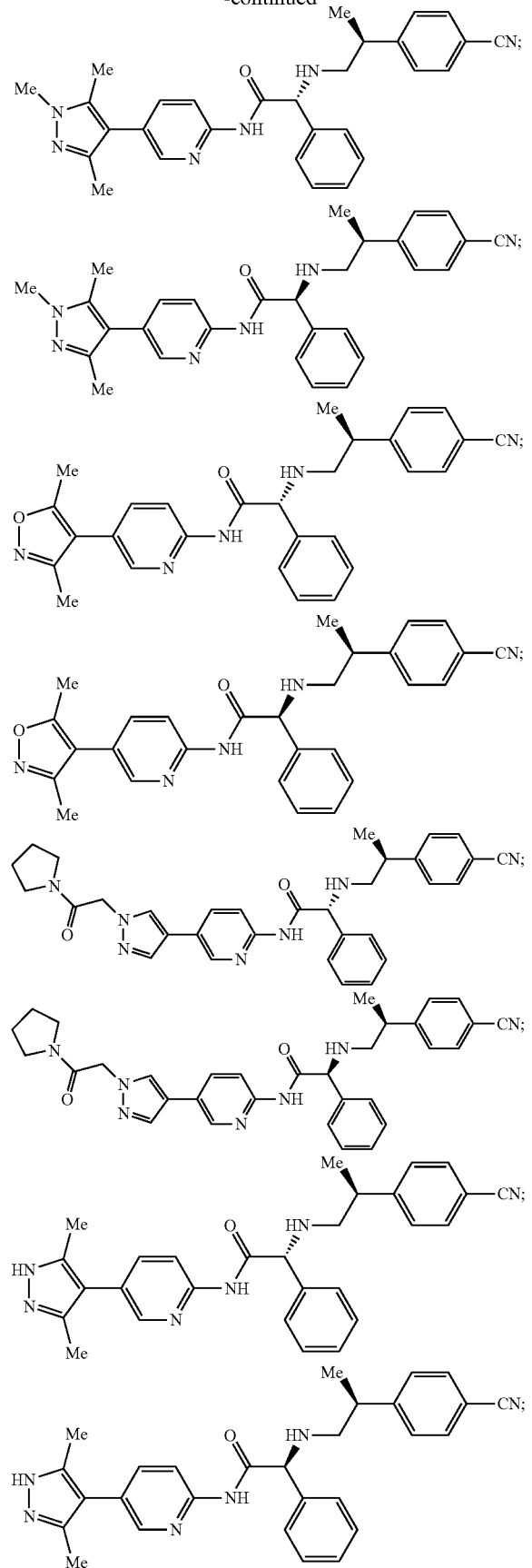
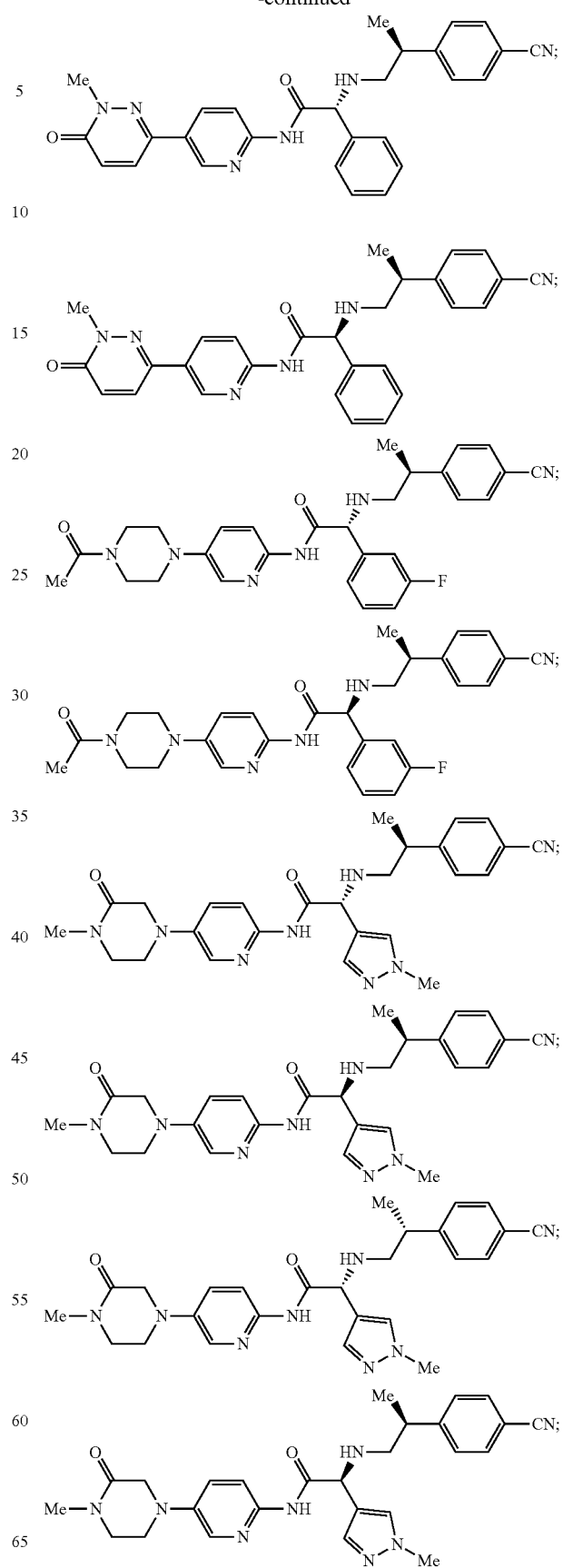

231
-continued
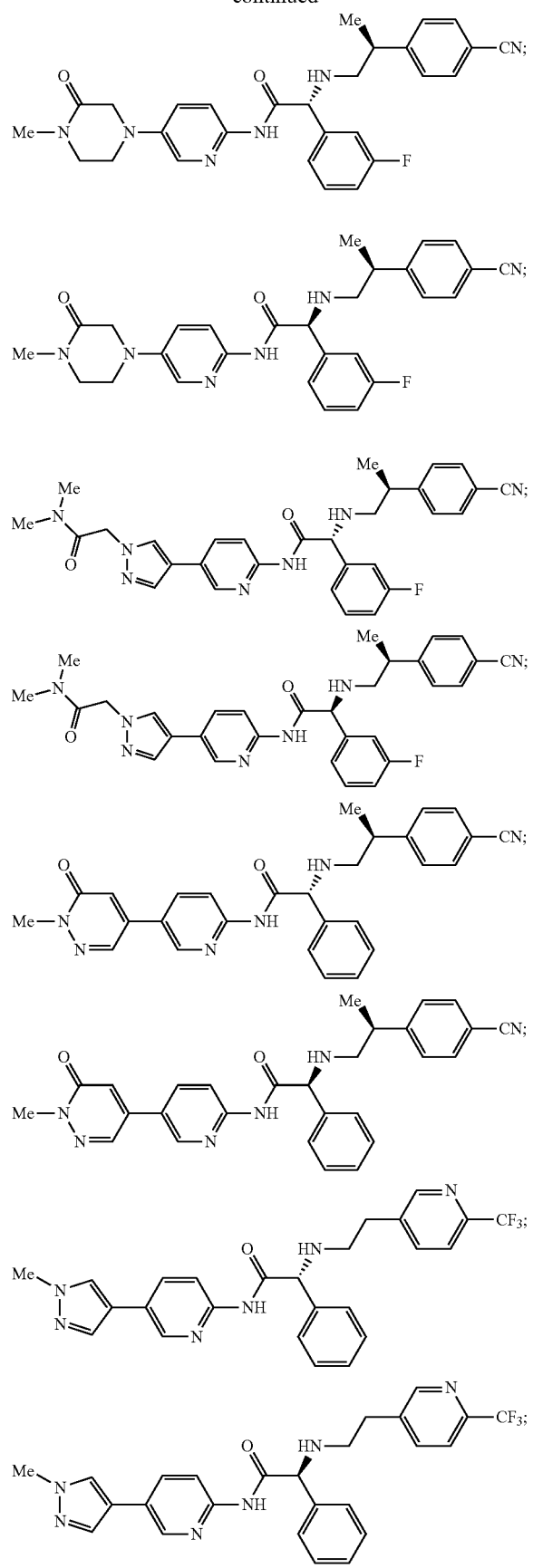
232
-continued
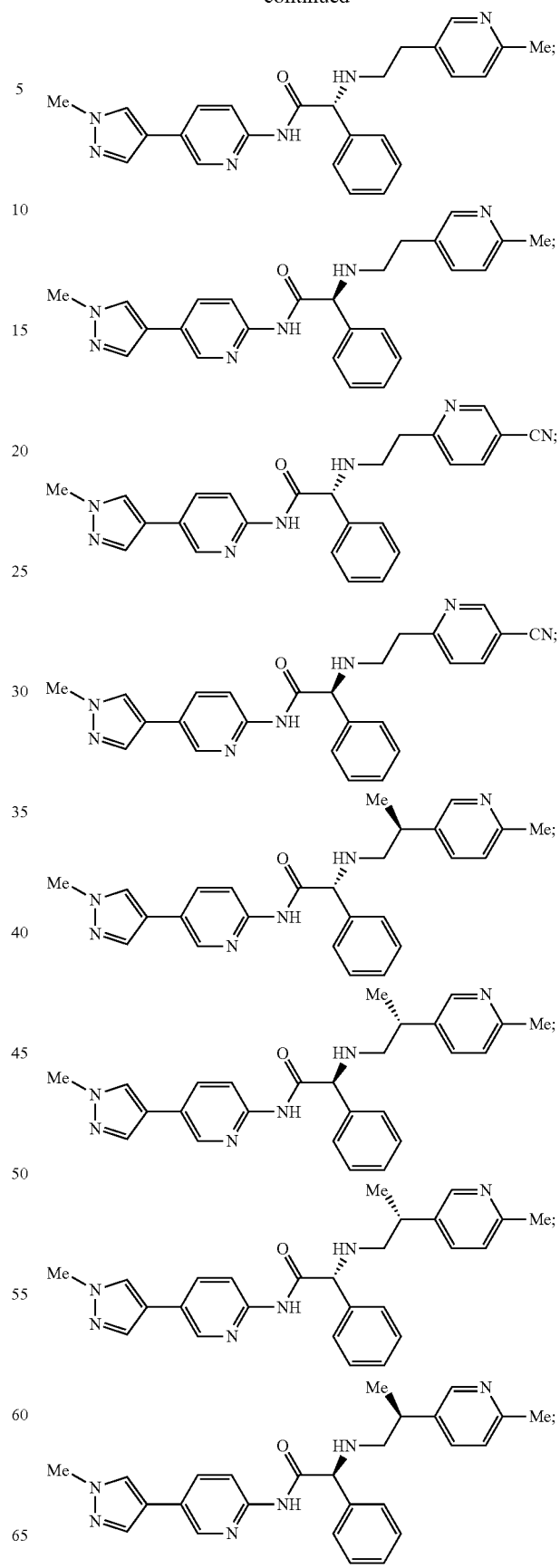

233
-continued
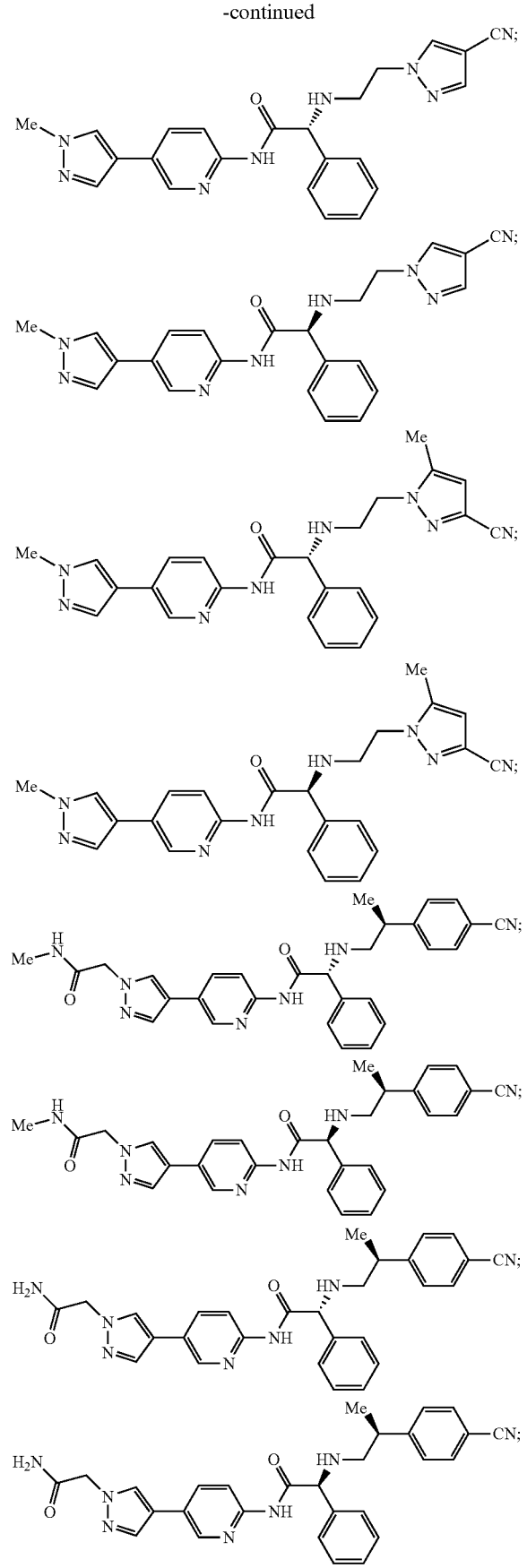
234
-continued
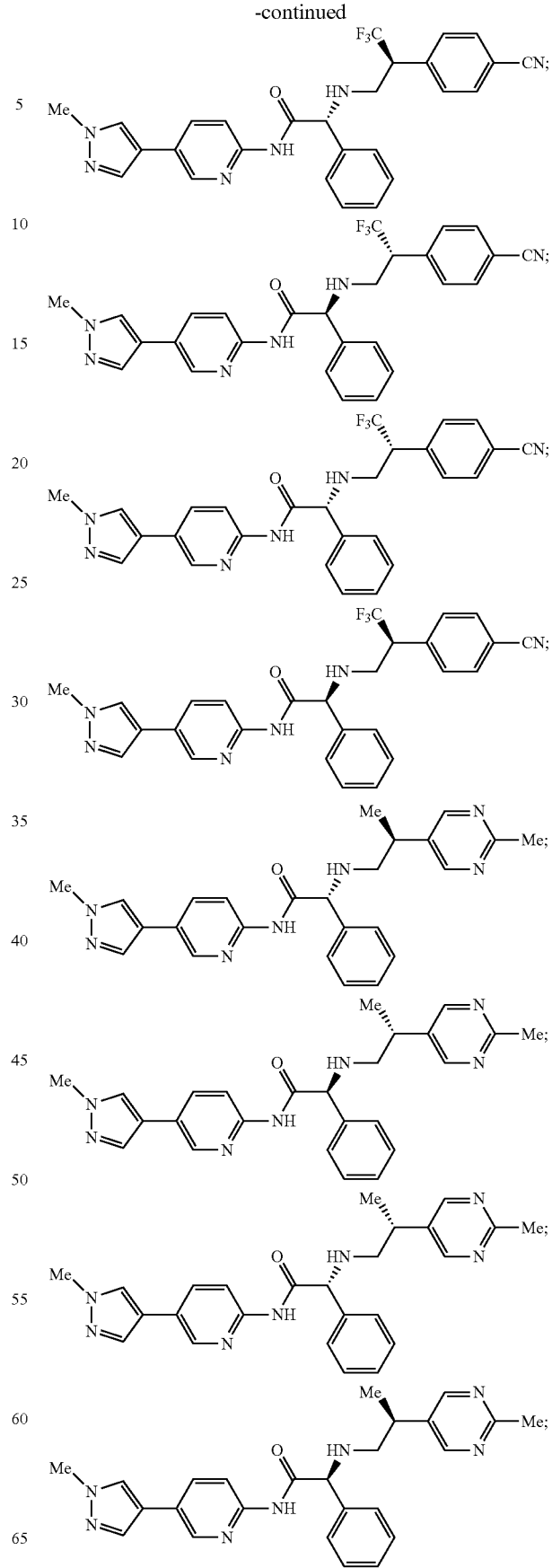

-continued

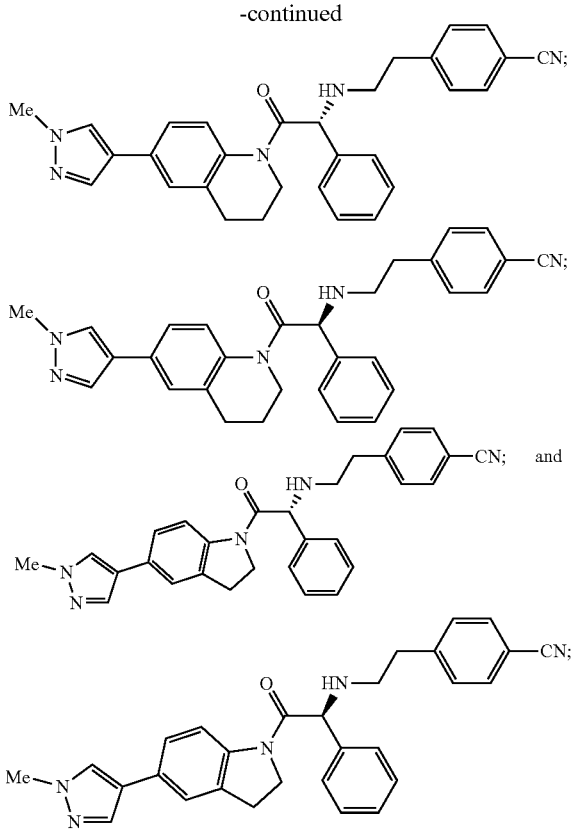

22. The compound of claim 1, wherein the compound is of the structural formula:

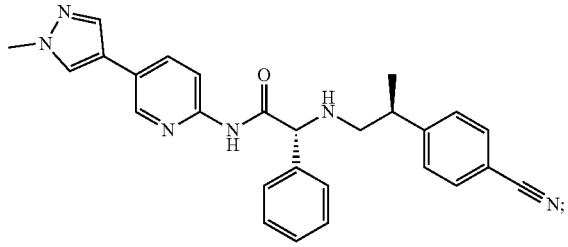 [SMILES: C[C@H](CN[C@@H](C(=O)Nc1ccc(-c2cnn(C)c2)cn1)c1ccccc1)c1ccc(C#N)cc1]

or a pharmaceutically acceptable salt thereof.

23. A pharmaceutical composition comprising
1) a compound of claim 1, or a pharmaceutically acceptable salt thereof; and
2) a pharmaceutically acceptable carrier.

24. A method of treating a CBP and/or EP300-mediated disorder in a subject in need thereof, comprising administering to the subject a therapeutically effective amount of a compound of claim 1, or a pharmaceutically acceptable salt thereof.

* * * * *